United States Patent
Chen et al.

(10) Patent No.: US 12,397,027 B2
(45) Date of Patent: Aug. 26, 2025

(54) PSEUDORABIES VIRUS FOR TREATING TUMORS

(71) Applicants: XIAMEN UNIVERSITY, Xiamen (CN); YANG SHENG TANG COMPANY, LTD., Hangzhou (CN)

(72) Inventors: Yixin Chen, Xiamen (CN); Guosong Wang, Xiamen (CN); Quan Yuan, Xiamen (CN); Jiali Cao, Xiamen (CN); Lina Lin, Xiamen (CN); Ningshao Xia, Xiamen (CN)

(73) Assignees: XIAMEN UNIVERSITY, Xiamen (CN); YANG SHENG TANG COMPANY, LTD., Hangzhou (CN)

( * ) Notice: Subject to any disclaimer, the term of this patent is extended or adjusted under 35 U.S.C. 154(b) by 1179 days.

(21) Appl. No.: 16/966,345

(22) PCT Filed: Feb. 1, 2019

(86) PCT No.: PCT/CN2019/074349
§ 371 (c)(1),
(2) Date: Jul. 30, 2020

(87) PCT Pub. No.: WO2019/149265
PCT Pub. Date: Aug. 8, 2019

(65) Prior Publication Data
US 2022/0110988 A1   Apr. 14, 2022

(30) Foreign Application Priority Data
Feb. 1, 2018   (CN) .......................... 201810100861.5

(51) Int. Cl.
*A61P 35/00* (2006.01)
*A61K 35/763* (2015.01)
*C12N 7/00* (2006.01)

(52) U.S. Cl.
CPC ............ *A61K 35/763* (2013.01); *A61P 35/00* (2018.01); *C12N 7/00* (2013.01)

(58) Field of Classification Search
None
See application file for complete search history.

(56) References Cited

U.S. PATENT DOCUMENTS

2009/0304735 A1   12/2009   Belz et al.

FOREIGN PATENT DOCUMENTS

| CN | 103952379 A | 7/2014 |
| CN | 105175551 A | 12/2015 |
| CN | 105368791 A | 3/2016 |
| CN | 106497890 A | 3/2017 |
| EP | 2 803 364 A1 | 11/2014 |
| WO | WO 2007/134385 A1 | 11/2007 |

OTHER PUBLICATIONS

Wollmann, et al. J Virol. May 2005;79(10):6005-22. doi: 10.1128/JVI.79.10.6005-6022.2005. PMID: 15857987. (Year: 2005).*
Cheung, et al. Am J Vet Res. Dec. 1994;55(12):1710-6, PMID: 7887515. (Year: 1994).*
Hummel, et al. (Mol Ther. Dec. 2005;12(6):1101-10. doi: 10.1016/j.ymthe.2005.07.533. Epub Sep. 1, 2005. PMID: 16140040. (Year: 2005).*
Parkinson, et al. J Virol. Nov. 2000;74(21):10006-17. doi: 10.1128/jvi.74.21.10006-10017.2000. PMID: 11024129. (Year: 2000).*
Zhang, et al. Oncotarget. Aug. 21, 2015;6(24):20345-55. doi: 10.18632/oncotarget.3884. PMID: 25972362. (Year: 2015).*
GenBank Accession JQ809329.1 (Dec. 1, 2016). (Year: 2016).*
GenBank Accession JF797217.1 (Nov. 2, 2011). (Year: 2011).*
Saha D, et al. Macrophage Polarization Contributes to Glioblastoma Eradication by Combination Immunovirotherapy and Immune Checkpoint Blockade. Cancer Cell. Aug. 14, 2017;32(2):253-267.e5. doi: 10.1016/j.ccell.2017.07.006. PMID: 28810147. (Year: 2017).*
Australian Examination Report issued Oct. 14, 2021 in Australian Patent Application No. 2019214179, 8 pages.
Extended European Search Report issued Oct. 28, 2021 in European Patent Application No. 19747565.0, 6 pages.
"Suid herpesvirus 1 strain Bartha, complete genome; NCBI accession No. JF797217.1," Retrieved from the Internet [URL: https://www.ncbi.nlm.nih.gov/nuccore/JF797217?report=girevhist], Jul. 24, 2012, 1 page.
Ai-Li Shiau, et al., "Development of a Conditionally Replicating Pseudorabies Virus for HER-2/neu-overexpressing Bladder Cancer Therapy," Molecular Therapy, vol. 15, No. 1, XP055852454, Jan. 2007, pp. 131-138.
Aotian Xu, et al., "A simple and rapid approach to manipulate pseudorabies virus genome by CRISPR/Cas9 system," Biotechnology Letters, vol. 37, XP037122173, 2015, pp. 1265-1272.
International Search Report issued May 5, 2019 in PCT/CN2019/074349, (submitting English translation only), 5 pages.
Written Opinion of the International Searching Authority issued May 5, 2019 in PCT/CN2019/074349, (submitting English translation only), 5 pages.
Combined Chinese Office Action and Search Report issued Sep. 18, 2020, in Chinese Patent Application No. 201910102988.5 (submitting English translation only), 11 pages.

(Continued)

*Primary Examiner* — Benjamin P Blumel
(74) *Attorney, Agent, or Firm* — Oblon, McClelland, Maier & Neustadt, L.L.P.

(57) ABSTRACT

A pseudorabies virus (PRV) or a modified form thereof, or a genome sequence or a cDNA sequence containing the PRV or the modified form thereof, or nucleic acid molecules of a complementary sequence of the cDNA sequence, for treating tumors of subjects and/or reducing or inhibiting tumor recurrence, and for preparation of a pharmaceutical composition used for treating the tumors of the subjects and/or reducing or inhibiting the tumor recurrence. A method for treating tumors and/or reducing or inhibiting tumor recurrence, comprising a step of administering, on a subject having a need, the PRV or the modified form thereof, or nucleic acid molecules of the genome sequence containing the PRV or the modified form thereof.

18 Claims, 7 Drawing Sheets
Specification includes a Sequence Listing.

(56) References Cited

OTHER PUBLICATIONS

Guido Wollmann. et al. "Oncolytic Virus Therapy of Glioblastoma Multiforme-Concepts and Candidates" Cancer J., vol. 18, No. 1, Dec. 31, 2012, pp. 69-81.
L. Lerma, et al., "Expression of the Immediate Early IE180 Protein Under the Control of the Htert and CEA Tumor-Specific Promoters in Recombinant Pseudorabies Viruses: Effects of IE180 Protein on Promoter Activity and Apoptosis Induction" Virology, vol. 488, 2016, pp. 9-19.
Tu, Yanyang et al. "Research Progress in Tumor Immunotherapy of Oncolytic Virus" E-Journal of Translational Medicine, vol. 4, No. 1, Dec. 31, 2017, pp. 20-23 (with English Abstract).
Yao, Hong, "Isolation and Identification of Pseudorabies Virus" Shandong Journal of Animal Husbandry and Veterinary Science, vol. 38, Dec. 31, 2017, pp. 16-17 (with English Abstract).
Zolt Boldogkoi, et al., "Evaluation of Pseudorabies Virus as a Gene Transfer Vector and an Oncolytic Agent for Human Tumor Cells" Anticancer Research, vol. 22, Jul. 31, 2002, pp. 2153-2160.
Yao Lin, Construction of Truncation Mutants of Pseudorabies Virus VP22 and Stud on their Function [D], Wuhan: Huazhong Agricultural University, 2006, 56 pages (with English Abstract) attached.

\* cited by examiner

PSEUDORABIES VIRUS FOR TREATING TUMORS

REFERENCE TO A SEQUENCE LISTING

In accordance with 37 CFR § 1.52(e)(5), the present specification makes reference to a Sequence Listing submitted electronically as a .txt file named "531837US_ST25.txt". The .txt file was generated on Aug. 17, 2020 and is 352 kb in size. The entire contents of the Sequence Listing are herein incorporated by reference.

TECHNICAL FIELD

The invention relates to the fields of virus and tumor therapy. In particular, the present invention relates to use of a pseudorabies virus (PRV) or modified form thereof, or a nucleic acid molecule comprising a genomic sequence of the PRV or modified form thereof, for treating a tumor and/or reducing or inhibiting tumor recurrence in a subject (e.g., a human), and use thereof in manufacture of a medicament for treating a tumor and/or reducing or inhibiting tumor recurrence in a subject (e.g., a human). The present invention also relates to a method for treating a tumor and/or reducing or inhibiting tumor recurrence, which comprises a step of administering to a subject in need thereof a PRV or modified form thereof, or a nucleic acid molecule comprising a genomic sequence of the PRV or modified form thereof.

BACKGROUND ART

The current means for treatment of malignant tumors mainly include surgical treatment, chemotherapy and radiotherapy. These traditional therapies are not satisfactory in the treatment of metastasized tumors, and may further cause great harm to the health of patients.

An oncolytic virus is a virus that can replicate itself in tumor cells, thereby killing or lysing tumor cells, or stopping the growth of tumor cells. When in vivo treatment is performed, oncolytic viruses exhibit specific selectivity for tumor cells and can directly induce the death of tumor cells, but have little or no effect on normal cells; meanwhile, oncolytic viruses can also stimulate the response of B lymphocytes and T lymphocytes in immune system, thereby indirectly killing tumor cells. Therefore, oncolytic viruses are considered to be a promising tumor treatment method.

Pseudorabies virus (PRV), also known as porcine herpesvirus type I, infectious bulbar paralysis virus, "mad itch" virus, Aujeszky's disease virus, belongs to the genus varicellovirus of subfamily α-herpesvirus. It is a herpesvirus that causes fever, severe itching (except for pigs) and encephalomyelitis as the main symptoms in a variety of domestic animals and wild animals such as cattle, sheep, pig, dog and cat. Pig is a natural host of pseudorabies virus, and exhibits symptoms of acute infectious diseases such as fever, diarrhea, dyspnea, encephalomyelitis and reproductive disorders after infection. Pseudorabies virus has the following characteristics: first, as a double-stranded DNA virus, there is not a process of integrating its genome into the host chromosome in a host; second, although pseudorabies virus has been endemic in some lower mammals, it has not been reported by official literature that it can infect human and cause disease; further, pseudorabies virus does not contain an oncogene. At present, pseudorabies virus is widely used as a veterinary vaccine, etc., but there is no report about pseudorabies virus having oncolytic activity in the art.

CONTENTS OF THE INVENTION

In the present invention, unless otherwise stated, the scientific and technical terms used herein have the meaning commonly understood by those skilled in the art. In addition, the operating steps for cell culture, virology, biochemistry, cell biology, nucleic acid chemistry and so on used herein are conventional steps widely used in the corresponding fields. Meanwhile, in order to better understand the present invention, definitions and explanations of related terms are provided below.

As used herein, the term "pseudorabies virus (PRV)" refers to a virus of the genus varicellovirus (Varicellovirus) of subfamily α-herpesvirus (Alphaherpesvirinae). The genome of the virus is a linear double-stranded DNA with a size of 130 kd to 150 kd. The genome of the virus includes a unique long region sequence (UL) and a unique short region sequence (US), and there are a terminal repeat sequence (TRR) and internal repeat sequence (IRS) on both sides of the US. The genes of PRV are named according to their regions and the order of discovery, but they can also be named by the proteins encoded by them. The genes encoding structural proteins include US2 (28K), US3 (PK), US4 (gG), US6 (gD), US7 (gI), US8 (gE), US9 (11K) and other genes in the US region, and capsid protein genes of UL9 (OBP), UL27 (gB), UL (gH), UL (TK), UL (gC), DNA polymerase gene and other genes in the UL region. The non-structural protein genes located in the UL region include UL54 which participates in transcriptional regulation. In the present invention, the expression "pseudorabies virus (PRV)" refers to a wild-type PRV, which can be isolated from a natural source and has not been intentionally modified by man, and the examples thereof include the wild strains Bartha-K61 (BK61) and HB-98, as well as various isolates from specimens (for example, the isolate described in Example 1 of the present invention). The wild-type PRV genome sequence is well known in the art, and can be found in various public databases (for example, GenBank database accession number: JF797217.1).

As used herein, the term "oncolytic virus" refers to a virus that can infect a tumor cell, replicate in the tumor cell, and cause the death and lysis of the tumor cell, or prevent the growth of the tumor cell. Preferably, the virus has minimal toxic effects on a non-tumor cell.

As used herein, the term "tumor-specificity" refers to selectively exhibiting a biological function or activity in a tumor cell. For example, in the present invention, when the term "tumor specificity" is used to describe the killing selectivity of a virus, it means that the virus can selectively kill a tumor cell without killing or hardly killing a non-tumor cell, or, the virus is more effective in killing a tumor cell than killing a non-tumor cell.

As used herein, the term "oncolytic activity" mainly comprises tumor-killing activity. When describing the oncolytic activity of a virus, the oncolytic activity of the virus can typically be measured by indicators such as its ability to infect a tumor cell, its ability to replicate in the tumor cell, and/or its ability to kill the tumor cell. The oncolytic activity of a virus can be measured using any method known in the art. For example, the ability of a virus to infect a tumor cell can be evaluated by measuring the viral dose required to infect a given percentage of tumor cells (e.g., 50% of cells); the ability to replicate in a tumor cell can be evaluated by measuring the growth of the virus in the tumor cell; the ability to kill a tumor cell can be evaluated by monitoring cytopathic effect (CPE) or measuring tumor cell activity.

As used herein, the term "modified form" of a virus refers to a modified virus obtained by modifying a wild-type virus, which retains the desired activity (e.g., oncolytic activity) of the wild-type virus. In the present invention, "modified form" of PRV includes, but is not limited to, a modified PRV virus, which has a substitution, insertion or deletion of one or more nucleotides compared to the genomic sequence of a wild-type PRV, and at least retains the oncolytic activity of PRV. It should be understood that the modified form of PRV or the modified PRV of the present invention is not limited by the method for production. For example, the modified form of PRV or the modified PRV of the present invention can be produced by homologous recombination, or can be prepared by culturing a host cell infected with the modified form or the modified PRV.

As used herein, the term "EP0 protein" refers to the early protein 0 of the PRV virus, which is encoded by the EP0 gene and is a transcriptional activator expressed early by the PRV virus. The amino acid sequence of the EP0 protein is known and can be found in, for example, public databases (for example, EM64001.1).

As used herein, the expression "do not express a functional EP0 protein" means that when a virus or viral genome infects a cell, the virus or viral genome cannot produce or express an EP0 protein with biological function or activity. For example, the virus or viral genome may not produce or express EP0 protein at all due to gene deletion, or may produce or express EP0 protein that has no biological function and activity due to a loss-of-function mutation.

As used herein, the term "loss-of-function mutation" refers to a mutation that causes the protein encoded and expressed by the mutant gene to lose its biological function and activity. Loss-of-function mutation includes, but is not limited to, missense mutation, nonsense mutation, frameshift mutation, base deletion, base substitution, base addition, and any combination thereof (e.g., deletion or substitution or addition of a gene fragment), as long as the gene containing the loss-of-function mutation cannot produce or express a protein with biological function or activity.

As used herein, the expression "cDNA sequence of PRV" refers to a DNA sequence obtained by reverse transcription using mRNA transcribed from the viral genome as a template, which differs from the genome sequence only in that the cDNA sequence does not contain the intron sequence in the genomic sequence.

As used herein, the term "exogenous nucleotide sequence" refers to an artificially introduced nucleotide sequence that is foreign to the original sequence. Exogenous nucleotide sequence includes, but is not limited to, any genes or nucleotide sequences not found in the viral genome. However, in some cases, it is preferred that the exogenous nucleotide sequence encodes a polypeptide having a therapeutic use, such as an immunomodulatory polypeptide, cytokine, chemokine, anti-tumor protein or polypeptide, and the like.

As used herein, the term "immunomodulatory polypeptide" refers to a polypeptide capable of modulating the function of an immune cell, examples thereof include, but are not limited to, CD40L, OX40L, inducible costimulatory molecule (ICOS), FTL3L, LIGHT, CD137L, CD70, 4-1BB, GITR, and CD28 (see, for example, Khalil D N, Smith E L, Brentjens R J, et al. The future of cancer treatment: immunomodulation, CARs and combination immunotherapy [J]. Nat Rev Clin Oncol, 2016, 13 (5): 273-290).

As used herein, the term "cytokine" has a meaning well known to those skilled in the art. However, in the present invention, when the oncolytic virus of the present invention is used to treat a tumor, it is particularly preferred that the cytokine is a cytokine that can be used for tumor treatment. Examples of "cytokine" include, but are not limited to, interleukins (e.g, IL-2, IL-12 and IL-15), interferons (e.g., IFNα, IFNβ, IFNγ), tumor necrosis factors (e.g., TNFα), colony stimulating factors (e.g., GM-CSF), and any combination thereof (see, for example, Ardolino M, Hsu J, Raulet D H. Cytokine treatment in cancer immunotherapy [J]. Oncotarget, 2015, 6 (23): 19346-19347).

As used herein, the term "chemokine" has a meaning well known to those skilled in the art. However, in the method of the present invention, when the oncolytic virus of the present invention is used to treat a tumor, it is particularly preferred that the cytokine is a chemokine that can be used for tumor treatment. Examples of "chemokine" include, but are not limited to, CCL2, RANTES, CCL7, CCL9, CCL10, CCL12, CCL15, CCL19, CCL21, CCL20, XCL-1, and any combination thereof (Homey B, Muller A, Zlotnik A. CHEMOKINES: AGENTS FOR THE IMMUNOTHERAPY OF CANCER [J]. Nat Rev Immunol, 2002, 2: 175-184).

As used herein, the term "anti-tumor protein or polypeptide" refers to a protein or polypeptide that has tumor therapeutic activity, including but not limited to: (1) a protein or polypeptide that is toxic to a cell, can inhibit cell proliferation, or induce apoptosis, its examples include but are not limited to, thymidine kinase TK (TK/GCV), TRAIL, and FasL (see, for example, Candolfi M, King G D, Muhammad A G, et al. Evaluation of proapoptotic transgenes to use in combination with Flt3L in an immune-stimulatory gene therapy approach for Glioblastoma multiforme (GBM) [J]. FASEB J, 2008, 22: 1077.13); (2) a protein or polypeptide with immunotherapeutic effect, such as immune checkpoint inhibitor, its examples include but are not limited to, anti-PD-1 antibody, anti-PD-L1 antibody, anti-TIGIT antibody, anti-BTLA antibody, anti-CTLA-4 antibody, anti-Tim-3 antibody, anti-Lag-3 antibody, anti-CD137 antibody, anti-OX40 antibody, anti-GITR antibody, anti-CD73 antibody, anti-KIR antibody, anti-ICOS antibody, anti-CSF1R antibody (see, for example, Nolan E, Savas P, Policheni A N, et al. Combined immune checkpoint blockade as a therapeutic strategy for BRCA1-mutated breast cancer [J]. Science Trans Med, 2017, 9: eaa14922; all of which are incorporated herein by reference); (3) a tumor-specific targeting antibody, its examples include but are not limited to, anti-HER2 antibody (e.g., Herceptin), anti-CD20 antibody (e.g, Rituximab), anti-VEGF antibody (e.g., Bevacizumab), anti-EGFR antibody (e.g., Cetuximab), or any combination thereof; (4) a protein or polypeptide that inhibits tumor angiogenesis, its examples include but are not limited to, anti-vascular endothelial growth factor (anti-VEGF) single chain antibody (scFv), VEGF-derived polypeptide (e.g., $_D$(LPR), KSRVRKGKGQKRKRKKSRYK, etc.), and ATN-161 (see, for example, Rosca E V, Koskimaki J E, Rivera C G, et al. Anti-angiogenic peptides for cancer therapeutics [J]. Curr Pharm Biotechnol, 2011, 12 (8): 1101-1116; all of which are incorporated herein by reference).

As used herein, the term "identity" refers to the match degree between two polypeptides or between two nucleic acids. When two sequences for comparison have the same monomer sub-unit of base or amino acid at a certain site (e.g., each of two DNA molecules has an adenine at a certain site, or each of two proteins/polypeptides has a lysine at a certain site), the two molecules are identical at the site. The percent identity between two sequences is a function of the number of identical sites shared by the two sequences over the total number of sites for comparison×100. For example, if 6 of 10 sites of two sequences are matched, these two sequences have an identity of 60%. For example, DNA sequences: CTGACT and CAGGTT share an identity of 50% (3 of 6 sites are matched). Generally, the comparison of two sequences is conducted in a manner to produce maximum identity. Such alignment can be conducted by for example using a computer program such as Align program (DNAstar, Inc.) which is based on the method of Needleman, et al. (J. Mol. Biol. 48:443-453, 1970). The percentage of identity between two amino acid sequences can also be determined using the algorithm of E. Meyers and W. Miller (Comput. Appl. Biosci., 4:11-17 (1988)) which has been incorporated into the ALIGN program (version 2.0), using a PAM120 weight residue table, and with a gap length penalty of 12 and a gap penalty of 4. In addition, the percentage of identity between two amino acid sequences can be determined by the algorithm of Needleman and Wunsch (J. Mol. Biol. 48:444-453 (1970)) which has been incorporated into the GAP program in the GCG software package (available at World Wide Web.gcg.com), using either a Blossum 62 matrix or a PAM250 matrix, and with a gap weight of 16, 14, 12, 10, 8, 6, or 4 and a length weight of 1, 2, 3, 4, 5, or 6.

As used herein, the term "vector" refers to a nucleic acid delivery vehicle into which a polynucleotide can be inserted. When a vector enables expression of a protein encoded by an inserted polynucleotide, the vector is called an expression vector. The vector can be introduced into a host cell by transformation, transduction or transfection, so that a genetic material element carried thereby can be expressed in the host cell. Vectors are well known to those skilled in the art and include, but are not limited to: plasmids; phagemids; cosmids; artificial chromosomes, such as yeast artificial chromosomes (YAC), bacterial artificial chromosomes (BAC), or P1 derived artificial chromosomes (PAC); phages such as λ-phage or M13 phage and animal viruses. Animal viruses that can be used as vectors include, but are not limited to, retroviruses (including lentiviruses), adenoviruses, adeno-associated viruses, herpesviruses (such as herpes simplex virus), poxviruses, baculoviruses, papillomaviruses, and papovaviruses (such as SV40). A vector may contain a variety of elements that control expression, including, but not limited to, promoter sequences, transcription initiation sequences, enhancer sequences, elements for selection, and reporter genes. In addition, the vector may contain a replication initiation site.

As used herein, the term "promoter" has the meaning well known to those skilled in the art, and refers to a non-coding nucleotide sequence located in the upstream of a gene that can activate the expression of a downstream gene.

As used herein, the term "pharmaceutically acceptable carrier and/or excipient" refers to a carrier and/or excipient that is pharmacologically and/or physiologically compatible with the subject and the active ingredient, which is well known in the art (see, for example, Remington's Pharmaceutical Sciences. Edited by Gennaro A R, 19th ed. Pennsylvania: Mack Publishing Company, 1995), and includes, but is not limited to: pH adjusting agents, surfactants, ionic strength enhancers, agents to maintain osmotic pressure, agents to delay absorption, diluents, adjuvants, preservatives, stabilizers, etc. For example, pH adjusting agents include, but are not limited to, phosphate buffered saline. Surfactants include, but are not limited to, cationic, anionic or non-ionic surfactants, such as Tween-80. Ionic strength enhancers include, but are not limited to, sodium chloride. Agents that maintain osmotic pressure include, but are not limited to, sugar, NaCl, and the like. Agents that delay absorption include, but are not limited to, monostearate and gelatin. Diluents include, but are not limited to, water, aqueous buffers (such as buffered saline), alcohols and polyols (such as glycerol), and the like. Adjuvants include, but are not limited to, aluminum adjuvants (such as aluminum hydroxide), Freund's adjuvants (such as complete Freund's adjuvant), and the like. Preservatives include, but are not limited to, various antibacterial and antifungal agents, such as thimerosal, 2-phenoxyethanol, parabens, trichloro-t-butanol, phenol, sorbic acid, and the like. Stabilizers have the meaning commonly understood by those skilled in the art, which can stabilize the desired activity (such as oncolytic activity) of the active ingredients in the drug, including but not limited to sodium glutamate, gelatin, SPGA, sugars (e.g., sorbitol, mannitol, starch, sucrose, lactose, dextran, or glucose), amino acids (e.g., glutamic acid, glycine), proteins (e.g., dried whey, albumin, or casein) or their degradation products (e.g., lactalbumin hydrolysates).

As used herein, the term "treatment" refers to treating or curing a disease (e.g., tumor), delaying the onset of a symptom of disease (e.g., tumor), and/or delaying the development of a disease (e.g., tumor).

As used herein, the term "effective amount" refers to an amount that can effectively achieve the intended purpose. For example, a therapeutically effective amount may be an amount that is effective or sufficient to treat or cure a disease (e.g., tumor), delay the onset of a symptom of disease (e.g., tumor), and/or delay the development of a disease (e.g., tumor). Such an effective amount can be easily determined by a person skilled in the art or a doctor, and can be related to the intended purpose (e.g., treatment), the general health, age, gender, body weight of subject, the severity of disease to be treated, complications, administration routes, etc. The determination of such effective amount is completely within the ability of those skilled in the art.

As used herein, the term "subject" refers to a mammal, such as a primate mammal, such as a human. In certain embodiments, the subject (e.g., human) has a tumor, or is at risk of having a tumor.

After extensive experiments and repeated explorations, the inventors of the present application have unexpectedly discovered that pseudorabies virus (PRV) has a broad-spectrum and significant tumor cell killing ability. Based on this discovery, the inventors have developed a new oncolytic virus for treating a tumor and a method for tumor treatment based on the virus.

Therefore, in a first aspect, the present invention provides a use of a pseudorabies virus (PRV) or modified form thereof or a nucleic acid molecule for treating a tumor and/or reducing or inhibiting tumor recurrence in a subject, or for the manufacture of a medicament for treating a tumor and/or reducing or inhibiting tumor recurrence in a subject; wherein the nucleic acid molecule comprises a sequence selected from the following:

(1) a genomic sequence or cDNA sequence of a PRV or modified form thereof;

(2) a complementary sequence of the cDNA sequence.

In certain preferred embodiments, the PRV is a wild-type PRV. In certain preferred embodiments, the PRV may be a strain isolated from an animal infected with a pseudorabies virus (PRV).

In certain preferred embodiments, the genomic sequence of the PRV or modified form thereof has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to the nucleotide sequence as shown in SEQ ID NO: 1. In certain preferred embodiments, the genomic sequence of the PRV or modified form thereof is the nucleotide sequence as shown in SEQ ID NO: 1.

In certain preferred embodiments, the modified form is a modified PRV, which has substitution, insertion or deletion of one or more nucleotides in its genome as compared to a wild-type PRV.

In certain preferred embodiments, the modified PRV has one or more modifications selected from the following as compared to a wild-type PRV:

(1) a deletion or mutation of one or more endogenous genes;
(2) a mutation, deletion or insertion of one or more nucleotides in an untranslated region (e.g., promoter);

(3) an insertion of one or more exogenous nucleotide sequences; and (4) any combination of the above three items.

In certain preferred embodiments, the modified PRV does not express a functional EP0 protein. As well known to those skilled in the art, the gene encoding the EP0 protein (EP0 gene) can be modified to prevent the functional expression of the protein. For example, a loss-of-function mutation can be introduced into the gene encoding the EP0 protein, or the gene encoding the EP0 protein can be deleted or replaced with an exogenous nucleotide sequence (e.g., a nucleotide sequence encoding an exogenous protein) to prevent the functional expression of the target protein.

Therefore, in certain preferred embodiments, the genome of the modified PRV of the present invention is modified as follows: the EP0 gene contains a loss-of-function mutation (e.g., addition, deletion and/or substitution of one or more nucleotides), or is deleted or replaced with an exogenous nucleotide sequence (e.g., a nucleotide sequence encoding an exogenous protein). In certain preferred embodiments, the loss-of-function mutation is selected from missense mutations nonsense mutation, frameshift mutation, base deletion, base substitution, base addition, and any combination thereof (e.g., a deletion or substitution or addition of a gene fragment).

In certain preferred embodiments, the EP0 gene is deleted. In such embodiments, the modified PRV does not express EP0 protein. In certain preferred embodiments, the EP0 gene is replaced with an exogenous nucleotide sequence (e.g., a nucleotide sequence encoding an exogenous protein). In certain exemplary embodiments, the exogenous protein is a fluorescent protein.

In certain preferred embodiments, the genomic sequence of the modified PRV has a sequence identity of at least 70%, at least 80%, at least 85%, at least 90%, at least 91%, at least 92%, at least 93%, at least 94%, at least 95%, at least 96%, at least 97%, at least 98%, at least 99%, or 100% to the nucleotide sequence as shown in SEQ ID NO: 4. In certain preferred embodiments, the genomic sequence of the modified PRV is shown in SEQ ID NO: 4.

In certain preferred embodiments, the modified PRV comprises a mutation, deletion or insertion of one or more nucleotides located in a non-coding region (e.g., a promoter).

In certain preferred embodiments, the genome of the modified PRV comprises the following modification: an original promoter of one or more PRV genes is replaced with a tumor-specific promoter. In the present invention, the original promoter of any PRV gene can be replaced with a tumor-specific promoter. In certain preferred embodiments, the tumor-specific promoter is selected from the group consisting of human telomerase reverse transcriptase (hTERT) promoter, alpha-fetoprotein promoter, carcinoembryonic antigen promoter, prostate-specific antigen promoter, Survivin promoter and cyclooxygenase COX-2 promoter.

In the present invention, the use of tumor-specific promoter is advantageous under certain circumstances, for example, it is conducive to improve the tumor specificity of an oncolytic virus. In normal cells, the activity of tumor-specific promoter is usually at a low level, while in tumor cells its activity is at a high level. Therefore, the use of tumor-specific promoter to regulate the transcription expression of some key proteins of PRV can allow the virus to obtain tumor-specific killing ability. Therefore, in some cases, replacing the original promoter of a key protein of PRV with a tumor-specific promoter can reduce the virus's ability to kill normal cells, thereby reducing toxic and side effects without affecting its ability to kill tumor cells.

In certain preferred embodiments, the modified PRV comprises an exogenous nucleotide sequence.

In certain preferred embodiments, the exogenous nucleotide sequence encodes an exogenous protein selected from the group consisting of fluorescent protein, immunomodulatory polypeptide, cytokine, chemokine, anti-tumor protein or polypeptide.

In certain preferred embodiments, the fluorescent protein is selected from the group consisting of green fluorescent protein, red fluorescent protein, blue fluorescent protein, yellow fluorescent protein, and any combination thereof.

In certain preferred embodiments, the immunomodulatory polypeptide is selected from the group consisting of CD40L, OX40L, inducible costimulatory molecules (ICOS), FTL3L, LIGHT, CD137L, CD70, 4-1BB, GITR, CD28, and any combination thereof.

In certain preferred embodiments, the cytokine is selected from the group consisting of interleukins (e.g., IL-2, IL-12 and IL-15), interferons (e.g., IFNα, IFNβ, IFNγ), tumor necrosis factors (e.g., TNFα), colony stimulating factors (e.g., GM-CSF), and any combination thereof.

In certain preferred embodiments, the chemokine is selected from the group consisting of CCL2, RANTES, CCL7, CCL9, CCL10, CCL12, CCL15, CCL19, CCL21, CCL20, XCL-1, and any combination thereof.

In certain preferred embodiments, the anti-tumor protein or polypeptide is selected from the group consisting of: cytotoxic peptides, such as thymidine kinase TK (TK/GCV), TRAIL, FasL, or any combination thereof; immune checkpoint inhibitors, such as PD-1 antibody, anti-PD-L1 antibody, anti-TIGIT antibody, anti-BTLA antibody, anti-CTLA-4 antibody, anti-Tim-3 antibody, anti-Lag-3 antibody, anti-CD137 antibody, anti-OX40 antibody, anti-GITR antibody, anti-CD73 antibody, anti-KIR antibody, anti-ICOS antibody, anti-CSF1R antibody, or any combination thereof; tumor-specific targeting antibodies, such as anti-HER2 antibody (e.g., Herceptin), anti-CD20 antibody (e.g., Rituximab), anti-VEGF antibody (e.g., Bevacizumab), anti-EGFR antibody (e.g., Cetuximab), or any combination thereof; proteins or polypeptides that inhibit tumor angiogenesis, such as anti-vascular endothelial growth factor (anti-VEGF) antibody, VEGF-derived polypeptides (e.g, $_D$(LPR), KSRVRKGKGQQRKRKRKKSRYK, etc.), ATN-161 or any combination thereof; and any combination of the above proteins or polypeptides.

In certain preferred embodiments, the modified PRV comprises at least one insertion of the exogenous nucleotide sequence as described above and/or at least one mutation, deletion or insertion in the untranslated region (e.g., promoter) as described above.

In certain preferred embodiments, the modified PRV does not express a functional EP0 protein and comprises at least one insertion of an exogenous nucleotide sequence as described above and/or at least one mutation, deletion or insertion in the untranslated region (e.g., promoter) as described above.

In the present application, the modified PRV of the present invention can be obtained by a technique well known in the art. For example, a loss-of-function mutation can be introduced into the viral gene through deletion, substitution or insertion of bases to inactivate the viral gene functionally. In certain exemplary embodiments, the viral gene is functionally inactivated by deletion (e.g., deletion of the entire gene or part thereof). In such embodiments, at least 25%, at least 50%, at least 75%, or 100% of the viral gene sequence of interest may be deleted, or at least 10 bp, at least 100 bp, or at least 1000 bp of the viral gene sequence of interest may be deleted. In certain exemplary embodiments, a frameshift mutation may be introduced by insertion or deletion of bases, thereby inactivating the viral gene functionally. In certain exemplary embodiments, the viral gene is functionally inactivated by replacing the entire gene of interest or a part thereof with an exogenous nucleotide sequence.

In certain preferred embodiments, the modified PRV of the present invention can be obtained by CRISPR/Cas9 technology. The CRISPR/Cas9 technology is known in the art, for example, see Ran F A, Feng Zhang et al. Nature, 2013, 2281-2308; which is incorporated herein by reference in its entirety. In such embodiments, the viral genome of wild-type PRV is typically modified (e.g., by insertion of an exogenous nucleotide sequence, deletion or mutation of an endogenous gene, or mutation in an untranslated region) to obtain the modified PRV.

The PRV or modified form thereof according to the present invention may be pretreated to reduce or eliminate the immune response against the virus in a subject, wherein the pretreatment may include: packaging the PRV in liposomes or micelles, and/or removing the viral capsid protein using a protease (e.g., chymotrypsin or trypsin) to reduce humoral and/or cellular immunity to the virus in a host.

In the present invention, the PRV or modified form thereof as described herein can be serially passaged for adaptation in tumor cells in tumor cells. In certain preferred embodiments, the tumor cells may be tumor cell lines or tumor cell stains known in the art, or may be tumor cells surgically excised or clinically isolated from the body of an individual (e.g., a subject) with a tumor. In certain preferred embodiments, the PRV or modified form thereof is serially passaged for adaptation in tumor cells obtained from an individual (e.g., a subject) having a tumor. In certain preferred embodiments, the tumor cells are surgically excised or clinically isolated from the body of an individual (e.g., a subject) with a tumor. In certain preferred embodiments, the method for serial passaging for adaptation comprises a plurality of (e.g., at least 5, at least 10, at least 15, at least 20) cycles consisting of the following processes: 1) infecting a target tumor cell with the virus; 2) harvesting the virus in a supernatant; and 3) reinfecting a fresh target tumor cell with the obtained virus.

In certain preferred embodiments, the PRV and modified form thereof as described above may be used in combination. Therefore, the medicament may comprise one or more of the PRV and modified forms thereof.

In certain preferred embodiments, the nucleic acid molecule consists of a genomic sequence or cDNA sequence of the PRV or modified form thereof as described herein, or a complementary sequence of the cDNA sequence.

In certain preferred embodiments, the nucleic acid molecule has a genomic sequence of the PRV or modified form thereof as described herein. In certain preferred embodiments, the nucleic acid molecule has a nucleotide sequence selected from the following:

(1) a nucleotide sequence as shown in SEQ ID NO: 1 or 4;

(2) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100%, to the nucleotide sequence as shown in SEQ ID NO: 1 or 4.

In certain preferred embodiments, the nucleic acid molecule is a vector (for example, a cloning vector or an expression vector) comprising a genomic sequence or cDNA sequence of the PRV or modified form thereof as described herein, or a complementary sequence of the cDNA sequence. In certain preferred embodiments, the nucleic acid molecule is a vector (for example, a cloning vector or an expression vector) comprising a cDNA sequence of the PRV or modified form thereof as described herein, or a complementary sequence of the cDNA sequence.

The nucleic acid molecule of the present invention can be delivered by any means known in the art, for example, by direct injection of naked nucleic acid molecule (e.g., naked RNA), or by using a non-viral delivery system. The non-viral delivery system can be prepared and obtained with various materials well known in the art, wherein the materials include but are not limited to those described in detail in "Yin H, et al. Nat Rev Genet. 2014 August; 15 (8): 541-55." and "Riley M K, Vermerris W. Nanomaterials (Basel). 2017 Apr. 28; 7 (5). Pii: E94.", all of which are incorporated herein by reference in their entirety, such as liposomes, inorganic nanoparticles (e.g., gold nanoparticles), polymers (e.g., PEG), etc.

In certain preferred embodiments, the medicament comprises a therapeutically effective amount of the PRV and/or modified form thereof, or a therapeutically effective amount of the nucleic acid molecule as described herein. In certain preferred embodiments, the medicament may be in any form known in the medical arts. For example, the medicament may be tablet, pill, suspension, emulsion, solution, gel, capsule, powder, granule, elixir, lozenge, suppository, injection (including injection liquid, lyophilized powder), and other forms. In some embodiments, the medicament is an injection liquid or a lyophilized powder.

In certain preferred embodiments, the medicament further comprises a pharmaceutically acceptable carrier or excipient. In certain preferred embodiments, the medicament comprises a stabilizer.

In certain preferred embodiments, the medicament optionally further comprises an additional pharmaceutically active agent. In a preferred embodiment, the additional pharmaceutically active agent is a drug with anti-tumor activity, such as an additional oncolytic virus, chemotherapeutic agent or immunotherapeutic agent.

In the present invention, the additional oncolytic virus includes but is not limited to adenovirus, parvovirus, reovirus, Newcastle disease virus, vesicular stomatitis virus, measles virus, or any combination thereof. The chemotherapeutic agent includes but is not limited to 5-fluorouracil, mitomycin, methotrexate, hydroxyurea, cyclophosphamide, dacarbazine, mitoxantrone, anthracyclines (e.g., epirubicin or doxorubicin), etoposide, platinum compounds (e.g., carboplatin or cisplatin), taxanes (e.g., paclitaxel or taxotere), or any combination thereof. The immunotherapeutic agent includes but is not limited to immune checkpoint inhibitor (e.g., PD-L1/PD-1 inhibitor or CTLA-4 inhibitor), tumor-specific targeting antibody (e.g., rituximab or herceptin), or any combination thereof.

In certain preferred embodiments, the medicament comprises a unit dose of the PRV and/or modified form thereof, for example, at least $1 \times 10^2$ pfu, at least $1 \times 10^3$ pfu, at (ICOS), FTL3L, LIGHT, CD137L, CD70, 4-1BB, GITR, CD28, and any combination thereof.

In certain preferred embodiments, the cytokine is selected from the group consisting of interleukins (e.g., IL-2, IL-12 and IL-15), interferons (e.g., IFNα, IFNβ, IFNγ), tumor necrosis factors (e.g., TNFα), colony stimulating factors (e.g., GM-CSF), and any combination thereof.

In certain preferred embodiments, the chemokine is selected from the group consisting of CCL2, RANTES, CCL7, CCL9, CCL10, CCL12, CCL15, CCL19, CCL21, CCL20, XCL-1, and any combination thereof.

In certain preferred embodiments, the anti-tumor protein or polypeptide is selected from the group consisting of: cytotoxic peptides, such as thymidine kinase TK (TK/GCV), TRAIL, FasL, or any combination thereof; immune checkpoint inhibitors, such as PD-1 antibody, anti-PD-L1 antibody, anti-TIGIT antibody, anti-BTLA antibody, anti-CTLA-4 antibody, anti-Tim-3 antibody, anti-Lag-3 antibody, anti-CD137 antibody, anti-OX40 antibody, anti-GITR antibody, anti-CD73 antibody, anti-KIR antibody, anti-ICOS antibody, anti-CSF1R antibody, or any combination thereof; tumor-specific targeting antibodies, such as anti-HER2 antibody (e.g., Herceptin), anti-CD20 antibody (e.g., rituximab), anti-VEGF antibody (e.g., bevacizumab), anti-EGFR antibody (e.g., cetuximab), or any combination thereof; protein or polypeptide that inhibits tumor angiogenesis, such as anti-vascular endothelial growth factor (anti-VEGF) antibody, VEGF-derived polypeptides (e.g., $_D$(LPR), KSRVRKGKGQQRKRKRKKSRYK, etc.), ATN-161 or any combination thereof; and any combination of the above proteins or polypeptides.

In certain preferred embodiments, the modified PRV comprises at least one insertion of the exogenous nucleotide sequence as described above and/or at least one of the mutation, deletion or insertion in an untranslated region (e.g., a promoter) as described above.

In certain preferred embodiments, the modified PRV does not express a functional EP0 protein and comprises at least one insertion of the exogenous nucleotide sequence as described above and/or at least one of the mutation, deletion or insertion in an untranslated region (e.g., a promoter) as described above.

In certain preferred embodiments, the PRV and modified form thereof as described above may be used in combination. Therefore, one or more of the PRV and modified forms thereof can be administered to the subject.

In certain preferred embodiments, the nucleic acid molecule as described herein is administered to the subject.

In certain preferred embodiments, the nucleic acid molecule consists of a genomic sequence or cDNA sequence of the PRV or modified form thereof as described herein, or a complementary sequence of the cDNA sequence.

In certain preferred embodiments, the nucleic acid molecule has a genomic sequence of the PRV or modified form thereof as described herein. In certain preferred embodiments, the nucleic acid molecule has a nucleotide sequence selected from the following:

(1) a nucleotide sequence as shown in SEQ ID NO: 1 or 4;
(2) a nucleotide sequence having a sequence identity of at least 70%, at least 80%, at least 85%, at least 90%, at least 91%, at least 92%, at least 93%, at least 94%, at least 95%, at least 96%, at least 97%, at least 98%, at least 99%, or 100%, to the nucleotide sequence as shown in SEQ ID NO: 1 or 4.

In certain preferred embodiments, the nucleic acid molecule is a vector (for example, a cloning vector or an expression vector) comprising a genomic sequence or cDNA sequence of the PRV or modified form thereof as described herein, or a complementary sequence of the cDNA sequence. In certain preferred embodiments, the nucleic acid molecule is a vector (for example, a cloning vector or an expression vector) comprising a cDNA sequence of the PRV or modified form thereof as described herein, or a complementary sequence of the cDNA sequence.

In the present invention, the nucleic acid molecule as described herein can be delivered by any means known in the art, for example, by direct injection of naked nucleic acid molecule (e.g., naked RNA), or by using a non-viral delivery system. The non-viral delivery system can be prepared and obtained with various materials well known in the art, wherein the materials include but are not limited to those described in detail in "Yin H, et al. Nat Rev Genet. 2014 August; 15 (8): 541-55." and "Riley M K, Vermerris W. Nanomaterials (Basel). 2017 Apr. 28; 7 (5). Pii: E94.", all of which are incorporated herein by reference in their entirety, such as liposomes, inorganic nanoparticles (e.g., gold nanoparticles), polymers (e.g., PEG), etc.

In certain preferred embodiments, the PRV and/or modified form thereof, or nucleic acid molecules as described herein, can be formulated and administered as a pharmaceutical composition. Such pharmaceutical composition may comprise a therapeutically effective amount of the PRV and/or modified form thereof, or a therapeutically effective amount of the nucleic acid molecule as described herein. In certain preferred embodiments, the pharmaceutical composition may be in any form known in the medical arts. For example, the pharmaceutical composition may be a tablet, pill, suspension, emulsion, solution, gel, capsule, powder, granule, elixir, lozenge, suppository, injection (including injection liquid, lyophilized powder), and other forms. In some embodiments, the pharmaceutical composition is an injection liquid or a lyophilized powder.

In certain preferred embodiments, the pharmaceutical composition further comprises a pharmaceutically acceptable carrier or excipient. In certain preferred embodiments, the pharmaceutical composition comprises a stabilizer.

In the present invention, the PRV and/or modified forms thereof, or the nucleic acid molecules as described herein can be administered to a subject by various suitable means. In some cases, the route of administration of the PRV and/or modified form thereof or the nucleic acid molecule as described herein depends on the location and type of tumor. For example, for a solid tumor that is easily accessible, the virus or nucleic acid molecule is optionally administered by injection directly into the tumor (e.g., intratumoral injection); for a tumor of hematopoietic system, the virus or nucleic acid molecule can be administered by intravenous or other intravascular routes; for a tumor that is not easily accessible in the body (e.g., metastases), the virus or nucleic acid molecule can be administered systematically so that it can run over the whole body and thereby reaching the tumor (e.g., intravenous or intramuscular injection). Optionally, the virus or nucleic acid molecule of the present invention can be administrated via subcutaneous, intraperitoneal, intrathecal (e.g., for brain tumors), topical (e.g., for melanoma), oral (e.g., for oral or esophageal cancer), intranasal or inhalation spray (e.g., for lung cancer) routes and so on. In certain preferred embodiments, the PRV and/or modified form thereof, or the nucleic acid molecule as described herein, can be administered via intradermal, subcutaneous, intramuscular, intravenous, oral routes etc.

In certain preferred embodiments, the method further comprises administering an additional pharmaceutically active agent having anti-tumor activity. Such additional pharmaceutically active agent may be administered before, simultaneously or after administration of the PRV and/or modified form thereof, or the nucleic acid molecule as described herein.

In certain preferred embodiments, the additional pharmaceutically active agent comprises additional oncolytic virus, chemotherapeutic agent, or immunotherapeutic agent.

In the present invention, the additional oncolytic virus includes but is not limited to adenovirus, parvovirus, reovirus, Newcastle disease virus, vesicular stomatitis virus, measles virus, or any combination thereof. The chemotherapeutic agent includes but is not limited to 5-fluorouracil, mitomycin, methotrexate, hydroxyurea, cyclophosphamide, dacarbazine, mitoxantrone, anthracyclines (e.g., epirubicin or doxorubicin), etoposide, platinum compounds (e.g., carboplatin or cisplatin), taxanes (e.g., paclitaxel or taxotere), or any combination thereof. The immunotherapeutic agent includes but is not limited to immune checkpoint inhibitor (e.g., PD-L1/PD-1 inhibitor or CTLA-4 inhibitor), tumor-specific targeting antibody (e.g., rituximab or herceptin), or any combination thereof.

In certain preferred embodiments, the PRV and/or modified form thereof can be administered in any amount of 1 to $1\times10^{15}$ pfu/kg of the subject's body weight, for example, the PRV and/or modified form thereof can be administered in an amount of at least $1\times10^3$ pfu/kg, at least $1\times10^4$ pfu/kg, $1\times10^5$ pfu/kg, $1\times10^6$ pfu/kg, at least $1\times10^7$ pfu/kg, at least $1\times10^8$ pfu/kg, at least $1\times10^9$ pfu/kg, at least $1\times10^{10}$ pfu/kg, at least $1\times10^{11}$ pfu/kg, or at least $1\times10^{12}$ pfu/kg of the subject's body weight. In certain preferred embodiments, the nucleic acid molecule as described herein can be administered in any amount of $1\times10^{10}$ to $5\times10^{14}$ (e.g. $3\times10^{10}$ to $3\times10^{14}$) virus genome copies per kg of the subject's body weight. In certain preferred embodiments, the PRV and/or modified form thereof or the nucleic acid molecule as described herein can be administered 3 times per day, 2 times per day, once per day, once every two days, or once per week, and the above-mentioned dosage regimen may be optionally repeated weekly or monthly as appropriate.

In certain preferred embodiments, the method further comprises administering an additional therapy. This additional therapy may be any therapy known for tumors, such as surgery, chemotherapy, radiation therapy, immunotherapy, hormone therapy, or gene therapy. This additional therapy can be administered before, at the same time, or after administration of the method as described above.

In certain preferred embodiments, the subject is a mammal, such as a human.

In certain preferred embodiments, the tumor is selected from neuroglioma, neuroblastoma, gastric cancer, liver cancer, renal cancer, lung cancer, breast cancer, colon cancer, lymphoma, ovarian cancer, cervical cancer, endometrial cancer, melanoma, pancreatic cancer, osteosarcoma, prostate cancer, nasopharyngeal cancer, squamous cell carcinoma of nasal septum, larynx cancer, thyroid cancer, ductal carcinoma of thyroid, bladder cancer, etc. In certain exemplary embodiments, the tumor recurrence is recurrence of liver cancer.

In a third aspect, the present invention also relates to a pharmaceutical composition, which comprises the PRV and/or modified form thereof as defined in the first or second aspect, or the nucleic acid molecule as defined in the first or second aspect.

In certain preferred embodiments, the pharmaceutical composition may be in any form known in the medical art. For example, the pharmaceutical composition may be a tablet, pill, suspension, emulsion, solution, gel, capsule, powder, granule, elixir, lozenge, suppository, injection (including injection liquid, lyophilized powder), and other forms. In some embodiments, the pharmaceutical composition is an injection liquid or a lyophilized powder.

In certain preferred embodiments, the pharmaceutical composition further comprises a pharmaceutically acceptable carrier or excipient. In certain preferred embodiments, the pharmaceutical composition comprises a stabilizer.

In certain preferred embodiments, the pharmaceutical composition optionally further comprises an additional pharmaceutically active agent. In a preferred embodiment, the additional pharmaceutically active agent is a drug with anti-tumor activity, such as an additional oncolytic virus, chemotherapeutic agent or immunotherapeutic agent.

In certain preferred embodiments, the pharmaceutical composition is used to treat a tumor and/or reduce or inhibit tumor recurrence in a subject.

In certain preferred embodiments, the subject is a mammal, such as a human.

In certain preferred embodiments, the tumor is selected from neuroglioma, neuroblastoma, gastric cancer, liver cancer, renal cancer, lung cancer, breast cancer, colon cancer, lymphoma, ovarian cancer, cervical cancer, endometrial cancer, melanoma, pancreatic cancer, osteosarcoma, prostate cancer, nasopharyngeal cancer, squamous cell carcinoma of nasal septum, larynx cancer, thyroid cancer, ductal carcinoma of thyroid, bladder cancer, etc. In certain exemplary embodiments, the tumor recurrence is recurrence of liver cancer.

In a fourth aspect, the invention also relates to the PRV and/or modified form thereof as defined in the first or second aspect, or the nucleic acid molecule as defined in the first or second aspect, for use as a drug.

Beneficial Effects of Invention

Compared with the prior art, the technical solution of the present invention has at least the following beneficial effects:

The inventors of the present application have discovered for the first time that pseudorabies virus (PRV) has a broad-spectrum tumor-killing activity. Based on this finding, the present invention further provides an oncolytic virus based on PRV. The oncolytic virus of the present invention can be used alone in the treatment of a tumor, can also be used as an auxiliary method for traditional tumor treatment, or as a treatment method in the absence of other treatment methods, and thereby having great clinical value.

The embodiments of the present invention will be described in detail below in conjunction with the drawings and examples, but those skilled in the art will understand that the following drawings and examples are only used to illustrate the present invention, not to limit the scope of the present invention. The various objects and advantageous aspects of the invention will become apparent to those skilled in the art from the following detailed description of the drawings and preferred embodiments.

BRIEF DESCRIPTION OF THE DRAWINGS

FIG. 7A shows the killing results of PRV-del-EP0 (BK61-dEP0) to various tumor cell lines, and FIG. 7B shows the killing results of PRV-del-EP0 (BK61-dEP0) to various diploid cell lines (similar to normal cell lines). The results show that PRV-del-EP0 had a tumor killing activity comparable to that of PRV-WT, and its killing activity to normal cells was reduced.

FIG. 9 shows the effects of PRV-del-EP0 on the tumor size of the mouse liver cancer model; FIG. 10 shows the effects of PRV-del-EP0 on the survival rate of the mouse liver cancer model. The results show that PRV-del-EP0 had a significant antitumor activity comparable to that of PRV-WT.

SEQUENCE INFORMATION

Figure 1A:
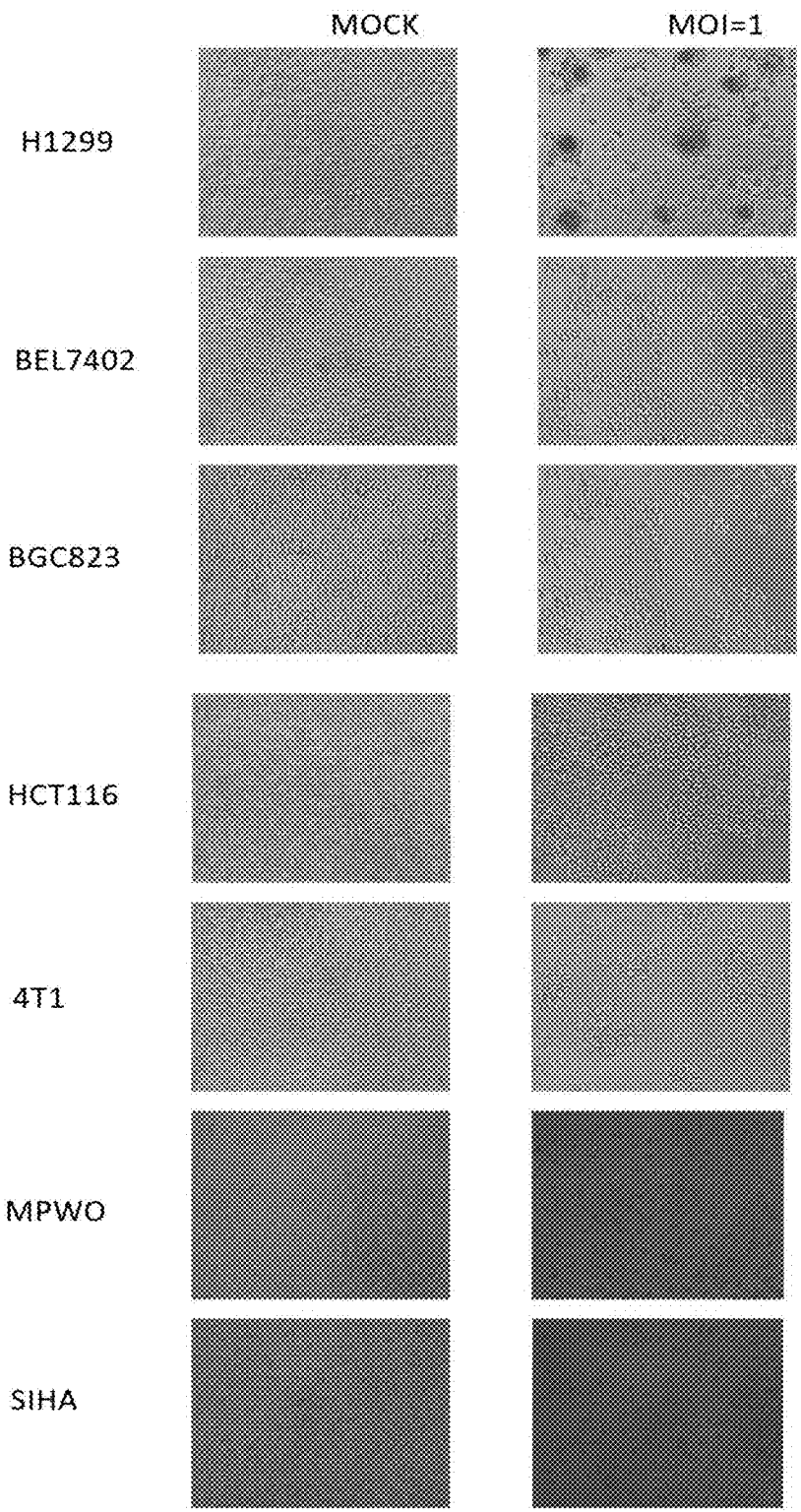
FIGS. 1A to 1C show the resultant micrographs of the in vitro killing experiments in Example 2 of wild-type PRV on human lung cancer cell line H1299, human liver cancer cell line BEL7402, human gastric cancer cell line BGC823, human colon cancer cell line HCT-116, mouse breast cancer cell line 4T1, human melanoma cell line MPWO, human cervical cancer cell line SIHA, mouse kidney cancer cell line Renca, human ovarian cancer cell line A2780, human nasopharyngeal cancer cell line CNE1, neuroglioma cell line GBM, human laryngeal cancer cell line Hep-2, human pancreatic cancer cell line Panc-1, human lymphoma cell line A20, mouse prostate cancer cell line Tramp C2, and human embryonic lung fibroblast MRC5, wherein MOCK indicates cells uninfected with the virus. The results show that the PRV showed a significant oncolytic effect on human and mouse tumor cell lines, but had less killing effect on MRC5 of human non-tumor cell, after 72 hours of infection at a multiplicity of infection (MOI) of 1.

The information of parts of sequences involved in the present invention is provided in Table 1 below.

TABLE 1

| SEQ ID NO: | Description |
| --- | --- |
| 1 | Genome sequence of wild type PRV (PRV-WT) |
| 2 | Nucleic acid sequence encoding the early protein EP0 in the PRV genome |
| 3 | GFP gene sequence |
| 4 | Genome sequence of PRV-del-EP0 |

EXAMPLES

The present invention will now be described with reference to the following examples intended to illustrate the invention (not to limit the invention).

Unless otherwise specified, the molecular biology experimental methods and immunoassays used in the present invention basically referred to J. Sambrook et al., Molecular Cloning: A Laboratory Manual, $2^{nd}$ Edition, Cold Spring Harbor Laboratory Press, 1989, and F M Ausubel et al., Short Protocols in Molecular Biology, $3^{rd}$ Edition, John Wiley & Sons, Inc., 1995. The use of restriction enzymes was in accordance with the conditions recommended by the product manufacturers. If no specific conditions were indicated in the examples, the conventional conditions or the conditions recommended by the manufacturers should be followed. The used reagents or instruments, of which manufacturers were not given, were all conventional products that were commercially available. Those skilled in the art know that the examples describe the present invention by way of example, and are not intended to limit the claimed scope of the invention. All publications and other references mentioned herein are incorporated by reference in their entirety.

Example 1: Acquisition and Preparation of PRV and Modified Forms Thereof 1.1 Isolation of Pseudorabies Virus (PRV) from Specimens (1) Pharyngeal swabs and anal swabs of sick pigs were from Xiamen Center for Disease Control and Prevention, China, and pig embryonic kidney cells (PK-15; ATCC NumberCCL-33™) were preserved by the National Engineering Research Center for Diagnostic Reagents and Vaccines for Infectious Diseases, Xiamen University, China, which were cultured in DMEM medium supplemented with 10% fetal bovine serum, glutamine, penicillin and streptomycin.

(2) Treatment of specimens: the pharyngeal swabs and anal swabs were placed in a specimen preservation solution and fully stirred so as to wash off the virus and virus-containing cells attached to the swabs, and then the specimen preservation solution was subjected to high speed centrifugation under 4000 rpm and 4° C. for 30 min;

(3) Inoculation and observation:

A. PK-15 cells were plated on a 24-well plate with $1 \times 10^5$ cells/well. The growth solution (DMEM medium, 10% fetal bovine serum, and glutamine, penicillin and streptomycin) was aspirated, and then each well was added with 1 mL of maintenance solution (DMEM medium, 2% fetal bovine serum, and glutamine, penicillin and streptomycin). Then except for the negative control wells, each well was inoculated with 50 µL of sample supernatant, and cultured in an incubator at 37° C., 5% $CO_2$.

B. The cells were observed under microscope every day for one week and the occurrence of specific cytopathic effect (CPE) in the inoculated wells was recorded.

C. If the pseudorabies virus-specific CPE appeared in the cells of the inoculated wells within 7 days, the cells and supernatant were collected and cryopreserved at –80° C.; if no CPE appeared after 7 days, the cells were subjected to blind passage.

D. If CPE appeared in the cells within 6 blind passages, the cells and supernatant were collected and cryopreserved at –80° C.; if CPE did not appear after 6 blind passages, the cells were determined as negative.

(4) Virus isolation and cloning:

The viruses isolated from clinical specimens were identified by PCR, the pseudorabies virus-positive cultures were selected and subjected to at least 3 virus plaque purification experiments; the clonal strains obtained from virus plaques in each round were also identified by PCR, and pseudorabies virus-positive clonal strains were selected and subjected to the next round of cloning; and a single strain of pseudorabies virus with strong growth viability was selected as the candidate strain of oncolytic virus.

1.2 Gene Editing of PRV Based on CRISPER/CAS9 Technology and Acquisition of the Modified Form Thereof This example used wild-type PRV strain that was also referred to as BK61-WT (SEQ ID NO: 1) as an example to show how to obtain the PRV and modified form thereof for the present invention through gene editing. The specific method was as follows.

(1) sgRNA design based on CRISPER/CAS9 technology: the PAM site near the site where an exogenous gene was to be inserted was found by virus genome analysis, and the sgRNA was designed according to the sequence near the PAM, so that the CAS9 protein could cleave the virus genome, and then homologous recombination was performed to obtain a new modified virus.

(2) Construction of donor target fragments: the target fragments were sent to Shanghai Shengong for synthesis. The acquisition of target gene fragments were also the key to successful modification, when homologous recombination was performed.

Modified form: The gene sequence of key protein EP0 of wild-type PRV (of which the DNA sequence was shown in SEQ ID NO: 2) was replaced by the gene sequence of green fluorescent protein (GFP) (of which the DNA sequence was shown in SEQ ID NO: 3) to obtain the genome (of which the DNA sequence was shown in SEQ ID NO: 4) of the recombinant virus (which was named as PRV-del-EP0, and also called BK61-dEP0).

(3) The sgRNA constructed above was transferred into 293T cells to form a stable cell strain, then the target fragment was transferred into the cells, followed by infection with PRV virus. And a new recombinant virus was formed by using intracellular homologous recombination technology.

(4) The progeny virus formed after infection with 293T was used to infect PK-15 cells. The successfully recombined progeny virus carried a fluorescent signal and could be used for the screening and isolation of the progeny virus.

Example 2: In Vitro Evaluation of Anti-Tumor Activity of Wild-Type PRV 2.1 Virus and Cell Lines as Used (1) Virus: In this example, the PRV-WT (SEQ ID NO: 1) provided in Example 1 was used.

(2) Cell lines: human rhabdomyosarcoma cell RD (ATCCR Number: CCL-136TM); human colorectal cancer cell lines SW1116 (ATCC® Number: CCL-233TM), SW480 (ATCC® Number: CCL-228TM) and HT-29 (ATCC® Number: HTB-38TM); human gastric cancer cell lines AGS (ATCC® Number: CRL-1739TM), SGC7901 (CCTCC deposit number: GDC150), BGC823 (CCTCC deposit number: GDC151) and NCI-N87 (ATCC® Number: CRL-5822TM); human esophageal cancer cell line TE-1 (purchased from the Cell Resource Center, Shanghai Institute for Biological Sciences, Chinese Academy of Sciences, No. 3131C0001000700089); human small cell lung cancer cell line DMS114 (ATCC® Number: CRL-2066TM); human non-small cell lung cancer cell lines SPC-A-1 (CCTCC deposit number: GDC050), NCI-H1975 (ATCCR Number: CRL-5908TM), NCI-H1299 (ATCCR Number: CRL-5803TM), A549 (ATCCR Number: CCL-185TM), NCI-H661 (ATCCR Number: HTB-183TM), EBC-1 (purchased from Thermo Fisher Scientific, Inc., Catalog #: 11875101) and NCI-H1703 (ATCC® Number: CRL-5889TM); human liver cancer cell lines C3A (ATCC® Number: CRL-10741TM), HepG2 (ATCC® Number: HB-8065TM), SMMC7721 (purchased from the Basic Medical Cell Center, Institute of Basic Medical Sciences, Chinese Academy of Medical Sciences, Number: 3111C0001CCC000087), BEL7402 (CCTCC deposit number: GDC035), BEL7404 (purchased from the Cell Resource Center, Shanghai Institutes for Biological Sciences, Chinese Academy of Sciences, number: 3131C0001000700064), Huh7 (CCTCC deposit number: GDC134) and PLC/PRF/5 (ATCCR Number: CRL-8024TM); human ovarian cancer cell lines SKOV3 (ATCC® Number: HTB-77TM) and Caov3 (ATCC® Number: HTB-75TM); human endometrial cancer cell lines Hec-1-A (ATCC® Number: HTB-112TM), Hec-1-B (ATCC® Number: HTB-113TM) and Ishikawa (ECACC No. 99040201); human cervical cancer cell lines Hela (ATCC® Number: CCL-2TM), Caski (ATCC® Number: CRL-1550TM) and C-33A (ATCC® Number: HTB-31TM); human melanoma cell lines SK-MEL-1 (ATCC® Number: HTB-67TM) and MeWo (ATCC® Number: HTB-65TM); human breast cancer cell lines BcaP37 (CCTCC deposit number: GDC206), BT-474 (ATCC® Number: HTB-20TM) and MDA-MB-231 (ATCCR Number: HTB-26TM); human kidney cancer cell lines A-498 (ATCC® Number: HTB-44TM) and 786-0 (ATCCR Number: CRL-1932TM); human pancreatic cancer cell lines Capan-2 (ATCC® Number: HTB-80TM) and HPAF-2 (ATCC®

Number: CRL-1997TM); human osteosarcoma cell line U2OS (ATCC® Number: HTB-96TM); human prostate cancer cell lines DU145 (ATCC® Number: HTB-81TM) and LNCap (ATCC® Number: CRL-1740TM); human neuroglioma cell line GBM (primary tumor cell line isolated from a patient tumor tissue); human neuroblastoma cell line SH-SY5Y (ATCC® Number: CRL-2266TM); human nasopharyngeal carcinoma cell line CNE (purchased from the Center for Basic Medical Cells, Institute of Basic Medical Sciences, Chinese Academy of Medical Sciences, No.: 3131C0001000700013); human nasal septum squamous cell carcinoma cell line RPMI 2650 (ATCC® Number: CCL-30TM); human laryngeal carcinoma cell line HEp-2 (ATCCR Number: CCL-23TM); human thyroid cancer cell line SW579 (preserved by the National Engineering Research Center for Diagnostic Reagents and Vaccines for Infectious Disease) and human ductal carcinoma of thyroid cell line TT (ATCC® Number: CRL-1803TM); human bladder cancer cell lines J82 (ATCCR Number: HTB-1TM) and 5637 (ATCC® Number: HTB-9TM); human Burkitt's lymphoma cell lines Daudi (ATCC® Number: CCL-213TM) and Raji (ATCC® Number: CCL-86TM); human normal cell lines including: human skin keratinocyte cell line HaCat (CCTCC, deposit number: GDC106), human embryonic lung fibroblast cell line MRC-5 (ATCC® Number: CCL-171TM), human foreskin fibroblast cell line HFF-1 (ATCC® Number: SCRC-1041TM), human prostate stromal cell line WPMY-1 (ATCCR Number: CRL-2854TM), human umbilical vein endothelial cell line HUVEC (purchased from Thermo Fisher Scientific, Inc., Catalog #: C01510C) and the differentiated human liver progenitor cell line HepaRG (with the characteristics of primary hepatocytes; purchased from Thermo Fisher Scientific, Inc., Catalog #: HPRGC10). The above cells were all preserved by the National Engineering Research Center for Diagnostic Reagents and Vaccines for Infectious Disease, Xiamen University, China. HepaRG cells were cultured in WME medium (added with 1.5% DMSO); AGS and TT were cultured in F-12K medium; SH-SY5Y was cultured in DMEM: F12 (1:1) medium; RD, C-33A, EBC-1, SK-MEL-1, J82 and DU145 were cultured in MEM medium; Raji, Daudi, 5637, 786-O, TE-1, Caski, NCI-H1299, NCI-H1703, NCI-H1975, NCI-H661, SGC7901, BGC823, SW1116, HEp-2 and LNCap were cultured in RPMI-1640 medium; and other cells were cultured in DMEM medium. These mediums were all supplemented with 10% fetal bovine serum, glutamine and penicillin-streptomycin. All the above cells were cultured under standard conditions of 37° C. and 5% $CO_2$.

2.2 Cultivation of Virus

The RD cells were evenly plated on 10 cm cell culture plates, and the culturing conditions were DMEM medium containing 10% fetal bovine serum, glutamine, penicillin and streptomycin, 37° C., 5% $CO_2$, and saturated humidity; when the cell confluence reached 90% or more, the cell culture medium was replaced with DMEM medium containing 2% serum, and each plate was inoculated with $10^6$ PFU of PRV-WT.

After 24 hours of continuous culture, the PRV-WT proliferated in RD cells and caused CPE in the cells. When more than 90% of the cells turned contracted and rounded, showed increased graininess, and became detached and lysed, the cells and culture supernatant thereof were harvested. After freezing and thawing for 3 cycles, the culture supernatant was collected and centrifuged to remove cell debris, in which the centrifugation conditions were 4000 rpm, 10 min, and 4° C. Finally, the supernatant was filtered with 0.22 μm disposable filter (Millipore) to remove impurities such as cell debris.

2.3 Determination of Virus Titer

The RD cells were plated on 6-well plates with cell density of $10^5$ cells/well. After the cells adhered, the virus was diluted 10-fold. 100 μl of the dilution of virus was added to each well to infect the cells, followed by shaking and mixing once every 15 minutes. After shaking and mixing 5 times, the supernatant was removed. 2% agarose solution prepared with pbs was dissolved by heating and then mixed with DMEM medium containing 10% serum at a volume ratio of 1:1, and was added to the cells. When it was cooled and solidified, it was inverted and placed in an incubator. After cultivating for three days, 10% formaldehyde solution was added for fixation for 1 hour, and then the gel was inverted and taken out, followed by staining with crystal violet staining solution for 15 minutes. The titer of the virus was determined by counting the number of plaques formed.

2.4 In Vitro Anti-Tumor Experiments of Virus

The human tumor cells and normal cells were inoculated into 96-well plates at $10^4$ per well. After the cells adhered, each well was replaced with corresponding cell culture medium without serum, and inoculated with viruses with MOIs of 10, 1, 0.1 and 0.01, respectively. Subsequently, CPE of the cells were monitored daily by a microscope.

Figure 1B:
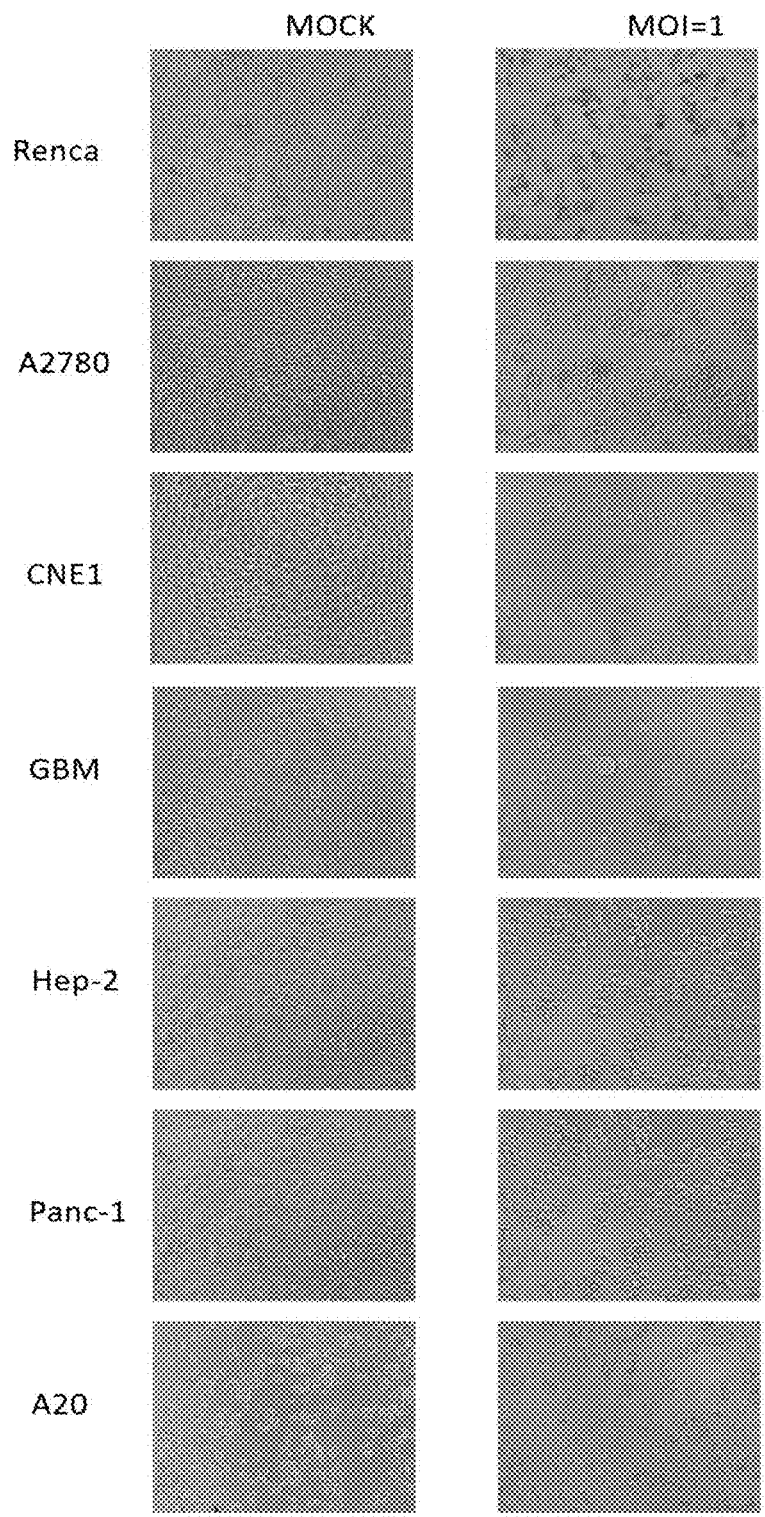
Figure 1C:
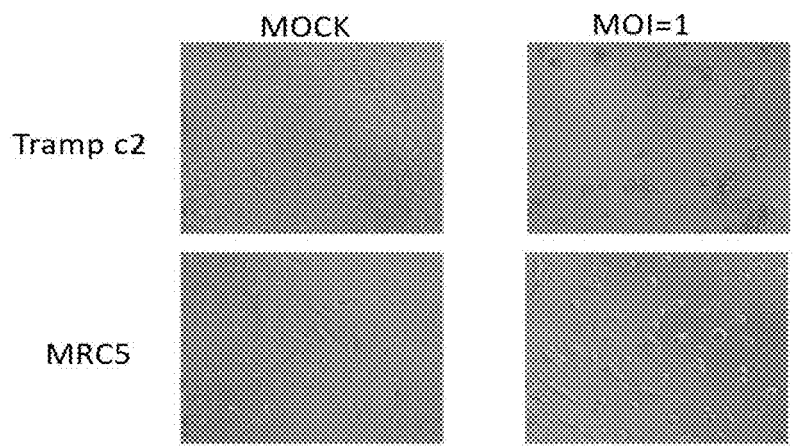
Figure 2:
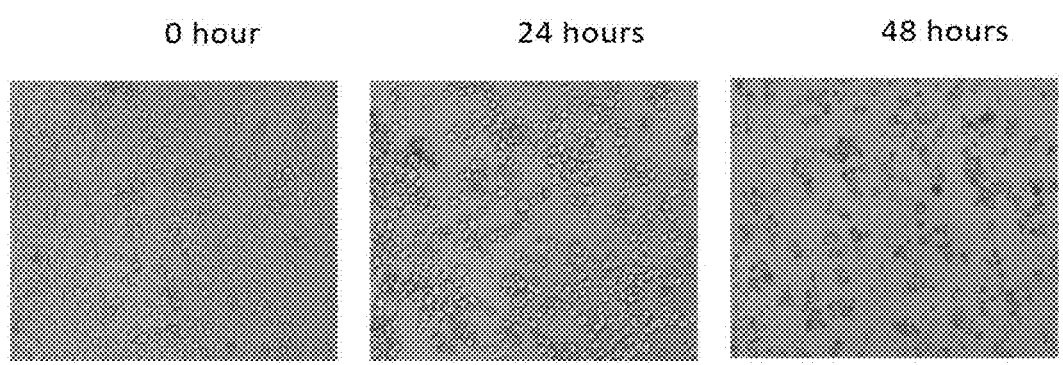
FIG. 2 shows the killing effect of the wild-type PRV virus on mouse kidney cancer cell line Renca in Example 2. The results show that the Renca cells infected with PRV exhibited very obvious CPE in 24 hours, and they were almost all lysed to death by 48 hours.

The micrographs are shown in FIGS. 1A to 1C. The results show that after 72 hours of infection with a multiplicity of infection (MOI) of 1, a significant reduction in the number of the tumor cells, marked shrinking and lysis and the like, were detected in the virus-infected groups; while the non-tumor cells infected with the virus had less change in cell morphology as compared to the non-tumor cells in the Mock group. The above results indicate that the PRV has a significant oncolytic effect on a variety of human and murine tumor cell lines, but has little effect on the non-tumor cell human embryonic lung fibroblast MRCS. In addition, after 24 hours of infection with a MOI of 1, the CPE of Renca cells was very obvious, and almost all of the cells were lysed to death by 48 hours (FIG. 2).

Cell Counting Kit-8 (CCK-8 kit; Shanghai Biyuntian Biotechnology Co., Ltd.) was used to detect cell survival rate after 72 hours of virus infection and culture. The specific methods were as follows:

For adherent cells, the original medium in a 96-well cell culture plate was directly discarded; for suspension cells, the original medium in a 96-well cell culture plate was carefully discarded after centrifugation; and then 100 μl of fresh serum-free medium was added per well. 10 μl of CCK-8 solution was added to each of the wells inoculated with cells, and an equal amount of CCK-8 solution was also added to the blank culture medium as a negative control, followed by incubation at 37° C. in a cell culture incubator for 0.5-3 hours. The absorbance was detected at 450 nm using a microplate reader at 0.5, 1, 2, 3 hours, respectively, and the time point where the absorbance was within a suitable range was selected as a reference for cell survival rate. The CCK-8 detection results of the cells against PRV-WT are shown in Table 2, where "−" indicated that the cell survival rate after virus treatment was not significantly different from that of the MOCK group; "+" indicated that after virus treatment, the cell number was reduced, the survival rate was still greater than 50% but was significantly different from that of the MOCK group; "++" indicated that the cell survival rate after virus treatment was less than 50%, and was significantly different from that of the MOCK group.

The calculation method of cell survival rate is:

$$\text{survival\_rate}(\%) = \frac{(\text{read\_of\_test\_group} - \text{read\_of\_negative\_control\_group})}{(\text{read\_of\_positive\_control\_group} - \text{read\_of\_negative\_control\_group})} \times 100\%$$

TABLE 2

Results of in vitro anti-tumor test of PRV-WT

| Cell line | MOI | | | |
|---|---|---|---|---|
| | 10 | 1 | 0.1 | 0.01 |
| A549 | ++ | ++ | ++ | + |
| H661 | ++ | ++ | ++ | + |
| H1299 | ++ | ++ | ++ | ++ |
| LLC | ++ | + | − | − |
| BEL7704 | ++ | ++ | ++ | ++ |
| BEL7402 | ++ | ++ | ++ | ++ |
| GSQ7701 | ++ | ++ | ++ | + |
| HEP1-6 | ++ | ++ | ++ | + |
| HUH7 | ++ | ++ | ++ | ++ |
| QGY7703 | ++ | + | + | − |
| SMMC7721 | ++ | ++ | ++ | + |
| AGS | ++ | ++ | ++ | ++ |
| BGC823 | ++ | + | + | + |
| SGC7901 | ++ | ++ | + | + |
| CT26 | ++ | ++ | + | + |
| HCT116 | + | − | − | − |
| SW1116 | ++ | + | + | + |
| MCF7 | ++ | ++ | + | + |
| 4T1 | ++ | + | + | + |
| MEWO | ++ | ++ | ++ | ++ |
| B16 | ++ | ++ | + | − |
| Renca | ++ | ++ | ++ | + |
| SKOV3 | ++ | ++ | ++ | ++ |
| A2780 | ++ | ++ | ++ | ++ |
| CNE1 | ++ | ++ | ++ | ++ |
| CNE2 | ++ | ++ | + | + |
| GBM | ++ | ++ | ++ | ++ |
| Hep-2 | ++ | ++ | ++ | + |
| Panc-1 | ++ | ++ | ++ | ++ |
| Raji | ++ | ++ | + | + |
| A20 | ++ | ++ | ++ | ++ |
| Tramp C2 | ++ | ++ | ++ | ++ |
| MRC5 | ++ | + | − | − |

Note:
"−" indicated that there was no significant difference in cell survival rate between virus treatment group and MOCK group; "+" indicated that after virus treatment, the number of cells was reduced, the survival rate was greater than 50% but was significantly different from that of MOCK group; "++" indicated that the cell survival rate after virus treatment was less than 50%, and was significantly different from that of the MOCK group.

It can be seen from Table 2 that the PRV-WT had a good killing effect on most of the detected tumor cells. In particular, the virus had a very significant killing effect on lung cancer, liver cancer, ovarian cancer, neuroblastoma, cervical cancer, lymphoma, and kidney cancer. On the other hand, the PRV-WT had a certain killing effect on non-tumor cell lines including human embryonic lung fibroblast cell line MRC-5.

Example 3: In Vivo Anti-Tumor Experiment of Wild-Type PRV 3.1 Virus, Cell Lines and Experimental Animals (1) Virus: In this example, the PRV-WT provided in Example 1 was used. For the virus cultivation and virus titer determination methods, see Examples 2.2 and 2.3, respectively.

(2) Cell lines: human nasopharyngeal carcinoma cell line CNE1, human Burkitt's lymphoma cell Raji (ATCC® Number: CCL-86™), human neuroglioma cell line GBM (primary tumor cell line isolated from patient tumor tissue), mouse colon cancer cell CT26, mouse liver cancer cell Hep1-6, mouse kidney cancer cell Renca and mouse breast cancer cell 4T1. Except Raji, the above cells were cultured in RPMI-1640 medium, and all other cells were cultured in DMEM medium; and the above mediums were all added with 10% fetal bovine serum, glutamine and penicillin-streptomycin. All the above cells were cultured under standard conditions of 37° C. and 5% $CO_2$.

(3) Experimental animals: 6-8 week-old female C.B17 SCID mice or Bab/c mice were from Shanghai Silaike Experimental Animal Co., Ltd.; according to the plan approved by Experimental Animal Center and Ethics Committee, Xiamen University, the mice were raised under SPF conditions.

3.2 In Vivo Anti-Tumor Experiments of Virus

For the human tumor transplantation model, SCID mice were used. The tumor cells used for subcutaneous tumor formation were digested with 0.01% trypsin, and then resuspended into a single cell suspension using cell culture medium containing 10% fetal bovine serum. The cell density of the suspension was counted. The cells were precipitated by centrifugation under 1000 g for 3 min, and then the cells were resuspended with an appropriate volume of PBS to reach a concentration of about $10^6$-$10^7$ cells/100 µl PBS. The tumor cells were subcutaneously inoculated in the back of SCID mice at $10^6$-$10^7$ cells/100 µl PBS/site with a syringe. When the tumor cells grew into a tumor mass of about 100 $mm^3$ under the skin of SCID mice after about 14-21 days, the tumor-bearing SCID mice were randomly divided into experimental groups treated with PRV-WT (BK61) and the negative control group (Mock). For the mouse tumor model, Bab/c mice were used, and were subcutaneously inoculated with tumor cells. After 7-14 days, the mice with tumor mass of about 100 $mm^3$ were selected for treatment.

The oncolytic virus PRV-WT at a dose of $10^6$ TCID50/100 µl serum-free medium/tumor mass and an equal amount of serum-free medium were intratumorally injected respectively, once every two days for a total of 5 times of treatment.

The tumor size was measured with a vernier caliper and recorded every two days. The calculation method of tumor size is:

Tumor size ($mm^3$)=tumor length value×(tumor width value)$^2$/2.

Figure 3:
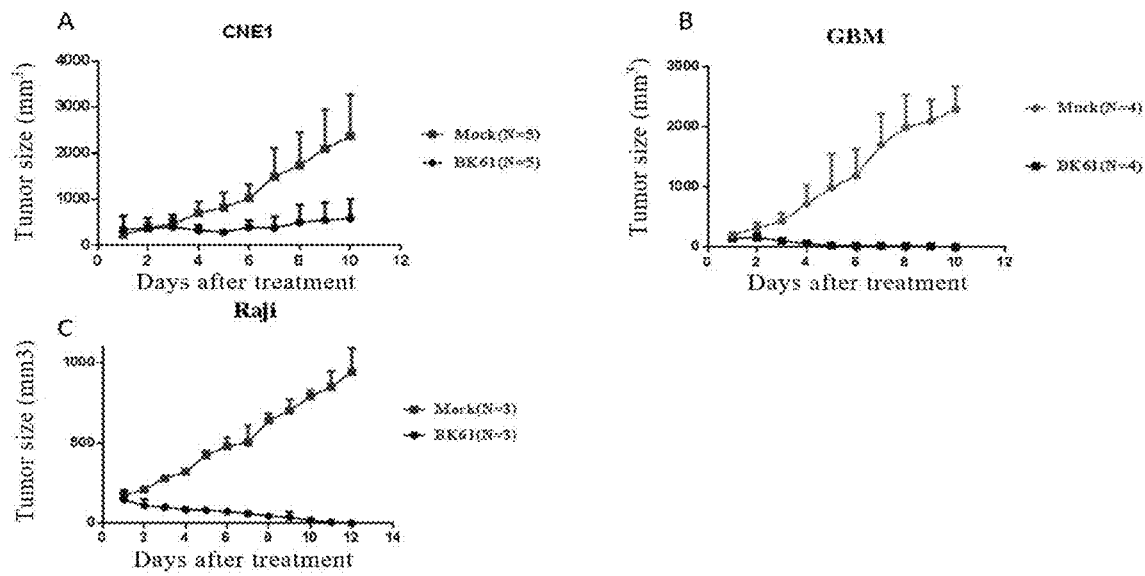
FIG. 3 shows the results of in vivo anti-tumor experiments in Example 3 of PRV-WT on human nasopharyngeal carcinoma model CNE1 (A), human Burkitt's lymphoma model Raji (B) and human neuroglioma model GBM (C). The results show that in the challenge groups, the growth of tumors formed by subcutaneous inoculation of CNE1, Raji or GBM cells significantly slowed down and arrested, and the tumors were even lysed and disappeared; in contrast, the tumors in the negative group (Mock) that were not treated with the oncolytic virus maintained normal growth, and their tumor volumes were significantly larger than those of the challenge groups.
Figure 4:
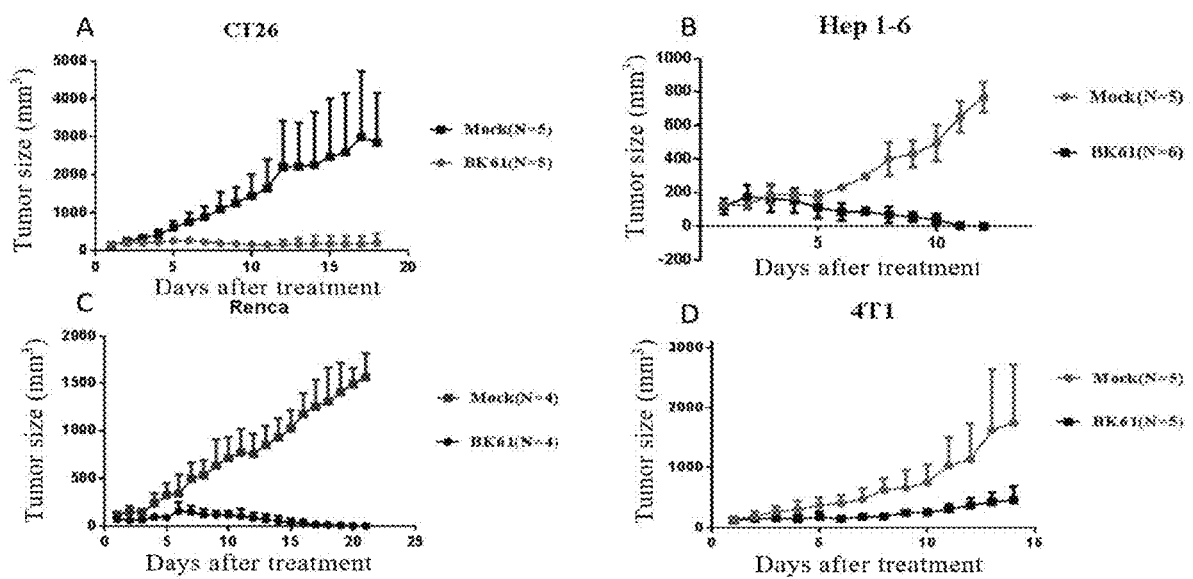
FIG. 4 shows the in vivo anti-tumor experiment results in Example 3 of PRV-WT on mouse colon cancer model CT26 (FIG. 4A), mouse liver cancer model Hep1-6 (FIG. 4B), mouse kidney cancer model Renca (FIG. 4C), mouse breast cancer model 4T1 (FIG. 4D). The results show that the PRV-WT had significant therapeutic effects in the above mouse tumor models.

The treatment results of PRV-WT on human tumor transplantation model and mouse tumor model are shown in FIG. 3 and FIG. 4, respectively. The results show that after treatment with PRV-WT, the growth of the tumors of CNE1 (FIG. 3A), GBM (FIG. 3B), Raji (FIG. 3C) and CT26 (FIG. 4A), Hep1-6 (FIG. 4B), Renca (FIG. 4C) and 4T1 (FIG. 4D) gradually slowed down and arrested, and the tumors were even lysed and disappeared; in contrast, the tumors in the negative group (Mock) maintained normal growth, and the tumor sizes were significantly larger than those in the experimental groups.

The above results indicate that PRV-WT exhibited significantly favorable antitumor activity in vivo.

Example 4: Safety Evaluation of Oncolytic Virus 4.1 Virus and Experimental Animals as Used (1) Virus: In this example, the PRV-WT provided in Example 1 was used. For virus cultivation and virus titer determination methods, Examples 2.2 and 2.3 were referred to, respectively.

(2) Experimental animals: 6-8 weeks old Bab/c mice were from Shanghai Silaike Experimental Animal Co., Ltd.; according to the protocol approved by the Experimental Animal Center and Ethics Committee, Xiamen University, the mice were raised under clean-grade conditions, and subsequently used for in vivo virulence assessment of pseudorabies virus.

Figure 5:
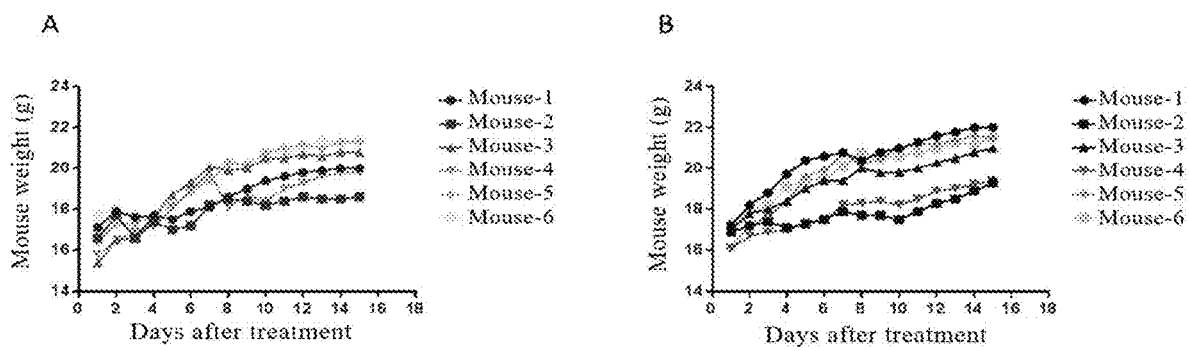
FIG. 5 shows the safety evaluation results of PRV-WT in the mouse intravenous injection model in Example 4. By intravenous injection of PBS (A) or $1*10^7$ PFU virus (B) into Bab/c mice, the body weight and survival rate of the mice were monitored. The results show that the mouse body weight of the PRV-WT group and the PBS group showed the same trend, and none of the mice died, confirming that the wild-type PRV-WT had very good safety in the mouse intravenous model.

4.2 Safety Evaluation of Virus in Mice (1) Bab/c mice were selected and subjected to single intravenous injection of PRV-WT or PBS, the challenge titer dose was $10^7$ TCID50/mouse (6 mice per group), and then the survival rate and body weight of the Bab/c mice of the challenge group were monitored and recorded every day. The statistical results of body weight of the mice after injection of PBS or PRV-WT are shown in FIGS. 5A-B, which showed that within 15 days after challenge, none of the mice in the challenge group died, and the trend of animal body weight growth of the challenge group was consistent with that of the control group, i.e., there was no statistical difference ($P>0.05$). This result indicates that PRV-WT had very good safety in the mouse intravenous model.

Figure 6:
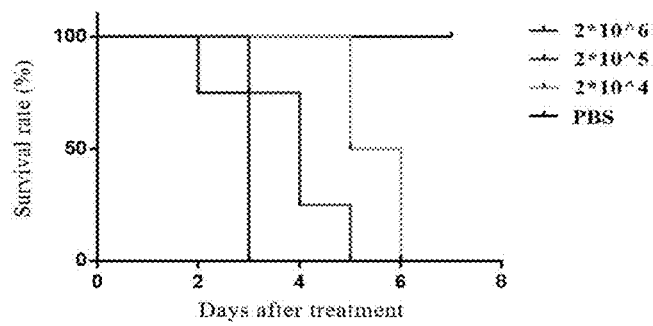
FIG. 6 shows the safety evaluation results of wild-type PRV-WT in the mouse intracranial injection model in Example 4. By intracranial injection of $2*10^6$, $2*10^5$, and $2*10^4$ PFU of PRV-WT into Bab/c mice, the survival rate of mice was monitored. The results show that the mice injected with the virus all died one after another, and showed a certain dose dependence. Such results suggest that the PRV-WT may have certain neurotoxicity.

(2) Bab/c mice were selected and intracranially injected with different doses of PRV-WT with challenge titers of $2*10^6$, $2*10^5$, $2*10^4$ PFU/mouse (4 mice per group). Subsequently, the survival rates of Bab/c mice in different dose challenge groups were recorded every day. The results are shown in FIG. 6, which showed that the death of mice occurred one after another, and this phenomenon was dose-dependent, indicating that PRV-WT had certain neurotoxicity.

Example 5: Anti-Tumor Activity and Safety Evaluation of Modified Form of PRV 5.1 Virus as Used:

In this example, the PRV-del-EP0 (SEQ ID NO: 4) provided in Example 1 was used. For virus cultivation and virus titer determination methods, Examples 2.2 and 2.3 were referred to, respectively.

5.2 In Vitro Oncolytic Activity Evaluation of PRV-Del-EP0

Figure 7:
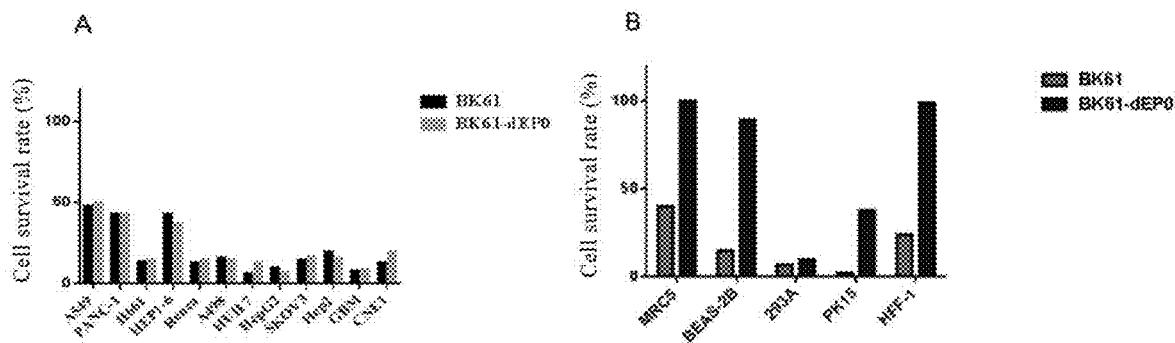
FIG. 7 shows the in vitro killing activity evaluation results of PRV-del-EP0 to tumor cell lines and diploid cell lines (similar to normal cell lines) in Example 5.

The target cells were treated with PRV-del-EP0 (BK61-dEP0) with MOI=1 according to the method described in Example 2, and the survival rate of cells after treatment with PRV-del-EP0 (BK61-dEP0) was detected using CCK8 method. FIG. 7A shows the killing results of PRV-del-EP0 (BK61-dEP0) on various tumor cell lines, and the results indicate that it substantially maintained a killing effect comparable to that of wild-type PRV of parental strain. FIG. 7B shows the killing results of PRV-del-EP0 (BK61-dEP0) on a variety of non-tumor cell lines, and the results indicate that PRV-del-EP0 showed a significantly reduced killing activity to diploid cell lines (similar to normal cell line) as compared to the wild-type PRV of parent strain. The above results indicate that PRV-del-EP0 not only retained the significant tumor-killing activity of wild-type PRV, but also had an improved safety to some extent.

5.3 In Vivo Safety Evaluation of PRV-Del-EP0

Figure 8:
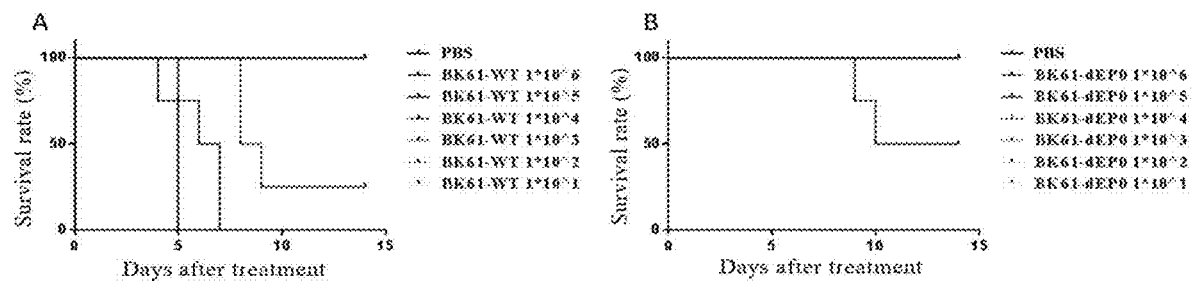
FIG. 8 shows the safety evaluation results of PRV-del-EP0 in the mouse intracranial injection model in Example 5. By intracranial injection of $1*10^6$, $1*10^5$, $1*10^4$, $1*10^3$, $1*10^2$, $1*10^1$ PFU of PRV-WT (A) or PRV-del-EP0 (B) into mice, the survival rate of mouse was monitored. The results show that PRV-del-EP0 had significantly improved in vivo safety as compared to the wild-type PRV.

ICR mice were selected and intracranially injected with different doses of PRV-WT and PRV-del-EP0 with challenge titer doses of $1*10^6$, $1*10^5$, $1*10^4$, $1*10^3$, $1*10^2$, $1*10^1$ PFU/mouse (4 mice per group), and then the survival rates of ICR mice in different dose challenge groups were recorded every day. The results of the PRV-WT (BK61-WT) group are shown in FIG. 8A, and the results of the PRV-del-EP0 (BK61-dEP0) group are shown in FIG. 8B. The results show that the mice in the PRV-WT group died one after another, all the mice in the $1*10^6$ and $1*10^5$ groups died, and the survival rate of the mice in the $1*10^4$ PFU group was only 25%; in contrast, among the PRV-del-EP0 groups, the death of mice only occurred in the $1*10^6$ group, and the survival rate was 50%. The above results indicate that the PRV-del-EP0 had significantly improved in vivo safety as compared to the wild-type PRV.

5.4 Evaluation of In Vivo Therapeutic Effect of PRV-del-EP0

The tumor cells Hep1-6 used for subcutaneous tumor formation in C57/B6 immune mice were digested with 0.01% trypsin, and then resuspended into a single cell suspension using cell culture medium containing 10% fetal bovine serum. The cell density of the suspension was counted. The cells were precipitated by centrifugation under 1000 g for 3 min, and then the cells were resuspended with an appropriate volume of PBS to reach a concentration of about $10^6$-$10^7$ cells/100 µl PBS. The tumor cells were subcutaneously inoculated in the back of C57/B6 mice at $10^6$-$10^7$ cells/100 µl PBS/site with a syringe. When the tumor cells grew into a tumor mass of about 100 mm³ under the skin of SCID mice after about 7-14 days, the tumor-bearing SCID mice were randomly divided into 3 groups, which were intratumorally injected with PRV-WT (BK61-WT), PRV-del-EP0 (BK61-dEP0) and PBS, respectively, once every two days, for a total of 3 treatments. The tumor size was measured with a vernier caliper and recorded every two days, and the method for calculating the tumor size was:

Tumor size (mm³)=tumor length value×(tumor width value)²/2.

Figure 9:
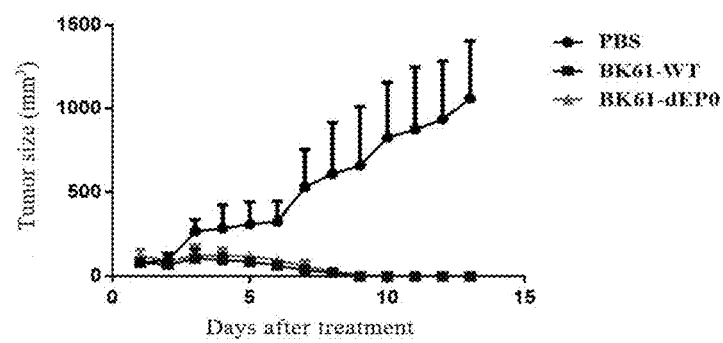
FIGS. 9 to 10 show the therapeutic effects of PRV-del-EP0 on mouse liver cancer model in Example 5. Among them.

The results are shown in FIG. 9. The tumors were completely cleared in the mice of the PRV-WT group and the PRV-del-EP0 group, indicating that the PRV-del-EP0 exhibited the same significant in vivo therapeutic effect as the wild strain.

Figure 10:
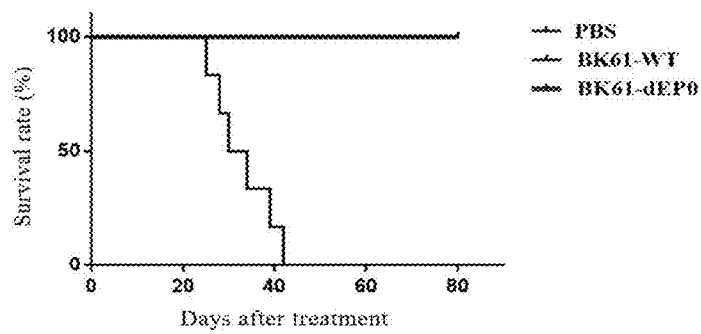

At the same time, the survival rates of the mice were determined. According to animal ethics, the mice were killed when the tumor size reached 2000 mm³. The results are shown in FIG. 10, which indicate that both PRV-WT and PRV-del-EP0 treatments could significantly improve the survival rate of the mice.

Figure 11:
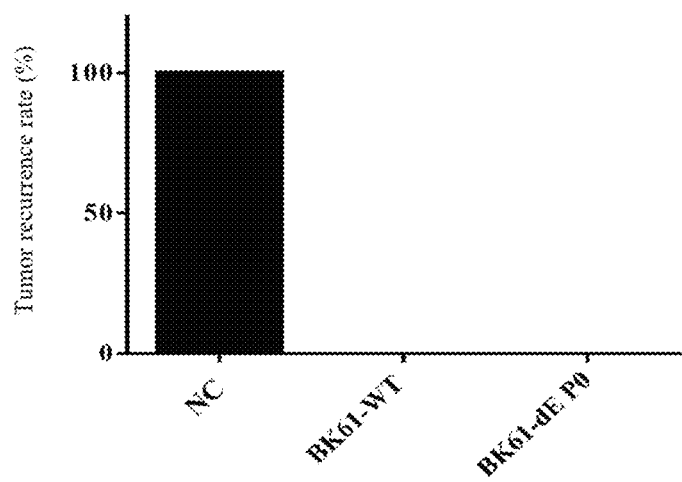
FIG. 11 shows the evaluation results of the tumor recurrence rate of the mice cured by PRV-WT and PRV-del-EP0 in Example 5. The results show that PRV-WT and PRV-del-EP0 could prevent tumor recurrence.

Further, the tumor recurrence rate in the mice was evaluated. Specifically, the mice that were cured in the above-mentioned PRV-WT group and PRV-del-EP0 group were inoculated again with tumors, and the number of inoculated cells was 10 times the number of the initially inoculated cells; and, the mice that were not treated with PRV-WT and PRV-del-EP0 were used as the control group (NC) and inoculated with the same amount of tumor cells. The tumor growth of the mice was monitored, the number of the mice with recurring tumors was counted, and the tumor recurrence rate was calculated as the following: tumor recurrence rate=(number of mice with recurring tumor/total number of mice inoculated with tumor)×100%. The results are shown in FIG. 11, which showed that none of the mice in the PRV-WT group and the PRV-del-EP0 group had recurring tumors, while tumors were observed in all of the mice of the control group that had not been treated with PRV-WT and PRV-del-EP0. This result suggests that mice cured by PRV-WT and PRV-del-EP0 had good anti-tumor immunity and tumor recurrence could be prevented.

Although the specific embodiments of the present invention have been described in detail, those skilled in the art will understand that various modifications and changes can be made to the details based on all the teachings that have been published, and these changes are within the protection scope of the present invention. The protection scope of the invention is given by the appended claims and any equivalents thereof.

What is claimed is:

1. A method for treating a tumor in a subject, the method comprising:
    administering to a subject in need thereof, an effective amount of a modified pseudorabies virus (PRV), or a nucleic acid molecule;
    wherein the nucleic acid molecule comprises a nucleotide sequence selected from the group consisting of:
    (1) a genomic sequence or cDNA sequence of the modified PRV; and
    (2) a complementary sequence of the cDNA sequence, and
    wherein the modified PRV does not express a functional EP0 protein compared to a wild-type PRV, and
    wherein the tumor is selected from the group consisting of neuroglioma.

2. The method of claim 1, wherein the genomic sequence of the wild-type PRV has a sequence identity of at least 70% to the nucleotide sequence of SEQ ID NO: 1.

3. The method of claim 1, wherein the genome of the modified PRV comprises the following modification:
    an original promoter of at least one PRV gene is replaced with a tumor-specific promoter.

4. The method of claim 1, wherein the modified PRV comprises an exogenous nucleotide sequence; and
    wherein the exogenous nucleotide sequence encodes an exogenous protein selected from the group consisting of a fluorescent protein, immunomodulatory polypeptide, cytokine, chemokine, and anti-tumor protein or polypeptide.

5. The method of claim 1, wherein the nucleic acid molecule has a genomic sequence of the modified PRV.

6. The method of claim 1, wherein the nucleic acid molecule is a vector comprising a cDNA sequence of the modified PRV or a complementary sequence of the cDNA sequence.

7. The method of claim 1, further comprising administering at least one additional pharmaceutically active agent having an anti-tumor activity to the subject.

8. The method of claim 1, wherein the subject is a human.

9. The method of claim 1, wherein a genome of the modified PRV comprises the following modification:
    (i) an EP0 gene comprising a loss-of-function mutation, or
    (ii) an EP0 gene which is deleted or substituted with an exogenous nucleotide sequence encoding an exogenous protein.

10. The method of claim 9, wherein the loss-of-function mutation is at least one selected from the group consisting of a missense mutation, nonsense mutation, frameshift mutation, base deletion, base substitution, base addition, and a combination thereof.

11. The method of claim 1, wherein a genomic sequence of the modified PRV has a sequence identity of at least 70% to the nucleotide sequence of SEQ ID NO: 4.

12. The method of claim 7, wherein the additional pharmaceutically active agent is at least one selected from the group consisting of an oncolytic virus, chemotherapeutic agent and immunotherapeutic agent.

13. The method of claim 12, comprising at least one selected from the group consisting of the following (i), (ii), and (iii):
    (i) the additional oncolytic virus is selected from the group consisting of adenovirus, parvovirus, reovirus, Newcastle disease virus, vesicular stomatitis virus, measles virus, and a combination thereof;
    (ii) the chemotherapeutic agent is selected from the group consisting of 5-fluorouracil, mitomycin, methotrexate, hydroxyurea, cyclophosphamide, dacarbazine, mitoxantrone, anthracyclines, etoposide, platinum compounds, taxanes, and a combination thereof; and
(iii) the immunotherapeutic agent is selected from the group consisting of an immune checkpoint inhibitor, a tumor-specific targeting antibody, and a combination thereof.

14. A method for reducing or inhibiting tumor recurrence in a subject, the method comprising:
administering, to a subject in need thereof, an effective amount of a wild-type pseudorabies virus (PRV), or a modified PRV, or a nucleic acid molecule;
wherein the nucleic acid molecule comprises a sequence selected from the group consisting of:
(1) a genomic sequence or cDNA sequence of the wild-type PRV or the modified PRV;
(2) a complementary sequence of the cDNA sequence;
and wherein the modified PRV does not express a functional EP0 protein compared to the wild-type PRV, and wherein the tumor is selected from the group consisting of neuroglioma.

15. The method of claim 14, wherein a genomic sequence of the wild-type PRV has a sequence identity of at least 70% to the nucleotide sequence of SEQ ID NO: 1.

16. The method of claim 14, wherein a genome of the modified PRV comprises the following modification:
(i) an EP0 gene comprising a loss-of-function mutation, or
(ii) an EP0 gene which is deleted or substituted with an exogenous nucleotide sequence encoding an exogenous protein.

17. The method of claim 14, wherein a genomic sequence of the modified PRV has a sequence identity of at least 70% to the nucleotide sequence of SEQ ID NO: 4.

18. The method of claim 14, wherein the nucleic acid molecule has a genomic sequence of the wild-type PRV or the modified PRV; or the nucleic acid molecule is a vector comprising a cDNA sequence of the wild-type PRV or the modified PRV, or a complementary sequence of the cDNA sequence.

* * * * *

SEQUENCE LISTING

<160> NUMBER OF SEQ ID NOS: 4

<210> SEQ ID NO 1
<211> LENGTH: 137764
<212> TYPE: DNA
<213> ORGANISM: Pseudorabies virus

<400> SEQUENCE: 1

```
ggcccagctc tccccgagc gcggatctct gaaaaaaaaa tttcccgccc ccgcgttttc      60
cattggggtg aatggggagg gggtggggga tgggcactca ctaagaattg caaggtgcc    120
aatttatatt ctggcatggt gccaaactac atacctggct ccctgccaac cccaatcccc    180
ctcctacctt ggctccctgc caaccccaat cccctccta ccctggcacc ctgccaaccc    240
caatccccca ccatcgtcgc ggtcttcatc cttggcacac agccaaccct agaaggcgag    300
ccgcgatgct gcggtcgggc ccacccgcgg caggaggttg tggatggcga tgggcgaggg    360
cgggcgcgcg tgtggtgggg acggtgtcgg tgcccgcgcc ggtggcgccc gcgagggttc    420
gccttgggtg cgctgggggc ccctccccat tcaccccaat ggaaaacgcg ggggcgggaa    480
attttttttt cagagatccg cgctcggggg agagctgggc cccagaccag agagttgtgg    540
gggggcccgg gggagagctg ggccccggc cagagagttg tggggggccg gggagagct     600
ggccccaga ccagagagtt gtgggggggg ggggcccggg ggagagctgg gcccggctct    660
cggtggggga caaccccctg gggagagcct gaccaattgc cagactagag gagagccccg    720
ccgggaccgg agaggagagc gcgccttccc ccaaccccct cgttccccc tttccccccaa    780
ccccctcgtt cccccttttc cccttccaa agcgggcgcc gcgagcgcgc gggcccccat    840
acggcgctcg ctctcgtccc ggccggtctg gccgccggga cggggcgctc ctcgccgcga    900
tgaccgacgc ctcgtcgcga cccggcgagg aagagccgat ggaggtggac gagcacgtcg    960
agcccgagtc ggagcccatg gaggtggacg agccccctgc gccggcgcag gcatcgggcg   1020
ccatcctcgc ggtgggcttc acccagcccg cgcaggtcct gcgggcgtac cagatcggtt   1080
gatgtgcgaa cgatgggcgg gggaaccagg gggtcagatg cacccacgtg gtgccacacc   1140
cgccccacgc cgcgctctttt tcccggggcc gcccgaccgg atcctcccgc agagccggac   1200
gtggggcgag agaccgggat ggacgtggag aggggagcgg ccgcggggcg cgtggaggtg   1260
gagctcgatg cccggccctc cggcaccaga gggcgcggcg cgagcccctc gcgtcgagcg   1320
cgggaccccc gaaccggccc gtgccctcgg ggcgggaccg accgcgtcc ccgggacaga   1380
accggcgacg ccaccggggc gcgcgccccg cgcccctccg ccctgggtat aacgccccg    1440
ggcaccgccg tccgccgcca gccgccgtgg gaggcagaca tgcctccaca acgagcccgc   1500
ggggcccgc cgcgccgccg cggcagcgac ccgcccgatc ccggcagcct cgccgggcgg   1560
ctctcgcccg gggggaggag cggcggagga tcgcgccgga ccctctcgcg cagcagctcg   1620
ctcacgtccg tcgcctcggc ccccgtggag acgcccgtcg ccgcggaggc tctcggactc   1680
ggcgccccg gctccagacc gccctcctac ggggacgtcg ttcgcgccgg gccgcgcccg   1740
caccgatcgc cggacacgcc gctgtttgcc cggggcccgc cccgtccta ctcggagacg    1800
ctcctgtttg accgcccgc gtacgcggtg accatccgg accgcccgc gtacgagccc    1860
accgtcatcg gaccgcagcc gccgaggccc cgcgactgga tctcctcgcc ctccgtggtg   1920
```

```
cagccgtcgc tgctgggccc cttcagccag tgcctcccgc agttgacctg ccccgactgc    1980
cgctaccccg aagaccgccc gatggtgctc gtgggcttcc tctgggggggg gctgctcctg    2040 ctggtgggcc tcgtgtttct gatcctgctc ccggtgctcc gggagtctgt cgtgtttccc    2100
tgaccaataa actcggctcg ccagtcctat cgatatccgc gtctcgcgtg tggtgttgcg    2160
acggggagag tgggagagg aggatgggga gaggaggatg gggagaggag atggggagat    2220
ggggagagga gatggggaga tggggagagg agatggggag atggggagag agatgggga    2280 gatgggagg acgacagact cgtgcacacc agagaggtac ggttcaacag ttttattcaa    2340
aacaggtggt tgcagtaaaa gtacttcccg tgcatgtaca cggggacgag ggtgtagctg    2400
cacgtcaggc ggcaggtggg cgcgtcgcag ccggttttgt gggagtccag cgcgtccatg    2460
atcccgccga ggcaggcgcc gggcacgtac tcctccagcg ggacgggcga gtccccagg    2520 tcctcgggca gcacgcagct cgagccgcgc tcgacgacg gggcgatgcg agccagcatc    2580
accagggtgt aggtgacgat gcagcgcacg tcccgcaggc ggcgccggcg cacgagctcg    2640
tcgacgggcg cgtcgcggag gtagcagcgc aggaacggcc cgagcttcag gcgcaggttc    2700
tgcagcaccg ccccgcggt ggccacgatg gggtccagcg tgcgcagcgt gagcccttg    2760 gtgaggatga gcttgaccca cgtgagcgtc tcgtccgccg aggcgaggga ctccgtcagg    2820
ccctcgttca ggagcaccat ctcgcggagc acgcgcgccg cctcggtggc gtgcggccgc    2880
acctcaaaca ggcggtgcag gtcggccccg tggaacatga gcgtctccca cgtgacgcgc    2940
cgcccgtccg gggtgaactg ctcggcgccg aactcgagga cggcggccca cggcgacgag    3000
cccgcggcgc ggaagccgtc gttgaacacg gggcgggaga ggtcgtgccg cgccgaggca    3060
aagagctcgt tgacgcgggt cgcgccgacc cgcgcgtgcg tcgcggagac ggcggcgcgc    3120
gcgctctccg acagacgatc gggggcgcg tcgggcccgc cgtccggacg atccgcctcc    3180
tgtcgccgcc gctggtgctg ctgctggcgc tgctgctgct gttgctgccg ccgccgctgc    3240
cgcagggcct gtcgggcggc gcgcccgccg cgacccccgc gccggcgccg gatgccccc    3300 agccgcgccc ggacgggccg ccgctcgggg gggcgcgagc ccaggcgctc acggaccggg    3360
cgccgctcct cgctccccga cctggacgcc tcgctgtcgc tgctgttgcc gctgtcctcc    3420
atgaccgtgg tgcgagcggg gccgcggtgt gcaggtggcg ggcggcgggg cgcctttaac    3480
ccgccgtccc cgcgcgacct tcatccaaat atggtaatgt gccgctcata gtgcagaaac    3540
agcaacacgc cccctaccag caggcagagg tacagcgcct tggcaaagat cccggcgagc    3600
acggtcgagc agcacgcgcc gcagacgcca agggcggcgc ggccgccgtc ggagcgcgcg    3660
ggcgtggccg tcgcgccgga gacgcgcgcg atgtgcggca gcgtcgccgc caggagctcc    3720
agcgccccga ccgccagcac aaagatccac acgagggcgc gggcgtacag cgggaagacg    3780
agggcgcacg gggcgcgtgt gacgccgagg gtcgtgaaca gcgccatgcg cgcccccagg    3840
cggagcccga gctcgaggag gatgagcgcg atcagcgtgg gatggcggtg tgccagcgta    3900 atgggtcct cgcggaggtc gcggctgagc gcggcgcggc gcgtcgcgag ctcggccatg    3960
taccaggcga acttggtgta gctgcagccg atgaccgtgg cggcgagcac gctcgccgcg    4020
tagttgagcg tgtacttctc cggggtcagg aactcggcgg ggtcgcggaa ggggccaaac    4080
atgcgccgct cctggcgcgc gtacacgaag gccgcgtaga ggagccacgc gacggccgcc    4140
aggcgaaagt gcacgtccca caggtaggcg cggcagtcgc ggcgcgcgta cacgacccgc    4200
gcgcggtcgc gcagcgccgg gctcagcgcg tccgtctcgt tggggccac gtagatggcc    4260 gtggcgttga aggcctccca gtccggcgcg ccccggcgg cgtcctcgcc gagcggcagc    4320
```

```
gccgcgtaca cgacggggtg gggcaggcgg gcgacggtcg cgtagtacgc gcccaggccg   4380
gcgtacgcgc ccatcacccc gaggacgagg aggtgcagcg ggcgcccgcc gaggagcatg   4440
attgccccac ctccgcggtg aaaatggtgc gcgtcgcgtt gctgccgcac tttgtagcga   4500
agcactgctg actcagcgag atacacagcc ggtcgtgggc gtcgacgctc agggccacga   4560
aggtgcgggc cggcgggctg cgcgcgtgcc gggcccgcag gcagctgaag cgcgcggacc   4620
cgcagagctg aagaggacc cagtcgggct tggccaccac ccgctgcgcg gtcgcgcccg   4680
cgtactcgtg cgcgcgcccg ttgaagtgcg cgtcgaggtg ccgcagcacg ggcgccatgg   4740
ccacgtccgc cacgaaggcc tcgagcgcgc gccggtcctc cgcgtccacg gccaggccgc   4800
gcagcatgtc caccagcggc gtgcgccggg cgaagaaggc ctcgcggttc cgcgccgcct   4860
tgcgctcgaa gaagctctcg tactccccc cgaggctgtg cagcacgcgc gtgacgcgt   4920 gcgccgggcg ggcgtggaag tgaaagttgc gcgggtcgtc gaagcccggg ggcgcgtccc   4980
cgaaggggag caggcgcccg tggcagccgc cgccgtcgac cttggcgaag aagggcagcc   5040
gcaggctgcg cccgtgcgcg tacacgcccg tgtccacgaa ggtgaagtcc tggaggtacg   5100
ggcccatggg ctcgatgaag tcccgctcca gcagcacggc ctgctggagc acgcgcgcca   5160
ggccgcggac cgtgtcggcg ccggccaccg cgtacggcga cggcacgggc gtgcacacgc   5220
ggaagcccat cttggcgcgg cagccgcacg cggggcgctc gtccgccggg acggggcgc   5280 ggacgagggc ggaggcgccg gggtccccgc ccgcgccccc gatcccgacc ccgacctcgt   5340
cgtcgtcgca cgtgtacacc tcggcgggga cgcccgcgtc ccagtccgcc cagtcctcgt   5400
cgcccggcgc ggcgccaaag tcggcgaggg cggcgtcgtc gtcccagggc gcctcctcga   5460
ggccgtcgtc ggaggaggcc gcggaggcgg accccgcggc ggcggcgagg cgccccccg   5520 gcgggcaggc gctcttgtac acgtagcagg ggtgcgcggc ccagtcgccg tcggcctcgg   5580
ggaagagcag cgcgagcgcg tcgagcaccg cgcggcggaa cccgcgcatg ccgcctcga   5640 gcgtgcccgc gggcaccggg cgcgcgaggc gaaagtcgac gtcgaggacg atgttggtca   5700
cggccagccg ggcgttgaac acctcgtggc ggctcacgta catctgcgcc gccggctcgt   5760
gcgcggccat ctccggcgcc gcgtcgcggc gcgccgtcgc gcgcccccag gcgtccccgg   5820
ccagcaccgc gaaggcctgg cgccggtgcg ccagctccac gcggtacacc ggcgccgggg   5880
ggcacgcgtc cggcaggccg agcagggcgc ccagcgccgt gcgcgcgcgc ccgccgcccg   5940
gcgcggcggc cagctccagc aggcgacgca ggacggcgcc gtcggcgccc ggctgctgct   6000
gctcctcgtc gggggcgcgc acccagccgt ggggcgcgag gcgctcctcg acggcggtca   6060
cgcggcgcgc gaggcggcg gccgcgtcgc agagcccgcg cggcgcgtcg gccgcgagcg   6120
cggcgtacgt gcgcgtcctcc acgtagccgg cgcccatggc cggggcgagg cgcgcgacgc   6180
tcggcgtcac gttctgggcg acgtagtcgc ggatgttgag ctgcgcccgc acgtggcgga   6240
agaaggcggc ggccgcgcgc tccccgaggg gcgagcgccc cacgggcgcc gcggggtccg   6300
tgacgttgac ggcgtccagg tgctcgcgga ccgcgcgcg gttgaagctc tcaaagtggg   6360
ccaggtagac gtacgtcacg aactcgcggt cggggagctt gaggctgccc cggtcgtggg   6420
agatgtagtc ccggaggacg cccatctcgg cgcggtcggc gcgcacgcgc tcgtcgacgt   6480
agcgcgcggc gtgcgccgcc gcggggcccc gcgcgtagcc gctcaggcag cagaagcgcg   6540
agagcgccgc gaacgagagc agcccgcgg ggtccaggcc gctggggttg gggtccacgc   6600
gcgggttgta cgtgagcagc aggtccttga gggcccgcag gtcgtaggcc ggccgcgggt   6660
```

```
ggaagaggtg gaggcgcgtg gccagcacca gcgtcttctc ctcggggccg aagcgcgcca    6720
cgtaccagaa gggcgtgttg tggttcccgt agaggcgccg gaaggcggcc agcgtctggg    6780
tctcgtggtg cacaaagagc gaggtcagcc cgcggcgccc gaccgcgatg gagcgcagcg    6840
ggcgctccgg cgcgtactcg gcgttgccgg tgcgcgggcg cacctgctcg aggaccatgg    6900
tcagggccgc gatgaggccg tcgtggaggg cgaaggtggc cgcctcgtcc atggcctcga    6960
ggacgtcccg cgccgcgagg ggctccccgc ggcagagcgc gcgcacgacc gccgggtcg     7020
cggcggcgac gaacacgggc gcacgcgga cgctggccac gtgcccggtg aggcagaacg     7080
tgacgccggg gcggcgcgct aaaagctcgg cctcggcgcg ctcgcccggc agtgagaagg    7140
cctcgtccag cccggcgccg tcccacgcgt acgagacgac gtagaccgcc cccgagggct    7200
cctggcccgt gagcagcatc agcgagtacg tgatcgcgca gccgtcctg gcgtacagga     7260
cgcggatcat gctgggcggc atcttctccg ggtggtgcgg gcgccgcggc cgtgggaggg    7320
cttatgagcc gccggacgaa ctccgcctcc gggagtcgct ggccgtgctc aacgtgatcc    7380
tccccgcccc gctcgccgcc gaggacgtga tggcctcggc cgaggccgcg cgccgcctgg    7440
cccgcgcgga cacgctggcg cgcacctacc aggcctgcca gcgcaacctg gagtgcctgg    7500
cgcgccacga ggcctccggc gacgacgcc tggacgccgt ggtcgcggcg cacgcggcca    7560
acgcgcggcg gctcgcggac acgtgcctgg cggcgctcat gcacctgtac ctctcggtcg    7620
gcgccgtcga cgcggacacg gacgacctcg tcgagcaggc cctgcgcatg accgccgaga    7680
gcaacgtggt gatgtccgac gtggccgtcc tggagcggac gctgggactg gcccggcggc    7740
ggcagccggc gcccgtccgg gccgcgcccg ccgggctggg tctgcccgtc cccgcccagc    7800
ccgccccgcg cgctaccgcc gcccgcccgg ccccgccgcc cccgcccgag gaggcggggg    7860
aagacgagga gggggaccgc cccgaggacg acgcggcccc gctgctgccc cccgcgcccc    7920
ccgccaagac gcgcccgccc gagaaggccc ggaggctggc cgaggcctgc aagatgtagc    7980
cggagagggc gggagggaag gaagggacgg agaccgccgg ggttgtctgt gcccaataaa    8040
catctttatt gaaaaatgag aagagcgggt ccgcgtgtg tgcgcgcgcg gtcgccaccg     8100
tccgggtccg gcgcgggccg ccgcggcctc acaggcccgt ggagccgaag ccgcgggccc    8160
cgcgcgcgct gctcggggcg acaaagtccc gcgcgaagag ccacgcgggg cggtgctgca    8220
tcggggcgcg cggggtggcg gggaacgggg accgtcccgt gatccagccc agcggctcgc    8280
gcgtcagcac cagctgggcc acgcgctggc ccgactccag ggtcaccggg tgcgcgccgc    8340
ggttctggat ccggaagcgg cacgggccgc tctcccaggg cgtggggaag acgacgatgc    8400
cgcggaggtt gagggacgag cgcccgaaga cgtaggccca gtggcggccg tccgtgcggt    8460
gcaccggcag cgtcacggtc tcggcgcccc cggggggcag caccagctcg cgcgggcagg    8520
ggatgtcgta tccggcgtcc tcgtcgcgct tcggcgcaaa gacctcgaag aagggcacgt    8580
ccgtggcgat gccggcgcg aggcgcagcg gcgtgcaata aaattgcgcc cgtgggcggc     8640
ccggggctac aatcgcctgc acctcgccgc gaaagcccgc gtccacgatc ccgttggtgg    8700
tgcgaccgcc cccgcgctgc gcgacgagca tcgcgtatcc ggtgggcagc gccaccttga    8760
ggcccagggg aaccttataa aatccctccg gcccggact ccgcacacc agcagccgcc      8820
ctccgtccac ggtcacgggc tcgctcgcac acaccaggat ggtctcctcc gccgggccct    8880
cgctgacgct cgtcgccgcg ctctgcgcgc tggtggcccc cgcgctctct tccatcgtct    8940
ccaccgaggg gccgctgccg ctgctgcgcg aggagtcgcg gatcaacttc tggaacgcca    9000
cctgcgccgc caggggagtc ccggtggatc agcccacggc cgccgccgtg acatttata    9060
```

```
tctgcctcct ggcggtgctc gtcgtggccc tgggttacgc cacccggacg tgcacccgga   9120
tgctgcacgc ctcccccgcg gggcggcgcg tataaagatc gatccgcacg cgcccgaccc   9180
cactcgctcg ccatgtccag ctcgagaaag acccgggtcg ccgccgacga gaccgcctcg   9240
ggggcgcgcc gccgcgccgg cagcgcctct cgcacccgga ccaccgcccc ggccgccgcg   9300
accccccagac gcccctcggc ctacgacgac tatgacgacg gcttctccta ccggtcggcg   9360
ccgtcctacg acgacgatga ctactacggc tacgatggct acggctcctc ccgcgccccc   9420
cgcgccgcca aggtgacgcc cgcggccgcc tcgcgggcct cgaccggggc caagagcgcc   9480
tcggccgcca agaccccgc gtccgcgcc aagaccaccc gctcggcccc ggccgccgcc   9540
ccggccgcca ccaccaccac caccaccgcc gccgccgccg cggaaccggc cgcccggcgc   9600
gcctcgacac gggccgcccc cggggagaac ctcgacgtgg gccgccgcg gctcgccttc   9660
agcgacaggc cgtgcgaggc caacgtgccc tggcgcggcg cgacgcacgc cttcaacaag   9720
cgcatcttct gcgcggccgt gggacgcgtg gccgaggccc acgcccgcgc cgccgccgag   9780
tccctctggg acatgaaccc cccgacgacg gacgcggcgc tcgaccgctt cctgcaggcc   9840
gcggtggtgc gcatcaccgt gtgcgagggg ctggacctga tcgaggcggc caacgccgtc   9900
ctggacgaga gcaccccgg gcggaaggga aaagtgtata aataaaggcg ttgcaaatgg   9960
caccccgctc agtcgtccgc tgtcttgctt gtgggggggt cggtgaggat gcgcgacgag   10020
gagtgcgtgg tcgcgttcga cgaggccctg ctgggggggcg cggccccggg ccggccgccc   10080
gtggtggccg tcccgcgggc ggccagcccg gacgcgctgt accagcgcct catcagcgac   10140
ctggccttcg acgagggccc ggcgctgctg ggcgccatgg agcgctggaa cgaggacctg   10200
ttctcgtgcc tgcccggcaa cgaggacctg tacgcgcgcc tggtcatgct gtcggcctcc   10260
gcggacgagg tggcggccca ggtccgggcg ccgacgcgcg acgcgagcgt cgacctgggg   10320
gtgcccgggg cggagcccat gccgcgggtc ccggccgtgg aggaggagct gcccgcgtac   10380
gtggcggccg tggagcgctt cttcgtgtcc acgctgcggg cgcgcgagga gcgctacgcg   10440
cgcctgctgg acgcctactg ccgcgcggtg ctgcgctacc tgcacgcgca ggcgcgccgc   10500
gacgagggca agctccggcg gctggtgcgc gggcgctact accgcgacgt cgcgcgcctg   10560
gcgcgcctgc tcttcctgca cctgtacgtg gccacggcgc gcgagctctc gtggcgcctg   10620
cacgcggacc aggtggtggc ccaggacgtg ttcatgtccc tgcgctacga gtgggaccag   10680
gcgcggcagc tgacgtgcct cttccacccg gtgctgttca accacggcgt ggtgctgctg   10740
tcgggcgcgc cggtgccggc cgcgcagctg cgcgccgtca accaccgccg gcgcgagctg   10800
ggcctgccgc tcgtgcgcgc cggcctcatc gaggaggacg cgccgacct ggtcgaggag   10860
ccgccgttct ccgccgcgct gccgcgcgcc ccggctacc tctcgcacca ggtgcggatc   10920
aagatggagg cctactcgcg cgagtaccgc gaccacacgt actgccgcc gccctcgccc   10980
gtggccagct acggcagcac cgcggaggcc ctgctgccgc cccgtcgcc ctcggccgtg   11040
ctgccctgcg acccgacgcc gccggcgcgc gtctcggccg cccgctcat caccacggtg   11100
acgctggccg aggccgagga ggatggcgcg ctgacgacgg cggcgcccgc ggccgcggtc   11160
gcggccgcga cggtcgcctc gcccgggccc gccaccccg cctaccacct catccccgc   11220
gacgcgctca accggatgtt tgagatgtga cgccgcgcgc ggtcggatct cggcgcccg   11280
accacctgtg ggcggggcgt ataaagccgc gggccggccc ggagggggg catttgccgc   11340
agcgaccacc atgagcgacg cggggcccgc gcggcgcccg aggcgctcgc aagagcagcg   11400
```

```
cttccagccg ttcccccgcg cggggctcct ggtgcacctg caggacgtgc tcgtgggcga    11460
ggtgcggcgc ccggacttcc gcccgccgcc cgacgaggag agcagcgagg aggaggagcc    11520
cgtctggacc gacgacgacg aggaggaaga ggggggggcg gaggaggaga ggatgagcgg    11580
gggccggcgc gggggtgagg gggggacga cgacggggac gaggaggagg aggagagcga     11640
ggggggcgcg tggtccgacg gggagctgta cgtggcggcc gaaggcgacg cgtgggacgc    11700
ggaggaggac gaggaggacg aggaggagga cgaggaagat gactacgacg atggggatga    11760
cggccacgac ggccgcggcg ccgcggtacc cgccgacgtg gactacctgt cgcgcgccct    11820
ccgcggcatg gagacggccc ccggtcccga cgagcgggag gccttcaccc gctacgccgg    11880
cacgctctac cgccgccagt tcagcccggg cggccggggg taccggcccc cgcgcccgcg    11940
cgaccccccg ccgccccgc ccccgcgggc ccggccaccg acgacggcga cggccgccgc     12000
cgcccactgc ggccccgccc gcgccgccga cggcgacgac tccgcgccgc gcctcgagcg    12060
ggacccggac gccgcgtacg ccagctggac gcgcgacatg cccgacggga ccttcctggc    12120
catgccgtcg tgggtggcgc tgcgccgcga ccgcgcgggg cccccgggcc gccccgtcgg    12180
gcccccggac atcctgcgcc gcgccccgcg ggcactgacg ttcacgccgc aggcggcctc    12240
ggcggcgctc gtgagccgcg accaggacgc ctgggaggcg ctggtgccgc tgcaccacct    12300
ccagatgcac tcgtggggcg gcagcgcgcc gccctcgcgc gggggcgtgt acgcgacgcc    12360
cgcgcccgag acgcgcggcg tgtggcgccg cgcgctgcgg caggccatcg ccctgcacca    12420
cgccatgttc ctggcgccgc tgcagtcctc gacggtcggc gcgcccgcgc tcgcgggcga    12480
ggcgctggcc ttcgcgctgg acgccgcggc gcgcgcggcc gtcaaccacg acgccgcggc    12540
gcgcgagctc cccgagcgcg cggcgcgcgc gctccgcgcc gtcggccggc gcgcggccgc    12600
ggcctcgggg ccgcgcgccg gcctcttccg cgccttctgc ggctccctgg cctactggcc    12660
ggagctgcgc gtcctcagcg ggcaccccga ggacgtccgc ttcgcggcct ccacctggc     12720 cgtggcagag gtgtacctgc tggcgcgcgc ccacggccag aacccgggct tcacggccga    12780
ggagcgcgag ctgctcgcgc ccatgttcac gctgaccgtg ctcgcgatgc accacgcgct    12840
gcgctggctc acgacggccg tggcgcgcgc cgtctcggac atccccgacg acgaggcctt    12900
ccgcgccgtg cgctcgcgcg tgccggcgtc gctggtgccg ctgggcagca tcgcgctctc    12960
ggacgccgag tacgccgtgc tgaacgcgac cgaggtggcg gcggcgcgcg acgccacggg    13020
cctgggccag gccgtgtcgc tgggctacgc cgccgcgcgc tccgcgctca cgggcctcat    13080
gcgggcccac gccggcggga gcgacgcgcct cgtcgccttc gcgctggtgc tgcagcgcct    13140 cgcggggccac gcgaacctgc tgctcaactg cctgctcggc gccgcggtcc acggcggccg    13200
gacggtgcgc gtgtacgagg cggcgctgga cgactacgcg gagctcatgg acgcgctcga    13260
cccgctggtg cgcgcgtgcc cgctcgcgga gttctgggag cagcgcgacg ccgtcatgcg    13320
ccagctgcgg ttgacggcgg ccccgggccc cccgtcggc ggcaagcggc tcgtcatcgc     13380
gcccgcgctg ccctccgagg acctggacgg gctcgtcccg cccacggccg tgcgccccgc    13440
ccacttgggg ccggacgtcg acctcgccga atacgccgcg cgccacccgg agctggtggg    13500
cgtgccggaa ccccgagcgc atttatcggc gcgccggccg ccccggggcc gctaacccgc    13560
ctctgcctcc gccatgctcc gccgcgcccg aggaacgcgc cgcgcttcgt ggaaggatgc    13620
ctcgcgccgc gtcaccgagg ggcgcacccg cgccagctgc ctgctggcgg ccccggggga    13680
ggtgctgacg gcggccgtgg cggccctgcg cgacgtggcc gagagccagt gcgcgccggc    13740
gctctttggc gcccagcgcg cctcggccct ggcgctcgtg cgcagcaact acgccccccga   13800
```

```
gtccgtgatc acggcgtgct cggcggagcc gcaccgcgag gtgtacgcgc gcgcggccga   13860
cgccgcgctg aagggcatca cggcggacgt ggcccggcgc gcggtgctgg ccacctactg   13920
gcgctacctg aaggccagct cgggcgtgga ggtgcgctcg gacgacgagc gcgacgcccc   13980
caccgtcatg ctgctgtggt cgacgttcgg caagccgctg tcgaagcacc cgttcaagca   14040
caaggcccag agcgccgcgt acggggccac gcgcgccgcg ctcgccgagg cgaccgaggc   14100
cgtggagcgg tacgcctact acatgcgccc gctcgacccc atggtctcca gcccccagac   14160
gagcgtgcgc ctgcacgaga tgctggcgta cgcggccacg ttgtaccgct ggctgctgtg   14220
gatgatggac acggtcgacg cgcgcgtggt ccgccacctg gggcgcacgc gcgggtggc   14280 gcgcgggccg cgcgagacga tgtcgcccga ggcgctcttt gggcggcacc gcgccggcgg   14340
gcccgccgtg gcctcgggct cgggcgaggt gctcgtgctg acgagccaca cggcgacggt   14400
gtttgacgcc ctggagatcc tcggcgccac gtgggccgag acgccctgga gagcggcgt   14460 gtgcggcctc acggccgccg tggaccttcgt gaccttcgtg caccaccacg cgcagaccct   14520
catcaacctg acgctggccg gctacgtgtg ctggctcgac gacgggatgg aggacccgta   14580
cctgcgcgcg gcgctgcgcg cgcagtgccg cttccaccac ctgatcggcg acctggcgcc   14640
cacgagctcg tcgcacgcct ggggcgccat ggagcgcggc acgctcgcct ggttcaacta   14700
cgccatcgcg cgcagcctgg cctcgtacgc cgggcccacg gagcgcttcg cgcgcgtgct   14760
ggcgacgacg ggccagcggg acatgcgctt cctgtcggtc gccccgcgc agccgccgct   14820 gccgccgctg ccgcgggcgt cgcagacgcc gtcgccgccg cccgcgacc gcgacgcgga   14880 gccgccgcac gagtacgtgg accccttcgc cgagtacctg aactggcccg tgcccgtctc   14940
gccgcccccg ctccccgagg ggcccccgag ctcggacgac gagctggagg tggacggcgg   15000
cgggcggcgc cccctccggc gcagccgcga cgccgccacg tacgtgaacc gcaaggacct   15060
cgcgccgccg cgcgcggcgg cggggggaggg cgacgacgag gaagaggagg aggatgaccg   15120
gttcccgcgc cgcgacgggg acgccgggac ctccacgagc tcgtcgcagg agagcgccgc   15180
cgacgaggag ttcccgcccg ggatcggcgt gcgcgacggc gaggaggacg acgaagacga   15240
gggggtggag gaggaagacg tgtacgtcga ccccgacggg gacggcgaac gaggcgccgg   15300
cggcggccac gacgacgacg ccccctgggc cccgctgacg cgccacggga gcatgcgcac   15360
cagcttccgg cgcggggtcc gcggctcgtt ccgcgccgcc cagcgcttcg tgcgccgccg   15420
gctctcgcgc acgagcgccg aggcgacccc gcgggctccc gtcgactcgg ccgcggcccc   15480 cgccacccg gcgtccccg cccagggcga gaccgaccac gtgtaccagc accccgccc   15540 gcggacccgc gcggacgacg gcctgtacca gcaccccga cccgtcatcg acctcaccgg   15600
ccaccgcgcg tcgcgccgca agagctggcg cgtgtgacgg ccccgcggac ccccgttgt   15660 atggtttccc cccgttgccc ccgtgtgtgg aaataaagtt ttttctaat tctgtacaca   15720 cggcgtgcgt gtcatcgtgg tcgcggtcgc gggacggagg ggagagggac ggaggggaga   15780
gggacggagg ggagagggac ggaggggaga gggacggagg ggagagggac ggaggggaga   15840
gggacggagg ggagagggac ggaggggaga gggacggagg ggagagggac ggaggggaga   15900
gggacggagg ggagagggac ggaggggaga gggacggagg ggagagggac ggaggggaga   15960
gggacggagg ggagagggac ggaggggaga gggacggagg ggagagggac ggaggggaga   16020
gggacgagac ggacgcgaga cgtgttgcca aacaagcgca tctttattgt ttcccgcggg   16080
agggggctac agggcgtcgg ggtcctcgct ctcgaggcgc tggtagtgcc ggcggcgcgt   16140
```

-continued

```
ggccatcgcc ccgacgcggc tggccagcag cgcgggcccg ctgttcttct tgcgcgcctt      16200
gtgctcctgc tgctcgaggg ccgacacgat ggacatgtac cggatcatgt cccgggcctg      16260
gtccagcttg gcctcgtcca cgtcgccctc gtcgacgccg tcctccttga gcgtcttcgt      16320
cgtgacgggg tacagggcct tcatggggtt gcgacgcagg cgcgagatgt gccggtaggc      16380
caggaaggcc gcgaccaggc cggccagcac cagcagcccg atggcgagcg ccccgaaggg      16440
gttggacagg aaggacacca tgccgccgac ggccgagatc acggccccg tggcgcccag       16500
gaccaccttg ccgacggcgg cgcccacgtc gccgaggccc tggaagaagt tggcgatgcc      16560
gcgcagcagc accacgttgt ggtccacctt gaccacgcgg tcgatgtcgt agaacttgag      16620
cgcgtgcagc tggttgcggc gctggatctc gctgtagtcc aggaggcccg tgtcggcgag      16680
ctcctcgcgc gtgtacacct cgaggggcag gaactcgcgg tcctccagca gcgtcaggtt      16740
cagggtcacc cgcgtgctga tcgtctcggg cacctccacc atgcgcacgt agctgtagtc      16800
ctcgtagtac acgtacccgc tccccagctt aaagtagcgc cggtggttgc cggtgcaggg      16860
ctcgatgagg tcgcgcgaga tgaggagctc gttgtcgtcg ccgagctggc cctcgatcac      16920
gcccgtgccg ttgtgctcga aggtgaccag cgggcggctg tagcacgtgc cgcgctcgcc      16980
gggcacgcgc atggagttct gcacgtacac gccgccgcgc acctccacgc accgcgagat      17040
ggccatcacg tcgccgagca tgcgcgccga gacgcgctgg ccgagcgcgg ccgtggccac      17100
ggcgctgggg ttcaggcgcg acatctcgct ccacagggtg cggtccttgt tctgcagctc      17160
gcaccaggcg gccgcgatgc ggcccagcat gtcgttcacg tgcgcctgga tgtggtcgta      17220
ggtgaactgc aggcgcgcaa actccgccga gcccgtggtg atgcgcaggt gccccgtgcc      17280
gttgacggcc ggcggctcgg gcgtccccgc ctgtccggcg gcgcgccggg cccgccgggc      17340
cgccgcgggg gacgcgggc ccacgacgcc ggcgaggccg aggcgctcga gctcgcgcgc       17400
gtacagctgc gccagctcgt tcgagatcag cgggcggaag gccaccacga agccccgcg       17460
ggcgaggtac acctcgggcc tgtcgccggc cagcacgtgc gtgttgttgt agcgccgctg      17520
gtagatggcg tcgatggcct ccgaggcctc gcggaggacg cagtcgccca ggtgcacgcg      17580
ctgcaggtcc agctgcgtga cgtcgctgac gaaggaggcg cccagggccc gcgacgtgaa      17640
gcggaaggac ccgtcgcgcg tctcgtcgcg gatcatctcc tcggcctcgc gccacttggc      17700
caggctgcac acgcgccgcg tcttgggggc ccagtcccag gccaccgtga agtgcggcgt      17760
gcgcagaaag ttgcgcgtca cgctctcgga ggcgcggagg cgcgagtcca ggtcgatggg      17820
gtagtagtgc tccacctgct ggaagcgccc gggcgcgtag ccgatgtgct ccccgtgggc      17880
cccctcgcgc aggccgtaga agggggacat gtacacaatg tccccgtgg acagggcgaa       17940
ggagtcgtag gggtacacgg agcgcgcctc cacctcctcg acgatgcagt tgacggaggt      18000
gcccgtgtgg tagaagcccg cggcgccgat cttggtgtgg gtgtcgttgg tggtgtgcca      18060
gccgcgggtg ccgagcgcgt tcaggcgcga ggggcgcagg tccacctcga cggggttctc      18120
gtcgcggtcg aaggcggtca ccttgtggtt gttgcgcacg tactcggcct tggagacgca      18180
cttgccgcgg cggtcgatca cgtccgtgat ctcctgcacg gggacgggca cgcggtccgt      18240
gaagcggttc gtgatggccg cgtacgtgct cccggaccac acgtcgtga cgatgacgtt       18300
cttgtagtag atgtgggcct tgaacttgtg cggggcgatg ttctccttga agagcacggc      18360
gatcccctcc gtgaagttgc gccccgcga gtactcgggg caggcctgct cgggctccag       18420
gcgcaccacc gtggagccgg acggcggcgg gcagacgtag aagcggtccc gctcggtcgc      18480
ggccgcgcgc acggccgtgc gcgcgtccag gtcgccgtac tcgccgtcgg gggcctccga      18540
```

```
ggggccgggg gtgaacgcct cgatctcctc gagggacgcc tccgcggaga cgtcgttggg    18600
ggtgaggccg gggctgcccg ggacgggcgt cggcgaggcc gaggcggccc gcgtcacggc    18660
cgccgcgccg cacggcgggg ccgcggcgag cgccagcagc agcagcgcta gcgcgacggc    18720
gccccgcgca gctgcagcgt ggtgtggagc aggccaaaga cgtccgaggc cagcaccgcc    18780
gtggtgcccg ggccgatgcc cgcggggccc gcgccaaaga ccgccaccag cgggcatgac    18840
gcctcgtagg tcaggtacag cccgtcgcgt ccggcgaagc gatccgcgcg gaggacctcg    18900
acgtccccgc agtggaagac ggacctgaag actgcaaccg ccagcaccag ctcgcggata    18960
tatcgccagg cctgccgctg ggtggcggtt acgccggccg tctggaagcg gtagaagccg    19020
cggaactcac tgacgcacca atcgcgggcc accatgaagc gcgccagctc ctccttcagg    19080
tgcggcagga ggcccacgtt ctccaccgca aagtagagcg ccgtgttggg gggctgggcg    19140
aaggcgtgcg tgtcgtgcgc gaagagcggc ccgttgacga gctcgaagaa cttgtgcgtg    19200
agcgccggga ggagcgcggc gtccacgggg tggcgctgca ccgtggcctt catgaagctg    19260
tgcgcgtcga agcagcccgt ctcgcgctcg tccacgacgg tgcccgcgcg cgcgacggcc    19320
tcgcagaacg cgccgcgc gcggaacccg gcggccaccg ccacgtacgt gtgcagcagc    19380
gcgtcgccgt acacgttcac gcgcagggtc ttctccagct cgcgccgctg ctcgcgcacg    19440
cactgcgcca ggctcgccgc cgagcgccgc gagaggcggt ccgcgtacag gcgccgccgg    19500
cgctcggcgt cgcgcagcgc cgcggccggc aggtccgccc acgccacggc gtccgccggc    19560 ggggcgcgc cgggcccgtc ttcgtcgccg acgcccccgt cgccggcgtc cgcgcccccc    19620
gcggcgccgc cgtcggcgtc cgcgtcgtcg ccgccctcga ggaggcgctc gagggcgtcg    19680
cggttggccc ggtccgggtc cagcatgcgc agcatgggcg tggacatgtg gtggtcgtag    19740
cacgcgcgga tgagcgcctc gaggcgctcg tcgggcgagg ccgcgcagcc gcccacgagc    19800
agcccgtcga tgatgtcgag ctcgcgggcc gcgcgggcgc ggtcaaagtg ctcgggccgc    19860
cgcccgaaga gcgcgagctc cacggccgcc gcgcgcacct cggcgcggcg ctcgcgccgc    19920
tccaggtcgt ccaggttgtg cgtgaacagg tcgagggccc gcaccgcctg gttcgtggac    19980
gccagccaaa actgcagctc gctcacgcg tacaggcgcc gcgaggcggg ccggaacacg    20040
tcgtgcgcgt ccaggagcgc gtccgcgcgc cggcgcgccg tctcgcccgc gtccccggcc    20100
tcggcgcccg cctccgcctc ccgggcctcg gcggcgtcca cggcggcgag cgccgccagc    20160
gcgcgcccgc ggcgcgcctc gtcgagcccg cgcacgtgcg gcaggttctt ggccacgtcc    20220
tcggggtcca cgcgcaccgc cagctgccgc gtgaggtggt cgcacacgca gccgagcagg    20280
cgccggtgcg tggcctcgcc ctggttggcc gtcacgcaca gctcctcgaa gcacaccgcg    20340 cacgctgcg ccgggtcgta cagctccggc ggcaccacga gccgccgcc gatcgtcgcg    20400 gcgaggaact cgtccacggc cgacaggtcc accgcgtggg gcgtgatcag gtggcagtag    20460
ttgagctgct tgagcaggtt ctcggcgtcg tggaggaact gcagctccgt ctccacgcgc    20520
ccgccgtacg tgtcgagcgc gacgcgcgcg tggaagcggc acgcgccgcc catggtgcgc    20580
tcaaagtagg cctcggcgtc gtccgcggcg gggccagcg cccccagcac gcggtccccc    20640
tcggcccgcg cgtacgcgag cgccaggcgc agcgcgcacg tgagcggcgt catctgcgcc    20700
tccagcggca gccgccgcgc gaggtagcgg cacatcagcg cgttcagctt gacgcgcggg    20760
gccagctcgc gcaccaccgc ggggtcgcag cgcttcagca tctccagctg aaacacgtac    20820
gtctgcacct gccccaggac cgccacgagc cgccgctccg ccatggccga gtccgccgc    20880
```

```
tcgctccctc cctccgcccg cccgcccgtc cgccgcgaga gaggccacgg gacgcgcgtg    20940
tgtgtctgtc aaacgcggtc atctttattg atacagccgg ggcgcccgc gcccgtcccc     21000 ccttcccctc ctcctcccct cacagcatgt cgaaggtcag ccgcttctcg ggcggggcgc    21060
ccatgtcaaa caggtcgtcc tccggggggcg ggcgcttgcc ccccagctcc gcgggcgcca   21120
gcgaggccgg cgcgagcccc gcgacgtccc cgcccgcgcc gcaggcccca aagtcgaagg    21180
cggtctcctc gccgccgtcc gcgcccgtct ggccctcgag gtcgcgcacc agctcggcgg    21240
ccgcctccac gctccagcgc ccgtcgcggt cggccacgcg cccgttgatc tccgccagcg    21300
cggccgccag gaactcgtcg tccacgatcg cccgccagtc gtcgggctcc aggtgctgcg    21360
tgcgggcgcc gagcgcgtgc agcacggccg cgtacacggc cgtctgcacc agcggcccgc    21420
cgtcggccag gatggtcttg acgtgctccc cgagggagtg gtcgtgcagc ccggcgccgc    21480
cgcccgtctg cgagcacgtg aagcccacgc gcgggcaggc cagcacaaag tgccgcgtgc    21540
ggtcaaacac catcaggggg cacacgtgct tgccgccgtt gagcccgctc cagttccccg    21600
cctggaagac gcggttgttg ccggccatgc cgtggtactt gctgacgccc aggcccagca    21660
ccaccagcgg gcgcgaggcc atgacggagc ggagcaggtg gctggacgtg tacgtggcca    21720
cccacgtgtc gtcgcgcggc gcgtccagca cctcgcgcgc cgcgcgctcc gcgtcggccg    21780
cgtccgccag cggccgccgc acccaggcca tgacggcggc cgggtcccgc gggcgcttcg    21840
actgcatcgt gatccccgtg aggctgttga tgaagaactg cttgtggtcg cagtagcgca    21900
ggatcaggtt ggccaggtag aactgggcca gctccgccac ggtgcccggg gtcaggttca    21960
cgtagttgat ggcgccgtag tccaccgaga agcgcttcac ggccgcgatg gtctcgatgt    22020
cgtccttggt cagcagccgc gccggcagct ggttgcgctg cagcagcgtc cagaaccact    22080
gcgggttggg gctctgcccg ccggggcggct tgccgcgggg gaacagcgtc gcgtggtgct    22140
gcttcagcag gaagcccagc gggccgttga gcacgtccac ggccgtgtcc gggcgctggt    22200
aggcgcccgc gagcccggcc acgcgggcgc gcgcggcgtc cgagaggctg cccgagcccg    22260
tcgagaacat gacccggctc ttgacgcgca gctcccgcag cacctcgaag ctcacgcgcg    22320
ccaggtcccc gtcgtggtcg cgcgccgggg gctccgcgct gcccttggtg gggtccgggg    22380
ccacgatgcc gtcggcgagc gtcaccgtca ccgtcttggc cgtgacgaag cccccgttga    22440
gcatgtccac cacgcggcgg cgcagcaccg gctggaactg attgcggaag ttgcgcccct    22500
ccacgggctg cccgtggagc acgccgtggc actggctcag ggccaggtcc tgcagcaccg    22560
ccagcagcgt gcgccgcgcc aggaagctcg tcgcccgggca cagcgcgccc gagtacgggt    22620
ccagcgagag ggacatggtg tggttggcgt cgtagagcgc gtcgcggagc ttgaagtcgc    22680
gcgtctccac gagcgtgcgc acgaagcggt ccgccgcctg ctccaccgtg tcgcgcaggg    22740
cgcgcagcgc gtgccggaag ccggcgtggt ccgccaccgt ctctccgatg cgcgcaccgg    22800
ccacgtccgc cagcagccgg tccacggcgg cgcggtacgt gtcctgcatg atcgccttcg    22860
ggggctcgct gtcgttgggg cgcttgaggg ccccgtacga ggcgtagttg ccgagcacgt    22920
cgcagtcgct gtaggcgctg ttcatggtcc cgaagacgcc catgggctg cgcgtcggcg     22980 cgccgaagcg cggaggcgg tggcgcaggc ggtgcagggt cgtgtgcgcg caggcggggc     23040
gcgaggcgcg gtcgcagagc gagcacggga cctcggcgtc gaggctgccg ccacgtagc    23100 gcacggcgtc cacgtcgccg cggcccacga acgtgcccgc gtcgcagcgc tccaggtaga    23160
acagcacgcg cgccagcagc tgcgggcaga agccgcacgc catcaccagg tggtccatgg    23220
cgaagtcgtg gttgcccggg gccgtcgcgg gctgcgaggc cgtgtgcggc agcacgcgcc    23280
```

```
cgtccttgtc cgtctgcggg ttcccggcca ggtagggcgc cgccacctgg tagaagcggt   23340
taaacgaggg gccggcgccc tccttgccgc cgccgtcggc ggcgcccgcg tcgtccacct   23400
ccgtcaggta cagcaccgag ttggagctaa acaccagcgc ccccacgagg ccggccgcgc   23460
ggctcacgta cgcgcccagc gccgcggcct gcgagacggg cgcgccccg gcggcgcccg    23520 cgccgccgcc gtccttggcg cccgcctcgg agagcacggg ccagtcgtcc agcgaggggg   23580
gctcctcgtc gtacacgccg gcggcgacga gcgcctccag cgacagcgcc gcgtcggcgc   23640
tcatgacgga cgccatgcgg cgctcgaggc cgccggcggc cgcgtcgccg ccgcggcggc   23700
gctgctcaaa gagcgtgaag gtcacgtcgg cgggcagcac ggcgctctcg tggttctcgt   23760
cgaaggccag gtgcgccgcg ccgcgcgcca ccgcgtccag gttccgcacg cgcgtggcca   23820
cggccgccgg gcccagcacg tagccgtgca gcaggcggca gagcgcgccg ttgaagaagg   23880
ggcgcgcgta cacaaactcc tcgctgatgg agcggttctt ggcgttgaag gggtccgcca   23940
cgagccggtt gacgtccggc atgaagaggt gcacggggta gagcggcacg cgccacgcct   24000
cgtgcccgtt gatggacacc gtgcccgcgc ccccgtagtg caggaaggcg ttgcacaggt   24060
acaccgcctc cttgaagccg tcggccaccg cgaggtaggc cgcgtgcgcg tccgcggcca   24120
ggccgagccg cgcgcacacc tccgcgcccg tcgtctcctc ggcgttgtcc accggcgtcc   24180
ggtaggccga gaacccgaag cgggcgcgcg ccgcctcgca ggcgcgcgag agggcgggcg   24240
cggcgctgct cgggggcacg cagtccccgt tgtggaagaa gaacacgttg gggtggaagt   24300
ggttgggcgt cagcttcagc gtgagcccgc cgccagcccc ggtggtccgg gcgcccgcca   24360
ccacggccac gtgcccggcg aagccggcct cgacggtgag gccgcgcacc agcggcgcca   24420
ccgccgcggc gtcgtcggcg ctgcgcgcca cgagcagcgc cagcaggtcg cggcgcagcg   24480
ccgcgatcgg cgtcacgtac acgtagccca gcggcgcggc gcgcacggtc acggtcttgg   24540
ccgcggcctc catcgtcgcg ggggagacga ggtgggcgcg acgagccgag acgagacggg   24600
gcgggagcgg gagagagaag gcgcggcgga cggagtcgag tctcggcccc tcttcgggcg   24660
gacgggtccg gcggcggggt gaagagaggc ggaggtgtcg gcgccgaggg gcgaacgcga   24720
cgtcggcggc ggcggtggag cccggcccgc cccggccggg tcttaaagcg tggggccccg   24780
ccctccgggg cgtggcgccc cgccccggag cctataccte ggccggcgac gttcgcacct   24840
ccgcgtggga cgagcgatgg cggcgcggca gggcagctac gtgacgcgcc tgagcgagtt   24900
caagttcatc gcgccgcggt gcctggacgc cccggagcag cgcggcgtgc acgtgggcac   24960
gctcgcgcgc gagcccacgg tctactgcgg cggcgccacg cggcccatcc tccgcgggga   25020
gcccttctgg ccgcggcgcg tcgccgcgtg ggagggggcc cccgagcggc ccgtgagtcc   25080
gcgcttcgag cgcttccacg tgtacgacat cgtcgagagc accgagtacg ccagcgcgga   25140
cccgcgcttc cccaacggca cggtggtcac gctgctgggg ctcagcgcct gcggcaagcg   25200
cgtggccgtg cacgtgtacg gcgtgcgcca ctacttcttc ctgggcaagg ccgaggccga   25260
cgccgccctc ggcgtggcga gcgccgagca gctcgcgcgc gcgctgtcgg cggcggccgc   25320
gcgcggcccg cgcctcgggc ccgccgacgt ggacgcgcgc gtcgtcgacg ccgcgcccgt   25380
ctactactac gacgccccc ggcggcccttt ctaccgcgtc tcgagcaaca gcgggcgcct   25440
ggtcgcgcac ctccgcgaga cggtgtgcgc cggcctggtg acgcacgagg ccggcgtgga   25500
cgcgaccacg cgcctgctgc tcgaccacga cctgcccagc ttcggctggt accgcctgcg   25560
gcccgggccc gcggggagc gcgtggtgct gcggcaccag cgcctcacgt ccagcgacgt   25620
```

```
ggaggtcaac tgcacgcccc tcaacctggc ccgcgacgag gacggcccgt ggcccgacta   25680
caagctcctg tgcttcgaca tcgagtgcaa ggccggcgac gacgcggcct tccccgccgc   25740
cgagaacccc gaggacctgg tgatccagat ctcgtgtctg ctctactcgc tcgccaccca   25800
gcggctggag cacacgctgc tcttctcgct gggctcgtgc gactcggacg accccgcggt   25860
gacggtcctc gagttcgaca gcgagttcga gctgctgctc gccttcgtga ccttcctgaa   25920
gcagtacgcg cccgagttcg ccacggggta caacatcatc aactttgact gggccttcgt   25980
ccacaccaag ctcacgaccg tctacgggct ggccctcgac ggctacgggc gcttcaaccg   26040
cggcggccag ttccgcgtct acgacgcggg ccagaacagc ttccagaagc gcagcaaggt   26100
caagatcaac ggcctcgtct ccctggacat gtacgccgtc gccgccgaca gctgaagct   26160 gccgagctac aagctcaacg ccgtggccga ggaggcgctc ggcgagcgca agctggacct   26220
ggactacaag gacatcccgc ggtactacgc cgcgggcccg cgcgagcgcg gcgtcatcgg   26280
gcgctactgc gtgcaggact cggcgctcgt gggcaagctc ttcttcaagt tcctgccgca   26340
cctcgagctc tcggccgtgg cgcggctcgc caacatcacg ctcgcgcgcg ccatctacga   26400
cggccagcag atccgcgtgt tcacgtgcct gctgaagctc gcgggctcgc gcggcttcgt   26460
gctgcccgac aagcgccgcg ccatcgccga cgaggacgac ggcggcggct accagggcgc   26520
caaggtgctc gagcccgact cgggcttcca cgtggacccg gtgctcgtgc tggactttgc   26580
cagcctgtac ccgagcatca tccaggcgca caacctgtgc ttcacgacgc tcgcgctcgc   26640
gcgcccggcg ggcctgcgcg aggacgagtt cagcgccttc gaggtcaacg gggagcggct   26700
ctactttgtg cacgcggggg tgcgcgagag cctgctctcg atcctgctgc gcgactggct   26760
ggccatgcgc aaggccatcc gcgcgcgcat cccgacgagc gcgcccgagg aggccgtgct   26820
gctggacaag cagcaggcgg ccatcaaggt ggtgtgcaac tcggtgtacg ggttcacggg   26880
cgtggccaac gggctgctcc cctgcctccc cgtggcggcc accgtgacga ccatcggccg   26940
cgacatgctg gtgccacgc gcgactacgt gcagacgcgc tgggccacgc gcgagctgct   27000
cgagcgcgac ctgcccgcgc gcccgcccgc gggcgagtac gccgtgcgcg tggtctacgg   27060
ggacacggac tcggtcttca tccgcttctc gggcatcgcg tacgacgacg tgtgcgagtc   27120
cggggagctc atggccgcgc gcatcacgcg cgacctcttc cgccccccca tcaagctcga   27180
gtgcgagaag accttccggc gcctgctgct catcacgaag aagaagtaca tcggcgtcat   27240
caacggcggc aagatgctca tgaagggcgt cgacctggtg cgcaagaaca actgcgcctt   27300
catcaacgcg tacgcgcgcc gcctggtgga cctgctcttt ggcgacgagg ccgtctcggc   27360
ggcagcggcc acgatcgcgc gcgcgcccgc ggcgcgctgg ctggagcgcc ccctgccgcg   27420
cggcttcgcc gccttcggc gcgtgctggc cgaggcgcac gcgcgcgtcg ccggcggcgc   27480
cggcctggac gtggccgact cgtcatgac ggccgagctc agccgccccc cggacgcgta   27540
cagcaacacg cgcctgccgc acctcaccgt ctaccacaag ctggccatgc gccacgggga   27600
ggtgccgagc gtcaaggagc gcgtgtccta cgtcatcatc gcgcccaccc cggaggccga   27660
gcgcgacgcg cgggccgtgc gcccgggcct cgcgcccggg aagctgctcg tcagcgacct   27720
ggccgaggac cccgcctacg tggtcgcgca cggcgtgccc ctcaacaccg agtactactt   27780
ctcccacctg ctgagcacgc tcagcgtcac cttcaaggcc ctctttggaa atgacaccaa   27840
gatcacggaa aggttgctca agcgctttat tccggaaacc gccccgggg acgcgccctt   27900 cgagcacgag gccttcgcgg cgctcacggg cgaggggggg gaaagtcttc aaacgctgcg   27960
tacaatcttt tgtactccaa cagcagctcc ccgtcgaagc tgatgtcccg catcttgcaa   28020
```

```
taaatgtcgc tcgcgctgac ggcgggcacg tcgtccgcgg gtctcccgtc tcccttcttt   28080
cgcaccacca acacgaacat ggtctgccac acgtgcgcga cgatgcggtg gccggcgcag   28140
gccccgagca ggcggtccag cacgcggtgg tgcacgtgca ccgacttctc ggggaacacc   28200
acgtacatca tgagcgcgcc ctgcgcgtcg ggtcctcga agaagagcac gcgcacgtcg   28260
cgcaggcccc cgtcgcgcag cacgtagtag gcgaaaaaga gctccgggtg cgcgagcacc   28320
tcctcgaggg cgcgctccga ggggtcccgc gcggccaccg aggccaggaa cacgcggtac   28380
tcgtagatgc tgttgagctg ctgcacgtag gccagcacga gggccgcgcg gtcgctgcgc   28440
ccgagccgcg gctcggcggc ggcgcacgtg gggcagcagc cgccgaggcc caggtagtag   28500
cccatgcccg agagcgacag gcagttgtcg gccaccgcct ggccgaggtc gaagggcagc   28560
gtcacggggg ccgtcttgat gagcgggttc gagaggccgc gcacggtggt cacctcgtcc   28620
gagggctgcg cggccgcgta ggcaaagtag ggcgcgtagc gatcgcgggc cgcgcgcgtc   28680
agcgtcttgc gccgcgcggc cgacgacttg cgccgcagga gccgccgtcg ctcaaacata   28740
gctgccgagc gtgtgctcga gggagacgag cgcgaggccg tggcgccgca gcagcgcgtg   28800
tgcgtcgcgc aggaaggcgg ctcgggcagt gggcttcggc gggaacagct ggtacgcttt   28860
aaatacgtac gccagggtcc acagctcccc gcacacgcgc ccctcgaagc ggttctcggc   28920
ggcgatctgc gccttgcgca gcgcgtcgcc gcgctcaaag agcacgcgcg gtccgcctg    28980 gcgctcggcc acggcgcaca gggggtcgca gaagaggtgc ttgtagacgg cgcgcgggcc   29040
cgcggcgcgc atcagcgcca ggaagcgcgc gtccgccacg aagccctcga gcacgggctc   29100
gatgcagtca agaggcccg cgttgttctc cgagtagctg agcacgccgc gccggaagcg    29160
gcgcagcgcc agccagtgcg cgcgcgtgag cagcatgttg cagagcaggc actcgccgtg   29220
cgtgcggttg cggccgcgca cgtgcttcag cgccagcgcc agcacgggcc ccagcgtgac   29280
gtccaccgcg cggtagcgcg cgtacgccgc ggcggtgttg cgggccagga agccctcgtg   29340
ctccgcccgg tactcgtcca cggcgcggtg ccggcgctcc tcggcggcgt ccgtctgcgc   29400
gttgggctcc cccgtggcca cgttgcccag cagcagcatg gcgaggtcgg cgtagccggg   29460
cccggcggcg tccgcgtccg cggccccgcc cccgtggcg gcggcgacgg ccgcgcgctc    29520
gtacgcgtcg tcctcgcgct ccgccgccgc gcagcacccg gcgcacgcgt cgtcgcccgt   29580
gtggtccttc cagccccca ggctcggcgg cgcgcgcgcg tccgccacgg tgaaaaacat    29640
cgcgcgcgtc gcggcctgga ccagaaagga ctggttcgag aagcggatct tgtcgccgac   29700
ggtgcggaag cagccgtgca ggaaaaagtg ccgctgcacg tccacgagcg tgagcacgcg   29760
cgtggcgaag gcgcgctgca gcgacgcgcg cccgcgaaag tgcttgtcca tcacgtacac   29820
gaactcgaag gcgccacga agacggccgt ggcgcacggg gggcaggcca gggccttggc    29880
gcacagcgcc gcgtagtccg ccagccaggg cggggccagc gagcgctcgc ggcggtacac   29940
gtcgatcgtg cggcacacgc ggcagggctc gtccagcgcc agcggcgccg cggcggcctc   30000
cacgaagccc gcgggcgagt cctcctcgtc cagcatcacg tgggcggcga agatcagctc   30060
gcggaagagg gcgtcgttct tggtcagcag cgcggggtcg aaggccgtgt acggcgcctc   30120
gaaggcgtcc tcgctccagc ccatggcgcg cggcggcggg gcggcgcgg cggtcgatct    30180 gcgcgcggcg atcccggagg ccgcgctgcg cgacttcgac gtggactttc tcgaggccaa   30240
ctacctgccc ccgcgggtgc gcgtctggtt cgaggacgtg atgccgcgcg agctggaagt   30300
gatcctcccc acgacggacg ccaagctaaa ttatctggcc cacacgcagc gcctggcggc   30360
```

-continued

```
ggcgacgagc gagcgcgact gcgcccacgg ggaggcgctg cgggcgcggc gcgatcgctt    30420
cgccgcggcc gtcaacaagt ttctggacct gcaccaggtc ctgcgtgacg gggtggagct    30480
gggcgcccta taaagtccgc cgcccgaccc ggggagctcc accagcccca ccaccaccac    30540
cgccgcccgc ccgccggccc cagctcccgc cgggaaaatc gccgccgccg cgtcgacgtc    30600
gtagccgcac cgctcacccc caccctcacg ctcgcgacga cgacgacgac catgagcggc    30660
accctggtcc aacgcctgaa gctcatcctc tccgggggga acctgcgctg cagcgacggc    30720
gagacggcct gcgaccccga gcgcccccg acgcggtgcg tcttccaggt ccacgggcag    30780
gacggctcca acgacacctt cccgctggag tacgtgctgc gcctcatgcg cagctgggcc    30840
cacgtcccct gcgacccta cgtgcgcgtg cagaacacgg gcgtgtcggt gctcttccag    30900
ggcttcttct tccggcccgc cgacgccccc ctggccgcga tcacggccga gcacaacaac    30960
gtgatcctgg cctcgacgca cagcaccggc atgagcctct cggcgctcga cgacatcaag    31020
cgcgccgggg gcgtggacac gcggccgctg cgcgccatga tgtcggtgag ctgcttcgtg    31080
cgcatgccgc gcgtgcagct ctcgttccgc ttcatgggcc ccgacgacgc ctcgcagacg    31140
cagcgcctcc tggaccgcgc cgagctgcgg cagcgctcgg tctcccgccc cgggggtgcc    31200
ggcggcggcg gcgacggcga ggggccctcg ccccgcgcgc ccatccgccc gaccgtcatc    31260
tcgcccgtgc ccgggcacgc ggccgccgcg ttcgtgggcc aggccgcgtg ccccccgccc    31320
gcgcggttcc cggcctcgct gctgcacacc ctcctggggc tgcggcgcct cgccggctac    31380
gccgtggcgt gcgtcaccgg cgctctcgcg atagtcatca tcctgaacat gcgttaaagg    31440
cggccgcgcg cgcgggggcg cgcacagacg cgcgctcccc gccgagccat catgtccttc    31500
gacccgaaca atccccggac gatcaccgcg cagacgctcg agggtgccct gcccgtggac    31560
attctgctcc ggctcaaccg cgcgacgggg ctgcagatgg atgcggccga ggcgcacgcg    31620
atcgtggagg acgcccgccg gaccctgttt atcggcacct ccctggccct cgtgaacctg    31680
cggcgcgcgc acgacaagca cctcgtggag cgccagccca tgttcgccac cagcgactac    31740
agcagctggg cccggcccac ggtcggcctg aagcggacct tctgccctcg ccccccgccc    31800
tagccccgcg cgatcaataa agcgagccgc gttgcaccat cctctcgact ctagcgtgtt    31860
gcttgggtgg ggtttccccc ggtctttccc cgatctcccc accgccgcgt ctttgggccc    31920
caatccccca aagtccccca atccccccaag tccccaagt ccccaagtcc    31980 cccaagtccc ccaagtcccc cgccaccgag tccggcccc gagctccccc aagtcccaca    32040
agttccccaa tcccccaat tcccccgat ctccccacca ccaagtcgtt gggcccgagt    32100
cccccgagtc ccccgaacac accaccgcag aggcaaacaa gttgggtaat aaacaattta    32160
ttaaccgaga atcaggcgga cctgaaatag gtccacgttg aagcggcggg cgctgcccctt    32220 gagggtcgtc cgcgtctccc gcaggcggcg cgctatcagg cggcacgcgg cgatgagcag    32280
ggccagggcc ccgagtccgg tggcgcgcat gtaccgcctg ttgatgagcg tgtccgactc    32340
caccacgcgc ggggggagca gctcctgggc cagagagacg tcctcgtccc cctcctcgtc    32400
ctccaggccc caggggtccg gctcgggcgc ctcctcggcg ggctcgcggg tcaagtcctc    32460
ccgggtgggc cagacgcggc cgaggccgcc caggggagag gccggcggcg gaggtctctg    32520
ctgctgccgc cgcggcggag gatgggcggg agggacgagc gccgtcaggt cgtcgaacca    32580 cgccggggc tggtggggt ccgccagcgg ggagcgcggg gccggcggcg caaactccgg    32640
cgggagctcg ggggtggtgc cgggcgcctc caacggcggc ggccacggca tccgctccag    32700
cggcgagcgc ggcggggtcg ccggggtctc ggcctctccc ccgctcgccc atagcggctg    32760
```

```
aggggcggc  ggtggcggca  gcggcggctc  ctctcgcccg  gggaactgga  acggcgggtc    32820
cgacggcggg  ggggtgaaga  gcgcgggcgg  gccggcagag  tccctcggct  cgggccacgt    32880
ccacggcgcc  tccgggggc   gctgctgaga  cggctgcggc  ggcagcggcg  gaggtgtgaa    32940
catgagccgc  gggggctccc  cgtgccgctc  cggcgtcggg  gccggccgcg  aaggtggtgg    33000
ggccggcggt  ggtgcggccg  gccgcgaagg  tggtggggcc  ggcggtggtg  cggccggccg    33060
cgaaggtggt  ggggccggcg  gtggtgcggc  ggggcggaa   gaggtggtgg  cggaagacga    33120
ggaggtggtg  gtggttgttg  ccgccgccgc  tgctgccgcc  gaggcggcgg  gccgctcgat    33180
ctcggagggg  gcggccagcg  acgtcgggc   cgccagcgga  gaccgcggcg  gctgggtctg    33240
cgccggggcg  ggagtctctg  gcgaggccgg  cagaggcacg  acgactccct  ccagctgcac    33300
aggctgcggc  ggcgggatgt  ggagacggag  gtgcccggcc  ggcgggcgcg  ggccggcggc    33360
tcgcctcact  gggcctccgg  gggcgggac   cacatcatct  ccggggccga  ctccggggc    33420
ggggacggct  gctgtagctg  ctgctgctgc  cgccgccggt  gggcccgctg  gagcagtcgc    33480
cggcgcttgg  gcttgggctt  gaggcgggcg  cggttcaagt  cctccgggag  gacggccctc    33540
gggttgagcc  gcgggcggaa  gacccccggt  ctggcgcggg  gccgatacgg  gccttcgcgg    33600
aacaagagcc  atggattttc  ggcgactgtg  gtctctaata  cccaccgacg  ttcgcgcctt    33660
ggtgcgtaga  acagcggagg  gaaggggctg  cgccactggg  gccgcgggga  gatgtcccgc    33720
aggttgatct  ccacggctcg  catccgcagc  cgggccaccg  tctcctcggc  gctggccacc    33780
actcccgggg  gctccaggag  gtgctcgggc  cgccgctccg  gctgctgagg  ggggacctcc    33840
gcgggcgcca  tcgctcggtg  ttccggccgg  ggaagaagag  gatgaggcgg  cttctcggga    33900
cggggtcgag  gcggcggagg  aggacgcgga  cgcgggctcg  gagtccgatg  tccccggagg    33960
agagcgggtc  cgatgctggt  ctggtccgac  cgtgtgttcg  cacttgtctg  cgcgcccgc    34020
tttataccgt  tcgtcatcga  ggggcggcc   cgggaggcg   gttcccgccg  ccttcccacc    34080
aaatttggcg  tcgcggacgt  ccggcggtgc  accggccctc  ggctctacga  tgcggtcacc    34140
atcggatttc  ttggccgatg  gggcggggcc  gggcgcgggg  ggcgtggggg  tcgccgccgg    34200
ggcagacggt  ggtggagggg  cgggcctggg  gagcgtagtc  tgagcagacg  gtggtggagg    34260
ggcgggcggt  gcggcgggcc  tggggagcgt  agtctgagca  gacggtggtg  ggggcgggg    34320
cggggcgggg  ggagcacccc  gcggcttggc  ggccggttgg  gacgacgggg  gctgaggggg    34380
gacctgcgcg  gccgcggtcg  cggcggatgg  tggagggggg  gcggtctgcg  tctgggcccg    34440
ggtcggcggc  tgagtctggg  gggtggcctt  gggcgcggtg  gtggcggcgg  cggtggcggg    34500
ctgcgccggg  ggcttctggg  caagggggc   ctgggccgac  ggggggctgcg  gcggcggtgg    34560
gggaccctgg  ggttgggggg  tcggcttggc  gcggcgggc   ggctgggcct  ggggggcctc    34620
cgggggggcc  gtctcgggcg  ccggggccgt  cgccgggtag  ggcgggttga  tgaccggcgg    34680
cgggggctcg  atgcgcgcct  tgagcgatgg  ctggatcttt  cgcggcgacg  agtgcgcgtt    34740
gggggcgggc  tcccggggct  gctgcttggg  ggccgcggcg  gccttggtgc  cggcggcggg    34800
cttcttgggg  gcggcggggg  gccctgctg   cggctgcggc  tgcggcttgg  tgagcgggt    34860
cgtctccacg  ggcttggcgg  gcggcggcgc  cggcggggcc  agcttggcgg  cgggagtcgt    34920
ctccacgggc  ttggcgggcg  gcggcgccgg  cggggccagc  ttggcggcgg  gagtcggctc    34980
cgcgggcttg  gcggcggcg   gcgccggcgg  ggccagcttg  gcggcgggag  tcggctccgc    35040
gggcttggcg  ggcggcggcg  ccggcgggc   cgccggggcc  aacggcggga  gcgtgggcgg    35100
```

```
gtcgaccggc ggcgacgggg gcggcggcag cgcgctggcc accaggtcgt cgccgagcag    35160
gtccagccac gggttggcgc caaagtcgtc gtccgggacg aacccgtcgt cctccccgc     35220 caactcgggg ggcagcccgg ggatcggggt cgcgggccgg gtgggcgtcg ccgacacggc    35280
gtacgggaac gggtcgccca ggttgcggaa gctcggccgg ccgtacagct cctccgaggt    35340
ggccgggtcc acgcgggcgt cgcccatgat gatggaggtg aacagcgggt ccgcggggtc    35400
catctccggc agctggtcct ccgtcgtctc caggaagggg atctcccgca gcagcgggtc    35460
gtcctcgagc gtgaagcccg ggcgtcgcgg cggctcgggc ggcgcccaga gcacgcgcga    35520
caccgccagc tgcgagtcca ccagcacgag gcaggccggc tcgccggcca ggggccgcgc    35580
cgcgatcagc gccgagagcc gctccagctg cggcgccagg cacgcgttct cgatgggtt     35640 gtcgtcgagc gccagcaggc gctcgcccca ggagctgagg tccgtggaca cgccgcggtg    35700
cagcgcgggg tcgcgcaggt cgcacagcgt cacggccagg gtcaggcccg agccgggcga    35760
gtacacgtcc aggttctcca tggcgatcac cagcggggcc ccgacgagca ccgccgccgc    35820
ggccaggtcc atggcgctca cgcgcgtcgc gctgctcggc ggcgagcccg tgacggtgaa    35880
cgtcatgccc gtgcccacgg gcgcgtacag gtcgccgggc gccggcgcgc cgagcgccgc    35940
ggcctcgcgc acgtgcgccg cggcgtccag gcgctcggtg accgcggcgt cgtacgcggc    36000
gttcgcctcc ggctgcaggg cggaccacag cgccgagagc agccgcgggg ggatgcacat    36060
gcgcgccagc acggtgaagg tggccagcgc gcccggcacg gcgcgcgcca gccgctggcc    36120
cgtctccgtg tgcgcccagg gcgcccacag ctccgtctcc gagaagcggc cctcggtcca    36180
gtcggcgacg cgcagcgtga acagcgcctg cccgtcgcgc agcgggcgcc gcggcgggcg    36240
cgcgcccgcg tccagcgtgt ccaccgcgtc cagcgcgcgg tccagcaccg cgtccagcgt    36300
cttggccatg tactcgtgct gcccggccag gtccacgcgc gtaaagttga acaggtcgt     36360 cggctcgccg gccaccgcgg ccaccatcag gtcggggagg gcgagccgca ccgccggctc    36420
cagcggcggg tgcgcgacgc ggtccagcgc cccgaaggtg cgcgagagcg tcgtggccag    36480
cacggccgcg tacgtctccg cggcggcctt ggccgccgag tcccagtcgg cgcggcggtg    36540
gcgcacgaag cgcgcgaagg tggcgaagcc cgtgtcgcgc gccttctcgt agttgagccg    36600
caggtggatg atctcgttca tgaggcgcat gcccgccacg gtcgccgtct ccatgagccc    36660
ctcggtgagc ggcgggcgca gctcggcgcc ctcgtcggtg cacagcatgg ccgccagctt    36720
gtcgccgacc gcgcggtagc acacctggta ctccacgggc acgttgttgt cgtccaggaa    36780
gaccgtgggg aacaccgcgt ccgcgtcgct ccgcgcctcg cgcaccgtgc agatgacgtc    36840
gcggtcgccc aggcgcgccg ccacgcgctg cttcaggcgc gcgcacggcg ccgtcgaggc    36900
gcgcggccgc gccggcgtcg gccccgcgcc gccgtaggcc gcgtagaact gcaggcgcag    36960
cgtgagcagc tcgcggtagg cggcgtactt gggcgggatc caccgcggca gccgctccgc    37020
gcgcgcgtcg aaggcggccg ccagcgcgcg cagggcgtcg tgccgcagct cgggcccgat    37080
gcgcgccgcc atgcggtcga gctcgcgcac gtcctcctcg acggcgccgg cgtcgcggaa    37140
gaagtcgccc agggcccggg cgcgcgccga gtacttgctc tcgatgcgcc ccacgaactt    37200
ggcgggcagg cgcgggtaga cggcgtcgct gcgcagcgcc agcacctcca tggtcgccgt    37260
ctgcagcgcg cgcgcgcggg cctcggccag gcgcgcctcg tcctcggagg cgccggcgcg    37320
gccgcgcgcg cgcccaaagt cctcccaggc ctcgtcccag gcgacctcgg cggccgtcag    37380
ccgctgccga gcgtgtccg cctcctggcg cagcgtctgc agcgcctcga tgcgctcggc     37440
gaactcgtcc atgggcccgc ggccgtcgac gcgcgtcgtc agcgggtgcg tgtcgatgat    37500
```

```
gagccgcgcc tggtgcagcc actcgacggc ctgcacgtcc agctcgggcg cctcctcgac   37560
ggcgccgagc agcagcgccg cctgcgtcac cagctcctcc gcggaggcgg cccggtcgat   37620
gttgagcgag gccggcggcg gcgtcacccg cagcaggttc ttgaggttgg ccagctcgag   37680
ggccccgtcg cggtcgcgcg ccgccgccg  gtccaccacc tcgcgcagca ggcgcgtggc   37740
gcgctccgtc gccgcggcct ggtccgcctc cgccgcggcg aggccgtcgc gcgccgccgc   37800
caggtcgcgg cgcacgagcg cgcgcatggc tccgcgtac  gccgtgcgct cgaagcgcgc   37860
aaagtcgaag cgctccaggt aggtcacggc gccgcgcagc agctcggtgc tcggcacgtg   37920
caggtgcacc ccctcgtcga gcgcgcgcgc gcgtcggcg  gccgcgcgca cgtacgtcac   37980
ctcctcgagc gcgcggcaga tctcggcgcc gcggctgccg ccggcctgca gcacgtccgc   38040
gcgccgcgcg cccagggcgg ccagctcggc ctcgtactcg gggaagccgc ggcggtaaaa   38100
gtccacgtac ttggccaggc ggggcacgtg cgccatgtcc gccccgacga agcccacggc   38160
gtcgtagtag ctgaagcgcc ccatgccggc ggcggcgcgg gccagcacgc cgccggcgat   38220
gcgggccagc cgcgagagcg gctccgtgtc ggcgccgaag agcgacccga tgacgggcgc   38280
cgcgacggtc tagtcgtcga gccacgtcag ccgctgcagc gcctgcagcg gcgggcccgc   38340
cgccgcgccg gcgttctcgg gcaggtgcgg gttgaaggcg aacacggcgt ccagcgccgt   38400
ggtcacggtc tcggcgttgg cgccgagcgc gcgctcggcg gcggggcgca gctccgcggc   38460
gtcgtagccg cggtcggccg ccacgtcgcg caggcgcacg aactcggccg cgtcgaaggc   38520
gtgctgctcg gcgcggcgca gcgccgcgtc ggcggcgcgc gcccagagct ggcgctgcgc   38580
gcgctccacc tccgccgcgc ggcgcgcctc cacgccgcc  acggccgcct ccagctcgcc   38640
gacgcgctgg cgcgccgcga gcgccatctt ctgcagctgc ggctcctcca cggcggccgc   38700
gcgcgccacc tccagcgcca ggtgccgcgc ctcgaccagc gtccctcgt  cgggctgcgc   38760 gcgcagccgc ccgagcatct ccacggccgc cgccacggcc gccgacagcg cggcctgcag   38820
cgccgccacg cgctccgact cgcgcagcgc cgcggcgcgc tcctcgcact gccgcgccag   38880
cggctccagg aagcccagct ccgggtgctc cacggcggcg cgcagcaccc ccgccgcgcg   38940
cgccgccttc tccgccgtgt ccgcgtccgc cagcgccgcc gccaccgcgt cggcgtgcgc   39000
gaggaagaag cgcgtgatgg gcgggttgtc cgcgagcgcg ttgaccagcg ccccgagcgg   39060
ctgcccggcg cccaccagcg cgccggggtc ggacgtcagc agctcgcggt agcgcgccac   39120
caggcgccac agcgccgcga gcaccgcgcc cggcacgggc gtggccgtga tgtgcgcgag   39180
caggtccacc gccgggccca gcgtggcaaa gtccccagc  agcgcgcgca gccgcatgta   39240
gaggtcgttc tgctcggcgg cgcgctgctg cgccgcctgc accagcgtgc gcagctcggc   39300
gtcgcgccgc gcgagccgcg cgcgcgtctc ctggctcagc acgtggccgc ccatggcgcg   39360
gatgtgccgc agcaggtcct ccatcgcgcg cacgcgcgtc tcctcgtccg ggcggccgc   39420 cagggcggc  tccatggcgt cgaagcgcgc caggtcggcg tcggccgagg cgcgcttggc   39480
cgcgcgctcg ttgatctggg tcacgtcgcg cgtgagcgtg tccagctcgc gccgctccag   39540
gtgcccgtgc gcctgcgcct cggccagcag cgcgaaccag gccccgaggc gctcgtccgt   39600
gctcacgtcc tcgcccgcct ccagcagctg cgccagcagc gcgccgtcgt gggcggcggg   39660
cgccgcgtcc agcgcgcgca gccgctcctc ggcggccgcc agcgagtcga cgaggcggcg   39720
caggcccgcc accgcggcgt tggccacgcg gaagcgctgc gcgccgttgc ggtccatcag   39780
catggccttg gcgctgtact gcgcgccgcg cagaaagtac tcgcggatgg cgtcgccgac   39840
```

-continued

```
catcagcgcc agcttgcgcg gcagcttggc cgcgcgctcc ttgacgtcgc gcgtgttcgg    39900
ctcggccgcg ccgcccgcgc ccggcgcccc cgcgtccacg gcgtcaaagt tggcgtgggc    39960
ggcctcgagc gccgcctcga gcgcgctcac gtcgcgcgcc cgctcgagcg cccgctgcga    40020
ctcgcgggac tcgcgcgcgc gggcgcgcgc aaacagggcc cgcgcgcgcg ccaccaccgt    40080
ctggtcgtag acgccgccgg ggtcccgcgc cgcggcgtcc atgaagcacg ccgagagctg    40140
cgcgtaggag ccctcggact cgagcgcgtc cagcgcccgg tgcatggcct cgttcgcggg    40200
ccgcgcgacg cgcgccgcga ccagcgccag cttggccacg ggcgcggacg cgtcgtcgcc    40260
ggccacgtcc agcagcgcgc gcgcctccgt cagcaccatg tgcgtggcgg ccacaaagtc    40320
cccggccggg ccgcgctccg gcagcgcgcc caggatgggc tcgaagagcg cggcgacggc    40380
gcacggcgcc tccccgtggg tgcgggcgcc gttctccacc agaaagtcct gcaggtgccc    40440
gaagaggagc tcggcgaagc gctccagcag cccggcgcgc ccggggaaca ggctccggcc    40500
cgcgcacgcg accacgtgct cctcgagctc gtcggcgtgg gcctgcagcg ggcccaggtc    40560
gagcggggcc agctccagct cccggacggc gaagcccatg ggctcgcggg tgcgcggggcg   40620
gaacttgcgc gacggccgcc cgccgaccgt gtgcgtgctg ctcaggtcct cctggctcgc    40680
cggccacggg ggcggcgcc gcttgggcat gctcggccgc ttctggaccc gcggcggcgg    40740
cgggagcggt gcgccgccgg gtgccggggc ggggcggcg ccgccgaga cggggacggc     40800
ggggacgggg gcgacggcga ggacgggat ggccccgggg ccccgcgtcg gcggcgcggc     40860
ggccgccggg tccggcggca gggccatcgg gtgcacggag ggcaccgccc gctccacgta    40920
cggctcgtcc acgaggtacg tctcgcccac gccgtagagc gcgggcacgg cggcgaactg    40980
gtcgtggggc aggaagaaca cgaaggcccc ggcccaccgg agctcgctgg cggcgtagcc    41040
cgcgacgtgc gcgtacacgt ccgccgggcg caggcgcgcc acgaaggcct gggtgatctg    41100
cccgtggccg tgcgggtcga agacgtacac gacgtcgccg cggcggtaga ggcccaggcc    41160
cacgcgccc accacgacca gcgtgaagga ctcggcgcgc tgcgcccaga ggccgtcgaa     41220
gaaggcgcgc gccgtgatct gcgtgctctg gaaaccctcg gcgggcggcg tgaaaaagtt    41280
gcactcgccg tgcacccgcg agaagacgca gtgcagcgcg gcgccgcccg cgccctcgta    41340
gacgatcttg ttcgggagct cgctgatggc gcacatgccc ccgccgggcc ccgtccacgc    41400
ctggccctcg cgcaggcacg cgtccacggc gtcggccgtc agggcggcct ccacgccgtt    41460
cgtgaagacc aggcgcagga aggagaggga ggagcgcagg cacgagacgc ccgacccggg    41520
ccccaggtcg gggtcatact gattacgata gccgacgacc accgcgtcgg ccgtcatggc    41580
tgaaataaca cacgcgcgtg ggggaaaaat ctttttattt ggacacggcg tcgacctcgg    41640
ccaggagccg atccacgggc acccacgttt cgcgcgagcag gggcacgccc gcgctcgcgt    41700
cgtcgggcgc gcgcgcgccg cggcgcagca cctccaggtt cacggcggcc cagtcgcgca    41760
cgttgacgct cgccgagagc ggcacggcgt cggggcccgc ctcgccgtcg cccgccacct    41820
cgtggtagtc gcccaggacg cggtccgcgg cctcgcgcag ctcctcgggc gtgaaggcgg    41880
gcgcgggcgg cgcctgctcc tcgcgcgcct cggtccaggt ctcgcggagc gtcgcgacga    41940
gcgccagcac gccgcgctcg tcgacggcgc ggcgcagcgc ggcgctgacc aggtcccagc    42000
gcgccaggaa gcgctccacg ggccgcagga cggtggcggc ctgcaggcgg ccggccgtga    42060
gggcggcgct cgtctgcagc ttgctcaggc gcgtggtc ggcgcacagc gtccggaaca      42120
cgggcgcctg caggccagc gcctcgcact cgcgcagcgc ctccgtcgtc tgcgccatca     42180
cgccgcgcag cgcccccgcg tcggcgcgca tgtccgagcg gtgcgtgttg acctcggcgc    42240
```

```
ggaaggcgcc cacggcgtcc acgacgtccg ccagacgcca cgtgcccagg cagggcccac   42300
cctccccggg cgcgaagacg gaggccgtgc gcccgcggaa gacgaagcgg caggtgaaga   42360
ggcgctcgag cgccaccacg cgctcggcca cggcgcccgc ggccgtggcc atcgagtcca   42420
gcaggtcgcc cgtgtgggtg gccatgtcct ccaggcggcg ccgagggcg cgcgccagca   42480 ggtccccgag gaaggcgctg gcggccagcg agggcggcgc cggcgccggc gcctcgagca   42540
cctcggcggc cgcgcgcacg accccgtgca gctcgtgcgc gagcgcctcg acgttgcgcg   42600
cgtgcgccac cgtcaggtcc tcgcgcgcca gcgccgccac gagcgcggcg agcttggtgc   42660
ggtagccgct gacgttgggg atgaggccgg cgccgtagtc gcgcgcccac gtcagcacct   42720
gcgccaggtc cgcgcggcgg tcgtaggagg ccgtcaggag gcagttgtag gcgtcggcca   42780
cggccgtcac gacgaagaag ggcgcgaagg acgggtcggc catggcctcg aggtgcacca   42840
tggacgggta gttcacgagg tccgcggcgg cggcgaggtc gacgagcgcc gcgctcgtcg   42900
gcgcctccat gggcgtctcc ccggcgccgt cggcgcgcag gccccagcgg ctctgcgcgc   42960
ggaaggcgag ccacgtgttg agggcctcgc gcgcggcgct gtgcgccagc ccggcgcggc   43020
gctcggccgc cgccacctcg cgcagcagcg ccgcgcgcgc cgcgcccacg tgctccgtgg   43080
gcgggcgcgg cgccatgcag tggcgcacca cgtgctccac gcccttctcg gggagcccca   43140
gcgccgccgt cacgtccccg tagaggggct ccagcgtgtc cgcgacgtcc gtgtaggcgc   43200
gcacgtagtc cagcccgggc ccgtagtcgt cgaggaggcg gtgcacgacg ccgccgacga   43260
ccgccgtgca gccgacggcg cgctgcgcgt ccgtcaggcg gggcgcgcgg tccagcacgg   43320
cgcgctcgag gaggtcgcag tggcggcgcg tgaagcccgc ggtcacgagc gcctccacga   43380
cctgcagcgg cgaggcgctg gcctgcaccg cctcccacac gcccgtggcg tccacctgcg   43440
tgtggtcgag gtccgcggcg gcggccacgt gcacggcctg cgccccgggg tccagcagcg   43500
ccagcacgcc ctggtccgtg cgcaggcgcc gcgccacggt gcccgggcgc agctcgcgca   43560
cgtacgcgtc cccgtgcgcg agggccgcgg agacgcgcac ctcgacggcc gtgcgcggcg   43620
tggcgttgac ctcgcccacg ggcaccagcc ccgcctcgtc cacggcccgc gccgcctcgg   43680
cgaactgctc gcgcagcgtc gggttctggc ggtcgtggaa gaactcgtcg gcgatcgtga   43740
gggcaaagag cgcgcgcgtc agcggcttca ggccctcgtt ctgcatctgg cgcaccgcca   43800 acgcagcgg cagcgcccag ttggtgtgct gcgccacgta gcgcaggccg tcctgcacaa   43860
agtccatgtc gtagagcgtc gcgaagcggg gctgcacgag cgcgcgcgcc gtctgctccg   43920
ggggcacgac gcggggcgcg gccaggacgt cgtcggcgga gcgcgcgccc gccagggcct   43980
cgtcgaaggc ggcgcaccac tcgctcacga ggcggaacat ggcgtcgggg ccgaactcgg   44040
ccgaggtgcg cagcccggcc tcggtgaggg cggccgtggt gtcgtcgccg ttgacgaccc   44100
ccaggagctc cagcagcggg gccgtgccct cgtcccagtc gtggcgcagg cgccacagcg   44160
ccaggccggc caggttctcg gcgagcacgg ccgcctcgca ggtgcccgtc tcgacgtagg   44220
cgcggcaggc caggcgcagc gcgcgcgccc agagcccgcg cacgcccgcg ggcgtctcgc   44280
ggcccgcggc catgaagaac tccaggatgc gcgactgcac caccgtggcg acggcgtggt   44340
cggcctcctc gagcgcgcgc acgagcgcct ccattataag agggtccgcg cgcgggcgcc   44400
gccgcgcact cgaccccgcg cggcgcgacg atgagcgtgc agatcggcaa cgggctgctg   44460
atggtggtcg cgccgggcac actaaccgtg ggctcggcgc gcgcgcgcct tatacgccag   44520
gtgacgctgg cggacttctg cgagcccag gccgagcgcc cggggctggt ggtgctcgcg   44580
```

```
ctgcgccacc ccgcggacct ggccggcgcc gcctacgcgg ccacgccgcc cggcaagaac    44640
caccgcgacc tggaggaggc gtggctcgcc ctcgacgagg gcgggcgcgg cctcggcggc    44700
gacggcatcc gcgcctccgt cgtctcgctc aacttcctgg tggcggccgc cgagaacgcg    44760
gacgacgcgc tgcgcgcgca cgtgacgacc aactaccgcg accggcgcac ggccgcgcgc    44820
ctcgagcgct tcgcgaccgt gctgcgcgcc atgatccgga gccacgtgtt cccgcaccgc    44880
gcgctgcacg tcctcggggg gctcctgggc cacgtgacgc aagaccggct ggccagcgtc    44940
acgtgcgtgg cccgcggcga ccaggaggcg gcgcgcacca cgacatggc cgcgcgccgc    45000 tcgcaggtgc acgtgcccgc gtgcgcgctg atggacgtgg accgcgagct gcgcctcggc    45060
ggcgacgacg gcctccgctt cgcgtacctg gtctttgtct acacgcagcg ccaccgccgc    45120
gaggcgctgc gcgtccacgt ggcggtgagc cgcctgcccg agctcggcga cgccctcagc    45180
ttcctcctgg ccggcacgcg cgtcgacaac gcgatccacg gcacggacga ggccgacgcc    45240
cccgccgcgc ccgccgccgc cgcggccttc cccgcgtacc tgttcaacga cccgcgcagc    45300
gcgcgctgcc cgacgggccg gctcaacacg cccgccgccg aggcgctgcc cgtgtgggcc    45360
cccgacatgc gcggccgcgc cacccggaac tcgtgcatgt acgccgccta cgtgcgcctc    45420
ggcaccgtcg agcgcgtcgt gcgccgggcc gagcgctgcg gctcggtgga cctgccgctg    45480
gcccacatgg agcgcttcac ctgggacgtg ggggcgtggg aggagtgttt cttctgaaaa    45540
aaccgggggg cgggtgtgtg agacggatgt gatgttgctg acgaggctaa taaaaaggcg    45600
ggcacacgcg cgcgtgtccc cccgctgacc ctccgtgccg cgtccgtgtc gtgtgtgact    45660 cacccccatcg tctctcccgc ccgcgatccc ggcccgtccc ggcttgtccc gccccgccca    45720
gacacgtccc atcatgtccc cgcgcgcgcc ccgcccgccg ggcgcggttt ccccgccctt    45780 tccccccattg gcgccccgc cgctaaaagc ccgcgcgccc cgagctcggg actctccgct    45840
cacctccccg cgtcgagcac acgccgccat ggcctccgtc gtcgcgcccg ccgcctcctc    45900
gtccgccgcc gccccggcg cggacgcatt cctcgacgcc gcctgccccg aggacgtcgc    45960
ccgggccctc gccgccgagc tcgaggcgct gcgcgccctc gggcacgacg tcggcgcgcc    46020
cgcgcccggc gcctcgcgcc gcgaggcggc gctgtttatc acgcgcgccg tggacgggct    46080
caaggccttc tcccgggtgg acgagcgcgt gtacgtggcc tgcggcaagc tggtgcacct    46140
gcgcgtgcgg aaccgcgagg cggacctgga cgcctggctc gcctcgccgg agctcgcgct    46200
gatccccgcg gtggcggccg ccgtgcgccg gcaccgcgcg cgcgtggagg cggccctccg    46260
ctggttctgg cgggaggcct acccggcgct ctacgcgcgc ggcctgcagt cggcgctcaa    46320
gtacgaggag atgtacctgg cccgcctcga gcacgggcgc tgcgaggcca tggaccagtt    46380 cttttgtgcgc ctcgccgcgg ccgccgccac ggcgacgcgg cgcccatgg cgctcgtgct    46440 ctgcggctcg gacgcgtggc ccgaggtctt tgacgcgtac tttcgcgcgc tggccacgca    46500
ggcgatcgtg cccgcaaccc cgctcatgct cttcgccggc cgcgcgcgcg gctcgctcgc    46560
cagctgctac ctgctgaacc ccctgccgcg caccaccgag gaggcggtgc gcgccatcac    46620
ggacgaggtg gccccatcc tgctgcgccg cggcggcgtc gggctctcgc tgcagagctt    46680
caaccgcacg ccctcgggcg actgcacgcg cggcatcatg gccgtgctca aggcgctgga    46740
ctcgatggcg gcggccatca acagcgacag cgagcgcccc acgggcgtgt gcgtgtacgt    46800
cgagccgtgg cacgcggacg tgcgcgccgt gctgaacatg gcggcatgc tcgccgcga    46860 cgagagcctc cgctgcgaca acatcttcag ctgcctctgg acgccggacc tgttcttcca    46920
gcgctaccag cggcacctgg acggcgagcg cgccgtcaag tggacgctct ttgacgaccg    46980
```

```
cgcctcgcac ctggcctcgc tgcacgggcc cgactttgcg cgcgagtacg agcgcctgga   47040
gcgcctcggc ctcggcgtcg agtccctgcc catccaggac atggccttcc tcatcgtccg   47100
cagcgccgtc atgacgggca gccccttcct catgatgaag gacgcgtgca accggcactt   47160
ccacacggac acgcgcggcg ccgccctcgc cacgtccaac ctctgcacgg agatcgtgca   47220
gcgggccacg cccggcgaga acggcgtctg caacctggcc agcgtgaacc tgcccgcgtg   47280
cctggcgggc ggcgccttcg actttgccgc gctgcgccgg gccgcgcgcg tcgccgccgt   47340
cttcgtcaac gccatgatgc gcatcgggaa ctacccgacg ggcgcctcgg tcgagggcgt   47400
gcggcgcagc cgctcgctgg gcatcggcct gcagggcctg cacacgaccg tgctggcgct   47460
ggacatggac atggccgacc cggcggcgcg gcgcctcaac gccgccatcg ccgaggagct   47520
gctctacggc gtcatggacg ccagcgtgga gctctgcgag cgcggcctgc gccccttcga   47580
cggcttcgag cacagccgct acgcgcgcgg ggtcatgccc tttgacgcct acgagcgcgt   47640
ctcgctccgc gagccgatgc gctgggacgc gctgcgcgtc cgcatcgcgg agcacggcgt   47700
gtacaacgcg cagtttgtgg cgctgatgcc caccgtgtcc tcgtcgcagg tcaccgagag   47760
cagcgagggc ttctcgccca ccttcaccaa catgttcagc aaggtcacca tctcgggga   47820 gctcctgcgc cccaacctgc cgctcatgga gacgctgcgg cgcctgtttc cgcgcgagtg   47880
cgcgcgccgg gacgccgtgg cgcggctgga gcgcgcgcag tggtccgtgg ccgcggcctt   47940
cggggagctg cccgccgggc acccgctggc caagttcaag acggccttcg agtacgacca   48000
ggagctgctc atcgacatgt gcgcggaccg cgccccccttt gtggaccaca gccagtccat   48060
gtccctcttc ctgaccgagc ccgccgacgg gaagttacac gcctcccgcg tcatgggcct   48120
cctcatgcgg gcatataacc tgggcctcaa gacgggcatg tactactgca agatcaggaa   48180
ggccaccaac aacggggtgt tcaccggcgg ggacctggtc tgcacgagct gccacctgtg   48240
agcgcgcgcc atggagtact tttacacgtc ccagtgcccc gacatggacc acctccgctc   48300
gctgagcgtg gccaaccgct ggctcgagac ggacctgccg ctgggcgacg acgccaagga   48360
cgtggccgcg ctcagcgagg ccgagctcga gttctaccgc ttcctcttcg ccttcctctc   48420
cgccgcggac gacctcgtca acgtcaacct gggcagcctc tcggagctct tcacgcagaa   48480
ggacatcctg cactactaca tcgagcagga gtgcatcgag gtggtgcact cgcgcgtgta   48540
cagcgccatc cagctgatgc tgttccgcgc cgacgccgcg gcgcgcgagc gctacgtgcg   48600
cgcggcgctg cgggacgagg ccatccgccg caaggtggag tggctcgact cgcgcgtcgc   48660
cgagtgcgcc tccgtcgcgg aaaagtacct gctcatgatc ctcatcgagg gcatcttctt   48720
cgcctcctcg ttcgcctcca tctcgtacct ccgcacgcac aacctctttg tggtgacctg   48780
ccagtccaac gacttcatca gccgcgacga ggccatccac acctcggcct cgtgctgcat   48840
ctacaacaac tacctggggg acgccccgcg ccccgacgag gcccgcatcc accagctctt   48900
cgccgaggcg gtggagatcg agtgcgagtt tctgcgggcg cgcgccccgc gcgacagcct   48960
cctgctggac ctgccggcca tcatctcgta cgtgcgctac agcgcggacc ggctgctgca   49020
ggccatcggc gcgagcccgc tctttgacgc gcccgccccc gcggcggact ttcccatggc   49080
gctgatggtc gccgagaaac acaccaactt tttcgagcgg cgcagcacca actacacggg   49140
gaccgtcgtg aacgacctgt agccccggcg accccgcccc tcccccctct tctctctctg   49200
cggcaaaaca ctaataaagc gttgagacac tagcgcgcgc ctccgccgt catccttggg   49260 gcgagggtga gacgggaacg gggatgggag agtgggatgg ggaaatgggg gatgatgacg   49320
```

| | |
|---|---|
| ggggaaggga gatggggccg gcggggggtgg acttggactg gggaaggatg gtggcggccg | 49380 |
| gcgcagagtg ggaggcggtg aggtggacgg aggggaggac cgatgtggga cggcggaggg | 49440 |
| acggcggagg gacggcggag ggacggcgga gggacggcgg agggacggcg acgacggaga | 49500 |
| gagaaggtgg gggagagggc gagcatcaca cgggccgcac aaccgaggat tttttcaagt | 49560 |
| tttttttattt tctcctatgg gcgttacagt cgtcccagta cgccacgagg acggcctggt | 49620 |
| agttcggggg cggggggtatg tgtttccaaa acaggcccgc cagctccttc gcccgcgtct | 49680 |
| cgttcttcac gtgccgcagc agcgagccaa agaccttgtt cacgtccgag ggctcctgca | 49740 |
| cgatggggac gcgccgcagc acgctcaggt gcccgtgccg cgccggcgtg agcatggcca | 49800 |
| ccacgtgctg gatgaactcg cgctcggcgc ggcgcgagcg cgcgtccccg gccgccggca | 49860 |
| gcagggcgag cgccttgccg gcgtcgcgca tgatgtcggg gcagcgggag gcgtacttga | 49920 |
| gcttgacgtc ctcgggggcc acctcgcggc cctccagcga ctcggccacc tgctgcaccg | 49980 |
| agtccacgtc cggcgcccgg tgcaggtccg tgtggcagcg cacgaacgcg gccaggaact | 50040 |
| ccgagtagtc caccccagg ctcgcgagga cgtcgcggca gcgcagcacc agcgggaaca | 50100 |
| cgggcgcgat gtcgaggatc atgtcgcacc cggtgaggat catgtccgtg tcggtcgtgt | 50160 |
| gcacctgcgc gaccgtgttg gtgtggtaga ggttggcgca gacgtcgtcc gcctccatgt | 50220 |
| ccgacacgtc cacgtaggcg tagcccatgt ggcggatgag gttgacgcag aggcggtgga | 50280 |
| cgatgcgcgg cgcgtgcagc atcgtgctcc agcgcggccg cggcggcgcg tcggcggccc | 50340 |
| cgtcgccgtc ggcgcgcacg gccgcggcca tgatggcctt ggcgccgcgc gcgatgcggc | 50400 |
| cgttcccgaa gatgccgcgg tccgagacga agatggggaa gtaggtgcgc ttgtgcagca | 50460 |
| tgcgcagcag gcgcagcagg cagcgggcgg tcgtggtcgc gttgtcctcg gtcgtctcct | 50520 |
| ggtagtgctt ctccatgagg gtgtacatga cgttccacag gtcgatgcg attggcgtga | 50580 |
| ggaccccgg cggcgtggag atggcctccg agcgcaccag acggtggcgg tgtgcgtact | 50640 |
| ttaaaaggcc aaagagcccc atgtctccgc tcgcacaccg aggcgccggt ctaaaatacg | 50700 |
| catgtggcgg ggcggggcca tccgcgcata taagccgggc ggtgattggt ctggcgcaca | 50760 |
| ccgcccgccc gagcccgctc gcccgccgcg atgtcgctgt tcgacgacgg cctcgaggac | 50820 |
| ctggaccgcc accccaccca cgcgcaccac ccggcgcagg tgatccacga cgggcccttc | 50880 |
| gtgctggagg acggcgagcc cctgcagcgc accggcatgc tggtgctcag cgacgagcac | 50940 |
| ctggagcacg cgcgcgccgc catcgccccg ctggccgcgc acctcgcgca cgccttcctc | 51000 |
| gtcttcagcg aggccgggct gctggtgcac gccagcgtgc gcggcgagca ggtctacgtg | 51060 |
| accctggccc cggaccagtt cagcacgttc gtgtggagcg ggccccaggc cgtgttcctg | 51120 |
| ggcaacgtcg acggcagcgg cggcgtgctc gacgcgctca aggtcgaccg gcggcggacc | 51180 |
| gtcttcaacg tcaccttcga ggtgtacggc gccttcccgg cgcggctgct gacgcggcgc | 51240 |
| gcgtactttg cggacgcggg cgtcctcgcg acggggcccg gctccccgag cgtcgcctgc | 51300 |
| gtctacaagc acgagttcaa cgactactgc atcatgctcc cctcgcgggc gcccgacgtg | 51360 |
| agcctgacgc tctcgcgccc ccaggtggcc aagctcgccg ccgtggcgaa gggcgccgcg | 51420 |
| gccgggacga ccttcgcgct cgcccgcggc ctcgacttct ccgtctcctc cagcgccggg | 51480 |
| gtcgtgacct tcccggcgcg cgaccgcgac gggaccgccg tgctggagcg cgccagccag | 51540 |
| cggcgccagg gcgtcgacgc ggtcggcgcg acggagccct tcgccatgac gctcgagacg | 51600 |
| gcgcacgggt gctgacgct gctgcagcgg ctgcgggccg ggaacgccga gctcacgttc | 51660 |
| aactttttca cgacgccgcg gcaggcgccc ctgttcagcg tgaccacctg cggcccggtg | 51720 |

```
agggcgacca ccttcttctt ctgcgcgccc gccgaccccg ccaccgtgcc cgccgccccc   51780
gcaggcgccg ccgccaccgt cgccgccgcc tgcggggcgg gcgcgtccgc cgcccccgcc   51840 gcggggggaca agcggcccgc cgccccgcgc atgtacacgc ccatcgccaa gcgcccgcgg   51900
gccgcctcgg gggaagggggg ccacgcctac ggagatttat tctaataaag tgtgcaggtg   51960 tataaagag aggtcgcacc tccgcgtctt tactcgccgt cgcgatgatc tcccagggga   52020
acggaggggg ttgccgcccc ggcgagccat gctggcgctg cgcgctcgag tccacccgct   52080
gcatcacgct gatgggcgtg ctcgtcgcgc tcctcgccgc ttgcatgctg tccgtcccgc   52140
ccgcggcgtc gacgatgctg ctcggcgtcg ccagcctcat ggccatgctg cgcctgccca   52200
tgcccctcgt ggaccggttc atccccgcgt gcatgggcct ccagctcgtc ggcgccgccg   52260
tcttcgccgc gggctgggcg ctggccagcc gcgacgcgat ctcggccggc gtcctgctgt   52320
gggccgtctg cgcgctcatc tcgcacatgt acaacgtcgt ctgcgtcgcc agcgggcccg   52380
acgcgcacta ccgccccgcc tgcctcgtca tgggcgtcgc cgcggcctgc ggcgcggcgg   52440
gggccctcgt gaacgtgcgc accgaggcgc gcctcggcat cgccctgggg ctggccgtca   52500
catgcgccac gaacaacgtc gcccgcagcc tgcgcggcac gtgcacctac gtcgccagcc   52560
gcgcccggtt cctggccgcg cccgcggacc tggggcgcgg ctacagcgtg gagaacgcgg   52620
acgccgaccc caccgccgag cccgagcggc gcgtctacga ggcgaccgtc ccgcacaccc   52680
acgcctacgc cggcagcatc gcgctcttcg ccctcgtctt atcggccgcc tcctccctcc   52740
agtggatggt ctcccagatg gtgggccgcg gcaaccagct cgtctcgccc accaccgcgg   52800
ccgcggccgg cgccgccggg ttcctggacg cggcggcgct ctcgctcttt gtgcgcccga   52860
gcacgcgcca cctctcggtg gccgtcaagg gcgcgcacac gctcctcatc ctcgcggcca   52920
tcgtcctcac ggccgtcggc gagcccatgg gcgtgcccat cagcctcgcg gcctccaccg   52980
gcctcgcgct gctcgaggcg gaccacgtcc gcctgcgcca cacccgcgcg taccggctcg   53040
ccgccgcgca cgtgacgcgg gccctgctgg tgcaggcgta cgtgaccgtc gccatgtgcg   53100
ccactagcat taaatccgtt tcctgattca cgcccacgct cgcgtcgttt ttaaaaccgc   53160
gatgggggga cgggggggcca ttcgcacgcg ccatggcctc gctcgcgcgt gcgatgctcg   53220
ctctgctggc gccctacgcg gcggccatcg ccgcggcgcc gtcgaccacg acggcgctcg   53280
gcacgacgcc caacggggggc ggcggcggca acagcagcgc gggcgaactc tcgccctcgc   53340
cgcccccgac ccccgcgccc gcctcgcccg aggcgggcgc ggtctccacg ccccgggccc   53400
cgccgccctc ggtctcgcgc aggaagcccc cgcggaacaa caaccggacg cgcgtccacg   53460
gcgacaaggc caccgcgcac gggcgcaagc gcatcgtgtg ccgggagcgg ctgttctcgg   53520
cgcgggtggg ggacgcggtc agcttcgggt gcgccgtctt cccgcgcgcc ggggagacct   53580
tcgaggtccg cttctaccgc cgcgggcgct tccgctcgcc cgacgccgac cccgagtact   53640
ttgacgagcc cccgcggtcg gagctcccgc gggagcggcc cctcttcagc tccgccaacg   53700
cctccctcgc ccacgcggac gcgctcaccc ccgtcgtcga ggacgagggc gggcgcgcga   53760
ccgtcgccaa cgtctcgggc gaggtgtccg tgcgcgtggc cgcggcggac gccgagaccg   53820
agggcgtcta cacgtggcgc gtgctgtccg ccaacgcac cgaggtccgg agcgccaacg   53880
tctcgctcct cctgtacagc cagcccgagt tcggcctgag cgcgccaccc gtcctcttcg   53940
gtgagccctt ccgggcggtg tgcgtcgtcc gcgactacta cccgcggcgc agcgtgcgcc   54000
tgcgctggtt cgcggacgag caccggtgg acgccgcctt cgtgaccaac agcaccgtgg   54060
```

```
ccgacgagct cgggcgccgc acgcgcgtct ccgtggtgaa cgtgacgcgc gcggacgtcc    54120
cgggcctcgc ggccgcggac gacgcggacg cgctcgcgcc gagcctgcgc tgcgaggccg    54180
tgtggtaccg cgacagcgtg gcctcgcagc gcttctccga ggccctgcgc ccccacgtct    54240
accacccggc ggcagtctcg gtgcgcttcg tcgagggctt cgccgtctgc gacggcctct    54300
gcgtgccccc ggaggcgcgc ctcgcctggt ccgaccacgc cgccgacacc gtctaccacc    54360
tcggcgcctg cgcggagcac cccggcctgc tcaacgtgcg gagcgcccgc ccgctgtcgg    54420
acctcgacgg gcccgtcgac tacacctgcc gcctcgaggg cctgccctcg cagctgcccg    54480
tcttcgagga cacgcagcgc tacgacgcct ccccgcgtc cgtgagctgg cccgtcgtga    54540
gcagcatgat cgtcgtcatc gccggcatcg ggatcctggc catcgtgctg gtcatcatgg    54600
cgacgtgcgt ctactaccgc cgggcggggc cgtgacgccc cgcgcgttcc ccccccacgt    54660
cgaatcaata aacgacagcg agtccgaccc gagccctcgc gtcttgtgtg tgtttgcgcg    54720
cgccctcccc caccctctcc cacccacact ctctcccgcc ccaccacacc ccgcaataaa    54780
ccacacgaga cggcggcgtg tacagcgcga ccgggcaatc tttattggtc gtcggggcg    54840 ggcgggaagg gagcggggcg cggcatcctc atcgctggga catcatctgc gagacgaaga    54900
tgtcggcgcc gcgctggcag gccacggcgg ccgagctggc gtcgatggtg ccggcggaga    54960
cgtccgccgg ggccgagacc gaggcctgga cgggcggctg gggggccgag gcgggcgcgg    55020
ccggggcggc ggcctgaacg ggggcggccg cggcggctgc cgctgctgga gccggagcgg    55080
gggcggccgc ggcggcggcg ggcacggcca ccggctgggc ctgcaccacc accggctgct    55140
gcgggaccac ctgggcgggg acgtgcgcga cggggggccgc caggccctgg aggcccggca    55200
ggcccgggag cgccggcacg gcgtgcgcca cgggcgaggg gggcggcgcg tgcagccccg    55260
gctgggggcg gtacatcggc gggtacagcg ccccggctgc gtggtgcggg tgcgggtgtc    55320
ccacgacggc cccgggtggc agcagctgct gcggcggcgc cgcgggcgcg tagtacggcg    55380
tcgggtagcg gagctgctgg gcgcgcaggt ggctgatctc gcgctggagc gacgagacca    55440
cggcggcgag gtcgctcgcg gggggcggcg cctccccggg gtagtacgcg ttgtcctggg    55500
cgtagtcgtc gtagcggcgc ttcctggcgg ggggccgggg ctcggcgag ggcgagcggc    55560 ggtggcggcg gtccatggcg gccgagacga tggcgccgag ctgggactcc aggctgggcg    55620
ccgggcgctg gttgaccacc agctggttgt actgcgccgc gggcacgaag atgtagtcgc    55680
cgggcgctgc gctcggcggg gctgccatgg ccgcactggg cccgggcgcc ggggaggccc    55740
cgcttttagg cagaagcccc gcccacatcg tcgcctgcag gtaggtgtgt ccgcgcacgc    55800
cggcctcgcg gcggcgcgcc gcgaccagct cccagcggtc gcgcagcagc atgttgttca    55860
cggccgtcga gagcagcgcg cgcgtgagcg cctcctcgct catgtgccac acgcgctcgc    55920
ggtccggcga ctcggcggcg cgcgccagca gctcggagcg cgcccgcgcc gagagctgcc    55980
ggaacggcgc cacggcggcc tcgggcgagg cgtcgtacac cacgatggtg cccacgcgcg    56040
gcccgatcac gcagagcgcc acgtgcgcaa agagcgtctc gtcgggggcc tcgccgggcg    56100
ccaggcgccg cgaggacagg gacgccgagg gcaggtagtt gctcagcagg tacagcagcc    56160
gctcctcgtc cgagagccgc atgtcccga agaagtccgg gccacgcg cgggcgagca    56220 cggcccccag ctgcgggcag ttgacgacgc cgaggaagaa ggggccgcgg tcgtcgtcga    56280
ccacggccag cacggcgccg atgtcgcagc gcggcggtg gtcgatgttg atgggcagcg    56340
ggcccgccgg gggcagcgcg gcggccacga tctcgcgcgt cagcgcgagc tccccgccgt    56400 cccctatcgta cagggccagg tagccggaca cgtacacggg ccccatggcg gcggcggcgc    56460
```

```
gcgcggagac tgcgggctca ggcggcggcg aactgcggga tatagcccag gcagagaaag   56520
tacaggaggt cgtagtcgct ggagacgcca aactgcccga ggcgcttgtc cgccgcgttg   56580
cgcaggtgcg gctgctgcag cagcaggccc agcccctcct cgtactgcac ggccacggcg   56640
tcgtgcgccg cgatgacctc gttgacgggg gccgtcacgc gctggcggtt ctgcagctcc   56700
agcgccacca ggcgcaccag gttgagctgg tggcgctgca cgcgcgcgcg gatcgagtgc   56760
gcgtccagcc ccagcgcggc cagcccgggg aagagctgcg tgagctccgt gcgctcgtcc   56820
gcgcggtagg ccacgacgac gtagtgggcc agcaggaagc gcaggttgcc gtcgccgctg   56880
cgcgaggcgg gcgcgtcccc gctggcgccg cgggcggcg gcgcgttggg cacgagcgcg   56940
ccgagctgga agttgttgcg caggcggtcc ccgtacacgt tgccgttgtg cagcaggcgc   57000
cgcagcagca gcaggcccgt gatggtgttc accgtggcgc gcagcagcgg cgcgtcctcg   57060
ccgaggaaga ggttctggcc gcggcccagg aaggcggccg cggcgcggtt gacctcgtcc   57120
acgaagcccg cgccgtcgac ctcgttggcg ccgacgttcg cgccggggac cacgcgcagg   57180
cgcgccagcg cggcgagcac gctgtggccc tccagcgcgt agcgcccgtg gagctgctcg   57240
cgcggcacgc gcgcgtagtt gtagcggtac gagatgcgcc cgccctcggc cagcgcctgg   57300
ctcagcgcgt ccaggtactc ggggacccgc tccagcaggt ccgcgatgcc cagcggggcg   57360
gcggcgcccg cggcgccggg cccctgccgc gcgcggtgca ccaggtgcag gcacagcgcg   57420
gcgctctcga gcgccgagta gtgccggttg cccacgtaca gacgcccgca ggcctgcagc   57480
gccgtggtcg tcacgcccat gaaggtcgcg gacatgcggc cgtcgcgcga gtcgatggcg   57540
cgcgagacct gcgggcgctc cgcgacgagc gtggcctgga gcgtggcgta ccacgtgccg   57600
aagagcacgc cggaggcggc gccgcgcgcg gcgtacacca tggccaggaa gtccagcgag   57660
aggttggcgt cgtaggcgag cgccacgtcg ttcttggcga tctgcacctc gcggccctcg   57720
tccgcggccg cggtcgcctc gggcgcctcc tcggcggcgc gcgccgcgtc cgcctcctcg   57780
gcggcgcgcg ccgtctcctc gagcaccacg agcgcttcgg ccacgcgctc cacctgccgc   57840
tccagcggcc gcagctgctc gtccacctcg gcctcgaggc gcgcgcccgc ggccatggcg   57900
ttgtccagcg ccgcggcggc cgcgcggcgg cgcgcgttcg cgtgcgccag cgcgaggcgc   57960
gcgtcgaggc cctcgccgaa gcccgggcgg gcccagaagc ccacggggaa cggggcgcg    58020 atgaagtggc gcgcgctgcc cgggatcgca gcggcctcga aggcgaacca cgcgcggtcc   58080
atggcgcggg gggacatggg ccgcgcgccg ccgcgcgccg ccttatcatc cccgctcccc   58140
gccgccgccc ggcccacgc gcgccgcgat cgcgatcacc gccgcggccc ggcgacgtac    58200
tcggcgaggc cgcgcacggt cgcggccatc gcgctcgcgt tgccgcgcgt ctgggtgcag   58260
ggcaggcgcg tcacgtcgag cacgcgcatg ctccgctggg ccacaaacac cagcaggggc   58320
acgagcgtga tctcctcgcc gcccgggggc acggcggcgg cgaggaggcg cgccgagtcg   58380
cgcagctggc acagccctc gtgccgctgc ccgcgcttgc tgggcgtgtt gaggttccgg    58440
gggaagcggc acgtcttgag ctcgatgacg aagcacaggt gcggccccac ccccagccgc   58500
accacgcaca cgcagtcggg gcggcgcacc ccgaggttga cttcaaaggc cagggtcaag   58560
gacgccttct taagcgtctc gcggggaagc ccgaagagac tctcgccgta cgcggacggg   58620
tcgcggcgca ggcgttcgta aagcggtttg tggcagcgga tccccgcccg gaagcgcgcc   58680
gggatgcgca tcctccggat ctacctcgac ggcgcctacg gcaccggcaa gagcaccacg   58740
gcccgggtga tggcgctcgg cggggcgctg tacgtgcccg agccgatggc gtactggcgc   58800
```

```
actctgttcg acacggacac ggtggccggt atttacgatg cgcagacccg gaagcagaac    58860
ggcagcctga gcgaggagga cgcggcccte gtcacggcgc agcaccagge cgccttcgcg    58920 acgccgtacc tgctgctgca cacgcgcctg gtcccgctct tcgggcccgc ggtcgagggc    58980
ccgcccgaga tgacggtcgt cttgaccgc cacccggtgg ccgcgacggt gtgcttcccg     59040
ctggcgcgct tcatcgtcgg ggacatcagc gcggcggcct tcgtgggcct ggcggccacg    59100
ctgcccgggg agccccccgg cggcaacctg gtggtggcct cgctggaccc ggacgagcac    59160
ctgcggcgcc tgcgcgcccg cgcgcgcgcc ggggagcacg tggacgcgcg cctgctcacg    59220
gccctgcgca acgtctacgc catgctggtc aacacgtcgc gctacctgag ctcggggcgc    59280
cgctggcgcg acgactgggg gcgcgcgccg cgcttcgacc agaccacgcg cgactgcctc    59340
gcgctcaacg agctctgccg cccgcgcgac gaccccgagc tccaggacac cctcttcggc    59400
gcgtacaagg cgcccgagct ctgcgaccgg cgcgggcgcc cgctcgaggt gcacgcgtgg    59460
gcgatggacg cgctcgtggc caagctgctg ccgctgcgcg tctccaccgt cgacctgggg    59520
cccctcgccg cgcgcctgcg ccgcggccgt ggggcgcagg cgcgcggcat ggaggtgacg    59580
gagtccgcgt acggcgacca catccggcag tgcgtgtgcg ccttcacgtc ggagatgggg    59640
gtgtgaccct cgccctcccc acccgcgccg cggccggatg gagaccgcga cggaggcaac    59700
gacgacggcg tgggaggggg ctcgggcgcg gtataaagcc atgtgtatgt catcccaata    59760 aagttgccg tgcccgtcac catgcccgcg tcgtccgtgc cctcccgct gcgcctcctg      59820 accctcgcgg gcctcctgge cctcgcgggg gccgccgccc tcgccgcgg cgcgccgcag    59880 ggtgggccgc cctcgccgca gggggtcc gcgcccaccg cggcgcccgc gcgcgggccc      59940
accctgttcg tcctggacgg cgacggctcc gcgtggttcg tcttccagct cggcgggctg    60000
ggggcgctca cgacacgcg catccgcggg cacctgctcg gccggtacct cgtctcgtac     60060
caggtggtgc cccgcccgt ctccgcgtgg tactttgtgc agcgcccgcg cgagcgcccg     60120
cgcctctcgg ggccgccctc gggcgcgag ctcgtggcct tcgacgcgcc cggcgtccgg     60180
cgcacgtaca ccacggcggc ggtgtggccc gcggaggtgg ccgtcctcgc ggacgcggag    60240
gcgcgctgcc ccgcggccgt cttcaacgtg acgctgggcg aggccttcct cggcctgcgc    60300
gtcgcgctgc gctccttcct gccgctggag gtcatcatct ccgccgagcg gatgcgcatg    60360
atcgcgcccc cggcgctcgg ctcggacctg gagccgccgg gccgcccgc gggccgcttc     60420 cacgtgtaca cgctcggctt cctctccgac ggggccatgc accagacgat gcgcgacgtg    60480
gccgcctacg tgcacgagag cgacgactac ctcgcccagc tgtcggcggc gcacgcggcc    60540
gccctggccg ccgtggtgca gcccgggccg tactactttt accgcgcggc ggtgcgcctc    60600
ggcgtggccc ccttcgtctt ctccgaggcg gcgcgccgcg accggcgcgc ctcggcgccg    60660
gcgctcctgc gcgtcgagag cgacgcgcgc ctgctctcgc gcctgctcat gcgcgcggcc    60720
ggctgccccg cgggcttcgc cgggctcttc gacgggcgcg ccgagcgcgt cccggtggcg    60780
cccgcggacc agctccgcgc cgcctggacc ttcggcgagg accggcgcc ccggctggac     60840 ctcgcgcggg cgaccgtcgc cgaggcgtac cgccgctccg tgcggggggaa gcccttcgac    60900 cagcaggcgc tcttcttcgc cgtcgccctg ctgctgcgcg ccggcggccc cggcgacgcg    60960
cgcgagaccc tgctccgcac cacggccatg tgcaccgcgg agcgcgccgc cgcggccgcc    61020
gagctcacgc gggccgcgct ctcgccgacg gccgcgtgga acgagcccctt cagcctgctc    61080 gacgtcctct cgtcgtgcgc cgtctcgctg cgccgcgacc tcggcgggga cgccaccctg    61140
gccaacctgg gcgccgcggc gcggctcgcg ctggcgcccg ccggggcccc gggcgcggcg    61200
```

```
gcggcgacgg acgaggggggc gggggaggag gaggacccccg tcgcgcgcgc cgcgcccgag    61260
atccccgccg aggcgctgct cgccctgccc ctgcgcgggg gcgccagctt cgtgttcacg    61320
cgccggcgcc cggactgcgg cccggcgtac acgctcggcg gcgtggacat cgccaacccg    61380
ctcgtgctcg ccctcgtcag caacgacagc gccgcgtgcg actacacgga ccgcatgccc    61440
gagtcccagc acctgccggc gacggacaac ccgtccgtgt gcgtgtactg cgactgcgtg    61500
ttcgtgcgct actcctccgc gggcacgatc ctggagaccg tcctcatcga gtccaaggac    61560
atggaggagc agctcatggc cggcgccaac tccaccatcc ccagcttcaa cccgacgctg    61620
cacggcggcg acgtcaaggc cctgatgctc ttccccaacg gcaccgtggt cgacctgctg    61680
tcgttcacgt cgacgcggct cgcgcccgtg tccccggcct acgtggtggc ctccgtcgtg    61740
ggggcggcca tcaccgtggg gatcctgtac gccctattca agatgctctg cagcttctcc    61800
tccgagggct attctcggtt aataaacgcc aggtcgtgag gcccgcgccg gccgcgaac    61860 ccagactctc tgcgtgcgcg tgttttttcct tgtcgggcgc gggagagacg ggggggagac    61920 gggaggggggg agagggacgg cacgggcgcc gtccgtcggg gagacggcgg gatgacatca    61980
cgagagtcgg gtggagggga tgcgggggagc gccatccacg ggggaaggct gctggatgac    62040
ataactagag ccagggatga ggatcccctt tccccgttc cccgagtata caccactctc    62100
tccccgcaca catttcccac cgggcgccta acgtggattg cacccccggtc cgcgctaccc    62160 ggttgtgtgt gagacgggcg gagagccgcc ctcgccccgg tcccccaaa actcctgcgg    62220 atgtgtggtc cgacgaagcc tccgcggatg tgtccgccgt accctcgtcc ccctctctcc    62280
cacagccctc tctcccacag ccctctctcc cacagccctc tctcccacag ccctctctcc    62340
cacagccctc tctcccacag ccagactccc gcctccccg tccccgatcg ccgaacgcct    62400
tcaagaattt tttacccgct ccgaggaagg ggtctctaag gggtctctaa ggggtctcta    62460
aggggtctct aaggggtctc taaggggtct ctaaggggtc tctaagggggt ctctaagggg    62520 tctctaaggg gtctctaagg ggtctctaag ggggaaccag agagtaaaga ccggagagta    62580
aagaccagag agtaaagacc agagagtaaa gaccggagag taaagaccag agacacattt    62640
tacaatttcg ttgtacccgg gtttattgaa aactttgttc aagagttaaa gtgtctgccg    62700
cttgccggtg tgccgcgccg aggccgcgat ccggccgccg tggaccgggg gcccgcgggc    62760
ctggattcga cgggacggcg ggtccgagcg acggcggtcc ggcggcgttt cggctcgcgg    62820
tcctcgcggc ggcgacgatc cggcggtccc acgacgatcc tggtccgggg gatccagcgg    62880
cgacggcggc gctccgggtt gtggcgccgg gctccggctc cccggtcttt tacccccaca    62940
cctcatgaat attcatgaat ggttggtatg tgcgaatttt tcggcgttcg cacttgttgt    63000
atataaaata ttatatccta tatatattag caattggtgc gaacgtgacg tggcccaatc    63060
attttccttg gatttgccca tgtgaccgag tttccaatag ctccgcccag atcgatcgcg    63120
gggccgatat tttgccgata atccatcaat attttcttcg gccgacgcgg gtttcacccg    63180
gccgtcccgc cggggaggcc cgtcccgggg cgcgggactc tcctctccgg acgccgcgcg    63240
gcgtcgagac cgcgccggga cgatggtgtc tgcgcatgcg cggctggggc cgagcgaccg    63300 ggaatccccct ctcatgacca gctccaccca tcgtcacatg cccgctcgct caccccccttc    63360 tcccgcgacc ggcgacgatg gggcggccgt ggcccagcca cgacgagggg gcgctcgctc    63420
gcgcgcgcgg gggcggtggg ggttgggttc tcgggcttcg gggcggatgt gtgtgttgtg    63480
cgtcggggga ctgggggcga gcgagcgggg ggtgttgtgg acgggggacg atccgggggg    63540
```

```
gccaccgaga ccgaggcggg cgggcgcgcg cgtgtgtgcg tgtcgcggat agagaacgga   63600
cgggggcgcg gacgtggtgt ttggttaacg gtttttattg aggacgatgg agatgttggc   63660
gcgggtcagg cgcgcccgaa acagctgaaa caggtactgg gccccgcgga gggccgcggg   63720
cgagtcgccg aaggcggtca ggagcgccgc ctcggcgcag acggcggacg tgggccgcag   63780
cgcgcgcccc acgggcgccg tcgcggcgac gaggccccgg ccggcgtaga gcccgtccag   63840
cacccgcgcc ccggccgcct ccaccagctc gcacgcgtcg gcgtccggcg cgttcgtctc   63900
cgcgtcgctc atcatgaccg ccagctccag gcccgtcgcc gcgtcctccc gggcgtgctt   63960
cgtcgtcggc ggcgaggccc ccgccgggtc cgcgatcgcg ggggcgtgca ccacggcggc   64020
gttcacgagc atccgcatca cctcgccgaa gacggtcgcc tcgcgcagca cgcggttggc   64080
ggcgtgggcc acggcgctcg cggcccgaga ccgccgtgg ccgccccctc ctcccccgtc   64140
tcctccgtcg tcgtcgtcgt cgtcgcccgc gcccgccccg gggcgctcgt ccagcctgtc   64200
gagcatgccc tccagcgcgg cgtagcagct cggcaggtgc cagcgggcca ggatgaactg   64260
gtacagcgcg aaccgctgcg cgcccgtgag cgacgtggag cccgtcccga agaagggtc    64320 cgccgcgacg gcggacacgg cctcgaccac ggcggccgag cgtcgtccg aggcgcccgc     64380 ggcccgccga aggatggcgt ccgccccggc cacgaggtcg cagagcatct gcaggacag    64440 gctcccgccg cgcgtcgccc agatgcgccg cgtcgccggg atgtagcgca cctgcacaaa   64500
gtcgctgacc accgtcgcgc gcagcgcgcg ctcggcgtac cggcgcgggc gcacgctcag   64560
cgtgggggcc gcgcgcccgc ccttcaccac cacggccgtg ggccgcgtct cgccgctgag   64620
cggggggcgc acgccgggga tgccgtcaaa gagcccctcc gtcagcacct gcagcgagct   64680
gggcagctcg gagaggtacg cctgcaccag cgcgaagcag gcctcgttca cggcgtacac   64740
gaagcccgag gaggggtgca cgatggcggg ctcggccagg agctccagga cgcggtcctg   64800
ctggcggtcg tgcacgagcg tcagcgagag cgccgacgcc ggcagcgaga ccatgcactc   64860
gacgaggtag gggtcgtaca cgtccagctc cgcgcggccg cagaggtcca gctccgtcag   64920
cggcagcagc agccccaggg cgtccacgaa gacgtcgtcg ctcccctgcg gggcggccca   64980
cgcgcggccc aggcgcgcca gctccgtgcg cacgtagttg gcgacgacgc ggttcccggg   65040
cgcgttcccg cgcagcgtga gcccgaactt gccgatctcc cgcgagcgcc ggcgcacgga   65100
cacgatgcag cccccgtgca caaagtacgc gcggtccccg ccgtcggcga cgtagaacag   65160 cacccctgg tgcacgatcg tgctctggta ctcaaactcc atggcggcgg gcacacgcgg    65220
cgcggcaaat gggtgagcga ggcggcgcga ccactccttt aaaccgccg gggggcgcct    65280 cccgccgcac acacgcggcg gcgcggggat ggaggacgcg gcggcggacg tggacgcggc   65340
ggcggacgcg aagatgacgg gggagaacga cgcgctgctg agctcggcct ttgtgggcgc   65400
gcgcccgccg cgcccgcgct tcagctcgca cgtggtgagc ctcctggccc tggcgctcgc   65460
gctccggccc gcgtgctgcc tcgtcctggc gctccacggc tcgcgggcca ccctcgcggc   65520
gctcctcacc gcgctggcct tctacgcgcg cgcggccgtc tgcgccgtcc tcgtggcgcg   65580
gaacgtggcc cggaccggga tgccgctctc gccggcgcag caggcggcgc tggggctcct   65640
ggcggcggcg cggctggcct tcctgtacgt cgccctggac gcgggccgcc actacgcgcg   65700
cgccctcgcc ggggcgctgt acggcgccga ctgcgtctgc gacgcgctcg ccttcctgct   65760
gccgcgcgcg tacgcgcgct ccatcatgca ttaaaaggcg gccgcggcgc gcccgcgcca   65820
ctctcccccc tgctccccag cgaccgcgca cacgcgcccg cacgcggtcg tcgccacacg   65880
atggagcgcc cggccatcct gccgtcgggg cagatcctgt ccaacatcga ggtgcactcg   65940
```

```
caccgcgcgc tgttcgacat cttcaagcgc ttccgctcgg acgacaacaa cctctacggt    66000
gccgagttcg acgcgctgct cggcacctac tgcagcacgc tctcgctcgt gcgcttcctg    66060
gagctcgggc tctcggtggc ctgcgtgtgc accaagttcc cggagctcag ctacgtggcc    66120
gagggcacca tccagtttga ggtgcagcag ccgatgatcg cgcgcgacgg gccgcacccg    66180
gccgaccagc ccgtgcacaa ctacatgatc aagcgcctcg atcgccgctc cctcaacgcc    66240
gccttctcga tcgccgtcga ggccctcggg ctcatctcgg gcgagaacct cgacggcacg    66300
cacatctcgt cggccatgcg gctgcgcgcc atccagcagc tcgcgcgcaa cgtgcaggcg    66360
gtgctggact cgttcgagcg cggcacggcc gaccagatgc tgcgcgtcct gatggagaag    66420
gcgccgcccc tgtcgctgct ggcgcccttc acgctctacg agggccggct cgcggaccgc    66480
gtggcctgcg ccgcgctcgt gtcggagctg aagcgccgcg tgcgcgacga caccttcttc    66540
ctcacgaagc acgagcgcaa caaggacgcg gtcctggacc ggctctcgga cctggtgaac    66600
tgcaccgcgc cctcggtggc cgtcgcgcgc atgacccacg cggacacgca ggggcgcccc    66660
gtcgacgggg tgctggtgac cacggccggc gtgcgccagc ggctcctgca ccacgtgctg    66720
acgctggcgg acacgcacgc ggacgtgccc gtgacctacg gcgagatggt gatcgccaac    66780
accaacctcg tgacggcgct ggtgatgggc aaggccgtca gcaacatgga cgacgtggcg    66840
cgctacctgc tcggcggcga gccggccccc gacgacggca gcccgtggg ctcggcgcgc    66900 gtgcgcgccg acctcgtcgt cgtcggcgac cgcctggtgt cctcgaggc cctcgagaag    66960 cgcgtgtacc aggccacgca ggtgccgtac ccgctggtgg gcaacctgga cgtgaccttc    67020
gtcatgcccc tgggggtctt caagccggcc gccgaccgct acgcgcgcca cgccggcagc    67080
ttcgcgccca cgccgggcct cccggacccg cgcacgcacc cgccccgcgc cgtgcacttc    67140
ttcaacaagg acggcgtgcc ctgccacgtg accttcgagc acgccatggg caccctctgc    67200 caccctcct tcctggacgt ggacgccacg ctggcggcgc tgcgccagga gcccgcggag    67260
gtgcagtgcg ccttcggcgc ctacgtggcc gacgcgcgcc ccgacgccct cgtcgggctc    67320
atgcagcgct tcctcgagga gtggcccggc atgatgcccg tgcgcccgcg ctgggccgcg    67380
ccggcggccg ccgaccagct gctggcgccc ggcaacgccg acctgcgcct ggagctgcac    67440
ccggcctttg acttcttcgt cgcgcccgag gtggacgtcc ccgggcccttc gccgtgccc    67500 caggtgatgg ggcaggtgcg cgcgatgccg cgcatcatca acggcaacat cccgctggcc    67560
ctgtgccccg tggactttag ggacgcgcgc ggcttcgagc tcagcgtgga ccggcatcgg    67620
ctggccccgg ccacggtggc cgcggtgcgc ggcgccttcc gcgacgccaa ctaccccatg    67680
gtgttctaca tcatcgaggc cgtgatccac gggagcgagc gcaccttctg cgcgctcgcg    67740
cggctcgtgg cgcagtgcat ccagagctac tggcgcaaca cgcacaacgc cgccttcgtg    67800
aacaacttct acatggtcat gtacatcaac acctacctgg gcaacgggga gctgcccgag    67860
gactgcgccg ccgtgtacaa ggacctgctg agcacgtgc acgccctgcg cgcgcctcatc    67920 ggcgagttca cgctgcccgg ggacccgctg gcaaccagc cccaggagga gctcaaccac    67980
gcgctggcgg acgccacgct gctgcccccg ctcatctggg actgcgaccc catcctgtac    68040
cgcgacgggc tcgccgagcg cctgccggag ctgcgcgtca acggcgcgca ctttcagcac    68100
atcctgtggg tcgagatggc ccaggtgaac tttcgcaacg tcggcggcgg cctggtgcac    68160
aaccggcccg tgcggaacga gaaccagccc ctgcacccgc accacgacgc cgagtggtcg    68220
gtgctgtcca agatctacta ctacgccgtg gtgcccgcct tctcgcgcgg caactgctgc    68280
```

```
accatgggcg tgcgctacga ccgcgtgtac cagctggtgc agacgatggt ggtgcccgag   68340
acggacgagg aggtgggcac ggacgacccc cggcacccgc tgcacccgcg caacctcgtg   68400
cccaactcgc tgaacgtgct cttccacaac gcctgcgtcg ccgtggacgc ggacgccatg   68460
ctgatcctgc aggagacggt gacgaacatg gccgagcgca cgacgcccct cctggcctcg   68520
gtggcgccgg acgcgggcat ggccacggtg gccacgcggg acatgcgcac gcacgacggc   68580
tcgctgcacc acggcctgct catgatggcc taccagccca acgacgccac gctgctcgag   68640
ggggccttct tctacccggc gcccgtgaac gcgctctttg cctgcgccga ccacctcggc   68700
gccatgcgcg acgtgggcgc cgaggtgcgc ccgccgcccc agcacgtgcc ctgcgtgccc   68760
cactttctcg gggccaacta ctacgccacg gtgcgccagc ccgtggccca gcacgcggcg   68820
cagagccgcg ccgacgagaa cacgctctcg tacgcgctca tggcgggcta cttcaagatg   68880
agccccgtgg ccttcaccca ccagctgcgg cgccagctgc accccggctt cgccctgacg   68940
gtggtgcgcc aggaccgctt cgccacggag aacgtgctct ttgcggagaa ggccagcgag   69000
tcgtacttta tgggccagat gcaggtggcg cgcaccgaga gcggcggcgg gctgcacctg   69060
cagctcacgc agccccgcgc caacgtggac ctgggcgtgg gcttcacggc cgcgtacgcg   69120
gcggccgcgc tgcgcgcccc cgtgacggac atgggcaacc tgccgcagaa cctcttcgcc   69180
acgcgcggcg ccccgcccat gctggacgcg gacgcggacg actacctgcg ccgcacggtc   69240
aacgccggca accgcctggc gcccgtgccc gtcttcggcc agatgctgcc ccaggtgccc   69300
gcgggcctgg cccgcgggca gcagtcggtg tgcgagttca tcgccacgcc cgtctccggtc   69360
```

```
gccaacgccg tgatccagct gggcagcgcc acgcgcgagc tcggccagct ggtgcggcag   70740
cccccgccgc cgctgccgca agaccacgcg cggcgcttct gcgtgttcga ggcgctggag   70800
gcctggatcg cctcggcctc gcggctgggc gacacgctcg gcacgcggcc cgtggcgcgc   70860
gtgtgcatct tcgacggccc cccgaccgtc ccccccggcg agaaggccgc ggtggtggag   70920
gtgtgacgac gcggcgcccg cggaggatgc ccgcccgtcc ccctcgcccc ccctccctcg   70980
caaataaacc cgtgaaggaa aaaacaaga gaaacgagtc gtgcgtgtct ggcgtttatt   71040
ttccgggccg gggtggcgag gcggggcgag ggaggagggg gcgcggggtg gccccgggag   71100
aggggggcgc gcgtcctccc ctcaggcaaa cagcccgtcg ggcagcgtgc tcaggtgcac   71160
ggccatgacg agggccacgg cgaggtcgtc ggcgcagccg ccgcgcttgc cggtgaagac   71220
gcggtgctcg ccgcccccg aggccgtctc cacgaggttc ccgagctggg cgttcaggta   71280
ctcgacgggg tcggcgcgcg cgcccacggt cacggacacg agctcctgcg aggccatgac   71340
ggcgcccgag ttgaactgct tgacgaaaaa gtcgaaggcg ggggtctttt gcttctgcag   71400
caggaagaag gggtagcgca cggcgcccgc gcccgcggcg ccgtggtggt agaagaccac   71460
ggccgggtcg gcgacgacgc gcgcggcgcg cagctccgcg agctcgcggc gcatggcgcc   71520
cacgatggcc acggccgagt cctggctgct gttgccctcg acggccacgc gcaccgccga   71580
gaaggcgccg tcgtgcagcg ccagcacgcg cgccaggcag cgcacgacgc agcgcgcgat   71640
ctcgtcggcg gaggcgcccg tgagcgcgcg caggaaaaag tgctccaggc cgagcacgat   71700
ccagctgcgc cggtagctgc ccacgacggc cacgccggtg ccggaggcgc gcgcgttggc   71760
cgtgaaggcc gggtccacgt acacgtgcag cgtgccggcc agcaggcggc ggttggccac   71820
cgaggagggg cggtagagca ggaagcgctc gccggcggcg cgcgtgagga cgggcgcctc   71880
gcgcgcggcc acggcgccgc cgaggatctc ctgcatgaag gagtccggga gcagccgctc   71940
ggccgtggtg cgcgtggcgg cgtccatggt gatgaagacg ggcttgttga gcacgtagca   72000
cgagcaggcg gtggcgtcgg tgtgcgccac cacgcggcgc atgtgctcgt cgcagacgta   72060
cgtgaccacg ttgagcatgt cggtgccgcg gaggttggtg aggaagctgg tgctggccct   72120
gccggtgttg gtggaggaga cgaagatgat cttgcagctg gcctggttca tgaagccgag   72180
gatggtctgc acggcatcgg ggcgtataaa gttggcctcg tcgacaaaga gcaggttaaa   72240
gtcctgtccg cggatcccct gtaacgacac gcggggagag agaggggggg acggtgagcg   72300
gcgccgcgat ggacgcccac atcgccaacg agaccaagca gcagatgacg cgcttcgcgc   72360
ccgcgctcgt gcacgtcatc gtcccggacc ccctcctggc gcgcgcgggc gtggacccgc   72420 tcgcgcccctt cgccgcccac gcgcagacgc gctaccacgg ctcgggcgtc tgcgagccgt   72480
gggtctccgt gttcgcgggc cacgtgcaga cgggcgccgt cgagagcgtg ctgacgctgc   72540
cgccgctgca gcgcccgcgc ggccccgggg ggctgttcgt ctcgctgccc ctggcgctcg   72600
gcgcccactt tgacggcttc acgacggcgg cgctgcgcgt gggcgcgcgc gagctggtct   72660
tcacctacga cgagctcctg ccggcccgca cgcgctacaa cgtggacggc gagcgcctgg   72720
agcgcctgtg ccgccagttc gccaactacg cgcgcgcgcg gcgcgtggcc ccggcggtcg   72780
cggccgcggg gggccacatc gacgcgctgc tgccccggc ggcggccacc atcgacggcg   72840
aggcgcagct gacgcgcggg ggcttcgacg acccggcggc gccgcacgcg cgggacgccg   72900
accgcgagat cctgtcgctg gtgcgccgcg cggccgagct cgtcgcggcg cggcacccgg   72960
tgcgcagcca cgtggcgagc gggctgatgc agggcgccct cgcgcggcgc ggcggcggag   73020
```

```
gagacggcgc gggggcgctc gaggcggcgg cgacggtgcc ggcgcccgcg gcgcgcgagg    73080
acgcgaacgg cggcggcgcc gcctggcgcg acgagctcct gctcacgccc caggacccoc    73140 ggccgctgac ggcgctcgac tggctggacg cgggctacgc cgcgctcgcg ggcggcgacg    73200
cgcccgcgca cgtgtggcgc cggcggcccg tgtccctggt ggcgcgccgc cactaccaga    73260
ccggcgagac gttcgtcgtc gtcgcctacg agcactccac cgcctggggc ggccggcgcg    73320
ggccccgggg cgagcccctg gcgcgcgtgc tcgccgagga gtgcgagcgg cacggcgtcg    73380
agcacccgcg cgccctgccc gcggaggcgc ggcgggagct ggtgcggcgg cacgccgagc    73440
tggccgtgcc gctgggggac gaggagccgc cgctgccggt ctttgacgcc accgcggagc    73500
tggtgctgct ggagcgcttc cgcaacgcct gcgtgcgcgc gctgctggcc ggcgtccgcg    73560
agtccgtgcg ccgcgagccg cgcatgcgcc agatcatcga gttcgcgatc cgcccgcgcg    73620
accgcgaggc cgtcctcgac gtggccgggc gcgcccggc gctgctggac gcgttcgcgc    73680
ggcgcctcga gcacacgccg gcgcgggaga tggtcgactc gggcctgatg acggccgcgg    73740
cggcgcacct cgccgcgcgc gccaccgccg gctacgtgac cttcgagagc ggcccgctgc    73800
tgggcggcgt tttcctcttc gactactaca gcgccggcgg ggaggttata agggtgacgc    73860
gggccccgct ggccgtggca gtggagccgg cgacgcgcgg gcagttcgcg tgtcgcttcc    73920
gaggcgcgtc gcatcgctgt ctcccgggcg agagctacgc gtacctctgc gtcggcgtgt    73980
cgcgggacct gcgcgcgctg gtggtgctgc ccggcggctt cggcttcttc gcgaccctcc    74040
ggctggagtg gcccgccgcg ctggtggacc ccgtgctcga gcgcctgtgc cgccgcgtgt    74100
agcggggcga ggggggcggg cgcgcgccat ggaggtggcc gcggccctga cggaggactt    74160
tgccgcctgg cggctgctgc gctccgactc gcgcgtcaag gtctacgccg ccctcgccgt    74220
cgtgggcgcg cgcctggccg ccgtggccgcc ggcgccgcg accgtcgccg cgcgcgtcta    74280
cctgacgcgc ccgcgggcgc tgcgcctggc gcagggccgc ttccacgtcg tggtcctgct    74340
caacgacgcc gcctacgcgc tggtggcggc cgtgaccacg accacgctcc gcgggagcgg    74400
cggcgagctc gtgcgcctga cgctgggcga cgcgagcctc gaggcgctgc ccgccgacct    74460
gcccgtcgcc gagcccgtgc ccgccgcgcc ggcgggccgc ctggacctgg acgccgccga    74520
gcccgtggcc gcggcgccgg cgggccgccg cgactgcgtg gtcctggccc ccggcgcgtg    74580
gtgggcgcgc ggccgcgtct acttcctgca gatggacccg aggctgctgg cgctgtgccc    74640
cgcgggctgg cgcgcgcgcc acctcggcgc cgtgctcgcc gggctgctga gccccgcga    74700 cgacgacggc ggcagctgct gccgcgagtg ccgcgtggag cacgtggacg ccctcaacgc    74760
gacgccgcac cccgacgggg ccgccgcgcc gtgcctgtgc gccgcgccgt gcctgtggcg    74820
ccaggcggac aagcgggagc tgcgcgcgag cgactcgggc ctcttccgcg tgctgttcct    74880
ggacgccgtg cggttcgtgc gcatgctccc ccgccgcaag atcgtcgacg tcgcctccga    74940
gctcatcggc gggctggacg cccgcgggcg ccacgtggtg gtcaacgacg ccggctggcg    75000
cctggtggcc ctggacccgg acgcgagccg cgcgctcgtg tgcgggtgcc cgctgctgcg    75060
cgcgctctgc gaccccccg cccgcgccat ccccgagcta ataaacgatt attgaaatga    75120 aaaaatggg tacttgcgtt tgtattgtgg ctggaggcga acacgatggt gctgcgcgcg    75180
ccgtcgggga aggtgacggt gatgttctcg cccttgacgt ggtccacgcg cgcgtcgcgg    75240
caccagcggc gcaggcgcgc gtggatctcc tcgaacacgg gctccgtggc cttgcggatg    75300
tgggccgtgt agccgacgcg gatgccgcgg aaggtggcca gcgcgagggc gatgagcggg    75360
accaggaacc aggtcttgcc gtggcgccgc ggcacgagga agaccgtgac gcgctggcga    75420
```

```
aagtggcgca ccgcgtcctc ggagaagagc ggcgtgtcga aggccgccag caggtaggcg   75480
gtggcgcgct cggcgtggtc cccgagcagc accgtggcca gaaagtacac cgcgtgcatg   75540
aggatcatct tctggaagag ctccagcgtg ccgcgcccgc cgccgccttt gccctcgccc   75600
ccgcctccgc ggccgcgccc gcctccatcg tggccctcct cggcggcgtc ctccggcgcg   75660
gggccgggcg cgcccttcgc gccgccccgg gccctctcgt ccttctcctc ttccccccca   75720
tcctcctcgt cgccgtcgtc gtccccgggc ccgccgccg ccgccgtccc gagggcggcc    75780
gtcgcggcgt cgcggaagga gcgccgcgac aggagcgcga agcggttgac gaagcgccgg   75840
agctggcgga aggccccgga cgtccgcatg gcgtccaccg ccgccatggc gctcgtgtac   75900
gcgttgcggt ggaaggccag gcgctcgccg tcgtaggcgg cgaagtcgag cgcctcggcc   75960
gcgcgcgcga gcgccgggtc cacgcgcgcg cggccgcgcg cgcccccgaa gagcgcggcg   76020
cgcgcgagcc cggcgaagat ccgcgcgctc tcgcagcagt tgtgcagcgt gccgaccgcc   76080
gggaccaccg tctggtggcg ctgtgggcg gcgatggcaa agttgaaaaa gcgggcctcc     76140
tcggcgcagt cgcgctcact ggcctcgcgc ttgcgcttga ggtccgcgta gtagcgccgc   76200
gtcgcgtcgc ccaggccgaa catgctcgcc tcggaccgcc gggagcgccg cgtgcgcctc   76260
gaggaggcct ttcggcgcga gagcgtcttc aaggcgcgca ccgtcgagct tctgcgcggg   76320
cgcgccgaca agaaaaaccc cgagttcgtc cgggccttta tggcggccaa acaggcccgg   76380
cgggatgtag agcgccacct gcggctggcc gcccgggtgg agtctgtgga acaaaaagcg   76440
cgcgcgctgc aggcccgcgt ggaagcccag gcggccgtcc gcggggtcct ggacaggcac   76500
cggcggttca cgcgggcgga ctttgcggag gcgctcgacg ccgcggagga cgcgctcgcg   76560
gccggcgagg accggctcga cgacgcggcc gcgctcgacg aggactgggc cggcggcggg   76620
gcgcccgacg aggacgaggg ggaggaggcg gacgaggccc tgctgaccca atggctgctg   76680
gaggaggcgg aggaggcgtg agccgggtcg cgctggcgcg gccgcccatc caccgcggca   76740
cgtccgcgcc gggcggcgcc atcgccgccg ccggcggcga cggggacggg gacgaggcct   76800
cccggctcct gggccgcgcg cagccgcgcg aggcccccta cctgatcccg cgcccggacg   76860
gggacctcgc cgtgccggac gacctgcagt acgcgaccct cgacctcacg ggcgaccccg   76920
tggccgtcgg ggccggatcg tacggcagcg tgctcgtgta cggctcggtg gccgtgaaga   76980
cgctccgcgc cggcttcggc cacgaggccg tcatgacgct gctggccgcg gaggaggcgc   77040
gctccgccgg cgtccgcggc gtggtgcgcc tgatgggact ctcggcgccg ctgcgccagc   77100
tcatgttccc ggcctacgag atggacatgg acgcgtaccg ccgctcgctc acggcgcgcc   77160
cggggcacgt ggtgcacgcc ctggggcgcg tcttcaccga gctcggccgc gcgctcgtgt   77220
tcctcaacgg ccgcgggctc agccacctgg acgtcaaggg cggcaacatc tttgtgcgca   77280
cgtgcggcaa catggtcgtg acggccgtca tcggggactt tagcctcatg gccctcaact   77340
cgcgcagcgc gctcgcggac ccgcgcttcc ggctcgcgcg ccgcaaggcg ctgaagatca   77400
cgtcgctggc gcggagcccg ccgacgggcg tcctcctggg gcatgcgcgc gaccggccca   77460
cgcgggtgct gatggacttt attaacgggc gccgccgcc gccgggcccc ctgccgtacg    77520
aggtgggcct ggcgatcgac ctgtgcgcgc tgggccacgt gctgctggac gtggcgctcg   77580
gcctgcgccc gcagcgcggc caggcgctga cgcgcgagta cgccgtggag gtgctcgcgc   77640
gccgctgcgt gctcttcgcg gccctgctcc cgccggcag cggcccctcc gccgaggccc     77700
tcgccgggga catcctcgag gaggagctgg ccgccggctt ccgcgagggc gtggccagct   77760
```

```
cgcgccccgg caaccagccc ccgcgcacgg tggccccgct gctcgagctc gtggcccggt    77820
tctgcggcga ggatggcggc gctcgttttg ccgaactcgc tgcctgagga gctgccgcg     77880 cgcaccttcc tgcggttcct gcgcggggcg ccgcgccccg cggccggcgg cgcggcgccg    77940
ctggcgtacc gcctggcgta cgtgcacgac ctgctcgtcg agctggcgcg ccacggcctc    78000 gccgccccg acgcggccgc ggcggccttt ggcggcgcgc gcccgccgcc cgcgcccgcg      78060
ggcgtccccg ccgcggcggc gcgcgccgcc atcctgacgg tggaggcggc cacgcgcgcg    78120
cagagcgaga gcgacctgtg gacgctgctg cgccgcgggc tggccacggc ctcgaccgtg    78180
cgctgggggg cggacggccc gcgcttcccg ccgacgtggt gcgaggccag cacggcgcgc    78240
tgcggcacgc ccgacaacgc ggcgctcatc tttggccgcg tcaacgagag cgtggcccgc    78300
gccgccgtcg cggccctgta cgccgaggcg cccacgccgg acctgccggg ggcgatcgcg    78360
ggcggcggcg acgatggcgg cggggacggg gcgaaggagg agatgttcac cttcgacgag    78420
acgggcgcgc ccccgccggg ccacgacctc ttctcgtgcg ggctgctgct ggacccgcgc    78480
accggcatgg tcgggccctc gctggacctg ctggtgtgcg atcgcgacgc gatcgggcgc    78540
ctggcgccgc accgcacgca gacggagatg cgcttcttcg agatcaagtg ccgcgccaag    78600
tacctgttct cggcggacga cgcgagcccc acggcgcgcg cgtacgcgcg cctgctcgag    78660
cgccccgacg cggacacgct gcgcgggttc ctgtactcca tcgcccggcc gggcgtggag    78720
ttcttcgagg gcgccccggg gccggcgag gcgctggcga cggcagaccc cgcctggcga     78780
cgcgggggcg ccgaggacgc cccgccgacg cgccggaggt gtggcgcctt cgacgggcgc    78840
cacgtcgccg cgaacgcgca cgcccagtcg gaggtctggc tatttagcga cccggtggac    78900
ggccgtcagg acattgtgcc ctgggcctcg ggcgagcgcg cgctgagggt gcccgtgttc    78960
gcgaacccgc gccacgccaa cttcggcag atcctggtgc agagctacgt ggtcgccggc     79020
gtcttccccg accgcccgc gcgcccccac ctggccacct tcttcggccg tcgccgccgc     79080
ccctgcgagc agaaccggac gctcgacctg gcctcgctgt gcgacgtgcc gccgcctgc     79140 gccgtgcccg tgctgctgat cgtcacgccc gtctccgtgt gcgaggaggc gttcgaggac    79200
ctgcggggcg cgcgccgagga ggccttcgc gtcaccgcgt cgcggacatg ggacagtgct     79260
gctgccgatt ctccagcaac cgcgtcgtga cgagctccgg cgaggtgctg accttcgacg    79320
cggacgcgtt cgaggacttt gagctcgagc ccatggtcgg cgagcccggc cccgtgcgcc    79380
ccaaggcccc gtgccgcgtg tcgcgcggga acctcgcga agcctcgcgg gcgtactgac     79440
tgcaataaac ccgtttgtca tactatcgca tcgttcccgt ctggtgtctg ggggagagga    79500 tggggagag gatgggggag aggatggggg agaggatggg ggagaggatg ggggagagga     79560 tggggagag gatgggggag aggatggggg agaggatggg ggagagagc cgtgggtgg       79620 ggcgagatgg aatggcacac gggccgcaaa gtgggacgat ggggacgggc ctcaacgcgg    79680
gacgagggcg gcggggcggg accggggaca agggacaagg gcggcgagag acggacacga    79740
gaggaccatg tgcgatcgaa acagaacgtt tattcaaagc cgaggttctc gtacacgacc    79800
tcgtcgccgt cgtcaaactc gtcgtcgccc gacccggggg ccagcaggta tcgtcgttg     79860 ccccggccgt gcaggcgctt ctgcaggtac cgccggccg tcgtccgcgc cttgtccacg     79920
ttggcgtaga accggctgcc ccgggcgcgg tgggcgatgc aggcgcggac caggcgcacg    79980
acgatcatcg ccagggcgat cagcgacagg accgccagga cggcgcgcgt cccgatgacg    80040
acgccgtgcg tctccccgag ggcctcgctg aacttggcga agtagcggtg gcggacacg     80100 ccgaaggccg cgctggccac gagcacgcag aaggccggcg tggggagcac ctgcacgtag    80160
```

```
ccggacacga cgacctcgac gaacaccatc agcgccagcg ccagcagcgt gaacacggcc   80220
agggcggcct ccgccgtctt ccagaggctg atgtggaagc tgttggccag gagcacgccg   80280
agcatcagcc cgaccacggc cgcgcccagg ccgaccgcgc cgaggacgac gttcgtcacg   80340
acggcgcgcg cgtgcaccgc cacgcggcgc agcgggggc tggccgccag ggcggcgcgc   80400
acgtcacccg tgcccttgca ggcgtggcac gccccaaaga gggcgagaaa cacaaaatgg   80460
gtgatgtagg cggcggcggc cagacccgcc tgcttgtggg ccatcagcag cacccacggcc   80520 tggagggtcc aggcgcagag cgcgccgagc atcagggtcc ccggggcggc caccgtcgac   80580
gccgcgtaga gcaccacgct gggctggaac ccagccggc cggcctcgcg ccgcagcacc   80640
acggcccccg cgaccgcgta cagggcgtgc gccagcagca cggtggccgt gaagccgaag   80700
aagctggtca cggtgggcgt ttccagaaac agggcggggg ccacgagcgg ctggcgcgtc   80760
cacacgccgc cgggggcgtc gttgagcgtg tcgtagtcgg ccacggtcgc gtaaaagcac   80820
gggaacccca tttccgggag cgaggcgaag ataagggtga ggaccagcgt cagggcggcc   80880
agggcgaacc cgcagacctc tatcagccag gagcgccagc tcacggcctc ggcgttgcgc   80940
ggcccgcaca tggcggcgcc cgcccgcgtc cgccgcggcg gggccgagga ggacggcggg   81000
gcgttcgcct cgagcgtgtc gctcgcgcgg atgctatacg gttgcgacct cccggccgtg   81060
gtgcgcagcc gctggccggg cgtctccctg gacctgcagc gcgacgcgcc cgtcgagctt   81120
ccgtccccgc acgataccgc ctgccgccgc gtcctcgtgg cgcgcgctcc gatgggctcg   81180
ggcaagacga cggcgctgtt gaaatggctc tccgcggcgc tggcggccac tgatatgagc   81240
gcgctggtcc tgtcctgccg acgcagcttc acccgcaccc tggcgagacg aatggacgac   81300
gcgggcctgg gatttgtgac gtacttcgac tcggacgcat acgtcatgac gggccggccc   81360
taccgccggc tgctggtgca gatcgagagc ctgaccgcgc tggacgagca cctgatcaac   81420
aactacgacg tgctcgtcgt cgacgaggtc atgtccacgc tcgggcagct ctactcgccc   81480
accatggcgc ggctggcccg cgtggacgcc ctgctcgcgc ggctgctgcg cggctgcccg   81540
cgggtcctcg tcatggacgc cacgatcaac gcgcagctcg tggagctgct cgtggagctg   81600
cgcggcgagc ccagcgtgca cgtggtggtg agcgactacg ccacggccgc cttcgcgagc   81660
cgccgctgcc tcgtgctccg gcacctcggg gccgaggtcg cggcgggcgc ggcgggcgcg   81720
cgggaggacg gcggcggcga cgggagcgag gacgcggcgc gggccgggag ccccgccccg   81780
acgacggcgg cggcgacgac ggcggtggag gcggcggggg cggcggggga cagcttcttc   81840
ggcctcctgg gcgcgcgcct cgccgcgggg gacaacgtct gcgtcttctc gtcgacgctg   81900
gccttctccg agctcgtggc gcgcttctgc gcgcgcttca cgccctccgt gctggtgctc   81960
aactcgcagc ggccccccga ggacgtgggc cgctgggccg tgcgcgccct cgtctacacc   82020
accgtggtca ccgtcgggct cagcttcgac gcgccgcact ttcacagcat gttcgcctac   82080
gtgaagccga tggcgcacgg cccggacatg gcctccgtct accagtccac ggggcgcgtg   82140
cggcggctgc tgcgcgacga gctcttcgtg tacgtggacg gctccggcgc gcgcggcgag   82200
cccatcttca cgcccgtgct gctgaaccac gtcgtgggct cgggctggcc ggcgcgcctg   82260
tcgcaggtga cgaacctcgt gtgcgcgcag ttccagcgcc gctgccgccc ggcgttcgcg   82320
gcggcgcgcg ggatgcgcct cttctcccgc ttcaagttca agcacctgtt cgagcgctgc   82380
acgctgacga gcgtcaacga cagcctcaac atcctgcacg cgctgctgga gaacaaccgc   82440
ctgcgggtgg cgctcgaggg ctgcgagccg ccgctgacgg cgcgcgcctt ctgcgacttt   82500
```

```
ctgcgcgacg cgcgcctgga cgccttcgcc agccagcagg tgctgcggca gctgcgcccc    82560
ccggaccggc cggtggcggc cgacatcgcg gacagcggcg aggtggccac cttcgtggag    82620
aagtacctcg tggccgacgt gcccgaggac gagctgcagg agctgctgcg cgcgctcgcc    82680
aaccccgtga cgcgggagca gtttgtgggc ctggccgtgc tcggcgcgtg cgcgcgcgtc    82740
cccgaggcgc tgcgcagcga gcgcgtcttc ggggccgtgt acgggcacta cgcctccggg    82800
gccgtgcccg tggtggccga cgggcggctg gagctggcgg cgctggcccc cgacttcaac    82860
gtgcccgcgc gctgggccct cacgcggcgc tgcgcgcgcg tcgcggaggc cgccgggctc    82920
ttcgagggcg cctcgccgga ggtggactcg gccgcggtcg cggcggcggc ggccgacgcc    82980
gagctggcgc cgctgctgct cgaggtgctg cggtgccacg tgctggacgc gacgacggcc    83040
gcgcggcgcc ccgtgcgcgc ggccctgagc gcgctggggg cgggcggggg cgcgggcccc    83100
ctgagccgcg ggcgccacgc cgcgctcgtg ttcaaggtga tgtgggagga ggccttcggc    83160
gtgcgcgtcg gccgcagccg gcagacgttc ccggggccca cgcgcgtgaa gaacctgcgc    83220
aaggccgaga tcgccgcgct gctgcgcgac gccggcctgg acccgcccgc gggcgccacc    83280
caccggcagc tgtacgccct gctgatggaa cgccgggggg actttgcggg ggagaggtat    83340
aaactgcgcc tgcccgcctg gagccggctc atgtacctga cccagggcgg cttcgacgcg    83400
ccgctggacg ccgcgctctc gctcgtgccc gcggaggcgt ggccgcgcac cgaggggggcc    83460 gtggactttg cggcgctatg acggccgcgg cggggggagcg cgtgtgcgcg gccgggatct    83520
acacggcctg gacggagccc ggcgcgccgg gcgagctcca cgcgctggcg cacctgctgt    83580
gccgcgacgg ggcggcgcg tacgcggcgc gcttcgtcca cgtgacggcg gtgccgtgga    83640
cgggctcggc ggccgcggtg gccgcggcgc tgcgcgacgc gagcggcacg ggggcgctgg    83700 cggaccggc gctgtggcgc ggcgcgcacg gcgcggtcat ggcggccctg cgccgcgccc    83760
tcccggcgct ggccttctac gagccgctgc gcttcgagac ggacccggcc acgaacctgg    83820
tcacggccgc gacgccggcg ggcggcggcg gcgaagagga cgaccgggg gagggcggcg    83880 aggaggacga ggacgaggcc ggcccgcgcg cgggcatcat ccacgtggac gccgacgtcg    83940
tcgtggaccg cgacgccgcg cgcgcgcacg ccaccgagcc gtggctgccg cacgcccagc    84000
tgcgcgccat ggccggctgc gccgcgctct ccgtcgagat cacgacgcgg cggaccagct    84060
tcgcgcgcgc ctacgcggag gccgcgcgc gccgctgaa cgccggggc gagatgagcg    84120 acctctttga cgtgcgcgag acggtgctgc ggcccgcggg ccggcgcgtg gcggcgcgcg    84180
tgctcgtccc gcgcggcttc gactgcctgg tgcccacgg cgtgagcaac gcggcgctgg    84240
tggcgctcta ccgccggtgg cacgcggccg cgtacggcgc gggcgacgcg accccgcccg    84300
tcttcgcctt cctgggcccc gagctcgccc gcgaggcgc ggacgaggac tactactgcg    84360
cgctgggctt ccccctgttt gcgacgatca aggtggccgc ggccgcgccg gaggcggtcc    84420
gcggcgcgct cgccgcccac cggctcacgg acgggctgtg gccccgcgctc ggcttccgcg    84480 ccttccacgc cctcgggccc gtgagctgcg gcctgcgcct gcgctgcgac gtctggccgg    84540
cggggcgcgc gaccagcgcc gtggagcacc cgtgcgccct ccgcggggcc tggctggcca    84600
agtttgactt cgcggccttc ttccccaacc tgtttctggc cctgtgcccg ggccacgagc    84660
ggctgcggcg cgccgtgcgg gcgcgcgcgg tcaagccggc gctcgtggcc ttcttcggcg    84720
ggctcaagca cacgtgcccg gaggcgtacc acagcgtcat cgcgctggcc aacggcgtct    84780
cgcgcgccgt cgaggcggcc gcggccgagg ccggcctggt cacgtgcgcc tacgtcaagg    84840
acggcttctg gggcgtgctc ggcgacgtgc ccgcggccgc gccggaggcg gccgccgcgg    84900
```

```
ccgcggccga gcgcgtgcgc gtcgcctgcg aggccgccgc ggcgcggcac ctggccgacg   84960 cggggggccgc cgcgacggac gtgacgctgc gctgcgaggg catcttcgac gcggcctgg    85020 cctggtcctg ccacgcctac tggctgcggg ggcgcgaggg ccccgcggac tttgtcggct    85080
tcccgtcgcg cagcggcttc ggccgcgccg ccaaggccgc gctggacgcc ctgctgcgcg    85140
aggccgtcga gggccgcgcg gacgccgagg ccgcgcgcgc cgcctgcgac ggcctcgtcg    85200
agcgggcctt cgcctcgcgc cacgaccccg acttctgggc cgcgccgggg gacgccctcg    85260 ccccgccgc gtgcgcaggg gcgaccgccg ggcgcggcgg cgcgcgctgc tcgcggcgct     85320
gcgtgcgcct gcgcggcgcc ggcccggtgc cctacgagca gctgcgcccc ccgctgatcc    85380
tgccctggat agactgtctg gcccacatgg agcccatctt cgccgccctc gtcggcatgt    85440
acaaccgcgc gctcgaggcg ctgagcgccg gcgacgcccc ggccgccttt gtgtttacat    85500
acacgccgga cgcgtttctg tttgggtaaa caataaagtc tgtttattgt cagaacgagc    85560 cacgggggtcc cgcgtcttgc tctcgtccgg ggtcggggggg gagcgagaga gggggagagg  85620 gggggaggggg tgagggaaga gagggatggg gaagggggaag agggagagga gggtgggggg  85680
aggaggggcg cgcttcactc gtagcgcaca aacatggtct tctcggtgag cgcgcgcggc   85740
gccgtcgtcc accagcggta cacggcctcg gccatctcgg gcgtgcgcag gggcgcggtg    85800
agcgcgccgc cggggcgcgt ccgcaccagc ccgtcgggcg gcggcgcgtc gcccggcagg   85860
ccgagcaggg gcccgaaccc ggcggcgaag agggcgtcca cgacgggcgg ggcccggggg   85920
gccgacagca ggcgctgggc gatgggtag tggggcagca cgcgcgtctc gtcgagcggg     85980
ctgaggtggg ccgcgaacat gagcgtgttg agcgcgcgcg tggcgccgac gtgcagcagg   86040
cgccgcagct tccgcgccgg cggggcgcgc gcgcgctcca gccaccggcc caggctcagg    86100
caccgcgcgg cgtccgcctc cgccgcgggg cagttctcca ggaacatctg cagcacgcag    86160
agcgcgaact ccgtcgggtc ctcggggcgc accagggcca ggcggtgcgg cagcgccacc   86220
ggcggcacgg ccagcgagag cacgcggtcc tcggcggccg tgaccaccgc gaaggcgaac   86280
ccgcggaagg cctccccggc gaggcagcgg cggcggtact cgtcgcagga caccgtctcg    86340
ccgctctcga ggcgcagcgt cagcgcgccg ccctcgacgc gcgcgtcagt caccgaggcg    86400
ctcgtgaaga ccgggatcag cccgggcacc tcgcgcacct cgcacaccag ccgcgggagg    86460
gcgtgccagg tcagctcgtc catcacggcc tccatcgcgg agccgctcgg tcgcccggcg    86520
cacgtccgcc gcgaacagcg ccgcgatctc ggtcaggtag gcctcgaggc gcgtcttctt    86580
aaacaccacg ccgcacaggt cctcctccga gcggtacacc tcctggctgg tgatgaggaa    86640
gccgaggtgg cgcacgcgca ggatggagaa gaagtacggc gcgaggatga gcgagatgga    86700
gctgttggag tacgagacgg acacctcctg gccctggttg ttggccacgc gcgtcagctt    86760
gaagcagcgg atcagctcct gctcccagag ccgcgagagg cgctccacgt ccgactcgta    86820
cggcggcacg tagcgcgact ggaagctgtt ggccacgtag gcgtcgtcgc ccatggcgcg    86880
cgtgatgtcg atgacctcgt ggccgaggtc ccgcggcggc tggccgtccg cggcgccggg   86940
cgcgcgcccc ccggcggggc cggcggccgc ggtcccgtcc gcgcccgcct gcgcggcgcg   87000
cagggcctgc tcgcgcaggc gccgcacctc ctgctcgcgc tcgcgcacct gctcgcggag   87060 gccccccgttg tccgccttca ggctctcgat ggtcttgaag aggttgttga cgtagccctc   87120
gagcatgccg ttgatgctgt tgaccacgga ggtgcggaag gcgtcctgca ccggctgcgc   87180
gccggcgccg tggtgcccga agcccggctg cgacgtgtcc acgctgtcca ggatgcgcgc   87240
```

-continued

```
cccggtctcg tcgaggtacg agcgcaccgt ctccgtgatg tcgccgatgt ggcgcatgcc    87300
cttcatgttc acgatgaggc gcacgaggcg cgccgcggcc gagcccgccg ggtcctcgcc    87360
gagcatcttc tccacggcgc cggccgggtg cccctcggcg ggcttgcgcc cgacgagcac    87420
cttcaccggc gccgtgttga gcagctggca gaggcgcgcg tgctcgcgca gcgcgtggca    87480
cgccagcacc tcgccgtgca cgcgctgcgc cggcgagtca aagagcagct cgccgtcgcg    87540
ccacagcggc tgccagagca ccaggcactc cccgcgctcg cccgtgagcg cgtcgcgcgc    87600
cagcacgcgc cggtgccggg gctcgtagta gagctgcacg cggtcgtagt ccatgatggt    87660
gacgccgcgc atggcctcgg cgagctcggc cacctcgtcc aggccctggc ccagcacgct    87720
gccggcgacg cgcaggtgcc cggccaggtc gtgctcgtcc acgcagcgct cgcgccgccg    87780 cttcccccg gggcgcgccc ggcgcaccgg gaccacgccg aggcacacga tccagtcgat    87840
gtacttggcg aagctggccg tgccgttgga ctcgctggcc gagaagcagg ccgcgatgcc    87900
gcgcacaaag tccaggaggg ccatctgcag cgtgcggtac caggtgtcga agaggcgctc    87960
ggccacggcg ggcgcctcgt cgccgaagcg ccgcgccagc gcctcggcgc cgaggccgcg    88020
cgcgcgcagg tgcgccatcc agtcccgggc cacgtcctcg tagcgcgccg cgttgagcgt    88080
gcgcgtgagc agcgtggact ggatctgccg cacggcggcc tcggtggagc gcaccgagtt    88140
gtagatgccc tggccctcgg tgtagcccag gttgcccatg aggatctcct tgaagaccat    88200
ggtgcgcggg gtggggtgga tgaggatccg cgagggggcg cccaacaggt tattagcctc    88260
ctccgcggcg ccgccggggc agagcccgtc cgcagccgcc gccgtcgcag ccgcagccga    88320
catgccgcgc gccgccgcag agggtccgcg cgccaccaac gccacctatc tgaactttac    88380
gtccatgcac ggcgtcgagc cgatcgtgga gcgcgtccgg gagctcgccg cgacgcccgc    88440
ggaggcgccc ccgccgctgg cgtggttcaa gtccctcgcc gcggcgggaca acccggtgga    88500 tatagaggcg ctggagctgc ccttcgccgc gtacctgatc agcggcaatg ccggctccgg    88560
caagagcacg tgcatccaga ccctcaacga gaccatggac tgcgtcatca cgggctcgac    88620
gcgcgtcgcc gcccagaacg tctacgccaa gctctcggcg gcgtactcga ccgctacgt    88680 gaacaccatc ttccaggagt tcggcttccg cgggaaccac gtgcaggcgc agctcggggcg    88740 ctacagctac gcgtgcccca cgagcccgcc gacggtgcgc gagctgcaga gcgcgacct    88800 ggtgtactac tgggaggtgc tgcaggacat ctcgcggcgc gtgctcgcgg ggagccacga    88860
ggagtttgcg cgcctgcgcg ccctggagcg gctcacgggg cgcgcggcgg agcacctggc    88920
cttcgcgtgc cacggctcgc tgccggcgtt cgcgcgcagc aacgtcatcg tgatcgacga    88980
ggccgggctg ctcgggcggc acctgctcac ggccgtcgtc tactgctggt ggctgatcaa    89040
cgccgcgtac gacacgacgc agtacgcggc gcgcgcgcgc cccgtgctcg tctgcgtggg    89100
ctcgcccacg cagacggact cgctcgagtc gcgcttcgag cacgcgcggc agctgtgccg    89160
cgtgcgcgcc agcgagaacc tgctcacgta cctgatcacc aaccgcgcgc tgcgcgagta    89220
cacggacctc tcgcgcaact gggccatctt catcaacaac aagcgctgcc aggagtacga    89280
gttcggcgag tcatgaagg cgctcgagta cggcctcccg ctgacggacg agcacctgcg    89340
cctcgtcgac agcttcgtgg tgcccgaggc ctacatcaac aacccggcga acctgcaggg    89400
ctggacgcgc ctgtactcgt cgcaccgcga ggtcagcgcg tacatgagcc gcctgcacgc    89460
gcacctcaag gtggcgggcg acggcgcagtt tgtggtcttc acgctcccgg cctacaccat    89520
cgtgcgcacg gcggccttcg accggtaccg cgaggccacg cagcagccgc acctgacgct    89580
ggaccgctgg ctcgcggcca acgccggccg catcaccaac tactcgcaga gccgcgacca    89640
```

```
ggacgccgcg gcgctgcgct gcgaggcgcg cgcgcagcag ggcgtcgtgc tcgcccgctg    89700
cgaggtcacg tacgtgctca acagccaggt ggccgtcacc acgcgcctca agaagctggt    89760
catcggcttc agcggcacct tcgaggcctt cgcggccgtc ctgcgcgacg acgccttcgt    89820
ccacgcgcag ggcggcagcg ccgagtacac gtaccgcttc ctgtcgagcc tgctgtttag    89880
cggcatgatc gccttctaca acttcctgca gcgccccggg ctggcgcccg aggccgtgac    89940
ggcggcctac cggcgcctgg ccgccgtcac ggcggcggcg ctgcgcgtgc ccgaggagca    90000
ctttgacttc tcgggcgcgg cggcgcccgc cgccccgcg ggccccgggg gcgcgccggc     90060
ggacgacgac gacgacctct tgcggcgct cagcgagaac atgctggaca tgctctactg     90120
ccactacgac tttgcgcgcc ccgagaccac gagcgaggtg tacgcgcagt tcctgatgct    90180
caagacgctc ttcgccgacc gctacgcggc gctctccgag ctcttcgggc ccgcgttcgc    90240
gcgcgcgccc ttcgagacgc acgtggacag cgtctcggtg cgcgggtgcg aggtgtttgt    90300
gggggggctg cgcggcgcgc tgctctcgac ggcgctgcag acggacagct acacgctcgt    90360
gggctatacg cacgcgacgg cgccggcctt cgccgaggag ctggcgcggc gcaagctgca    90420
cgccggcacc gcggagctgc tcgcctcgct ggacacgccg cgcgtggtgc tgcgcgacca    90480
gagcggcttc ctgtccatcc tcaacgtcaa cctcagcgac tttgtcgagt cgctggacga    90540
cctggagctg gacatggcca cctacgtcga ctacggcatc agctccaagc tggccatgac    90600
catcgcgcgg tcgcagggcc tgagcctgga gcgggtggcc gtgtgcttca cgcgcgccaa    90660
cctgcgcatg aacagcgtct acgtggccat gtcccgcgtg atctcgtcgc gcttcctgcg    90720
catgaacatg aacccgctgc gcgaggagcc cgagcgggac aacggcatca gcgagcatat    90780
attggccgcg ctgcgcgacg gcggtgca catcgtgtac tgacccgccg tccacccgcc      90840 cgagggggc cgagggacca agggaccgag cgagaccgac catgacggcg ctggtggcct     90900 actcgttta cgaaataaag ctgcccggcg gctgggcgca gtcgggctgt gggcagaccg     90960
tgtgcgagta cgagcgcggc gtccgcgtca tggccacgga cgggtgcacg cgctgcgacg    91020
cgctcgcccc gggccgcgtc acgatccagc acgggccggt gctcacggtc ctggccgtgg    91080
acggggagcc ggagcggtgc tcgtacgtgt tcgcgcggac ctggcggcg gccccgagg      91140 gcgcgctcgt gatgcccttc tcgacctgga gctgcgccga gcgctcgcgc cgctgcgcg     91200 ggcccgcggg cggcctgctg gccacccctcg tcgtggagcg ggccctgcac gtcaccatca    91260
ccgcgtaccg gcccgacgtg ctccgggacg ccctgcgcga ggcccgcatc ctggagtgag    91320
aggcggagag gggcgggcga gcggaggagg ccgccgccat caccatcgcc accaccgtca    91380
ccatccccat cccaccccga caataaacga cgacggccgc gcgtgcgcgg aaagagagac    91440
cgaaccggtt gtgtcttttg tctggtccgt gggcatccgc cctttattga tcgcggtagc    91500
aacaggaggc ggggggcgcg cgccggcccc gggacggggt ccggggcgc gggagggcgg     91560 ccgccgaggg gacggcggcg tgggccgagg cgtggacgct gcgctggcgg ggtctcggca    91620
gctggggcgt cggggcggcc gtcgtcgagg cgttgatgct ccgttgccgg ggccggggca    91680
gctggaccgc cggggcggcc gtcgccgagg cgtggacgct gccgcggcgg cgcggggtg     91740 cggccgcgca cgactcgggt ccgcccgcgg ccgtcgccga ggcgtgcacg ctgccgcggc    91800
ggcgtggggc ccgctgctgt tgttgttgct gctgctgctg cggatgctga gagcggtggt    91860
ggtgctgctg ctgctggtgg tggtgggtag gctggacgac ggtggcgtag acggggtccg    91920
gctcggtcgc gccgcgctgg cgcgagcgcc cgcgggcggt gcccaggccg ccggcgcgca    91980
```

-continued

| | |
|---|---|
| ggggcgcctc ctcgtcgggg gggccgcgcg aggaccgcgg ggcccgcgtc tcgccccgc | 92040 |
| cggcggagac gcggcgggag gccgcggcca ggcgccgggc ggccgtctcg ttggcctgca | 92100 |
| ggaaccggtg gtagtcatcg accgtggcca cggacgcgcg tccgaaggtg ctcatggcgc | 92160 |
| cgcaaacacg ttgtcccggt gcagccgcac cggctcgggg gtgatgaact cgtggatgaa | 92220 |
| caccggcgcg gccggccgcg ctcgtccgct cgtcgggcgc gcgcggggct cgcgtgggcg | 92280 |
| tcgggcgcgc accgcggacc ggagctgatc gcgtacgcgc gccgcgtggg ctctgcggca | 92340 |
| caggataaac atctgcaggc ttttatggcc gcgcccgggg gcgccgcgcg ggccgcgcgc | 92400 |
| gcggcgcgca aacgcggacg tcttggtgca ggcgacgggg aggccggcca gggccgcggc | 92460 |
| caggtcccgg cggatcgtgt ccgtcagccg ccggcgcccg agctcgtcca cggacgcgac | 92520 |
| cataaacagc gtgtcaaact ccacgtgctg cgcccggcgc gggcccgccg ccgccgtcgt | 92580 |
| cccttcgtcc cccccgtctt cctcgtcttc cgtctcctcc ttctccgtcg ccttcccctc | 92640 |
| ctcgccgtct tccacgtccc cctctccgtc ttcgctcccg cgcaccccct cccggggagg | 92700 |
| gggtgcgctc tccgggggcg cgtccgcgtc ctccgggcac ggcccggagg gctcgacctc | 92760 |
| ctccacggcc catccccact cgcgcagcac cgccaggacc ggcagcgcgc tggccggggc | 92820 |
| gccgcgagc gcgggctcca tcatccgctc tcctccgtcc atcccaccca cccccctccc | 92880 |
| cccctcctcg tcctccgccg gcggtgtgcg cgcacgcccg actcagtcca cgctccagtc | 92940 |
| gacgggggcc cggcccgtct ggacgaggta cgcgttcgcc tctccaaagt gcgggcaggt | 93000 |
| cctgaagggc gtgcgggaca cggcgacgg atggctgaag gtgagcacct tgtggcggcg | 93060 |
| cgggtccggc gcgcaggcct tttgagcgtg ggcgccccag agcatgaaca ccagcttggg | 93120 |
| gcgggtctcg cagagccgct ggacgacggc gcgcacgagc cgcgcccagc cgagcggggc | 93180 |
| gtgggagccg gggaccccgc gccgcacggt cagcgtcgtg ttcagcagca gcaccccgcg | 93240 |
| gcgcgcccag gcctccaggc agccgtgggc gggcgcgggc agcgtcgggt acgtcgcccg | 93300 |
| gaccgccgcg aagatgttgg ccaggctcgg ggggatcggg accccgcgcc ggacgctgaa | 93360 |
| ggccagcccg tgggcctggc ccggcccgtg gtacgggtcc tggccgatga tgaccacctt | 93420 |
| gacgtcctcg ggcgccgtga ggcgcgtcca ggcgaacacg tcctcgcgcg cgggcagcac | 93480 |
| ctcctcggtc aggcagcggc cgcggtactc ggccagcagc aggcgcgcgt acggcttggc | 93540 |
| gatctcgggc tccagcagcg cgcgccacga ggggccacg tcgaactcgg cggcgaaggc | 93600 |
| gtcccacgtg ggcgccccgg ggtcgggggc cggggcggag gcgtcggccc ccgtggctgt | 93660 |
| tgttgccgcc gacgccgcgg gcgtgccctt cgcgggccgg gcggcggcgg agggtcgggc | 93720 |
| cggcttcgag gcccccgccc ctgccccggc ggggctgct gctgcagcgg cggtggcggc | 93780 |
| gttagaggca gaagcggcgg cggcggcagg cacgacgagg cgcacccggg gcggcaggcc | 93840 |
| gcagggtctc ttactcggcg gggggccctc cattatagcg cagcggcggc agggagtcct | 93900 |
| tgtgcacggc cacctctccg agctccttca gggccgcctc atttaagggc tctccgatgg | 93960 |
| ccagggcctg gatggcgaca aaggggttga ccaggtaggg ggtgcccgac gcccacagga | 94020 |
| tgacctccgg tggcgagcag tagggcttca cgaccacgct cgtgacggcg gtcatgtccg | 94080 |
| gcggcagcga gtacgcgatg tagggtggc agcgcgatcc cacggcggc tcgaggccca | 94140 |
| gcagcgggtg gtcttcatcg tcccattcca gctcctcgcg ccggggagcg cgggtggggg | 94200 |
| gcgcgggcgt gaccggcggc tcgaagatgg catcgagccc atggggttt cccgcgacgc | 94260 |
| cggtgccagg aaccccagc gccgcgaaa aaaacaccag caccgccacg agcggcgaca | 94320 |
| tcgcggctgg tgtatccttt ttcggcgcgg ggtcccggct tttatctccg gaaagaggaa | 94380 |

| | | | | | |
|---|---|---|---|---|---|
| attgagacat | aaactagacg | tccgcataat | cccctttgat | ttacgggggg | gaaatacgtg | 94440
| ccacgtgccg | gggggcgggg | caactggagc | gtggcgaagc | ggaacggggc | gcgatggggc | 94500
| gcatcgaggc | gcggacgcgt | cccgggggag | tcgggggga | gtcgggggg | agtcgggggg | 94560
| gagtcggggg | ggagtcgggg | gggaattcca | gctcggcgcg | atcgccgcat | cgcgcaaagt | 94620
| ccggctgcag | taaatttact | gcggatgcag | ttcccgggac | ggccgcaccg | gccaaatggc | 94680
| gctgcagtat | agatactgcg | gctgcagttt | actacagttg | cagtaccgcg | cgccgccgcc | 94740
| aaatactaca | gtagatttcc | tgcggccgcc | gcgtactgca | gtttaccgcg | gctgcagtaa | 94800
| actgcagtat | cgcgcggtaa | attgtagtct | ggcagccgcg | cgttactgca | attagcggtg | 94860
| gctcccgaca | ctctggccaa | ttggtgctaa | tgggccgtga | tggtccacgc | ggggtgatg | 94920
| taaccgccgg | gccccggttg | ggcactcaga | tggtagccgg | gcgccaggcc | aaagtgctgt | 94980
| ctgagtgcca | ctttatgact | ttgtttttct | caaacaacat | caattatgga | tgcacatcgt | 95040
| gtatataatc | cccggtccgc | gctccgccca | cccatcacag | cagccgcgga | cgctgcgcgc | 95100
| cggagcggtc | catctcgcca | gccagccaac | cagccgagcc | gcccagccga | cccgagagcc | 95160
| ccgagagcca | gactccctca | tccatagaag | acaccgggcg | ggagagacgg | actgaaaaaa | 95220
| tatatctttt | tttattttgt | ctgggcctgg | agacccgcag | caggagcgga | ggtgggtgcg | 95280
| gggccgggag | ccggagcagg | accgggaaca | ggaacaggaa | caggagtggg | gccgggagca | 95340
| ggagcaggag | cgggagccga | agtgggggca | ggagcggcgg | cggccgcggc | agcaacaggg | 95400
| tcgccccagt | ccgcggcgag | gaagaggag | ctcagtcgtc | gtcctgggtg | aggtcgatga | 95460
| agatggtagc | ggagcggggg | gatcccgacg | agctagacgc | cggaggcccg | ccccgggggg | 95520
| cggcggtctc | gggggcagag | gcagagggcg | acgggcgccg | catcgaggag | gagggtgaag | 95580
| acgaggggga | ggagcgagcc | gaagcggcgg | tgttcgccga | ccccgggccg | gccccggccc | 95640
| ccgaggcacc | atgctgcgca | gaggaccccct | cgccggacga | tggcgcctcc | ggagtctcgc | 95700
| cctgggcctg | tccgcccgtc | cggccgcgcc | gcaggcatcg | ggtccgtctc | tgctcgcgcc | 95760
| tcagcacggc | cgcccgtcgg | gccctgcgcg | gggagcgcct | gggcgccggc | ctctggtcgt | 95820
| ccgcggactc | ggaggcctcc | gtcagatcct | ccgtgtgcac | cccgctgctc | gaggcgcccg | 95880
| agtcttcctc | gtcggggggaa | gacacctcag | agtcagagtg | tgcctcggac | tcggacgtgt | 95940
| cgatatagtt | cacaccctgg | tggctcatcg | gggctcgcct | ctgcatccgc | cgcatccact | 96000
| gcgccgatat | gtcaaacagc | gcatcgacga | gggcgtgggt | gtttgcccca | aacatgggga | 96060
| gcatggcctc | ggtcacgcgc | tggcggttca | tcccgtgctc | ctggataatc | tcgacgatgt | 96120
| tgtccacgac | ggcctcgcgg | atggggtcgc | tctcgatgac | cgtcgagacc | tgcccataaa | 96180
| gccagttgaa | gacggggact | ctgggcgggg | cgcgagaccc | agaccggag | ccctgccctt | 96240
| cggcctcctc | gtggcgcacc | tcctcggtat | agtcttcacc | ccagatgacc | gcgaagcccc | 96300
| cccctaccgg | ctcatcctct | tccccgtcga | catccgtcgc | ccctccacg | ggcgtctcca | 96360
| caaacgaagc | gtcgctgtcc | acgtggtgga | ggatggaggt | gacgcgggcc | ttgcacagcg | 96420
| ggcaggcggt | gctcgactgg | gtccagcgct | ggatgcagtc | cagacagaac | ttgtgcatgc | 96480
| acggcagcgt | ctgagcctcg | gtggccgcga | cgtccagaca | gatggggcag | tccatgacgg | 96540
| tgagtggcag | tgacaggcgc | tgcggcggcg | gcgaggggct | tctgggcgg | tagaagccaa | 96600
| agatccccca | ggcgctggaa | gcctcggcgg | tggtcgtccg | tctccgagag | accgtgcagc | 96660
| ccatggtgtc | gagggccccg | ttttttaacc | gggtgcccgg | cccctttgtt | tgtcttcgcc | 96720

```
cggggcgtcc acgccccctt ccgcccgccc cgtcggggct ccccccgccc cctcgggccg    96780
tcccgggacg atggcccggg cgcgccgtcg tgggaagcgg ccctcccgc ggtgggtcga     96840 cggctcctgg gtctgaaagc ggcgctgcgg atccccgct ctcacccctg ggtccgtcgc    96900
cgccccgcgt tgcgtgcgac gcccgcgaac ccccggccca caacacaccg gcaccaccac    96960
caccatcatc gtccccctc tccacataca cgctcgcact cgggccacac gctcccgtcc     97020
tccgccgcca ccctcccagc ctcccggcct cgcgggtcct cgggacgacc gccgctcacc    97080
ccgacggggg gactgggaca gggagcaagg ggggaggagg acgggggggg gggagagggg    97140
aacgcgagcg cggcgcaccc cgtcgccgtc cgtggtggcg ggcacgccac cccgtccgtc    97200
catccagccc ccttctcctt tttccgcctc ccgtcccacg gcacggcccc atcgacgcca    97260
caccgcgcgg tgcgcgccct ccagccgtcc catccccca cacccccac gcttcccca      97320 ttcgcttctc atcccgtcag acctgcgcca tggagttcga ggacgggcgc ggggcaacgg    97380
tggtgagagg cgagccgggg gggtcgagtg ggcctcgcac tttacgcgca cacgcccctc    97440
tcgcgcacca cacaccaccg cacaccgccg aggtcggggcg agagagggcg cccccccctc    97500
cacgaccccg ctcgccccgg tcccgacgcc ctcgcacccc cacagcaccc cctttcaccc    97560
cccgcttctc cccgctctct ccgcgcgatc gcacacacaa cacccgcgcg catgctcggc    97620
ttcttcacac ggaggacacc atgggcagca gatggtacgg tcagccgccg gccgccgtgc    97680
gcatgtgtcg ggctgccgcg gccaagagta tcagcgtggc tttttgttg gtcagggtgt    97740 gaaaaaggca cgctgatgcg tccgccgctg cagcggagct cctcggcagc gagatcatcg    97800
accaccacca ccaccatc gctcttctcg cccgcgcttc cccaccgcca ccccacacca     97860
tcccccaccc ccccgtcca ccctcaccc ccatcgcgtc gcgagagctc tcaacacatg      97920
cttacatgca catgcacacg cgcccctccc tcctcggcgc ccccgcggcg ggaccgtcgc    97980
aaccctctcc ccgccgtcc caccccgtccg cggccctcct ctccttttcc ccttcccctc    98040
cccttcgcat ccccgttccc ccctgttccg catttccccg ctccctccac catcgactct    98100
catcgacggg cttctccgcc atcatcacca ccaaccacca tcaccatctc ccgccgccgc    98160
ccggacggcg acccgcggtg ctcccagggg cgcgttccca ctcacaaccc ggtggtttcg    98220
atggccgccc ccgggggggtt gatggggatg ggcgctcggg ggtgatcgtc tgctaccaaa    98280
ccgcaccacc gtccccctgt ccctcatcca cttctcgacg gccggctccc cgcgggggcgg   98340 gggctgctgg ggggtgggtg ggtgggtgat agagcaggcg ggcaggtcgg ggcggccggg    98400
gagggccccc ggcccctctc cctcctctct cttccccccc cctaccccc tctccgcgcc     98460 gactcgacga gcggggcga ggcagggtgc gtaccgaccc gcctaccagg caggctagaa     98520
gcctcacgct gctgcttggc agcgggtggg tacccaaccc ctcccctcag gacgcgaccg    98580
accggtgtga agagagaaag atgcccgtct ccccccgcccc caccgtcccc gatttttcgg   98640
ttcctctccc cgtcgcgccg gcgggcccct cgtcgccagg gggttttttgg tggaaggccc   98700 gccggggtaa gggggggtgg gtggtgtgtg tgcgacggaa cgggccgcag gaggatcggg    98760
atgtatgcac ggtcgtcccc gtctcaaact tcctcgtgtc ccctgttccc catccttcca    98820
cccatgcatt catccgtgcg gtggtgggga tgagtggatg gatggaggcg agggacgcgg    98880
tggaccatgc caggcaagac ctgcatcact cgaagaaagg gtgcctggat tggccttcgc    98940
atctttgccg gccacgagcg acggccacca ccgcccccga cggtctctcc ccccctcccg    99000
cttctcctct ttcctctccg gcgcgtaccc cccccccgtt ttctcgacga ggttcgagga    99060 cccccccca aagcagagcg agagcacccc acacccgcac gcactccccg gtgtcgctcc     99120
```

```
tttcccccc cggcagcgcc ggaaccgggt gcgggcggtg ggggcgaaga ttgggttggg   99180
tgagagacta gaaccggtgt tctcaaccct tctggagccc taccctctgt gcctggactt   99240
tccagcgcgc gacacggggg ggagcgggca cgcggcggtg gcgatggtgg cgacggcggt   99300
ggctgggcgc gatcgaggag atgtggaggg gtgccaagcg cccgccgccc tccccgcat   99360 ctcttctctc tcgcacacgc acacgacccg cggatggcga ggatgtgggg ggagaggtct   99420 cccgcgtta gtgggtgcta tttgattctc ctctaacccc ctctccctcg cggcccctc    99480 gaccatcgtc gtgcagcggc gacggcggct cccactccgt ctctctcccc cacacgacct   99540
cgacgcgtcc cgccacccg cccagtcacg tcccaccccc cggggagagg ggagagggat    99600 gcacggggt agggtcccc gcccctctc tctgattcca agacggtgat tgttgtctcc      99660
gtctccggct cgcacgcaca catccccgcc gcggatgcc cggccagacc aaccgagggg    99720
ggggaggaga gggggaggag gaggaggaag tataggcctc tcgggacgg gcggcgcgtg    99780 gcgccggaga ggggggtggc ggggaagagg gaaacctaga aggcggccca tcccccgaga   99840
tgacgagaga ggagagaggc gctaaacggc gcccggggag ttggggagg aggagacggc    99900 gcgcgaggag ctgggggagg aggaggagac ggcgcgcgag gaggaagacg accggtccaa   99960
cccttgggac gagaggtctc gaatcttgac accatttccc ctcccctccg ctccactccc   100020
gtcgcagctt cgcgcgggga ggaaaataat ccgatccgac cccgggggcg agaggctcgc   100080
gatcccaccc ccccgctccc cggggccgc gaaaaaggg ggcggggctt aaggggggg     100140 ggctaatttg cataaatttg catacatttg catagccccg cccctcatt tgcataaatt   100200 agcatggccc ctccccctca tttgcatgca tttgcataac ccctcccct gatctgcata   100260 accccacccc ctcatttgca tacatttgca tagccccgcc ccctaatctg cataacccct   100320
ccccctaatc tgcataaccc ctccccctaa tctgcataac ccctcccct aatctgcata    100380 accccctcccc ctaatctgca taaccccctcc cctaatctg catatgacaa cttcctccgg  100440
aagtgacgct ctggcccctc ccccccatt taaatatgac cgcttccccc ggacgtgacg    100500
ccgggctcct ccccccccca tttgcatatg accgcttccc ggacgtgacg tttttgccga   100560
tgacgacttc cgcctcattt gcgtatgacc gcttcccgcg cgcaacttcc gccgacgtg    100620 acgccggccc ccacggatct catctgcata tcgcgccggc cccttccgct tcccccggac   100680
gtgacgccgg cttccggggc gcggccgggg cgggctccgc ggatcgcatc ggcgcgccga   100740 gcctgccct tccgtcgcac cggggggtccg cgggcgggg cttccgctcc gcggcgcccg    100800
ccccattggc tccctcgcg ccacgcggtc gccgtcgtca tcgtcccgcc ggccaatcgg    100860
tggcagcggg ggaggctggg agtggggacg gaagacggaa gccagatgaa cctgttccgc   100920
ccgctctccc accgcctttc ccgccctcc acgacgacca cccgggacca ccaccaccaa    100980
caacaccacc accccccccc ccccccctca cgcacacgct ttactactat caccaccagg   101040
gggcgatggt tgcaacggca gttccctgta ctgaccacca ccgtgttttt ttctctcttt   101100
ctctctttcc ccccaccccc ctcgaccacc gcaggaccac catcgtccaa ctcccgcccg   101160
ggaccaccgg gaccctcggg accatctacc tcccaccagg accgccggg accaccaacg    101220 ccgtccacct cccaccacca ccatcaagga ccccaacat ccccaagacc ctctacttct    101280
tcccaccaag accctccggg aggagggccc ccatctgcta agacccacca gggaccccca   101340
tctgctaaga cccaccacca ccaagaccct ccaggaggag gaccccccatc cacttcttcc   101400 caccaccacc accaccacca agaccctcca ggaggaggac ccccgtcacc ctcaccaaga   101460
```

```
ccctccacct cttcttcttc ctcccaccag ggaccccccat ccacaagacc acctccaccc   101520
cagagaccac cgccaagatg gccgcctcca tctccccaaa aaatctcaga gactcgagcc   101580
ggttcagaaa atacagcaca aactttattt tctcgctctg aaaataaact cttttctcac   101640
ccgatgggag aaggaggaga aggggaccgg gggaccgcgg gaggaggagg agaaggggac   101700
cgggacgatc ctccgccgcc gagccctccg ccgcggccgc cgccgccgct tccaccaccg   101760
ccgccacctc cgccgccgcc gcagccacct ccggccgggg gatccgcgcg gaggagaagg   101820
agaggaggag gaggagggcc accgggccgg ggaggcaggc gccggggagg caagcgccgc   101880
cgggccgagg ggaccgaggc cgccgccgcg gacgcagagg aggaggagga cggggacgag   101940
gacgaggacc gggccgaggg cgaggggaga gaagacggag gagaagggcc tcgaggagcc   102000
ggcggagggg ccgagagtc agagtcagag tccggccggg ccgaggggc gccccgctca    102060 gcggagcagc aggtaggggt tgccggcgtc ctcggcctcc tcgtcgtccg agatggcctc   102120
caccttgatg ggcccgagcg ggccgcgggg ccggccgtcg ccgccgcgga cgccgacgat   102180
ctccacagag tccccgtcct cgccggggcc ggccccggcg cccgaggccc ccgcgggccg   102240
gcgggtctcc acggcgcccc cggcggcggc gcggacgctg gtctcgaagg gcgcaaagtc   102300
ccagagcacg gccggcgggg cgcccgcggc ggcgacggcg cccggggtca gcaccagcgg   102360
ggcggcctcg gcgtcgggct ccagcagcgc cgcggcgcag aaggcgcgca gctcggccgg   102420
caggccctcg gggccgcgga gctcggcgag gccccggcgg ccgcaggaga cgaagacggg   102480
ccgcagcggg gcgccgagcc ccagcggtt ggccgcgcgg tgcccgaagg cggcgcccgc     102540
gtcaaagtcc gggtccccga gcccgagcgc ggagcgctgg cgggccatgt ccttgcagcc   102600
gtccacggtg gggagcacgc gctggcggta ggcgcgcggc ggcagcggga ccggggtccg   102660
gggcccggcg cgggtgctca ccgtgtagcg cacgttgtcc tggcggcaga ggcgcagcgg   102720
ctcggccccg gggtgcaggc gggcgaagga ggcctccgcg cgggcgaagc aggccgggcc   102780
cacgatggag ctagagtcca gcacggccgc gcggagctcg cggcacccgg ccagcgcac    102840 ggcgcactgg gcggccgggt ccaggcgggc gcggacgtag acgtggtagt cccccacggc   102900
cgggccgtcc gcgggccagt cctcgatggt gtccagcacg atgagccggc gccgcgccgc   102960
gccgagccgc gagcagaggt actccacggc gccggcgaag ccgaggtccc gcgccgagag   103020
cagcagcacc cctgggcgt tgaggcggcc gatgtcgggg cgcccggtcc agttcccggc   103080
ccaggcgtgc gagtccggcg tgcagaggcg gtgggcgaag gcggcgagca gccgagag    103140 gccgccgcgg cgcgggtccc aggccgggcg cggggcgccc tcggcgggct cggcgcagag   103200
ctcctcgtgg ggcagcgggt cgtagagcac caccacgcgc acgtcctcgg ggtcggctat   103260
ctgccgcatc caggcggcgc ggcggcggag cggggcgccc gcggcccgc ggcgcgcggc     103320 gatgtgcgcc agggcggccg ggtcgaaggt gagcgccggg cgccagagtt cggggaagac   103380
ctcctggtcc acgagggcgc gggccacctc gggcgggcag taggcggcga gggccgcctc   103440
ggagggccgc ggcgtgtggg tctcgccggc cgggacgcgc cggaagccgc cgtcgggcgc   103500
ggggtgctcg ggcatgggcc cgagcgggcg ccggagccgg tcgtcctcgg aggaggagga   103560
ggaggacagc agcgcgggag cggggtccgg agcgggcccc agtccgaggg agcggcgctt   103620
gcgccggggc ccccggtcct cttcgtcgtc gcggtggccg tggccgtccc cgcggagggc   103680
cgcgccggag agccctcgt cctcctcgcc gtccccgggg cggcgggccc cgggcgcgcg    103740
gcgcttcttc ttgcgccgct cgggcgctgg gtccggggccg gcggcggggg agctggcgta  103800
gccggaggag ccggagaggc cggacttggt gccggagctg gacttggtgc tggagccgga   103860
```

```
ctcggtgctg gagctggact tggtgctggc ggggctggag ggcccggagc cggggaggcc    103920 ggaggggggcg cccgccgccg ccggcgccgg cgctgggacg acgaggccgg gctgctcggg   103980
ccagagcggg ggcaggccgg gcgcgggctc cgcgggcccg ggccgcgcgg cggcctcggc    104040
gagccgggcc gcggccacgt tggccggggc gaagagggcc gcggcgtagg tccaggcggc    104100
ctcgcgggcg cgggcccgt ccacgctgta gcgcaccagc ggcgccacgg tgcgggcgac     104160
gagggcgaca gcgtccgcgg cctgctgccg ctcggccggg ccggcccgg ggatcgcgtc     104220 gcggagcgcg agcagcgcgg ccgtcacctc ctcgaggcag gcgggcccga gggcggccgg    104280
ggcgcgggcg ggcgcgggca gccggagcgg gcagggcagc aggcgctcga ggacgccgcg    104340
gcaggccagg acgcaggcgt ccgccagctc gcggggcacg cggccgggct gcgcggcggc    104400
gaaggcggcg cggacgcggg cgcagagggc ctcgacggtc gcctccccgg gcgcggggtc    104460
cgcggcgcgg cccgggtagg ccatgtcggc gtaggcccgg cggaggctct gcaggatgaa    104520
ggtcttctgg gtgcgatcgt agcggcggct catggccacg gcgctcaccg cgtgcggcag    104580
ggcccagagc gggtcctggg cggccatggc gtccccgatg tgcggcagcg gcgggtcac    104640 gctgccggtg atgaaggagc cgtggccgtg gggcgcgtgg acccggcgct ggcagaactg    104700
gttgaagcgc tggtcggggg cctgcatccg cgggttctgc agccaggaca tggcctcgcc    104760
ggcggccccg ctgtagatga ggcgcacgag ggcctcgtgc tgcttcctcg agtcccccat    104820
ctccgggatg aagacgggca cgggcccggc cgcggcgcgg tagcggggccg cggcctggcg   104880 gacgtcgtcc tcgtcccaga gcccctcgcg ggagtcccg cgccgccgt agcggacgcg      104940 gccgtcggcc ggagggtcgg agccgggcca gggctccccg agcggggtga gcagcggccc   105000
gtcggtcggc gggggcccgt cggccatgag cgagaggtgg ttgttggtgg agcggcgctt   105060
cctgcgcggg ggccgggcgg gctccggggc cggggccggg gaggccgcgg cggaggagga    105120
ggcggaggag gccgagggcc gcggggccgc ggcgggcgcc ggcggagacg gtggcggccc    105180
ggcgcgggcg agtgggcgc cgggccggac tccttcgtct tcttctccct cggaggagga    105240
cgaggacgag gaggacgagg aggacgagga cgaggaggag gccgagcgcc gcgcggcggc    105300
ggcggcgagg gccggggggg cggagggcga gcggccgggg gagaggtccg agtcgctgcc    105360
gccgctgctg gagctgctga agccgcggcc gcggcggagg gcgccctctc cggcgcggcg    105420
ccggcggggc tgtctctgcg ggggcgcccc gccgtccccg gcggggccga gtccgtcctc    105480
gtccttctcg gggccgcggg cgacgggctc gacggcgacg gtggtggtgg agctggagtt   105540
ggagttgggg ttgaggagag cggggctccg ggcgccaagc ggccgaggat cgagccgcct    105600
cgcggcggcg ggctcgtcga gcaggggctc gcggtgctgg tgatggtgac gaccgcggtc   105660
ccctccggcg gagggggcgc cgccgccgcc gggcgccgag accggccggg cggcgggggg    105720
ggctggggaa gcgggccccc gccgtgccgg cgctgcggcc accgctgctg gctgtgctgg    105780
tggcgccggg gtccgaggcc gcgccgccgg cccgggctca ccgaccgggt cccccgcggg    105840
ggaccatctc cgcgggggctg ccgaggggcc ggggggagccg gaggaggagg ccggggaggc  105900
cgcggagggg gacgagcgcc cggggccgcc ggggcccccg gcctctgccg ctgcgagtgc    105960 tgccgggggtc ggcggccggg gccggagcc ggccccgggac cggggcccga ggacgaggtg    106020
accgtgctcg gagccctgat ggagagcccg accgggggac ccggcggccg gggacccggg   106080
ctcgtcctcc tcctcgtctt cgtcgtctag caccacgatc tcgcccgagc ccggcgggg    106140 ctgctgctgc tgggccgaag gaggacgggg cggcctcgtg gctccggccg cggccgcgag    106200
```

```
gacggcggcc tcggcctcgg cctcggcggc gtcgtcggag aagaggccgc ccgggccgaa   106260
gaggagatcc tcgccggagg agccgcggcg ccgggagccc tggctgccgc cgtcggggcc   106320
ggacgcgatg ccctcttcct cggccgcggc ggcggcggcc gccaggagct ggctgaagtt   106380
gccctcggtc tcgatgaagt caaagagatc gtcggccatg gtctcgatcg ggtctttcct   106440
gcctgagcga ggctgggcgc cgagcgcgga gagcgggcgg cggagaagaa ggaggaaggc   106500
ggccggagga ggagaagaag aagactcttc tctggtgggc cgagagcctc ggtgggtcgg   106560
gcgtccgtcg agggctgata gccgccggag agccggagtc ttcagagtcc gcgccggagc   106620
ggagacggtc ggatcccctc gggttggcag agaacgatgc tgtccgtacc tgcaccgcag   106680
tgaagtgcta cgatggagac cgcgcttata agcgccccga ggagagcccg ccccaggta    106740 agcggaccaa tggccgattt cgccgcggga cttccccgac ggccggccaa tgggattttt   106800
ctcgcccgct tcctctcgcg tctgctttgc atgcccggcc caagatggcg gccgccggcc   106860
aatgggattt cgcgaggaac ttcctcgcga ggaccatttg catgcccggc ccccgcggcg   106920
gccatcttgc ccactcgacg gccaatggga tttctctcgc ccacttcctc tcgcgtctac   106980
tttgcatgtc cggccccgag ggcgccatct tggcccctcg acggccaatg ggatttctct   107040
cgcccacttc ctctcgcgtc tactttgcat gcccggcccc cgcggcggcc atctcggccc   107100
gcccgggcca atgggcgcgc ggaggcgtct cccgcgcgcc tctgatttgc atgcccggcc   107160
cgctctgcgg ccatcttggc cgcgggcggc caatgagatt gtccgaaaat ccctcgcgcg   107220
ggcgcgaggc gcatgctcgg cacgcgaccc accccgtggt gctagcgagc caatcagatg   107280
attttcgggg aagcttccgt gtgcacgtca tttgcatgct cgcccacgt ggccgccctc    107340 ggccaatggg gcctcacggt gcaagcttcc gtgtgtctgc acgtggtccg catgtgttgt   107400
ggtggtctct gtgttgtggt ggtccgcatg tgttgtgtgg tggtctctgt gttgtggtgg   107460
tccgcatgtg ttgtgtggtg gtctctgtgt tgtggtggtc tctgtgttgt gtggtggtct   107520
ctgtgttgtg gtggtctctg tgttgtgtgg tggtctcacc gcctcccct gccactcgcg    107580 agaccccgag acccccgttt ccccctcccc gagacccctg agaccccga gaccctcccg     107640 cgaccccgc ggtcgcccca cccgcgcctg cgcgctcggc gcgcgctccg agggcgcccc     107700
cagccggtcg gagagacgag cggaaccgcc gtcggaccgg ggaccggcga ccggaccga     107760 accgggaagc gacgccgggg cgggagaacc ggacccgaac ctcgagcccg gacccgcccg    107820
gacccggaag gaaggagccg gacagccacg ccttggatac ttttgtcgcc cacccacccc    107880
ctcctctccc ccccccctc tatctctctc tcccggtccc cctcccacc ccacgagaca     107940 cgccccagag tgaaaaaat aaaagttgtt ctcgttgcac cgtcttccgg ctcgtgtcgt      108000
ccttccgcgg tacctcgggc gggcgggagg gggcgcgaga ccggctcggc ctcgtcggga   108060
gagagggagt tgggggggagg ggagccaaga tggcgacggg gcgtggcggg gcgtggcaga  108120
gggggagggg gggggtcgg agcgcggacc ccgcccggtg ggggggggcg ggtgcaaagg    108180
ggcggggccc aaaatggacc tcgggccggg acccgggggg cgctccggga gacgaagagg   108240
gccgggcccc cttcccggcg gggagggccg ggcggcgcg ccgggacgcc cctccggggg    108300
aaagcgtgtc cccgcgcggg cgccgcgtcc cgccccgagc ccccggggc gcgcgggcct    108360 cgatcgcgcc cgccggacgc ggaggcgcga ggcccccgcc cccgggggg tccgggatgg    108420 gggggtcaa tttttgctgt gtgtgcaggg aaggctcgct ctctctctct cgtggagggt    108480
cgggaggacg gatggtcggt cggacggggc gggcgggag ggtgtcgtct gtgtgtctgt     108540
gcgcggggag cgtgtgatgt gggggtgtgc gagagagagc gtgcgtgcgt gtgggtgggt   108600
```

```
gtgagggccg gtgcgagtat gggggccggt gcggtgtgtga gggtccgtgt gggtgtcggt    108660
ggtgcgggtg ttactggcga taccggtacc gacggtggtg gccgggcggg cggtctctcg    108720
gtctccgtct ccgccgtcgc ctcggtccga ggaggggggg tgcccgggcg tgtctcgcct    108780
ttcccccagt tcgcctcctc cttctcctcc tctctcgcct ctcctctctc tctccgcgtg    108840
tgtgcgcgcg cctctccccg tgcgtgtctc gctcgccctc tccgcctctg tcctccgccc    108900
gactttccga ctctcctccg tctcctcctcc tccgtctcct ctcctcctct ccccgccccc    108960
gcccccgccc ccgcccctg tcccggtccc ggtcccggtc ccggtccgg tcccggtccc      109020 acgcgcgcgc gccccgggga agggtcgggc gatggccgcc gccaccgccc cacccttccc    109080
ccggaccccc tcccgcccgc cggggcgccc cgcgtgctcc gggggcgccg gccggccatc    109140
cccccacacc tccttcctc cccgcccccc gacccgcctc gcactcgccc gacactcggc     109200
ccgcggcacg cgcgcccaga ccttcctctc ccccctccac cgcccgccct cgccccctc     109260 cgtctcatgc cacccgcggc agcatccccc cctccccgtc gtcctcagcc aacggccaac    109320
agccgacaac ccacagccga cagcctcact ctcgcgctct cccgtcgcg ggaaaaaaac     109380 acggcaccac aggcgggagc ggggtcgctc ggggaaggt ttcattcaaa cgacaggcga     109440
caggaggggg ccccgcgcg ggtcgggcct tcttccccat ccccgccggc cccctcttt     109500 ctctctctct cttcttccgc gtcttcttcc gcgtccgctt cggccccccg cggccgcggc   109560
gtgggagagc ggggcgtgtg gggaaggaag agggacggg ggggggaaga agaagaaacg     109620
gggaagcggg ggaaggaaca gacggggaag gggggaaagg gaaacgggga aacgggggaag   109680 gggccggcgg gggggggga agcgggaggg agaggcgcgg cgccccgcgc ttccccttcc    109740
cgcttccccc tccgcccggc cgcgggtgcc cgggagacgg gagcgaaagg aggagagggg    109800
aggaaaaaaa gtctagagcg gggaggagaa gtcaccgtag tagtcatagt agtagtcata    109860
gtagtagtca tagtaatata gtaggagtag gagtagtagg agtagtagta ggagagtctg    109920
tgcttaccga gagaggagaa taagaagcag aagccggggc gcttcctccc cggcggtccg    109980
ggaagaaagc cccggcgcct cgggcctcgg agatggggac gcggagaagg aaacacccaa    110040
aggcggagga ggaggaggaa gaaggagagg aaggaaaaaa aaacctcgag agcggcgcg     110100 gcggtcgccg cggccaggag gaaaaacggg ggagcgggag cggctcccga gtccgggaat    110160
gaaaggcggg cggaggaagg cgggtgcgga ggaggaagcg ctcgcgcccc tcgctctctc    110220
tccccctgtc ccctctccg cgtctcttcc ccgcgtcccc tctctgcgtt cgccggtcgc     110280
ggcgcgggcg gcggctgcag aggcggctgc ggacgcggag gggggcgagg ggacacagaa    110340 ctcttttgt cctcctcgcc ggctcccagg cggcgggcgc gtcccgcgtc ccggcgtca     110400 tcacgcggga cccccccggtc cccgtgacgc aggacgcggg aggggagggg ggtcgggggg    110460
aagggaggga ggggggggga atgaggggga gagcgggtg acgccgcggg tgggccgagg     110520 ccggcggga gggaggagga ggacgcgcg cggtgaagg aggaaagccg cccggcgcgc       110580
gcccgccgcc gcaggcgcgt cccggcgcg ggcgcctctc cacgcccgt tccgcccggc     110640 gcccaatggc gcggccggct cggcggcccg gccttcctc cgccctcctc cctccccgcc    110700
gcccgcgcgc ccgcgtgcgc tcgtgccggc gcggcatccc cgcccaggcg gcgggggagc   110760
gcggagcgcg ccgccccccc gtgatcacgt tcgcgcaccg cggcgccagc aggaaaaaaa    110820
caacacagag acacacctcc ctctccgtct ccctcgcctt ctccgttttg ggggagacc    110880 gatgccggtg ccacatacac atacacacac gcgcgcgcac cccgtccccc ccccccttc    110940
```

```
cccttcccct tccccttcgcc ccggccccc  ggcttggtgc cggagaaaag ggggtgccgg   111000
cgcggaccgg  ggtcgggccc gcggcgccga gggtgggcgc gcgtgtccgt gtgagagttt   111060
acggtgtggg  tgggtgtcac ggtggagcgg gccggggccc ccggctcgcc cgctcgctcg   111120
ctcgctcgcc  gggccggcct ggacgcgggc cacactgtgc ggcggaccgt gccaagttta   111180
gggcgctgcg  acccagagag agcgccgagc taaaagctat tttatcgccg ctgcggtttc   111240
ccctggcgcg  cgcctagac  accgtttctg cagacagagc cctctctaat ggcgcgtccg   111300
ggaaggcttc  tccgggccg  cgagggccgc ggcggcgacc ccttcctcc  ctcctcctcc   111360
ccgtccccgt  cccccgtcccc cgcccgctct cccgggccgc cgcgataccg cgcgggcgat   111420
accgcgcggg  ccgcccgcgg gcgctaccgc gccgctccgc tcgccgcctc ttcccccctc   111480
ctcctccgcc  gccgccgcca gtcctcctcg ctcctctccg cccacgcaac tcctcccgcc   111540
cgcgtgcccc  cggggccatc ggctggaaca ccccgagcct tcgctgagtg ctgccccgc    111600
cccgcccgcg  gcactccggg cccgcgtgag agggtacaga gcgaacccgg ccccgacccc   111660
cccccgccc  gccggggag  gcttcccgga accggcgcgg ccatcaaccc cctcccccac   111720
ccacccgcac  agcgcgcacg ccgaccgccc gcgtttgcta cgatccctgc gcccgacggg   111780
gccgcgggac  ggcgcgtgcg gcgcggaacg agaggggggag cggggtgcg  ggggcggggc   111840
gcgggcgagt  gagcgtgcgc gaaggggggga gagggcgcgt gggcgagagg ggcggggtgg   111900
ggtgggggc  ggcggcggct cgccctccgt cctcccctcc ttcctctccc cgtcgactcg   111960
cgtcgcggcg  attcgggccg catcgaggcg cgtcggggtt ttcgcgccct cgcgccgccg   112020
ccgcctcctc  atctttcgtg gttaacacac accaccacac atacacaccc tcccccgcg    112080
ccgctgtctg  tggcgcccgt cgtctctccc gccggcgcaa ccccgggccc tgagagcttt   112140
ctccgctttc  tatttcggcc ccggcctccc cgacctctct caccgccct  cccgcgctct   112200
cttctcccaca cacacaagag gctcgccctc gttccatcat ctcggcgtac tcgccgcctc   112260
gtacactaca  tccgtctacc gccgccagca acccttttt  ttccccgctc actcctcctc   112320
ccccctcctc  ctcctcctcc tcctcccccc tcctgcctcc attcatcaat ctcgtccagg   112380
ccgcgggccc  attcaccatc gccgcggtcc gagctcggcc aggagagatg gatgatgga   112440
ttgggggaag  gaggggcggg gagcgcgagc gggagaaggt tggcgaagga gagagcgaga   112500
gcgggaactg  gagaggggggc tgggtggggt gaggcgagtg accgccaccg ccctctacca   112560
ccaccacccc  tccccctccct ctcctctctc tccccggtcc cgtgtgcaca cacagagagt   112620
gtttttttt  ccttcttctt cccggttcct cttcgtcctc cgggccctcg gtgccgcgat   112680
ccccccacccc gccccgcccc ccttcctcct ccccccattt ccccccaccccc caattccccc   112740
actcctccca  caccagcccc caccgccgcg gccgcagccg ccgcgatccg tcctccccat   112800
tcatcttttt  tccagaggcc attcatcgcc ccgctcatcc gtcttcatcg ccgcggaggg   112860
ctggctcgag  gccagcgcgc cctttcctct cccggcgcgc ccgctccctc cgcgtccct    112920
ctccccgccg  cccccgcgg  ccacaccgag ccttctccgc gcggtcccgc ctctcctctc   112980
ctctccccc  atcccgcccc gctccccgcc ccctctcccc ccccctctcc cgccggtgtt   113040
ttcccacgcc  cacactcact ttctccgctc ccacccccacc ctcctgactc accccgtcccg   113100
ggggattccc  tgtccctcgg ggcgcggccg accggcggt  gacccatccc cacccccgccg   113160
cgccccttt  tcctcgagag cgggcgtccg ggaagggaga ggtcgcggcg ggtcacgcgc   113220
gctccccgcga  cttcccggcc cgcgatgcgg tcccggaaat ttccgggacg gtcgccgcgg   113280
ccgtctcggg  gcccgcggcg ccgccaactc gagtcttggc acgctgccag cgttcgcact   113340
```

```
tgttgtatat aagatataat actagtatat attagcaatt ggtgcgaacg tgacgtggcc   113400
caatcaaatc cggccctcgg gcccacgtgc cccattggca atttatcgac cgctttccga   113460
agggatcgaa ccccgggggca cccgcctccg gggacgcgcc agccaatgcg ggctcccggg   113520
acgcgggcac ggctccccca ttggccggtc ccggacgccc gtcccgcggg ccggaccgcc   113580
cccttcccgg gacttggcac gcatccagcg ttcgcacttg cggtatataa gatataatac   113640
tagtatatat tagcaattgg tgcgaacgtg acgtggccca atcaaatctc tccacgggcc   113700
ccacgtgccc ccattggcga tttatcgatc gctttccgaa gggatcgaac cccgggggcg   113760
ggcgccccgg ggacgcgccg gccaatgggg gagccgggcc cgcgtccccg gggcccacgt   113820
gtgaggcccc ggccaatggg cccgtcggcc cggcccctc dacggggcga taagggggtg   113880
cgcggcggcc cggccgacgg cactcgccgc cccaacgacg ccgacgggga tcgaccggga   113940
gaggcgcgag cgcgcccga gccgacgagg agccgcgccc cgctcgagga cgcccggacg   114000
acgacggtga cgtcggcatc ggcttcgacg acgacgatcg cgggacccga cggtaccgga   114060
tgcgggggat ccccggtcg gggtggggccg ggagtggggcg tggcaactcc tccccgtccc   114120
ccctccccac cccgcgcgat cgcgctcatc gtatccgttc tcgtttcagg tgccgcatcg   114180
ttccggaaga aacgcctcgg gggtcgcgcg tccgtcgcct aggtgagtcg ggggggcttcc   114240 cgggtgcggc tccccccctc cccctcccc tccccgggt tgggttgggc gggtgggcgg   114300
gggtcgggag ggatcggggg aaggggaggg ggtcgtggct cacgctgacg tcatgcgttt   114360 tcttccccc cccacaggg acgcgagcgg gaccggctgg tcgaccaccc attcaatcca   114420
tccaatccat ccagccaccc ccacccgtcg gggcggccgg gctcggttcc gggtcggcgt   114480
cggggagcct cgcccaccca cccggccccc gtcccagccc agccccccc acgccccat   114540 cgcaccccct cccaccccac cccgttccca ccaccccgcc gaccccccgc tcgaccgccc   114600 gccccgacc caccgcgtcc gccgcgccca tggaccgggt ctgggccgac tggtacgagc   114660
ccgtgccctc cccgccgttc tcgcccgtcg accgccccgg gccccggccc acgacccgc   114720 tccggggag cagccccccg tccccgcct cgacccccac gccccccaag cgcggggcgct   114780 acgtcgtcga gcaccccgag tacgggcccc cgcccgaccc cgaggaggtg cgcgtccacg   114840
gcgcgcgggg cccggcgcc ttctgcgcgg cccctggcg ccccgacacg cggcgcctcg   114900
gggccgacgt gaaccgcctc tttcgcggca tgccgtctc ggccgccgac gtgacgggcg   114960
acacgcgcgc cctgcgccgc gccctctttg actttttacgc catgggctac acgcgccagc   115020 gccccctcggc ccctgctgg caggccctgc tccagctctc gcccgagcag agcgccccgc   115080
tgcgcagcgc gctgcgcgag ctcaacgagc gcgacgtcta cgacccgcgc gtcctctccc   115140
cgccggtcat cgagggcccg ctctttgggg aggagtgcga cgtcgacgag gacgacgccg   115200
gctcggacac caccgtcgcg tccgagttta gcttccgcgg ctcggtgtgc gaggacgacg   115260
gggaggacga ggacgaagag gaagacgggg aggaggaaga cgaggacgag gaggggaag   115320 aggaagaaga cgaggaggaa gaggaagacg aggacgagga ggaagaggaa ggggacgagg   115380
acggggagac ggacgtgtac gaggaggacg acgaggacga ggacgggctc tgtgaggacg   115440
aggccgagga cgaggaggac gaggaggacg gggacgactt tgacgggggcc agcgtgggcg   115500 acgacgacgt gtttgagccc cccgaggacg gctcggacgg agagggctcg ggctcggacg   115560 acggcggga cggggaagag gaagacgaag atgaagacga ggacgaggac gatggagagg   115620
acgaggagga cgaggaagag gaggacgggg gggaagacgg cgaagacggt gaagaagacg   115680
```

```
aagacgaaga cggagagggc gaggagggcg ggaaggacgc cgcccgccgg gggacgcgcg   115740
ccccgacgcg gcccgccgcc gccccgtgag gcgggcctcg ccccgcgctg ttcttcccac   115800
tccccccccc ccccacccca ccgtccgccc catcgtttgc ccctctcccc ttcccctctg   115860
ttgtgccctc aataaacacg gcggcccgcc gctcgaacct caactctctc gtctctcggg   115920
cgttttttcc ctcccggccc tcgtggggaa gggagatggg gtgggggaga gggggacggt   115980
gggggagagg ggtggaggga gagaaaggac agaggccggg cgcgtcgggt tcgagagcga   116040
gggcgtttat tgttaaagtt gttggtgggg gggagtccgg gggagtccgg gggagtcagg   116100
gggagtcagg gggagtccgg gggagtcagg gggagtcagg gggagtccgg gggagtccgg   116160
gggagtcctc ggcggctagg agatggtgca aggagtgggg gggtgaggtc ctcggcggct   116220
attggtggga aggggagtg acgtcaggc agcggggga aagggggggg aagggggga   116280 gagcgagtgg gtggcggcgg cgagagtctg tcggatggcg ccaggggggg cgggcgggcg   116340
gccgcgggga gggaggacgg gcgcgcgtga ggcggcggcg ccccgtcgcg gtcgagaacc   116400
accgccgccg tcaccgccgc ctcccatccg atgtgatatc gcggcacgcc ggccgtcccg   116460
gcgttcattc acaccgcacc cgttcgccca cgtccccgcg ggcaagcacg cacacacccg   116520
gtcgcgcatc atgctggcga tgtggagatg ggtcaccaag aggtcgcggc tccgccgagg   116580
ccacgcccat cttgggggaa ataaaggagt ccggggaatt tgttccttat accttgccgg   116640
gctcagcagg gggttgtcgc gcgtccacgc ccagcgctcg cacgcagcaa caatggccga   116700
cgccggaatc cccgacgaga tcctgtactc ggacatcagc gacgacgaga tcatcatcga   116760
cggcgacggc gacagcagcg gggacgagga cgacgatgac gggggggctga cgcggcaggc   116820 cgcggcgcgc atcgtcacgg acctgggctt cgaggtgctg cagcccctgc agtcgggctc   116880
ggagggccgc gtcttcgtgg cccgccggcc gggcgaggcg gacacggtgg tgctgaaggt   116940
gggccagaag ccctcgacgc tgatggaggg catgctgctg cagcgcctgt cccacgataa   117000
cgtcatgcgc atgaaacaga tgctcgcccg gggcccggcg acgtgcctgg tcctgccgca   117060 cttcggtgc gatctgtaca gctacctgac catgcgggac gggccgctgg acatgcgcga   117120
cgccgggtgc gtgatccggg ccgtgctccg cgggctcgcc tacctgcacg ggatgcgcat   117180
catgcaccgc gacgtcaagg cggagaacat cttcctcgag gacgtggaca cggtgtgcct   117240
gggggacctc ggggccgcgc gctgcaacgt ggcggcgccc aacttttacg ggctcgccgg   117300
gaccatcgag accaacgccc ccgaggtgct cgcgcgcgac cgctacgaca ccaaggtcga   117360
cgtctggggc gcggggtgg tgctcttcga gacgctggcc taccccaaga cgatcaccgg   117420
cggggacgag cccgcgatca acggggagat gcacctgatc gacctcatcc gcgccctcgg   117480 ggtgcaccc gaggagttcc cgcccgacac gcgcctccgg agcgagttcg tccggtacgc   117540
cgggacccac cgccagccgt acacgcagta cgcgcgcgtg gctcgcctcg ggctgccga   117600 gacgggggct ttcctgattt acaagatgtt gacgtttgat cccgtccgcc gcccttccgc   117660
tgatgagata ctcaactttg gaatgtggac cgtataaaac gggccggctc cgagcggtag   117720
gacacacaca cctttgcgca tctccacagc tcaacaatga agtgggcaac gtggatcctc   117780
gccctcgggc tcctcgtggt ccgcaccgtc gtggccagag aggcccctcg ggagctctgc   117840
tacggccacc ccgtccacga cgaccggcgg cccgtcgggc ccgcgaccga cgcccagccc   117900
gtgaacccgc tcgcccccgc caacgccacc gggacggact actctcgcgg ctgcgagatg   117960
cgcctcctgg atccgcctct cgatgtatcg tcccgctcct cggaccccgt caacgtgacc   118020
gtcgcctggt tctttgacgg cggccactgc aaggtgcccc tcgtccaccg cgagtactac   118080
```

```
ggctgccccg gggacgccat gccctccgtc gagacgtgca ccggcgggta ctcgtacacc   118140
cgcacgcgca tcgacaccct gatggagtac gccctcgtga acgccagcct cgtgctgcag   118200
cccgggctgt acgacgccgg cctgtacatc gtcgtgctcg tctttggcga cgacgcctac   118260
ctcggcaccg tctccctgtc ggtggaggcc aacctggact accctgcgg catgaagcac    118320 gggctcacga tcacccgccc cggggccacc ctcccaccca tcgccccac ggccggcgac    118380 caccagcgct ggcgcgggtg cttcccctcg accgacgagg gcgcctggga gaacgtgacc   118440
gccgccgaga agggcctgtc cgacgactac gccgactact acgacgcgca catcttccgc   118500
ctggagtctg acgacgaggt cgtccacggc gatgccccg aggcccccga gggcgaggag    118560
gtgaccgagg aggaggccga gctgacctcc agcgacctcg acaacatcga gatcgaggtc   118620
gtgggctctc ccgccgctcc cgtcgagggc ccggcgacg gcgaggaggg gcacagggac    118680
gaggaggacg aggagctgac ctccagcgac cttgacaaca tcgagatcga ggtcgtgggc   118740
tcgcccgcgg ccgccgcgtt cttcgccgcc tccaccaccc ccgcgcccc cacccgcgcg   118800 gccgagatca cgaccatgac cacggtcacc accgtgcgga cgaccgagga ccccagcggc   118860
atcaccgact gccgccggag cgactttgtc tcgccctctg acatcttcgt gaccccccacc  118920 ggcagccccg ctctgctcct gggcttcctg ggcagcgcgc tcgcctcgcg cccccctgcac  118980 ctgacggccg gggagacggc ccagcacgtg cgcgaggccc agcagaagag ccgccacatc   119040
cgctccctcg gcggcctcca gctctcggtc gagaccgaga ccaccaacac caccaccacc   119100
cagacgggcc tgtcgggcga catccgcacc tcgatctaca tctgcgtcgc cctcgccggc   119160
ctggtcgtcg tgggcatcgt catcatgtgc ctccatatgg cgatcaccag ggcccgggcc   119220
cggaacgacg gctaccgcca cgtggcctcc gcctgacccg gccccgcccg actccccgc    119280 gatccccccc ctctcaccgg gtgtccatct tcaataaagt atgtctcaaa cacctaattt   119340
gcgtacggcc ttgcttacgg gggtgcgccc cacgcccagc ggtccataaa attgggttgg   119400
ggccccaggt tcccatacac tcacccgcca gcgccatgct gctcgcagcg ctattggcgg   119460
cgctggtcgc ccggacgacg ctcggcgcgc acgtggacgc cgtgcccgcg ccgaccttcc   119520 ccccgccccgc gtacccgtac accgagtcgt ggcagctgac gctgacgacg gtcccctcgc   119580
ccttcgtcgg ccccgcggac gtctaccaca cgcgcccgct ggaggacccg tgcggggtgg   119640
cggcgctgat ctccgacccg caggtggacc ggctgctgag cgaggcggtg gcccaccggc   119700
ggcccacgta ccgcgcccac gtggcctggt accgcatcgc ggacgggtgc gcgcacctgc   119760
tgtactttat cgagtacgcc gactgcgacc ccaggcagat cttttgggcgc tgccggcgcc   119820 gcaccacgcc gatgtggtgg accccgtccg cggactacat gttccccacg gaggacgagc   119880
tggggctgct catggtggct ccggggcggt tcaacgaggg ccagtaccgg cgcctggtgt    119940
ccgtcgacgg cgtgaacatc ctcaccgact tcatggtggc gctccccgag gggcaagagt   120000
gcccgttcgc ccgcgtggac cagcaccgca cgtacaagtt cggcgcgtgc tggaacgacg   120060
agagcttcag gcggggcgtg gacgtgatgc gattcctgac gccgttctac cagcagcccc   120120
cgcaccggga ggtggtgaac tactggtacc gcaagaacgg ccggacgctc ccgcgggcct   120180
acgccgccgc cacgccgtac gccatcgacc ccgcgcggcc ctcggcgggc tcgccgaggc    120240
ccaggccccg gccccggccc cggccgaagc ccgagcccgc cccggtgacg cccgcgcccc   120300
ccggccgcct gccgagccg gcgacgcggg accacgccgc cggggccac cccacgcgc     120360 gaccccccgag gcccgagacg ccgcaccgcc ccttcgcccc gccggccgtc gtgcccagcg   120420
```

```
ggtggccgca gcccgcggag ccgttccagc cgcggacccc cgccgcgccg ggcgtctcgc  120480
gccaccgctc ggtgatcgtc ggcacgggca ccgcgatggg cgcgctcctg gtgggcgtgt  120540
gcgtctacat cttcttccgc ctgaggggggg cgaagggta tcgcctcctg gcggtcccg   120600
cggacaccga cgagctaaaa gcgcagcccg gtccgtagcc tccgcagtac cggcgtcgat  120660
gatgatggtg gcgcgcgacg tgacccggct ccccgcgggg ctcctcctcg ccgccctgac  120720
cctggccgcc ctgaccccgc gcgtcggggg cgtcctcttc aggggcgccg gcgtcagcgt  120780
gcacgtcgcc ggcagcgccg tcctcgtgcc tggcgacgcg cccaacctga cgatcgacgg  120840
gacgctgctg tttctggagg ggccctcgcc gagcaactac agcgggcgcg tggagctgct  120900
gcgcctcgac cccaagcgcg cctgcttgcg gacgcggtcc gaccccacgg cgccgttcta  120960
catcaccacc gagacgcacg agctgacgcg gcgcccccg gcggacggct cgaagcccgg  121020
ggagcccctc cgtatcagcc cgccccgcg gctggacacg gagtggtcgt ccgtcctgaa  121080
cgggatccag tacctgaact cgggggcccg gggcacggcc ccgatccacc tgtggatcct  121140
gggcgccgcc gacctctgcg accaggtgct cctggccgcc tcccgcagca ccgccgccgg  121200
agccccggc gccccgacgg gcgcgcgcct gacccggcgg cggcccgggc tgacggacgc  121260
cgacgccctg gacgtgatcg tcgccgggat cccgccacc cgcgccatgt tcgcgcgggt  121320
ccacaaccgc tcctggcgcc acgccggcga gtggacggag gccctgcatg cccagatcgt  121380
gacccggggc gacgtgcgcc ggcgccgagg cgggcgcgcg aacggacgcg agcgcgcccc  121440
gcgatgtacc atctcctaga cggcaggatc tctccgcatc ccccacaccc ccccaaaaaa  121500
acaaacaata aacgctctcg ctctggcacc cgatgcacg cctccgtcct ctctctcccct  121560
ccccccatct cccctttccc cccctttcc ccccgctgcc ctgacgtcac tcccccttcc  121620
caccaatagc cgccgaggac ctcaccccc cactccttgc accatctcct agccgccgag  121680
gactccccg gactccccg gactccccct gactccccct gactccccg gactccccct  121740
gactccccct gactccccg gactccccg gactcccccc caccaacaac tttaacaata  121800
aacgccctcg ctctcgaacc cgacgcgccc ggcctctgtc cttctctctcc ctccaccccct  121860
ctcccccacc gtccccctct cccccacccc atctcccttc cccacgaggg ccgggaggga  121920
aaaaacgccc gagagacgag agagttgagg ttcgagcggc gggccgccgt gtttattgag  121980
ggcacaacag aggggaaggg gagaggggca aacgatgggg cggacggtgg ggtgggggg  122040
gggggagtg ggaagaacag cgcggggcga ggcccgcctc acggggcggc ggcgggccgc  122100
gtcggggcgc gcgtccccg gcgggcgcg tccttcccgc cctcctcgcc ctctccgtct  122160
tcgtcttcgt cttcttcacc gtcttcgccg tcttcccccc cgtcctcctc ttcctcgtcc  122220
tcctcgtcct ctccatcgtc ctcgtcctcg tcttcatctt cgtcttcctc ttccccgtcc  122280
ccgccgtcgt ccgagcccga gccctctccg tccgagccgt cctcgggggg ctcaaacacg  122340
tcgtcgtcgc ccacgctggc cccgtcaaag tcgtccccgt cctcctcgtc ctcctcgtcc  122400
tcggcctcgt cctcacagag cccgtcctcg tcctcgtcgt cctcctcgta cacgtccgtc  122460
tccccgtcct cgtccccttc ctcttcctcc tcgtcctcgt cttcctcttc ctcctcgtct  122520
tcttcctctt cccctcctc gtcctcgtct tcctcctccc cgtcttcctc ttcgtcctcg  122580
tcctccccgt cgtcctcgca caccgagccg cggaagctaa actcggacgc gacggtggtg  122640
tccgagccgg cgtcgtcctc gtcgacgtcg cactcctccc caaagagcgg ccctcgatg  122700
accggcgggg agaggacgcg cgggtcgtag acgtcgcgct cgttgagctc gcgcagcgcg  122760
ctgcgcagcg gggcgctctg ctcgggcgag agctggagca gggcctgcca gcaggggcc  122820
```

```
gaggggcgct ggcgcgtgta gcccatggcg taaaagtcaa agagggcgcg gcgcagggcg    122880
cgcgtgtcgc ccgtcacgtc ggcggccgag acggcgatgc cgcgaaagag gcggttcacg    122940
tcggccccga ggcgccgcgt gtcggggcgc caggggaccg cgcagaaggc gccggggccc    123000
cgcgcgccgt ggacgcgcac ctcctcgggg tcggcgggg gcccgtactc ggggtgctcg    123060
acgacgtagc gcccgcgctt ggggggcgtg ggggtcgagg cggggacgg ggggctgctc    123120
cccgggagcg gggtcgtggg ccggggcccg ggcgggtcga cgggcgagaa cggcggggag    123180
ggcacgggct cgtaccagtc ggcccagacc cggtccatgg gcgcggcgga cgcggtgggt    123240
cgggggcggg cggtcgagcg gggggtcggc ggggtggtgg gaacggggtg gggtgggagg    123300
gggtgcgatg ggggcgtggg gggggctggg ctgggacggg ggccgggtgg gtgggcgagg    123360
ctccccgacg ccgaccccgga accgagcccg gccgccccga cgggtggggg tggctggatg    123420
gattggatgg attgaatggg tggtcgacca gccggtcccg ctcgcgtccc tgtgggggg    123480
gggaagaaaa cgcatgacgt cagcgtgagc cacgaccccc tccccttccc ccgatccctc    123540
ccgacccccg cccacccgcc caacccaacc cgggggaggg gaggggggag gggggagcc    123600
gcacccggga agcccccgga ctcacctagg cgacggacgc gcgaccccg aggcgtttct    123660
tccggaacga tgcggcacct gaaacgagaa cggatacgat gagcgcgatc gcgcggggtg    123720
gggagggggg acgggagga gttgccacgc ccactcccgg cccacccga ccggggatc    123780
ccccgcatcc ggtaccgtcg ggtcccgcga tcgtcgtcgt cgaagccgat gccgacgtca    123840
ccgtcgtcgt ccgggcgtcc tcgagcgggg cgcggctcct cgtcggctcg gggcgcgctc    123900
gcgcctctcc cggtcgatcc ccgtcggcgt cgttggggcg gcgagtgccg tcggccgggc    123960
cgccgcgcac cccttatcg ccccgtcgag ggggccggggc cgacgggccc attggccggg    124020
gcctcacacg tgggccccgg ggacgcgggc ccggctcccc cattggccgg cgcgtccccg    124080
gggcgcccgc ccccgggggtt cgatcccttc ggaaagcgat cgataaatcg ccaatggggg    124140
cacgtgggggc ccgtggagag atttgattgg gccacgtcac gttcgcacca attgctaata    124200
tatactagta ttatatctta tataccgcaa gtgcgaacgc tggatgcgtg ccaagtcccg    124260
ggaaggggggc ggtccggccc gcgggacggg cgtccgggac cggccaatgg gggagccgtg    124320
cccgcgtccc gggagcccgc attggctggc gcgtccccgg aggcgggtgc ccgggggttc    124380
gatcccttcg gaaagcggtc gataaattgc caatggggca cgtgggcccg agggccggat    124440
ttgattgggc cacgtcacgt tcgcaccaat tgctaatata tactagtatt atatcttata    124500
tacaacaagt gcgaacgctg gcagcgtgcc aagactcgag ttggcggcgc cgcgggcccc    124560
gagacggccg cggcgaccgt cccggaaatt tccggaccg catcgcgggc cggaagtcg    124620
cgggagcgcg cgtgacccgc cgcgacctct cccttcccgg acgcccgctc tcgaggaaaa    124680
aggggcgcgg cggggtgggg atgggtcacc gccgggtcgg ccgcgccccg agggacaggg    124740
aatccccggg gacgggtgag tcaggagggt ggggtgggag cggagaaagt gagtgtgggc    124800
gtgggaaaac accggcggga gagggggggg gagaggggc ggggagcggg gcgggatggg    124860
gggagaggag aggagaggcg ggaccgcgcg gagaaggctc ggtgtggccg cggggggcgg    124920
cggggagagg ggacgcggag ggagcgggcg cgccgggaga ggaaagggcg cgctggcctc    124980
gagccagccc tccgcggcga tgaagacgga tgagcggggc gatgaatggc ctctggaaaa    125040
aagatgaatg gggaggacgg atcgcggcgg ctgcggccgc ggcggtgggg gctggtgtgg    125100
gaggagtggg ggaattgggg gtgggggaaa tgggggggagg aggaagggg gcggggcggg    125160
```

```
gtgggggatc gcggcaccga gggcccggag gacgaagagg aaccgggaag aagaaggaaa   125220
aaaaaacact ctctgtgtgt gcacacggga ccggggagag agaggagagg gaggggaggg   125280
gtggtggtgg tagagggcgg tggcggtcac tcgcctcacc ccacccagcc ccctctccag   125340
ttcccgctct cgctctctcc ttcgccaacc ttctcccgct cgcgctcccc gcccctcctt   125400
cccccaatcc atccatccat ctctcctggc cgagctcgga ccgcggcgat ggtgaatggg   125460
cccgcggcct ggacgagatt gatgaatgga ggcaggaggg gggaggagga ggaggaggag   125520 gagggggag gaggagtgag cggggaaaaa aagggttgc tggcggcggt agacggatgt   125580
agtgtacgag gcggcgagta cgccgagatg atggaacgag ggcgagcctc ttgtgtgtgt   125640
gggaaagaga gcgcgggagg gcgggtgaga gaggtcgggg aggccgggc cgaaatagaa   125700 agcggagaaa gctctcaggg cccgggttg cgccggcggg agagacgacg ggcgccacag   125760
acagcggcgc ggggggaggg tgtgtatgtg tggtggtgtg tgttaaccac gaaagatgag   125820
gaggcggcgg cggcgcgagg gcgcgaaaac cccgacgcgc ctcgatgcgg cccgaatcgc   125880
cgcgacgcga gtcgacgggg agaggaagga ggggaggacg gagggcgagc cgccgccgcc   125940 ccccaccca ccccgcccct ctcgcccacg cgccctctcc ccccttcgcg cacgctcact   126000
cgcccgcgcc cccgccccgc acccccgctc ccctctcgt tccgcgccgc acgcgccgtc   126060
ccgcggcccc gtcgggcgca gggatcgtag caaacgcggg cggtcggcgt gcgcgctgtg   126120
cgggtgggtg ggggagggg ttgatggccg cgccggttcc gggaagcctc ccccggcggg   126180 cgggggggg gtcggggccg ggttcgctct gtaccctctc acgcgggccc ggagtgccgc   126240 gggcggggc ggggcagcac tcagcgaagg ctcggggtgt tccagccgat ggccccgggg   126300
gcacgcgggc gggaggagtt gcgtgggcgg agaggagcga ggaggactgg cggcggcggc   126360
ggaggaggag gggggaagag gcggcgagcg gagcggcgcg gtagcgcccg cgggcggccc   126420
gcgcggtatc gcccgcgcgg tatcgcggcg gcccgggaga gcgggcgggg gacggggacg   126480 gggacggggga ggaggaggga ggaaggggt cgccgccgcg gccctcgcgg cccgggagaa   126540
gccttcccgg acgcgccatt agagagggct ctgtctgcag aaacggtgtc taggcgccgc   126600
gccaggggaa accgcagcgg cgataaaata gcttttagct cggcgctctc tctgggtcgc   126660
agcgccctaa acttggcacg gtccgccgca cagtgtggcc cgcgtccagg ccggcccggc   126720
gagcgagcga gcgagcgggc gagcgggggg ccccggcccg ctccaccgtg acacccaccc   126780
acaccgtaaa ctctcacacg gacacgcgcg cccaccctcg gcgccgcggg cccgaccccg   126840
gtccgcgccg gcaccccctt ttctccggca ccaagccggg gggccgggc gaggggaagg   126900 ggaaggggaa gggggggggg ggacggggtg cgcgcgcgtg tgtgtatgtg tatgtggcac   126960
cggcatcggt ctccccccaa aacgagaag gcgagggaga cggagaggga ggtgtgtctc   127020
tgtgttgttt ttttcctgct ggcgccgcgg tgcgcgaacg tgatcacggg ggggcggcgc   127080
gctccgcgct ccccgccgc ctgggcgggg atgccgcgcc ggcacgagcg cacgcgggcg   127140 cgcggcggc ggggagggag gagggcggag gaagggccgg gccgccgagc cggccgcgcc   127200
attgggcgcc gggcggaacg gggcgtggag aggcgcccgc gccggggacg cgcctgcggc   127260
ggcgggcgcg cgccggcgg ctttcctcct tcaccgccgc cgcgtcctcc tcctccctcc   127320
ccgccggcct cggcccaccc gcggcgtcac cccgctctcc ccctcattcc ccccccctcc   127380
ctcccttccc cccgaccccc ctcccctccc gcgtcctgcg tcacggggac cgggggtcc   127440 cgcgtgatga cgccggggac gcgggacgcg cccgccgcct gggagccggc gaggaggaca   127500
aaaagagttc tgtgtcccct cgcccccctc cgcgtccgca gccgcctctg cagccgccgc   127560
```

```
ccgcgccgcg accggcgaac gcagagaggg gacgcgggga agagacgcgg agaggggac   127620 aggggagag  agagcgaggg gcgcgagcgc ttcctcctcc gcacccgcct tcctccgccc   127680
gcctttcatt cccggactcg ggagccgctc ccgctccccc gttttcctc ctggccgcgg   127740 cgaccgccgc cgccgctctc gaggtttttt tttccttcct ctccttcttc ctcctcctcc   127800
tccgcctttg ggtgtttcct tctccgcgtc cccatctccg aggcccgagg cgccggggct   127860
ttcttcccgg accgccgggg aggaagcgcc ccggcttctg cttcttattc tcctctctcg   127920
gtaagcacag actctcctac tactactcct actactccta ctcctactat attactatga   127980
ctactactat gactactact atgactacta cggtgacttc tcctcccgc tctagactt    128040 ttttcctccc ctctcctcct ttcgctcccg tctcccgggc acccgcggcc gggcggaggg   128100
ggaagcggga aggggaagcg cggggcgccg cgcctctccc tcccgcttcc ccccccccg    128160 ccggcccctt ccccgtttcc ccgtttccct ttccccccctt cccgtctgt tccttccccc   128220 gcttcccgt  ttcttcttct tcccccccc gtccctctt ccttcccac acgcccgct     128280 ctcccacgcc gcggccgcgg ggggccgaag cggacgcgga agaagacgcg gaagaagaga   128340
gagagagaaa gaggggggcc ggcggggatg gggaagaagg cccgacccgc gcggggcccc   128400
cctcctgtcg cctgtcgttt gaatgaaacc ttcccccgag cgacccgct cccgcctgtg   128460 gtgccgtgtt ttttccccgc gacggggaga gcgcgagagt gaggcgtcg gctgtgggtt   128520 gtcggctgtt ggccgttggc tgaggacgac ggggagggg ggatgctgcc gcgggtggca   128580
tgagacggag gggggcgagg gcgggcggtg gaggggggga aggaaggtct gggcgcgcgt   128640
gccgcgggcc gagtgtcggg cgagtgcgag gcgggtcggg gggcggggag gaaggagt    128700 gtgggggggat ggccggccgg cgccccccgga gcacgcgggg cgcccgcg ggcgggaggg   128760 ggtccggggg aagggtgggg cggtggcggc ggccatcgcc cgacccttcc ccggggcgcg   128820
cgcgcgtggg accgggaccg ggaccgggac cgggaccggg accggacag ggggcggggg   128880 cggggcggg  ggcggggaga ggaggagagg agacggagga gaggagacgg aggagagtcg   128940
gaaagtcggg cggaggacag aggcggagag ggcgagcgag acacgcacgg ggagaggcgc   129000
gcgcacacac gcggagagag agaggagagg cgagagagga ggagaaggag gaggcgaact   129060
gggggaaagg cgagacacgc ccgggcaccc ccctcctcg gaccgaggcg acggcggaga   129120
cggagacgga gagaccgccc gcccggccac caccgtcggt accggtatcg ccagtaacac   129180
ccgcaccacc gacacccaca cggaccctca cacccgcacc ggcccccata ctcgcaccgg   129240
ccctcacacc cacccacacg cacgcacgct tctctcgca caccccaca tcacacgctc    129300 cccgcgcaca gacacacaga cgacaccctc cccgcccgcc ccgtccgacc gaccatccgt   129360
cctcccgacc ctcacgaga  gagagagagc gagccttccc tgcacacaca gcaaaaattg   129420
acccccccca tcccggaccc cccccggggc ggggccctcg cgcctccgcg tccggcgggc   129480
gcgatcgagg cccgcgcgcc cccggggct cggggcggga cgcggcgccc gcgcggggac    129540
acgctttccc ccggagggc gtcccggcgc gccggcccgg ccctcccgc cgggaagggg    129600 gcccggccct cttcgtctcc cggagcgccc ccggggtccc ggcccgaggt ccatttgggg   129660
ccccgcccct ttgcacccgc ccccccccac cgggcgggt ccgcgctccg accccccccc    129720
ctccccctct gccacgcccc gccacgcccc gtcgccatct tggctcccct ccccccaact   129780
ccctctctcc cgacgaggcc gagccggtct cgcgccccct cccgcccgcc cgaggtaccg   129840
cggaaggacg acacgagccg gaagacggtg caacgagaac aactttttatt ttttcactc   129900
```

```
tggggcgtgt ctcgtggggt gggagggggg accgggagag agagatagag gggggggggg    129960
agaggagggg gtgggtgggc gacaaaagta tccaaggcgt ggctgtccgg ctccttcctt    130020
ccgggtccgg gcgggtccgg gctcgaggtt cgggtccggt tctcccgccc cggcgtcgct    130080
tcccggttcg ggtccggtcg ccggtccccg gtccgacggc ggttccgctc gtctctccga    130140
ccggctgggg gcgccctcgg agcgcgcgcc gagcgcgcag gcgcgggtgg ggcgaccgcg    130200
ggggtcgcgg gagggtctcg ggggtctcag gggtctcggg gagggggaaa cggggggtctc   130260
ggggtctcgc gagtggcagg gggaggcggt gagaccacca cacaacacag agaccaccac    130320
aacacagaga ccaccacaca acacagagac caccacaaca cagagaccac cacacaaacac   130380
atgcggacca ccacaacaca gagaccacca cacaacacat gcggaccacc acaacacaga    130440
gaccaccaca acacatgcgg accacgtgca gacacacgga agcttgcacc gtgaggcccc    130500
attggccgag ggcggccacg tggggcgagc atgcaaatga cgtgcacacg gaagcttccc    130560
cgaaaatcat ctgattggct cgctagcacc acggggtggg tcgcgtgccg agcatgcgcc    130620
tcgcgcccgc gcgagggatt ttcggacaat ctcattggcc gcccgcggcc aagatggccg    130680
cagagcgggc cgggcatgca aatcagaggc gcgcgggaga cgcctccgcg cgcccattgg    130740
cccgggcggg ccgagatggc cgccgcgggg gccgggcatg caaagtagac gcgagaggaa    130800
gtgggcgaga gaaatcccat tggccgtcga ggggccaaga tggcgccctc ggggccggac    130860
atgcaaagta gacgcgagag gaagtgggcg agagaaatcc cattggccgt cgagtgggca    130920
agatggccgc cgcgggggcc gggcatgcaa atggtcctcg cgaggaagtt cctcgcgaaa    130980
tcccattggc cggcggccgc catcttgggc cgggcatgca aagcagacgc gagaggaagc    131040
gggcgagaaa aatcccattg gccggccgtc ggggaagtcc gcggcgaaaa tcggccattg    131100
gtccgcttac ctgggggcgg gctctcctcg gggcgcttat aagcgcggtc tccatcgtag    131160
cacttcactg cggtgcaggt acggacagca tcgttctctg ccaacccgag gggatccgac    131220
cgtctccgct ccggcgcgga ctctgaagac tccggctctc cggcggctat cagccctcga    131280
cggacgcccg acccaccgag gctctcggcc caccagagaa gagtcttctt cttctcctcc    131340
tccggccgcc ttcctccttc ttctccgccg cccgctctcc gcgctcggcg cccagcctcg    131400
ctcaggcaga aagaccccga tcgagaccat ggccgacgat ctctttgact tcatcgagac    131460
cgagggcaac ttcagccagc tcctggcggc cgccgccgcc gcggccgagg aagagggcat    131520
cgcgtccggc cccgacggcg gcagccaggg ctcccggcgc cgcggctcct ccggcgagga    131580
tctcctcttc ggcccgggcg gcctcttctc cgacgacgcc gccgaggccg aggccgaggc    131640
cgccgtcctc gcggccgcgg ccggagccac gaggccgccc cgtcctcctt cggcccagca    131700
gcagcagccc cgccggggct cgggcgagat cgtggtgcta gacgacgaag acgaggagga    131760
ggacgagccc gggtccccgg ccgccgggtc cccggtcggg gctctccatc agggctccga    131820
gcacggtcac ctcgtcctcg ggcccgggtc ccgggccggc tccggccccc ggccgccgac    131880
cccggcagca ctcgcagcgg cagaggccgg ggccccccggc ggccccgggc gctcgtcccc    131940
ctccgcggcc tccccggcct cctcctccgg ctcccccggc ccctcggcag cccgcggag    132000
atggtccccc gcggggacc cggtcggtga gccggggccg gcggcgcggc ctcggacccc    132060
ggcgccacca gcacagccag cagcggtggc cgcagcgccg gcacggcggg ggcccgcttc    132120
cccagccccc ccgccgccg ggccggtctc ggcgccccgg ggcggcggcg ccccctccgc    132180
cggaggggac cgcggtcgtc accatcacca gcaccgcgag cccctgctcg acgagccgc    132240
cgccgcgagg cggctcgatc ctcggccgct tggcgcccgg agcccccgtct cctccaaccc   132300
```

```
caactccaac tccagctcca ccaccaccgt cgccgtcgag cccgtcgccc gcggcccga   132360 gaaggacgag gacggactcg gccccgccgg ggacggcggg gcgcccccgc agagacagcc   132420
ccgccggcgc cgcgccggag agggcgcccct ccgccgcggc cgcggcttca gcagctccag  132480
cagcggcgga agcgactcgg acctctcccc ggcccgctcg ccctccgccc cccgggcccct  132540 cgccgccgcc gccgcgcggc gctcggcctc ctcctcgtcc tcgtcctcct cgtcctcctc   132600
gtcctcgtcc tcctccgagg gagaagaaga cgaaggagtc cggcccggcg ccccactcgc   132660
ccgcgccggg ccgccaccgt ctccgccggc gccccgccgcg gccccgcggc cctcggcctc   132720
ctccgcctcc tcctccgccg cggcctcccc ggccccggcc ccggagcccg cccggccccc   132780
gcgcaggaag cgccgctcca ccaacaacca cctctcgctc atggccgacg gccccccgcc   132840
gaccgacggg ccgctgctca ccccgctcgg ggagccctgg cccggctccg acctccggc    132900 cgacggccgc gtccgctacg gcggcgccgg ggactcccgc gagggctct gggacgagga    132960 cgacgtccgc caggccgcgg cccgctaccg cgccgcggcc gggcccgtgc ccgtcttcat    133020
cccggagatg ggggactcga ggaagcagca cgaggccctc gtgcgcctca tctacagcgg   133080
ggccgccggc gaggccatgt cctggctgca gaacccgcgg atgcaggccc cgaccagcg   133140 cttcaaccag ttctgccagc gccgggtcca cgcgccccac ggccacggct ccttcatcac   133200
cggcagcgtg accccgccgc tgccgcacat cggggacgcc atggccgccc aggacccgct   133260
ctgggccctg ccgcacgcgg tgagcgccgt ggccatgagc cgccgctacg atcgcaccca   133320
gaagaccttc atcctgcaga gcctccgccg ggcctacgcc gacatggcct acccgggccg   133380
cgccgcggac ccccgcgccg gggaggcgac cgtcgaggcc ctctgcgccc gcgtccgcgc   133440
cgccttcgcc gccgcgcagc ccggccgcgt gccccgcgag ctggcggacg cctgcgtcct   133500
ggcctgccgc ggcgtcctcg agcgcctgct gccctgcccg ctccggctgc ccgcgcccgc   133560
ccgcgccccg gccgccctcg ggcccgcctg cctcgaggag gtgacggccg cgctgctcgc   133620
gctccgcgac gcgatccccg gggccggccc ggccgagcgg cagcaggccg cggacgctgt   133680
cgccctcgtc gcccgcaccg tggcgccgct ggtgcgctac agcgtggacg gggcccgcgc   133740
ccgcgaggcc gcctggacct acgccgcggc cctcttcgcc ccggcaacg tggccgcggc   133800 ccggctcgcc gaggccgccg cgcggcccgg gccgcggag cccgcgcccg gcctgccccc   133860
gctctggccc gagcagcccg gcctcgtcgt cccagcgccg gcgccggcgg cggcgggcgc   133920
cccctccggc ctccccggct ccgggccctc cagccccgcc agcaccaagt ccagctccag   133980
caccgagtcc ggctccagca ccaagtccag ctccggcacc aagtccgcc tctccggctc    134040 ctccggctac gccagctccc ccgccgccgg cccggaccca gcgcccgagc ggcgcaagaa   134100
gaagcgccgc gcgcccgggg cccgccgccc cggggacggc gaggaggacg aggggctctc   134160
cggcgcggcc ctccgcgggg acggccacgg ccaccgcgac gacgaagagg accggggcc    134220 ccggcgcaag cgccgctccc tcggactcgg gccgctccg gaccccgctc ccgcgctgct   134280
gtcctcctcc tcctcctccg aggacgaccg gctccggcgc ccgctcgggc ccatgcccga   134340 gcacccccgcg cccgacggcg gcttccgccg cgtccggcc ggcgagaccc acacgccgcg    134400
gccctccgag gcggccctcg ccgcctactg cccgcccgag gtggcccgcg cctcgtgga    134460 ccaggaggtc ttccccgaac tctggcgccc ggcgctcacc ttcgacccgg ccgccctggc   134520
gcacatcgcc gcgcgccgcg gggccgcggg gccccgctc cgccgccgcg ccgcctggat   134580
gcggcagata gccgacccccg aggacgtgcg cgtggtggtg ctctacgacc cgctgcccca   134640
```

```
cgaggagctc tgcgccgagc ccgccgaggg cgcccgcgc ccggcctggg acccgcgccg    134700
cggcggcctc tcggcgctgc tcgccgcctt cgcccaccgc ctctgcacgc cggactcgca    134760
cgcctgggcc gggaactgga ccgggcgccc cgacatcggc cgcctcaacg cccagggggt    134820
gctgctgctc tcggcgcggg acctcggctt cgccggcgcc gtggagtacc tctgctcgcg    134880
gctcggcgcg gcgcggcgcc ggctcatcgt gctggacacc atcgaggact ggcccgcgga    134940
cggcccggcc gtgggggact accacgtcta cgtccgcgcc cgcctggacc cggccgccca    135000
gtgcgccgtg cgctggcccg ggtgccgcga gctccgcgcg gccgtgctgg actctagctc    135060
catcgtgggc ccggcctgct tcgcccgcgc ggaggcctcc ttcgcccgcc tgcacccccgg   135120 ggccgagccg ctgcgcctct gccgccagga caacgtgcgc tacacggtga gcacccgcgc    135180
cgggccccgg accccggtcc cgctgccgcc gcgcgcctac cgccagcgcg tgctccccac    135240
cgtggacggc tgcaaggaca tgcccgcca cgcctccgcg ctcgggctcg ggacccgga    135300 ctttgacgcg ggcgccgcct tcgggcaccg cgcggccaac cgctggggc tcggcgcccc    135360 gctgcggccc gtcttcgtct cctgcggccg ccggggcctc gccgagctcc gcggcccga    135420 gggcctgccg gccgagctgc gcgccttctg cgccgcggcg ctgctggagc ccgacgccga    135480
ggccgccccg ctggtgctga ccccgggcgc cgtcgccgcc gcgggcgccc cgccggccgt    135540
gctctgggac tttgcgccct tcgagaccag cgtccgcgcc gccgccgggg gcgccgtgga    135600
gacccgccgg cccgcggggg cctcgggcgc cggggccggc cccggcgagg acggggactc    135660
tgtggagatc gtcggcgtcc gcggcggcga cggccggccc cgcggccgc tcgggcccat    135720 caaggtggag gccatctcgg acgacgagga ggccgaggac gccggcaacc cctacctgct    135780
gctccgctga gcggggcgcc ccctcggccc ggccggactc tgactctgac tctccggccc    135840
ctccgccgga tcctcgaggc ccttctcctc cgtcttctct cccctcgccc tcggccggt     135900 cctcgtcctc gtccccgtcc tcctcctcct ctgcgtccgc ggcggcggcc tcggtcccct    135960
cggcccggcg gcgcttgcct ccccggcgcc tgcctcccg gcccggtggc cctcctcctc    136020
ctcctctcct tctcctccgc gcggatcccc cggccggagg tggctgcggc ggcggcggag    136080
gtggcggcgg tggtggaagc ggcggcgcg ccgcggcgg agggctcggc ggcggaggat     136140
cgtcccggtc cccttctcct cctcctcccg cggtcccccg gtccccttct cctccttctc    136200
ccatcgggtg agaaagagt ttatttcag agcgagaaa taagtttgt gctgtattt          136260 ctgaaccggc tcgagtctct gagattttt ggggagatgg aggcggccat cttggcggtg     136320
gtctctgggg tggaggtggt cttgtggatg gggggtcctg gtgggaggaa gaagaagagg     136380
tggagggtct tggtgagggt gacggggtc ctcctcctgg agggtcttgg tggtggtggt     136440
ggtggtggga agagtggat gggggtcctc ctcctggagg gtcttggtgg tgtgggtct      136500 tagcagatgg gggtccctgg tgggtcttag cagatggggg ccctcctccc ggagggtctt    136560
ggtgggaaga agtagagggt cttgggggatg ttggggggtcc ttgatggtgg tgtgggagg   136620 tggacggcgt tggtggtccc ggcgggtcct ggtgggaggt agatggtccc gagggtcccg    136680
gtggtcccgg gcgggagttg gacgatggtg gtcctgcggt ggtcgagggg ggtgggggga    136740
aagagagaaa gagagaaaaa aacacggtgg tggtcagtac agggaactgc cgttgcaacc    136800 atcgcccct ggtggtgata gtagtaaagc gtgtgcgtga gggggggggg gggggtggt      136860 ggtgttgttg gtggtggtgg tcccgggtgg tcgtcgtgga ggggcgggaa aggcggtggg    136920
agagcgggcg gaacaggttc atctggcttc cgtcttccgt ccccactccc agcctccccc    136980
gctgccaccg attggccggc gggacgatga cgacggcgac cgcgtggcgc gaggggagcc    137040
```

```
aatgggcgg gcgccgcgga gcggaagccc ccgcccgcgg accccggtg cgacggaagg  137100 ggcaggctcg gcgcgccgat gcgatccgcg gagcccgccc cggccgcgcc ccggaagccg  137160
gcgtcacgtc cggggaagc ggaaggggcc ggcgcgatat gcagatgaga tccgtggggg  137220
ccggcgtcac gtccggcgga agttgcgcgc gggaagcggt catacgcaaa tgaggcgaa  137280 gtcgtcatcg gcaaaaacgt cacgtccggg aagcggtcat atgcaaatgg ggggggagg  137340 agcccggcgt cacgtccggg ggaagcggtc atatttaaat gggggggag gggccagagc  137400 gtcacttccg gaggaagttg tcatatgcag attaggggga ggggttatgc agattagggg  137460
gaggggttat gcagattagg gggagggtt atgcagatta ggggagggg ttatgcagat  137520 taggggggagg ggttatgcag attagggggc ggggctatgc aaatgtatgc aaatgagggg  137580
gtggggttat gcagatcagg gggagggtt atgcaaatgc atgcaaatga ggggagggg  137640 ccatgctaat ttatgcaaat gaggggcgg ggctatgcaa atgtatgcaa atttatgcaa  137700
attagccccc ccctttaag ccccgcccc ttttttcgcg ccccccgggg agcgggggg  137760 tggg                                                              137764

<210> SEQ ID NO 2
<211> LENGTH: 1104
<212> TYPE: DNA
<213> ORGANISM: Pseudorabies virus

<400> SEQUENCE: 2
atggactgcc ccatctgtct ggacgtcgcg gccaccgagg ctcagacgct gccgtgcatg   60
cacaagttct gtctggactg catccagcgc tggacccagt cgagcaccgc ctgcccgctg  120
tgcaaggccc gcgtcacctc catcctccac cacgtggaca cgacgcttc gtttgtggag  180 acgcccgtgg aggggcgac ggatgtcgac ggggaagagg atgagccggt aggggggggc  240
ttcgcggtca tctggggtga agactatacc gaggaggtgc gccacgagga ggccgaaggg  300
cagggctccg ggtctgggtc tcgcgcccgc cccagagtcc ccgtcttcaa ctggctttat  360
gggcaggtct cgacggtcat cgagagcgac cccatccgcg aggccgtcgt ggacaacatc  420
gtcgagatta tccaggagca cgggatgaac cgccagcgcg tgaccgaggc catgctcccc  480
atgtttgggg caaacaccca cgccctcgtc gatgcgctgt tgacatatc ggcgcagtgg  540 atgcggcgga tgcagaggcg agcccgatg agccaccagg tgtgaacta tatcgacacg  600 tccgagtccg aggcacactc tgactctgag gtgtcttccc ccgacgagga agactcgggc  660
gcctcgagca gcggggtgca cacggaggat ctgacggagg cctccgagtc cgcggacgac  720
cagaggccgg cgcccaggcg ctccccgcgc agggcccgac gggcggccgt gctgaggcgc  780
gagcagagac ggacccgatg cctgcggcgc ggccggacgg gcgacaggc ccagggcgag  840 actccggagg cgccatcgtc cggcgagggg tcctctgcgc agcatggtgc ctcgggggcc  900
ggggccggcc cggggtcggc gaacaccgcc gcttcggctc gctcctcccc ctcgtcttca  960
ccctcctcct cgatgcggcg cccgtcgccc tctgcctctg ccccgagac cgccgccccc 1020 cggggcgggc ctccggcgtc tagctcgtcg ggatccccccc gctccgctac catcttcatc 1080
gacctcaccc aggacgacga ctga                                       1104

<210> SEQ ID NO 3
<211> LENGTH: 717
<212> TYPE: DNA
<213> ORGANISM: Artificial Sequence
<220> FEATURE:
```

<223> OTHER INFORMATION: Polynucleotide sequence of GFP

<400> SEQUENCE: 3

| | | | | | |
|---|---|---|---|---|---|
| atgtcgaagg | gcgaggagct | gttcaccggc | gtcgtcccga | tcctggtcga | gctggacggt | 60 |
| gacgtcaacg | gccacaagtt | ctccgtctcc | ggcgagggtg | agggcgacgc | cacctacggc | 120 |
| aagctgaccc | tgaagttcat | ctgcaccacc | ggtaagctgc | cggtcccgtg | gccgaccctg | 180 |
| gtcaccaccc | tgacctacgg | cgtccagtgc | ttctcccgct | accggaccca | catgaagcgc | 240 |
| cacgacttct | tcaagtccgc | catgccggag | ggttacgtcc | aggagcgcac | catctccttc | 300 |
| aaggacgacg | gtaactacaa | gacgcgtgcc | gaggtcaagt | tcgagggcga | caccctggtc | 360 |
| aaccgcatcg | agctgaaggg | catcgacttc | aaggaggacg | gtaacatcct | gggccacaag | 420 |
| ctggagtaca | actacaactc | ccacaacgtc | tacatcaccg | cggacaagca | gaagaacggc | 480 |
| atcaaggcca | acttcaagac | ccgccacaac | atcgaggacg | gtggcgtcca | gctagccgac | 540 |
| cactaccagc | agaacacccc | gatcggcgac | ggccccgtcc | tgctgccgga | caaccactac | 600 |
| ctgtccaccc | agtccgccct | gtccaaggac | ccgaacgaga | agcgcgacca | catggtcctg | 660 |
| ctggagttcg | tcaccgccgc | cggcatcacc | cacggcatgg | acgagctgta | caagtaa | 717 |

<210> SEQ ID NO 4
<211> LENGTH: 137377
<212> TYPE: DNA
<213> ORGANISM: Artificial Sequence
<220> FEATURE:
<223> OTHER INFORMATION: Polynucleotide sequence of PRVdelEP0

<400> SEQUENCE: 4

| | | | | | |
|---|---|---|---|---|---|
| ggcccagctc | tcccccgagc | gcggatctct | gaaaaaaaaa | tttcccgccc | ccgcgttttc | 60 |
| cattggggtg | aatggggagg | gggtgggggga | tgggcactca | ctaagaattg | gcaaggtgcc | 120 |
| aatttatatt | ctggcatggt | gccaaactac | atacctggct | ccctgccaac | cccaatcccc | 180 |
| ctcctacctt | ggctccctgc | caaccccaat | ccccctccta | ccctggcacc | ctgccaaccc | 240 |
| caatccccca | ccatcgtcgc | ggtcttcatc | cttggcacac | agccaaccct | agaaggcgag | 300 |
| ccgcgatgct | gcggtcgggc | ccacccgcgg | caggaggttg | tggatggcga | tgggcgaggg | 360 |
| cgggcgcgcg | tgtggtgggg | acggtgtcgg | tgcccgcgcc | ggtggcgccc | gcgagggttc | 420 |
| gccttgggtg | cgctggggc | ccctccccat | tcacccccaat | ggaaaacgcg | ggggcgggaa | 480 |
| attttttttt | cagagatccg | cgctcggggg | agagctgggc | cccagaccag | agagttgtgg | 540 |
| gggggcccgg | gggagagctg | ggccccggc | cagagagttg | tggggccccg | ggggagagct | 600 |
| gggcccccaga | ccagagagtt | gtgggggggg | ggggcccggg | ggagagctgg | gcccggctct | 660 |
| cggtgggggga | caaccccctg | gggagagcct | gaccaattgc | cagactagag | gagagccccg | 720 |
| ccgggaccgg | agaggagagc | gcgccttccc | ccaaccccct | cgttccccc | tttcccccaa | 780 |
| cccctcgtt | cccccctttc | cccttccaa | agcgggcgcc | gcgagcgcgc | gggcccccat | 840 |
| acggcgctcg | ctctcgtccc | ggccggtctg | gccgccggga | cggggcgctc | ctcgccgcga | 900 |
| tgaccgacgc | ctcgtcgcga | cccggcgagg | aagagccgat | ggaggtggac | gagcacgtcg | 960 |
| agcccgagtc | ggagcccatg | gaggtggacg | agccccctgc | gccggcgcag | gcatcgggcg | 1020 |
| ccatcctcgc | ggtgggcttc | acccagcccg | cgcaggtcct | gcgggcgtac | cagatcggtt | 1080 |
| gatgtgcgaa | cgatgggcgg | gggaaccagg | gggtcagatg | cacccacgtg | gtgccacacc | 1140 |
| cgccccacgc | cgcgctcttt | ttcccggcc | gcccgaccgg | atcctcccgc | agagccgac | 1200 |
| gtggggcgag | agaccgggat | ggacgtggag | aggggagcgg | ccgcggggcg | cgtggaggtg | 1260 |

```
gagctcgatg cccggccctc cggcaccaga gggcgcggcg cgagccctc gcgtcgagcg    1320
cgggaccccc gaaccggccc gtgccctcgg ggcgggaccg accgcgtcc ccgggacaga    1380
accggcgacg ccaccggggc gcgcgccccg cgccctccg ccctgggtat aacgccccg    1440
ggcaccgccg tccgccgcca gccgccgtgg gaggcagaca tgcctccaca acgagcccgc    1500
ggggccccgc cgcgccgccg cggcagcgac ccgcccgatc ccggcagcct cgccgggcgg    1560
ctctcgcccg gggggaggag cggcggagga tcgcgccgga ccctcgcgcg cagcagctcg    1620
ctcacgtccg tcgcctcggc ccccgtggag acgcccgtcg ccgcggaggc tctcggactc    1680
ggcgcccccg gctccagacc gccctcctac ggggacgtcg ttcgcgccgg gccgcgcccg    1740
caccgatcgc cggacacgcc gctgtttgcc cggggcccgc cccgtcccta ctcggagacg    1800
ctcctgtttg acccgcccgc gtacgcggtg accatcccgg accgcccgc gtacgagccc    1860
accgtcatcg gaccgcagcc gccgaggccc cgcgactgga tctcctcgcc ctccgtggtg    1920
cagccgtcgc tgctgggccc cttcagccag tgcctcccgc agttgacctg ccccgactgc    1980
cgctaccccg aagaccgccc gatggtgctc gtgggcttcc tctgggggg gctgctcctg    2040
ctggtgggcc tcgtgtttct gatcctgctc ccggtgctcc gggagtctgt cgtgtttccc    2100
tgaccaataa actcggctcg ccagtcctat cgatatccgc gtctcgcgtg tggtgttgcg    2160
acggggagga tgggggaggg aggatggggga gaggaggatg gggagaggag atggggagat    2220
ggggagagga gatgggggaga tggggagagg agatgggggag atggggagag gagatgggga    2280
gatggggagg acgacagact cgtgcacacc agagaggtac ggttcaacag tttttattcaa    2340
aacaggtggt tgcagtaaaa gtacttcccg tgcatgtaca cggggacgag ggtgtagctg    2400
cacgtcaggc ggcaggtggg gcgtcgcag ccggttttgt gggagtccag cgcgtccatg    2460
atcccgccga ggcaggcgcc gggcacgtac tcctccagcg ggacgggcga gtcccccagg    2520
tcctcgggca gcacgcagct cgagccgcgc tcgacgacgc gggcgatgcg agccagcatc    2580
accagggtgt aggtgacgat gcagcgcacg tcccgcaggc ggcgccggcg cacgagctcg    2640
tcgacgggcg cgtcgcggag gtagcagcgc aggaacggcc cgagcttcag gcgcaggttc    2700
tgcagcaccg ccccgcggt ggccacgatg gggtccagcg tgcgcagcgt gagccccttg    2760
gtgaggatga gcttgaccca cgtgagcgtc tcgtccgccg aggcgaggga ctccgtcagg    2820
ccctcgttca ggagcaccat ctcgcggagc acgcgcgccg cctcggtggc gtgcggccgc    2880
acctcaaaca ggcggtgcag gtcggccccg tggaacatga gcgtctccca cgtgacgcgc    2940
cgcccgtccg gggtgaactg ctcggcgccg aactcgagga cggcggccca cggcgacgag    3000
cccgcggcgc ggaagccgtc gttgaacacg gggcgggaga ggtcgtgccg cgccgaggca    3060
aagagctcgt tgacgcgggt cgcgccgacc cgcgcgtgcg tcgcggagac ggcggcgcgc    3120
gcgctctccg acagacgatc gggggcgcg tcgggcccgc cgtccggacg atccgcctcc    3180
tgtcgccgcc gctggtgctg ctgctggcgc tgctgctgct gttgctgccg ccgccgctgc    3240
cgcagggcct gtcgggcggc gcgcccgccg cgaccccgc gccggcgccg gatggccccc    3300
agccgcgccc ggacgggccg ccgctcgggg gggcgcgagc ccaggcgctc acggaccggg    3360
cgccgctcct cgctccccga cctggacgcc tcgctgtcgc tgctgttgcc gctgtcctcc    3420
atgaccgtgg tgcgagcggg gccgcggtgt gcaggtggcg ggcggcgggg cgcctttaac    3480
ccgccgtccc cgcgcgacct tcatccaaat atggtaatgt gccgctcata gtgcagaaac    3540
agcaacacgc cccctaccag caggcagagg tacagcgcct tggcaaagat cccggcgagc    3600
```

-continued

```
acggtcgagc agcacgcgcc gcagacgccg agggcggcgc ggccgccgtc ggagcgcgcg    3660
ggcgtggccg tcgcgccgga gacgcgcgcg atgtgcggca gcgtcgccgc caggagctcc    3720
agcgccccga ccgccagcac aaagatccac acgagggcgc gggcgtacag cgggaagacg    3780
agggcgcacg gggcgcgtgt gacgccgagg gtcgtgaaca gcgccatgcg cgcccccagg    3840
cggagcccga gctcgaggag gatgagcgcg atcagcgtgg gatggcggtg tgccagcgta    3900
atggggtcct cgcggaggtc gcggctgagc gcggcgcggc gcgtcgcgag ctcgccgatg    3960
taccaggcga acttggtgta gctgcagccg atgaccgtgg cggcgagcac gctcgccgcg    4020
tagttgagcg tgtacttctc cggggtcagg aactcggcgg ggtcgcggaa ggggccaaac    4080
atgcgccgct cctggcgcgc gtacacgaag gccgcgtaga ggagccacgc gacggccgcc    4140
aggcgaaagt gcacgtccca caggtaggcg cggcagtcgc ggcgcgcgta cacgacccgc    4200
gcgcggtcgc gcagcgccgg gctcagcgcg tccgtctcgt tggggccac gtagatggcc    4260 gtggcgttga aggcctccca gtccggcgcg ccccggcgg cgtcctcgcc gagcggcagc    4320
gccgcgtaca cgacggggtg gggcaggcgg gcgacggtcg cgtagtacgc gcccaggccg    4380
gcgtacgcgc ccatcacccc gaggacgagg aggtgcagcg ggcgcccgcc gaggagcatg    4440
attgccccac ctccgcggtg aaaatggtgc gcgtcgcgtt gctgccgcac tttgtagcga    4500
agcactgctg actcagcgag atacacagcc ggtcgtgggc gtcgacgctc agggccacga    4560
aggtgcgggc cggcgggctg cgcgcgtgcc gggcccgcag gcagctgaag cgcgcggacc    4620
cgcagagctg gaagaggacc cagtcgggct tggccaccac ccgctgcgcg gtcgcgcccg    4680
cgtactcgtg cgcgcgcccg ttgaagtgcg cgtcgaggtg ccgcagcacg ggcgccatgg    4740
ccacgtccgc cacgaaggcc tcgagcgcgc gccggtcctc cgcgtccacg gccaggccgc    4800
gcagcatgtc caccagcggc gtgcgccggg cgaagaaggc ctcgcggttc cgcgccgcct    4860
tgcgctcgaa gaagctctcg tactccccc cgaggctgtg cagcacgcgc gtgacggcgt    4920
gcgccgggcg ggcgtggaag tgaaagttgc gcgggtcgtc gaagcccggg ggcgcgtccc    4980
cgaaggggag caggcgcccg tggcagccgc cgccgtcgac cttggcgaag aagggcagcc    5040
gcaggctgcg cccgtgcgcg tacacgcccg tgtccacgaa ggtgaagtcc tggaggtacg    5100
ggcccatggg ctcgatgaag tcccgctcca gcagcacggc ctgctggagc acgcgcgcca    5160
ggccgcggac cgtgtcggcg ccggccaccg cgtacggcga cggcacgggc gtgcacacgc    5220
ggaagcccat cttggcgcgg cagccgcacg gcgggcgctc gtccgccggg acggggcgc    5280 ggacgagggc ggaggcgccg gggtccccgc ccgcgcccc gatcccgacc cgacctcgt    5340 cgtcgtcgca cgtgtacacc tcggcgggga cgcccgcgtc ccagtccgcc cagtcctcgt    5400
cgcccggcgc ggcgccaaag tcggcgaggg cggcgtcgtc gtcccagggc gcctcctcga    5460
ggccgtcgtc ggaggaggcc gcggaggcgg accccgcggc ggcggcgagg gcgccccccg    5520
gcgggcaggc gctcttgtac acgtagcagg ggtgcgcggc ccagtcgccg tcggcctcgg    5580
ggaagagcag cgcgagcgcg tcgagcaccg cgcggcggaa cccgcgcatg gccgcctcga    5640
gcgtgcccgc gggcaccggg cgcgcgaggc gaaagtcgac gtcgaggacg atgttggtca    5700
cggccagccg ggcgttgaac acctcgtggc ggctcacgta catctgcgcc gccggctcgt    5760
gcgcggccat ctccggcgcc gcgtcgcggc gcgcgtcgc gcgcccccag gcgtcccgg    5820 ccagcaccgc gaaggcctgg cgccggtgcg ccagctccac gcggtacacc ggcgccgggg    5880
ggcacgcgtc cggcaggccg agcagggcgc ccagcgccgt gcgcgcgcgc ccgccgcccg    5940
gcgcggcggc cagctccagc aggcgacgca ggacggcgcc gtcggcgccc ggctgctgct    6000
```

```
gctcctcgtc gggggcgcgc acccagccgt ggggcgcgag gcgctcctcg acggcggtca    6060
cgcggcgcgc gaggccggcg gccgcgtcgc agagcccgcg cggcgcgtcg gccgcgagcg    6120
cggcgtacgt gcggtcctcc acgtagccgg cgcccatggc cggggcgagg cgcgcgacgc    6180
tcggcgtcac gttctgggcg acgtagtcgc ggatgttgag ctgcgcccgc acgtggcgga    6240
agaaggcggc ggccgcgcgc tccccgaggg gcgagcgccc cacgggcgcc gcggggtccg    6300
tgacgttgac ggcgtccagg tgctcgcgga gccgcgcgcg gttgaagctc tcaaagtggg    6360
ccaggtagac gtacgtcacg aactcgcggt cggggagctt gaggctgccc cggtcgtggg    6420
agatgtagtc ccggaggacg cccatctcgg cgcggtcggc gcgcacgcgc tcgtcgacgt    6480
agcgcgcggc gtgcgccgcc gcggggcccc gcgcgtagcc gctcaggcag cagaagcgcg    6540
agagcgccgc gaacgagagc agcccgcgcg ggtccaggcc gctggggttg ggtccacgc    6600 gcgggttgta cgtgagcagc aggtccttga gggcccgcag gtcgtaggcc ggccgcgggt    6660
ggaagaggtg gaggcgcgtg gccagcacca gcgtcttctc ctcggggccg aagcgcgcca    6720
cgtaccagaa gggcgtgttg tggttcccgt agaggcgccg gaaggcggcc agcgtctggg    6780
tctcgtggtg cacaaagagc gaggtcagcc cgcggcgccc gaccgcgatg gagcgcagcg    6840
ggcgctccgg cgcgtactcg gcgttgccgg tgcgcgggcg cacctgctcg aggaccatgg    6900
tcagggccgc gatgaggccg tcgtggaggg cgaaggtggc cgcctcgtcc atggcctcga    6960
ggacgtcccg cgccgcgagg ggctccccgc ggcagagcgc gcgcacgacc gccggggtcg    7020
cggcggcgac gaacacgggc cgcacgcgga cgctggccac gtgcccggtg aggcagaacg    7080
tgacgccggg gcggcgcgct aaaagctcgg cctcggcgcg ctcgcccggc agtgagaagg    7140
cctcgtccag cccggcgccg tcccacgcgt acgagacgac gtagaccgcc cccgagggct    7200
cctggcccgt gagcagcatc agcgagtacg tgatcgcgca gccgtccgtg gcgtacagga    7260
cgcggatcat gctgggcggc atcttctccg ggtggtgcgg gcgccgcggc cgtgggaggg    7320
cttatgagcc gccggacgaa ctccgcctcc gggagtcgct ggccgtgctc aacgtgatcc    7380
tccccgcccc gctcgccgcc gaggacgtga tggcctcggc cgaggccgcg cgccgcctgg    7440
cccgcgcgga cacgctggcg cgcacctacc aggcctgcca gcgcaacctg gagtgcctgg    7500
cgcgccacga ggcctccggc gacgacggc tggacgccgt ggtcgcggcg cacgcggcca    7560
acgcgcggcg gctcgcggac acgtgcctgg cggcgctcat gcacctgtac ctctcggtcg    7620
gcgccgtcga cgcggacacg gacgacctcg tcgagcaggc cctgcgcatg accgccgaga    7680
gcaacgtggt gatgtccgac gtggccgtcc tggagcggac gctgggactg gcccggcggc    7740
ggcagccggc gcccgtccgg gccgcgcccg ccgggctggg tctgcccgtc ccgcccagc    7800 ccgccccgcg cgctaccgcc gcccgccggg cccgccgcc ccgcccgag gaggcggggg    7860 aagacgagga gggggaccgc cccgaggacg acgcggcccc gctgctgccc cccgcgccc    7920 ccgccaagac gcgcccgccc gagaaggccc ggaggctggc cgaggcctgc aagatgtagc    7980
cggagagggc gggagggaag gaagggacgg agaccgccgg ggttgtctgt gcccaataaa    8040
catctttatt gaaaaatgag aagagcgggt cccgcgtgtg tgcgcgcgcg gtcgccaccg    8100
tccgggtccg gcgcggggccg ccgcggcctc acaggcccgt ggagccgaag ccgcgggccc    8160
cgcgcgcgct gctcggggcg acaaagtccc gcgcgaagag ccacgcgggg cggtgctgca    8220
tcggggcgcg cggggtggcg gggaacgggg accgtcccgt gatccagccc agcggctcgc    8280
gcgtcagcac cagctgggcc acgcgctggc ccgactccag ggtcaccggg tgcgcgccgc    8340
```

```
ggttctggat ccggaagcgg cacgggccgc tctcccaggg cgtggggaag acgacgatgc   8400
cgcggaggtt gagggacgag cgcccgaaga cgtaggccca gtggcggccg tccgtgcggt   8460
gcaccggcag cgtcacggtc tcggcgcccc cggggggcag caccagctcg cgcgggcagg   8520
ggatgtcgta tccggcgtcc tcgtcgcgct tcggcgcaaa gacctcgaag aagggcacgt   8580
ccgtggcgat gcccggcgcg aggcgcagcg gcgtgcaata aaattgcgcc cgtgggcggc   8640
ccggggctac aatcgcctgc acctcgccgc gaaagcccgc gtccacgatc ccgttggtgg   8700
tgcgaccgcc cccgcgctgc gcgacgagca tcgcgtatcc ggtgggcagc gccaccttga   8760
ggcccagggg aaccttataa aatccctccg gccccggact ccggcacacc agcagccgcc   8820
ctccgtccac ggtcacgggc tcgctcgcac acaccaggat ggtctcctcc gccgggccct   8880
cgctgacgct cgtcgccgcg ctctgcgcgc tggtggcccc cgcgctctct tccatcgtct   8940
ccaccgaggg gccgctgccg ctgctgcgcg aggagtcgcg gatcaacttc tggaacgccg   9000
cctgcgccgc caggggagtc ccggtggatc agcccacggc cgccgccgtg acattttata   9060
tctgcctcct ggcggtgctc gtcgtggccc tgggttacgc cacccggacg tgcacccgga   9120
tgctgcacgc ctcccccgcg gggcggcgcg tataaagatc gatccgcacg cgcccgaccc   9180
cactcgctcg ccatgtccag ctcgagaaag acccgggtcg ccgccgacga gaccgcctcg   9240
ggggcgcgcc gccgcgccgg cagcgcctct cgcacccgga ccaccgcccc ggccgccgcg   9300
acccccagac gcccctcggc ctacgacgac tatgacgacg gcttctccta ccggtcggcg   9360
ccgtcctacg acgacgatga ctactacggc tacgatggct acggctcctc ccgcgccccc   9420
cgcgccgcca aggtgacgcc cgcggccgcc tcgcgggcct cgaccggggc caagagcgcc   9480
tcggccgcca agaccccgc gtccgcggcc aagaccaccc gctcggcccc ggccgccgcc   9540
ccggccgcca ccaccaccac caccaccgcc gccgccgccg cggaaccggc cgcccggcgc   9600
gcctcgacac gggccgcccc cggggagaac ctcgacgtgg gccgccgccg gctcgccttc   9660
agcgacaggc cgtgcgaggc caacgtgccc tggcgcggcg cgacgcacgc cttcaacaag   9720
cgcatcttct gcgcggccgt gggacgcgtg gccgaggccc acgcccgcgc cgccgccgag   9780
tccctctggg acatgaaccc cccgacgacg gacgcggcgc tcgaccgctt cctgcaggcc   9840
gcggtggtgc gcatcaccgt gtgcgagggg ctggacctga tcgaggcggc caacgccgtc   9900
ctggacgaga gcaccccgg gcggaaggga aaagtgtata aataaaggcg ttgcaaatgg   9960
caccccgctc agtcgtccgc tgtcttgctt gtgggggggt cggtgaggat gcgcgacgag  10020
gagtgcgtgg tcgcgttcga cgaggccctg ctggggggcg cggccccggg ccggccgccc  10080
gtggtggccg tccgcgggc ggccagcccg gacgcgctgt accagcgcct catcagcgac  10140
ctggccttcg acgagggccc ggcgctgctg gcgccatgg agcgctgaa cgaggacctg  10200
ttctcgtgcc tgcccggcaa cgaggacctg tacgcgcgcc tggtcatgct gtcggcctcc  10260
gcggacgagg tggcggccca ggtcggggcg ccgacggcgg acgcgagcgt cgacctgggg  10320
gtgcccgggg cggagcccat gccgcgggtc ccggccgtgg aggaggagct gcccgcgtac  10380
gtggcggccg tggagcgctt cttcgtgtcc acgctgcggg cgcgcgagga gcgctacgcg  10440
cgcctgctgg acgcctactg ccgcgcggtg ctgcgctacc tgcacgcgca ggcgcgcgc  10500
gacgagggca agctccggcg gctggtgcgc gggcgctact accgcgacgt cgcgcgcctg  10560
gcgcgcctgc tcttcctgca cctgtacgtg gccacggcgc gcgagctctc gtggcgcctg  10620
cacgcggacc aggtggtggc ccaggacgtg ttcatgtccc tgcgctacga gtgggaccag  10680
gcgcggcagc tgacgtgcct cttccacccg gtgctgttca accacggcgt ggtgctgctg  10740
```

```
tcgggcgcgc cggtgccggc cgcgcagctg cgcgccgtca accaccgccg gcgcgagctg   10800
ggcctgccgc tcgtgcgcgc cggcctcatc gaggaggacg cgcgccgacct ggtcgaggag   10860 ccgccgttct ccgccgcgct gccgcgcgcc gccggctacc tctcgcacca ggtgcggatc   10920
aagatggagg cctactcgcg cgagtaccgc gaccacacgt actgccgccc gccctcgccc   10980
gtggccagct acggcagcac cgcggaggcc ctgctgccgc ccccgtcgcc ctcggccgtg   11040
ctgccctgcg acccgacgcc gccggcgcgc gtctcggccg ccccgctcat caccacggtg   11100
acgctggccg aggccgagga ggatggcgcg ctgacgacgg cggcgcccgc ggccgcggtc   11160
gcggccgcga cggtcgcctc gcccgggccc gccacccccg cctaccacct catccccgc    11220 gacgcgctca accggatgtt tgagatgtga cgccgcgcgc ggtcggatct gcggcgcccg   11280
accacctgtg ggcggggcgt ataaagccgc gggccggccc ggaggggggg catttgccgc   11340
agcgaccacc atgagcgacg cggggcccgc gcggcgcccg aggcgctcgc aagagcagcg   11400
cttccagccg ttccccgcg cggggctcct ggtgcacctg caggacgtgc tcgtgggcga    11460
ggtgcggcgc ccggacttcc gcccgccgcc cgacgaggag agcagcgagg aggaggagcc   11520
cgtctggacc gacgacgacg aggaggaaga ggggggggcg gaggaggaga ggatgagcgg   11580
gggccggcgc gggggtgagg gggggacga cgacggggac gaggaggagg aggagagcga   11640 gggggcgcg tggtccgacg gggagctgta cgtggcggcc gaaggcgacg cgtgggacgc    11700
ggaggaggac gaggaggacg aggaggagga cgaggaagat gactacgacg atgggatga    11760 cggccacgac ggccgcggcg ccgcggtacc cgccgacgtg gactacctgt cgcgcgccct   11820
ccgcggcatg gagacggccc ccggtcccga cgagcgggag gccttcaccc gctacgccgg   11880
cacgctctac cgccgccagt ttcagcccgg gcggccgggg taccggcccc cgcgccgcg    11940 cgacccccg ccgccccgc cccgcgggc ccggccaccg acgacggcga cggccgccgc     12000
cgcccactgc ggccccgccc gcgccgccga cggcgacgac tccgcgccgc gcctcgagcg   12060
ggacccggac gccgcgtacg ccagctggac gcgcgacatg cccgacggga ccttcctggc   12120
catgccgtcg tgggtggcgc tgcgccgcga ccgcgcgggg cccccgggcc gccccgtcgg   12180 gccccggac atcctgcgcc gcgccccgcg ggcactgacg ttcacgccgc aggcggcctc    12240
ggcggcgctc gtgagccgcg accaggacgc ctgggaggcg ctggtgccgc tgcaccacct   12300
ccagatgcac tcgtggggcg gcagcgcgcc gccctcgcgc gggggcgtgt acgcgacgcc   12360
cgcgcccgag acgcgcggcg tgtggcgccg cgcgctgcgg caggccatcg ccctgcacca   12420
cgccatgttc ctggcgccgc tgcagtcctc gacggtcggc gcgcccgcgc tcgcgggcga   12480
ggcgctggcc ttcgcgctgg acgccgcggc gcgcgcggcc gtcaaccacg acgccgcggc   12540
gcgcgagctc cccgagcgcg cggcgcgcgc gctccgcgcc gtcggccggc gcgcggccgc   12600
ggcctcgggg ccgcgcgccg gcctcttccg cgccttctgc ggctccctgg cctactggcc   12660
ggagctgcgc gtcctcagcg ggcaccccga ggacgtccgc ttcgcggcct tccacctggc   12720
cgtggcagag gtgtacctgc tggcgcgcgc ccacggccag aacccgggct tcacggccga   12780
ggagcgcgag ctgctcgcgc ccatgttcac gctgaccgtg ctcgcgatgc accacgcgct   12840
gcgctggctc acgacggccg tggcgcgcgc cgtctcggac atccccgacg acgaggcctt   12900
ccgcgccgtg cgctcgcgcg tgccggcgtc gctggtgccg ctgggcagca tcgcgctctc   12960
ggacgccgag tacgccgtgc tgaacgcgac cgaggtggcg gcggcgcgcg acgccacggg   13020
cctgggccag gccgtgtcgc tgggctacgc cgccgcgcgc tccgcgctca cgggcctcat   13080
```

```
gcgggcccac gccggcggga gcgacgccct cgtcgccttc gcgctggtgc tgcagcgcct    13140
cgcgggccac gcgaacctgc tgctcaactg cctgctcggc gccgcggtcc acggcggccg    13200
gacggtgcgc gtgtacgagg cggcgctgga cgactacgcg gagctcatgg acgcgctcga    13260
cccgctggtg cgcgcgtgcc cgctcgcgga gttctgggag cagcgcgacg ccgtcatgcg    13320
ccagctgcgg ttgacggcgg ccccgggccc ccccgtcggc ggcaagcggc tcgtcatcgc    13380
gcccgcgctg ccctccgagg acctggacgg gctcgtcccg cccacggccg tgcgccccgc    13440
ccacttgggg ccggacgtcg acctcgccga atacgccgcg cgccacccgg agctggtggg    13500
cgtgccggaa ccccgagcgc atttatcggc gcgccggccg ccccgggggcc gctaacccgc    13560 ctctgcctcc gccatgctcc gccgcgcccg aggaacgcgc cgcgcttcgt ggaaggatgc    13620
ctcgcgccgc gtcaccgagg ggcgcacccg cgccagctgc ctgctggcgg ccccccgggga    13680 ggtgctgacg gcggccgtgg cggccctgcg cgacgtggcc gagagccagt gcgcgccggc    13740
gctctttggc gcccagcgcg cctcggccct ggcgctcgtg cgcagcaact acgccccga    13800 gtccgtgatc acggcgtgct cggcggagcc gcaccgcgag gtgtacgcgc gcgcggccga    13860
cgccgcgctg aagggcatca cggcggacgt ggcccggcgc gcggtgctgg ccacctactg    13920
gcgctacctg aaggccagct cggggcgtgga ggtgcgctcg gacgacgagc gcgacgcccc    13980
caccgtcatg ctgctgtggt cgacgttcgg caagccgctg tcgaagcacc cgttcaagca    14040
caaggcccag agccgccgcgt acggggccac gcgcgccgcg ctcgccgagg cgaccgaggc    14100
cgtggagcgg tacgcctact acatgcgccc gctcgacccc atggtctcca gcccccagac    14160
gagcgtcgcg ctgcacgaga tgctggcgta cgcgccacg ttgtaccgct ggctgctgtg    14220
gatgatggac acggtcgacg cgcgcgtggt ccgccacctg gggcgcacgc gcgggtggc    14280 gcgcgggccg cgcgagacga tgtcgcccga ggcgctcttt gggcggcacc gcgccggcgg    14340
gcccgccgtg gcctcgggct cgggcgaggt gctcgtgctg acgagccaca cggcgacggt    14400
gtttgacgcc ctggagatcc tcggcgccac gtgggccgag acgccctgga gagcggcgt    14460 gtgcggcctc acggccgccg tggacctcgt gaccttcgtg caccaccacg cgcagaccct    14520
catcaacctg acgctggccg gctacgtgtg ctggctcgac gacgggatgg aggacccgta    14580
cctgcgcgcg gcgctgcgcg cgcagtgccg cttccaccac ctgatcggcg acctggcgcc    14640
cacgagctcg tcgcacgcct ggggcgcgcat ggagcgcggc acgctcgcct ggttcaacta    14700
cgccatcgcg cgcagcctgg cctcgtacgg cgggcccacg gagcgcttcg cgcgcgtgct    14760
ggcgacgacg ggccagcggg acatgcgctt cctgtcggtc gccccccgcgc agccgccgct    14820 gccgccgctg ccgcgggcgt cgcagacgcc gtcgccgccg ccccgcgacc gcgacgcgga    14880
gccgccgcac gagtacgtgg accccttcgc cgagtacctg aactggcccg tgcccgtctc    14940
gccgcccccg ctccccgagg ggccccgag ctcggacgac gagctggagg tggacggcgg    15000
cgggcggcgc cccctccggc gcagccgcga cgccgccacg tacgtgaacc gcaaggacct    15060
cgcgccgccg cgcgcggcgg cggggaggg cgacgacgag gaagaggagg aggatgaccg    15120
gttcccgcgc cgcgacgggg acgccgggac ctccacgagc tcgtcgcagg agagcgccgc    15180
cgacgaggag ttcccgcccg ggatcggcgt gcgcgacggc gaggaggacg acgaagacga    15240
gggggtggag gaggaagacg tgtacgtcga ccccgacggg gacggcgaac gaggcgccgg    15300
cggcggccac gacgacgacg ccccctgggc cccgctgacg cgccacggga gcatgcgcac    15360
cagcttccgg cgcggggtcc gcggctcgtt ccgcgccgcc cagcgcttcg tgcgccgccg    15420
gctctcgcgc acgagcgccg aggcgacccc gcgggctccc gtcgactcgg ccgcggcccc    15480
```

```
cgccaccccc gcggtccccg cccagggcga gaccgaccac gtgtaccagc accccgccc     15540
gcggaccege gcggacgacg gcctgtacca gcaccccega cccgtcateg acctcaccgg    15600
ccacegegeg tegegcegea agagctggcg cgtgtgacgg ccccgcggac ccccgttgt     15660
atggtttccc cccgttgccc ccgtgtgtgg aaataaagtt ttttttctaat tctgtacaca   15720
cggcgtgcgt gtcatcgtgg tcgcggtcgc gggacggagg ggagagggac ggaggggaga    15780
gggacggagg ggagagggac ggaggggaga gggacggagg ggagagggac ggaggggaga    15840
gggacggagg ggagagggac ggaggggaga gggacggagg ggagagggac ggaggggaga    15900
gggacggagg ggagagggac ggaggggaga gggacggagg ggagagggac ggaggggaga    15960
gggacggagg ggagagggac ggaggggaga gggacggagg ggagagggac ggaggggaga    16020
gggacgagac ggacgcgaga cgtgttgcca aacaagcgca tctttattgt ttcccgcggg    16080
aggggggctac agggcgtcgg ggtcctcgct ctcgaggcgc tggtagtgcc ggcggcgcgt   16140
ggccatcgcc ccgacgcggc tggccagcag cgcgggcccg ctgttcttct tgcgcgcctt    16200
gtgctcctgc tgctcgaggg ccgacacgat ggacatgtac cggatcatgt cccgggcctg    16260
gtccagcttg gcctcgtcca cgtcgccctc gtcgacgccg tcctccttga gcgtcttcgt    16320
cgtgacgggg tacagggcct tcatggggtt gcgacgcagg cgcgagatgt gccggtaggc    16380
caggaaggcc gcgaccaggc cggccagcac cagcagcccg atggcgagcg ccccgaaggg    16440
gttggacagg aaggacacca tgccgccgac ggccgagatc acggcccccg tggcgcccag    16500
gaccaccttg ccgacggcgg cgcccacgtc gccgaggccc tggaagaagt tggcgatgcc    16560
gcgcagcagc accacgttgt ggtccacctt gaccacgcgg tcgatgtcgt agaacttgag    16620
cgcgtgcagc tggttgcggc gctggatctc gctgtagtcc aggaggcccg tgtcggcgag    16680
ctcctcgcgc gtgtacacct cgaggggcag gaactcgcgg tcctccagca gcgtcaggtt    16740
cagggtcacc cgcgtgctga tcgtctcggg cacctccacc atgcgcacgt agctgtagtc    16800
ctcgtagtac acgtacccgc tccccagctt aaagtagcgc cggtggttgc cggtgcaggg    16860
ctcgatgagg tcgcgcgaga tgaggagctc gttgtcgtcg ccgagctggc cctcgatcac    16920
gcccgtgccg ttgtgctcga aggtgaccag cgggcggctg tagcacgtgc cgcgctcgcc    16980
gggcacgcgc atggagttct gcacgtacac gccgccgcgc acctccacgc accgcgagat    17040
ggccatcacg tcgccgagca tgcgcgccga gacgcgctgg ccgagcgcgg ccgtggccac    17100
ggcgctgggg ttcaggcgcg acatctcgct ccacagggtg cggtccttgt tctgcagctc    17160
gcaccaggcg gccgcgatgc ggcccagcat gtcgttcacg tgcgcctgga tgtggtcgta    17220
ggtgaactgc aggcgcgcaa actccgccga gcccgtggtg atgcgcaggt gccccgtgcc    17280
gttgacggcc ggcggctcgg gcgtccccgc ctgtccggcg gcgcgccggg ccgccggcc    17340
cgccgcgggg gacgcggggc ccacgacgcc ggcgaggccg aggcgctcga gctcgcgcgc    17400
gtacagctgc gccagctcgt tcgagatcag cgggcggaag gccaccacga agcccccgcg    17460
ggcgaggtac acctcgggcc tgtcgccggc cagcacgtgc gtgttgttgt agcgccgctg    17520
gtagatggcg tcgatggcct ccgaggcctc gcggaggacg cagtcgccca ggtgcacgcg    17580
ctgcaggtcc agctgcgtga cgtcgctgac gaaggaggcg cccagggccc gcgacgtgaa    17640
gcggaaggac ccgtcgcgcg tctcgtcgcg gatcatctcc tcggcctcgc gccacttggc    17700
caggctgcac acgcgccgcg tcttgggggc ccagtcccag gccaccgtga agtgcggcgt    17760
gcgcagaaag ttgcgcgtca cgctctcgga ggcgcggagg cgcgagtcca ggtcgatggg    17820
```

-continued

```
gtagtagtgc tccacctgct ggaagcgccc gggcgcgtag ccgatgtgct ccccgtgggc    17880
cccctcgcgc aggccgtaga aggggggacat gtacacaatg tcccccgtgg acagggcgaa    17940
ggagtcgtag gggtacacgg agcgcgcctc cacctcctcg acgatgcagt tgacggaggt    18000
gcccgtgtgg tagaagcccg cggcgccgat cttggtgtgg gtgtcgttgg tggtgtgcca    18060
gccgcgggtg ccgagcgcgt tcaggcgcga ggggcgcagg tccacctcga cggggttctc    18120
gtcgcggtcg aaggcggtca ccttgtggtt gttgcgcacg tactcggcct tggagacgca    18180
cttgccgcgg cggtcgatca cgtccgtgat ctcctgcacg gggacgggca cgcggtccgt    18240
gaagcggttc gtgatggccg cgtacgtgct cccggaccac acggtcgtga cgatgacgtt    18300
cttgtagtag atgtgggcct tgaacttgtg cggggcgatg ttctccttga agagcacggc    18360
gatcccctcc gtgaagttgc gcccctgcga gtactcgggg caggcctgct cgggctccag    18420
gcgcaccacc gtggagccgg acggcggcgg gcagacgtag aagcggtccc gctcggtcgc    18480
ggccgcgcgc acggccgtgc gcgcgtccag gtcgccgtac tcgccgtcgg gggcctccga    18540
ggggccgggg gtgaacgcct cgatctcctc gagggacgcc tccgcggaga cgtcgttggg    18600
ggtgaggccg gggctgcccg ggacgggcgt cggcgaggcc gaggcggccc gcgtcacggc    18660
cgccgcgccg cacggcgggg ccgcggcgag cgccagcagc agcagcgcta gcgcgacggc    18720
gccccgcgca gctgcagcgt ggtgtggagc aggccaaaga cgtccgaggc cagcaccgcc    18780
gtggtgcccg ggccgatgcc cgcggggccc gcgccaaaga ccgccaccag cgggcatgac    18840
gcctcgtagg tcaggtacag cccgtcgcgt ccggcgaagc gatccgcgcg gaggacctcg    18900
acgtccccgc agtggaagac ggacctgaag actgcaaccg ccagcaccag ctcgcggata    18960
tatcgccagg cctgccgctg ggtggcggtt acgccggccg tctggaagcg gtagaagccg    19020
cggaactcac tgacgcacca atcgcgggcc accatgaagc gcgccagctc ctccttcagg    19080
tgcggcagga ggcccacgtt ctccaccgca aagtagagcg ccgtgttggg gggctgggcg    19140
aaggcgtgcg tgtcgtgcgc gaagagcggc ccgttgacga gctcgaagaa cttgtgcgtg    19200
agcgccggga ggagcgcggc gtccacgggg tggcgctgca ccgtggcctt catgaagctg    19260
tgcgcgtcga agcagcccgt ctcgcgctcg tccacgacgg tgcccgcgcg cgcgacggcc    19320
tcgcagaacg cgcgccgcgc gcggaacccg gcggccaccg ccacgtacgt gtgcagcagc    19380
gcgtcgccgt acacgttcac gcgcagggtc ttctccagct cgcgccgctg ctcgcgcacg    19440
cactgcgcca ggctcgccgc cgagcgccgc gagaggcggt ccgcgtacag cgccgccgg    19500
cgctcggcgt cgcgcagcgc cgcggccggc aggtccgccc acgccacggc gtccgccggc    19560
gggggcgcgc cgggcccgtc ttcgtcgccg acgcccccgt cgccggcgtc cgcgcccccc    19620
gcggcgccgc cgtcggcgtc cgcgtcgtcg ccgccctcga ggaggcgctc gagggcgtcg    19680
cggttggccc ggtccgggtc cagcatgcgc agcatgggcg tggacatgtg gtggtcgtag    19740
cacgcgcgga tgagcgcctc gaggcgctcg tcgggcgagg ccgcgcagcc gcccacgagc    19800
agcccgtcga tgatgtcgag ctcgcgggcc gcgcgggcgc ggtcaaagtg ctcgggccgc    19860
cgcccgaaga gcgcgagctc acggccgccc gcgcgcacct cggcgcggcg ctcgcgccgc    19920
tccaggtcgt ccaggttgtg cgtgaacagg tcgagggccc gcaccgcctg gttcgtggac    19980
gccagccaaa actgcagctc gctcacgcg tacaggcgcc gcgaggcggg ccggaacacg    20040
tcgtgcgcgt ccaggagcgc gtccgcgcgc cggcgcgccg tctcgcccgc gtccccggcc    20100
tcggcgcccg cctccgcctc ccgggcctcg gcggcgtcca cggcggcgag cgccgccagc    20160
gcgcgcccgc ggcgcgcctc gtcgagcccg cgcacgtgcg gcaggttctt ggccacgtcc    20220
```

```
tcggggtcca cgcgcaccgc cagctgccgc gtgaggtggt cgcacacgca gccgagcagg    20280
cgccggtgcg tggcctcgcc ctggttggcc gtcacgcaca gctcctcgaa gcacaccgcg    20340
cacggctgcg ccgggtcgta cagctccggc ggcaccacga gcccgccgcc gatcgtgcgc    20400
gcgaggaact cgtccacggc cgacaggtcc accgcgtggg gcgtgatcag gtggcagtag    20460
ttgagctgct tgagcaggtt ctcggcgtcg tggaggaact gcagctccgt ctccacgcgc    20520
ccgccgtacg tgtcgagcgc gacgcgcgcg tggaagcggc acgcgccgcc catggtgcgc    20580
tcaaagtagg cctcggcgtc gtcgccggcg gcggccagcg cccccagcac gcggtccccc    20640
tcggcccgcg cgtacgcgag cgccaggcgc agcgcgcacg tgagcggcgt catctgcgcc    20700
tccagcggca gccgccgcgc gaggtagcgg cacatcagcg cgttcagctt gacgcgcggg    20760
gccagctcgc gcaccaccgc ggggtcgcag cgcttcagca tctccagctg aaacacgtac    20820
gtctgcacct gccccaggac cgccacgagc cgccgctccg ccatggccga gtccgcccgc    20880
tcgctccctc cctccgcccg cccgcccgtc cgccgcgaga gaggcacagg gacgcgcgtg    20940
tgtgtctgtc aaacgcggtc atctttattg atacagccgg ggcgccccgc gcccgtcccc    21000 ccttccccte ctcctccect cacagcatgt cgaaggtcag ccgcttctcg ggcggggcgc    21060
ccatgtcaaa caggtcgtcc tccggggggcg ggcgcttgcc ccccagctcc gcgggcgcca    21120
gcgaggccgg cgcgagcccc gcgacgtccc cgcccgcgcc gcaggcccca aagtcgaagg    21180
cggtctcctc gccgccgtcc gcgcccgtct ggccctcgag gtcgcgcacc agctcggcgg    21240
ccgcctccac gctccagcgc ccgtcgcggt cggccacgcg cccgttgatc tccgccagcg    21300
cggccgccag gaactcgtcg tccacgatcg cccgccagtc gtcgggctcc aggtgctgcg    21360
tgcgggcgcc gagcgcgtgc agcacggccg cgtacacggc cgtctgcacc agcggcccgc    21420
cgtcggccag gatggtcttg acgtgctccc cgagggagtg gtcgtgcagc ccggcgccgc    21480
cgcccgtctg cgagcacgtg aagcccacgc gcgggcaggc cagcacaaag tgccgcgtgc    21540
ggtcaaacac catcagggggg cacacgtgct tgccgccgtt gagcccgctc cagttccccg    21600
cctggaagac gcggttgttg ccggccatgc cgtggtactt gctgacgccc aggcccagca    21660
ccaccagcgg gcgcgaggcc atgacggagc ggagcaggtg gctggacgtg tacgtggcca    21720
cccacgtgtc gtcgcgcggc gcgtccagca cctcgcgcgc cgcgcgctcc gcgtcggccg    21780
cgtccgccag cggccgccgc acccaggcca tgacggcggc cgggtcccgc gggcgcttcg    21840
actgcatcgt gatccccgtg aggctgttga tgaagaactg cttgtggtcg cagtagcgca    21900
ggatcaggtt ggccaggtag aactgggcca gctccgccac ggtgcccggg gtcaggttca    21960
cgtagttgat ggcgccgtag tccaccgaga agcgcttcac ggccgcgatg gtctcgatgt    22020
cgtccttggt cagcagccgc gccggcagct ggttgcgctg cagcagcgtc cagaaccact    22080
gcgggttggg gctctgcccg ccgggcggct tgccgcgggg gaacagcgtc gcgtggtgct    22140
gcttcagcag gaagcccagc gggccgttga gcacgtccac ggccgtgtcc gggcgctggt    22200
aggcgcccgc gagcccggcc acgcgggcgc gcgcggcgtc cgagaggctg cccgagcccg    22260
tcgagaacat gacccggctc ttgacgcgca gctcccgcag cacctcgaag ctcacgcgcg    22320
ccaggtcccc gtcgtggtcg cgcgccgggg gctccgcgct gcccttggtg gggtccgggg    22380
ccacgatgcc gtcggcgagc gtcaccgtca ccgtcttggc cgtgacgaag cccccgttga    22440
gcatgtccac cacgcggcgg cgcagcaccg gctggaactg attgcggaag ttgcgcccct    22500
ccacgggctg cccgtggagc acgccgtggc actggctcag ggccaggtcc tgcagcaccg    22560
```

```
ccagcagcgt gcgccgcgcc aggaagctcg tcgccgggca cagcgcgccc gagtacgggt    22620
ccagcgagag ggacatggtg tggttggcgt cgtagagcgc gtcgcggagc ttgaagtcgc    22680
gcgtctccac gagcgtgcgc acgaagcggt ccgccgcctg ctccaccgtg tcgcgcaggg    22740
cgcgcagcgc gtgccggaag ccggcgtggt ccgccaccgt ctctccgatg cgcgcaccgg    22800
ccacgtccgc cagcagccgg tccacggcgg cgcggtacgt gtcctgcatg atcgccttcg    22860
ggggctcgct gtcgttgggg cgcttgaggg ccccgtacga ggcgtagttg ccagcacgt    22920 cgcagtcgct gtaggcgctg ttcatggtcc cgaagacgcc catggggctg cgcgtcggcg    22980
cgccgaagcg cgggaggcgg tggcgcaggc ggtgcaggt cgtgtgcgcg caggcggggc     23040
gcgaggcgcg gtcgcagagc gagcacggga cctcggcgtc gaggctgccg gccacgtagc    23100
gcacggcgtc cacgtcgccg cggcccacga acgtgcccgc gtcgcagcgc tccaggtaga    23160
acagcacgcg cgccagcagc tgcgggcaga agccgcacgc catcaccagg tggtccatgg    23220
cgaagtcgtg gttgcccggg gccgtcgcgg gctgcgaggc cgtgtgcggc agcacgcgcc    23280
cgtccttgtc cgtctgcggg ttcccggcca ggtaggcgc cgccacctgg tagaagcggt    23340
taaacgaggg gccggcgccc tccttgccgc cgccgtcggc ggcgcccgcg tcgtccacct    23400
ccgtcaggta cagcaccgag ttggagctaa acaccagcgc cccacgagg ccggccgcgc    23460 ggctcacgta cgcgcccagc gccgcggcct gcgagacggg cgcgccccg gcggcgcccg     23520 cgccgccgcc gtccttggcg cccgcctcgg agagcacggg ccagtcgtcc agcgaggggg    23580
gctcctcgtc gtacacgccg gcggcgacga gcgcctccag cgacagcgcc gcgtcggcgc    23640
tcatgacgga cgccatgcgg cgctcgaggc cgccggcggc cgcgtcgccg ccgcggcggc    23700
gctgctcaaa gagcgtgaag gtcacgtcgg cgggcagcac ggcgctctcg tggttctcgt    23760
cgaaggccag gtgcgccgcg ccgcgcgcca ccgcgtccga gttccgcacg cgcgtggcca    23820
cggccgccgg gcccagcacg tagccgtgca gcaggcggca gagcgcgccg ttgaagaagg    23880
ggcgcgcgta cacaaactcc tcgctgatgg agcggttctt ggcgttgaag gggtccgcca    23940
cgagccggtt gacgtccggc atgaagaggt gcacggggta gagcggcacg cgccacgcct    24000
cgtgcccgtt gatggacacc gtgcccgcgc cccgtagtg caggaaggcg ttgcacaggt     24060
acaccgcctc cttgaagccg tcggccaccg cgaggtaggc cgcgtgcgcg tccgcggcca    24120
ggccgagccg cgcgcacacc tccgcgcccc tcgtctcctc ggcgttgtcc accgcgtcc    24180 ggtaggccga gaacccgaag cgggcgcgcg ccgcctcgca ggcgcgcgag agggcgggcg    24240
cggcgctgct cggggcacg cagtccccgt tgtggaagaa gaacacgttg gggtggaagt     24300
ggttgggcgt cagcttcagc gtgagcccgc cgccgagccc ggtggtccgg cgcccgcca    24360 ccacggccac gtgcccggcg aagcggcct cgacggtgag gccgcgcacc agcggcgcca    24420
ccgccgcggc gtcgtcggcg ctgcgcgcca cgagcagcgc cagcaggtcg cggcgcagcg    24480
ccgcgatcgg cgtcacgtac acgtagccca gcggcgcggc gcgcacggtc acggtcttgg    24540
ccgcggcctc catcgtcgcg ggggagacga ggtgggcgcg acgagccgag acgagacggg    24600
gcgggagcgg gagagagaag gcgcggcgga cggagtcgag tctcggcccc tcttcgggcg    24660
gacgggtccg gcgcgcgggt gaagagaggc ggaggtgtcg gcgccgaggg gcgaacgcga    24720
cgtcggcggc ggcggtggag cccggcccgc cccggccggg tcttaaagcg tggggccccg    24780
ccctccgggg cgtggcgccc cgccccggag cctataccct ggccggcgac gttcgcacct    24840
ccgcgtggga cgagcgatgg cggcgcggca gggcagctac gtgacgcgcc tgagcgagtt    24900
caagttcatc gcgccgcggt gcctggacgc cccggagcag cgcggcgtgc acgtgggcac    24960
```

```
gctcgcgcgc gagcccacgg tctactgcgg cggcgccacg cggcccatcc tccgcggga    25020
gcccttctgg ccgcggcgcg tcgccgcgtg ggagggggcc cccgagcggc ccgtgagtcc    25080
gcgcttcgag cgcttccacg tgtacgacat cgtcgagagc accgagtacg ccagcgcgga    25140
cccgcgcttc cccaacggca cggtggtcac gctgctgggg ctcagcgcct gcggcaagcg    25200
cgtggccgtg cacgtgtacg gcgtgcgcca ctacttcttc ctgggcaagg ccgaggccga    25260
cgccgccctc ggcgtggcga gcgccgagca gctcgcgcgc gcgctgtcgg cggcggccgc    25320
gcgcggcccg cgcctcgggc ccgccgacgt ggacgcgcgc gtcgtcgacg ccgcgcccgt    25380
ctactactac gacgcccccc ggcggcccct taccgcgtc tcgagcaaca gcgggcgcct    25440
ggtcgcgcac ctccgcgaga cggtgtgcgc cggcctggtg acgcacgagg ccggcgtgga    25500
cgcgaccacg cgcctgctgc tcgaccacga cctgcccagc ttcggctggt accgcctgcg    25560
gcccgggccc gcggggagc gcgtggtgct gcggcaccag cgcctcacgt ccagcgacgt    25620
ggaggtcaac tgcacgcccc tcaacctggc ccgcgacgag gacggcccgt ggcccgacta    25680
caagctcctg tgcttcgaca tcgagtgcaa ggccggcgac gacgcggcct tccccgccgc    25740
cgagaacccc gaggacctgg tgatccagat ctcgtgtctg ctctactcgc tcgccaccca    25800
gcggctggag cacacgctgc tcttctcgct gggctcgtgc gactcggacg accccgcggt    25860
gacggtcctc gagttcgaca gcgagttcga gctgctgctc gccttcgtga ccttcctgaa    25920
gcagtacgcg cccgagttcg ccacggggta acatcatc aactttgact gggccttcgt    25980
ccacaccaag ctcacgaccg tctacggggct ggccctcgac ggctacgggc gcttcaaccg    26040
cggcggccag ttccgcgtct acgacgcggg ccagaacagc ttccagaagc gcagcaaggt    26100
caagatcaac ggcctcgtct ccctggacat gtacgccgtc gccgccgaca agctgaagct    26160
gccgagctac aagctcaacg ccgtggccga ggaggcgctc ggcgagcgca agctggacct    26220
ggactacaag gacatcccgc ggtactacgc cgcgggcccg cgcgagcgcg cgtcatcgg    26280
gcgctactgc gtgcaggact cggcgctcgt gggcaagctc ttcttcaagt tcctgccgca    26340
cctcgagctc tcggccgtgg cgcggctcgc caacatcacg ctcgcgcgcg ccatctacga    26400
cggccagcag atccgcgtgt tcacgtgcct gctgaagctc gcgggctcgc gcggcttcgt    26460
gctgcccgac aagcgccgcg ccatcgccga cgaggacgac ggcggcggct accagggcgc    26520
caaggtgctc gagcccgact cgggcttcca cgtggacccg gtgctcgtgc tggactttgc    26580
cagcctgtac ccgagcatca tccaggcgca caacctgtgc ttcacgacgc tcgcgctcgc    26640
gcgcccggcg ggcctgcgcg aggacgagtt cagcgccttc gaggtcaacg gggagcggct    26700
ctactttgtg cacgcggggg tgcgcgagag cctgctctcg atcctgctgc gcgactggct    26760
ggccatgcgc aaggccatcc gcgcgcgcat cccgacgagc gcgcccgagg aggccgtgct    26820
gctggacaag cagcaggcgg ccatcaaggt ggtgtgcaac tcggtgtacg ggttcacggg    26880
cgtggccaac gggctgctcc cctgcctccc cgtggcggcc accgtgacga ccatcggccg    26940
cgacatgctg gtggccacgc gcgactacgt gcagacgcgc tgggccacgc gcgagctgct    27000
cgagcgcgac ctgcccgcgc gcccgcccgc gggcgagtac gccgtgcgcg tggtctacgg    27060
ggacacggac tcggtcttca tccgcttctc gggcatcgcg tacgacgacg tgtgcgagct    27120
cggggagctc atggccgcgc gcatcacgcg cgacctcttc cgccccccca tcaagctcga    27180
gtgcgagaag accttccggc gcctgctgct catcacgaag aagaagtaca tcggcgtcat    27240
caacggcggc aagatgctca tgaagggcgt cgacctggtg cgcaagaaca actgcgcctt    27300
```

```
catcaacgcg tacgcgcgcc gcctggtgga cctgctcttt ggcgacgagg ccgtctcggc   27360
ggcagcggcc acgatcgcgc gcgcgcccgc ggcgcgctgg ctggagcgcc ccctgccgcg   27420
cggcttcgcc gccttcgggc gcgtgctggc cgaggcgcac gcgcgcgtcg ccggcggcgc   27480
cggcctggac gtggccgact tcgtcatgac ggccgagctc agccgccccc cggacgcgta   27540
cagcaacacg cgcctgccgc acctcaccgt ctaccacaag ctggccatgc gccacgggga   27600
ggtgccgagc gtcaaggagc gcgtgtccta cgtcatcatc gcgcccaccc cggaggccga   27660
gcgcgacgcg cgggccgtgc gcccgggcct cgcgcccggg aagctgctcg tcagcgacct   27720
ggccgaggac cccgcctacg tggtcgcgca cggcgtgccc ctcaacaccg agtactactt   27780
ctcccacctg ctgagcacgc tcagcgtcac cttcaaggcc ctctttggaa atgacaccaa   27840
gatcacggaa aggttgctca agcgctttat tccggaaacc gccccgggg acgcgccctt   27900 cgagcacgag gccttcgcgg cgctcacggg cgaggggggc gaaagtcttc aaacgctgcg   27960
tacaatcttt tgtactccaa cagcagctcc ccgtcgaagc tgatgtcccg catcttgcaa   28020
taaatgtcgc tcgcgctgac ggcgggcacg tcgtccgcgg gtctcccgtc tcccttcttt   28080
cgcaccacca acacgaacat ggtctgccac acgtgcgcga cgatgcggtg gccggcgcag   28140
gccccgagca ggcggtccag cacgcggtgg tgcacgtgca ccgacttctc ggggaacacc   28200
acgtacatca tgagcgcgcc ctgcgcgtcg gggtcctcga agaagagcac gcgcacgtcg   28260
cgcaggcccc cgtcgcgcag cacgtagtag gcgaaaaaga gctccgggtg cgcgagcacc   28320
tcctcgaggg cgcgctccga ggggtcccgc gcggccaccg aggccaggaa cacgcggtac   28380
tcgtagatgc tgttgagctg ctgcacgtag gccagcacga gggccgcgcg gtcgctcgcg   28440
ccgagccgcg gctcggcggc ggcgcacgtg gggcagcagc cgccgaggcc caggtagtag   28500
cccatgcccg agagcgacag gcagttgtcg gccaccgcct ggccgaggtc gaagggcagc   28560
gtcacggggg ccgtcttgat gagcgggttc gagaggccgc gcacggtggt cacctcgtcc   28620
gagggctgcg cggccgcgta ggcaaagtag ggcgcgtagc gatcgcgggc cgcgcgcgtc   28680
agcgtcttgc gccgcgcggc cgacgacttg cgccgcagga gccgccgtcg ctcaaacata   28740
gctgccgagc gtgtgctcga gggagacgag gcgcgaggcc tggcgccgca gcagcgcgtg   28800
tgcgtcgcgc aggaaggcgg ctcgggcagt gggcttcggc gggaacagct ggtacgcttt   28860
aaatacgtac gccagggtcc acagctcccc gcacacgcgc ccctcgaagc ggttctcggc   28920
ggcgatctgc gccttgcgca gcgcgtcgcc gcgctcaaag agcacgcgcg gtccgcctg   28980 gcgctcggcc acgcgcaca gggggtcgca aagaggtgc ttgtagacgg cgcgcgggcc   29040
cgcggcgcgc atcagcgcca ggaagcgcgc gtccgccacg aagccctcga gcacgggctc   29100
gatgcagtca aagaggcccg cgttgttctc cgagtagctg agcacgccgc gccggaagcg   29160
gcgcagcgcc agccagtgcg cgcgcgtgag cagcatgttg cagagcaggc actcgccgtg   29220
cgtgcggttg cggccgcgca cgtgcttcag cgccagcgcc agcacgggcc ccagcgtgac   29280
gtccaccgcg cggtagcgcg cgtacgccgc ggcggtgttg cgggccagga agccctcgtg   29340
ctccgcccgg tactcgtcca cggcgcggtg ccggcgctcc tcggcggcgt ccgtctgcgc   29400
gttgggctcc cccgtggcca cgttgccag cagcagcatg gcgaggtcgg cgtagcgggg   29460
cccggcggcg tccgcgtccg cggccccgcc cccggtggcg gcggcgacgg ccgcgcgctc   29520
gtacgcgtcg tcctcgcgct ccgccgccgc gcagcacccg gcgcacgcgt cgtcgcccgt   29580
gtggtccttc cagcccccca ggctcggcgg cgcgcgcgcg tccgccacgg tgaaaaacat   29640
cgcgcgcgtc gcggcctgga ccagaaagga ctggttcgag aagcggatct gtcgccgac   29700
```

```
ggtgcggaag cagccgtgca ggaaaaagtg ccgctgcacg tccacgagcg tgagcacgcg   29760
cgtggcgaag gcgcgctgca gcgacgcgcg cccgcgaaag tgcttgtcca tcacgtacac   29820
gaactcgaag gcggccacga agacggccgt ggcgcacggg gggcaggcca gggccttggc   29880
gcacagcgcc gcgtagtccg ccagccaggg cggggccagc gagcgctcgc ggcggtacac   29940
gtcgatcgtg cggcacacgc ggcagggctc gtccagcgcc agcggcgccg cggcggcctc   30000
cacgaagccc gcgggcgagt cctcctcgtc cagcatcacg tgggcggcga agatcagctc   30060
gcggaagagg gcgtcgttct tggtcagcag cgcggggtcg aaggccgtgt acggcgcctc   30120
gaaggcgtcc tcgctccagc ccatggcgcg cggcggcggc ggcggcgcgg cggtcgatct   30180
gcgcgcggcg atcccggagg ccgcgctgcg cgacttcgac gtggactttc tcgaggccaa   30240
ctacctgccc ccgcgggtgc gcgtctggtt cgaggacgtg atgccgcgcg agctggaagt   30300
gatcctcccc acgacggacg ccaagctaaa ttatctggcc cacacgcagc gcctggcggc   30360
ggcgacgagc gagcgcgact gcgcccacgg ggaggcgctg cgggcgcggc gcgatcgctt   30420
cgccgcggcc gtcaacaagt ttctggacct gcaccaggtc ctgcgtgacg gggtggagct   30480
gggcgcccta taaagtccgc cgcccgaccc ggggagctcc accagcccca ccaccaccac   30540
cgccgcccgc ccgccggccc cagctcccgc cgggaaaatc gccgccgccg cgtcgacgtc   30600
gtagccgcac cgctcacccc caccctcacg ctcgcgacga cgacgacgac catgagcggc   30660
accctggtcc aacgcctgaa gctcatcctc tccgggggga acctgcgctg cagcgacggc   30720
gagacggcct gcgaccccga cgcccccccg acgcggtgcg tcttccaggt ccacgggcag   30780
gacggctcca acgacacctt cccgctggag tacgtgctgc gcctcatgcg cagctgggcc   30840 cacgtccccct gcgaccccta cgtgcgcgtg cagaacacgg gcgtgtcggt gctcttccag   30900
ggcttcttct tccggcccgc cgacgccccc ctggccgcga tcacggccga gcacaacaac   30960
gtgatcctgg cctcgacgca cagcaccggc atgagcctct cggcgctcga cgacatcaag   31020
cgcgccgggg gcgtggacac gcggccgctg cgcgccatga tgtcggtgag ctgcttcgtg   31080
cgcatgccgc gcgtgcagct ctcgttccgc ttcatgggcc ccgacgacgc ctcgcagacg   31140
cagcgcctcc tggaccgcgc cgagctgcgg cagcgctcgg tctcccgccc cggggtgcc   31200 ggcggcggcg gcgacggcga ggggccctcg ccccgcgcgc ccatccgccc gaccgtcatc   31260
tcgcccgtgc ccgggcacgc ggccgccgcg ttcgtgggcc aggccgcgtg cccccccgccc   31320 gcgcggttcc cggcctcgct gctgcacacc ctcctggggc tgcggcgcct cgccggctac   31380
gccgtggcgt gcgtcaccgg cgctctcgcg atagtcatca tcctgaacat gcgttaaagg   31440
cggccgcgcg cgcgggggcg cgcacagacg cgcgctcccc gccgagccat catgtccttc   31500
gacccgaaca atccccggac gatcaccgcg cagacgctcg agggtgccct gcccgtggac   31560
attctgctcc ggctcaaccg cgcgacgggg ctgcagatgg atgcggccga ggcgcacgcg   31620
atcgtggagc acgcccgccg gaccctgttt atcggcacct ccctggccct cgtgaacctg   31680
cggcgcgcgc acgacaagca cctcgtggag cgccagccca tgttcgccac cagcgactac   31740
agcagctggg cccggcccac ggtcggcctg aagcggacct tctgccctcg ccccccgccc   31800
tagccccgcg cgatcaataa agcgagccgc gttgcaccat cctctcgact ctagcgtgtt   31860
gcttgggtgg ggtttccccc ggtctttccc cgatctcccc accgccgcgt ctttgggccc   31920
caatcccccc aagtccccca atccccaag tccccaagt ccccaagtcc   31980 cccaagtccc ccaagtcccc cgccaccgag tccgggcccc gagctccccc aagtcccaca   32040
```

```
agttccccaa tcccccaat  tcccccgat  ctccccacca ccaagtcgtt gggcccgagt   32100 ccccgagtc  ccccgaacac accaccgcag aggcaaacaa gttgggtaat aaacaattta   32160
ttaaccgaga atcaggcgga cctgaaatag gtccacgttg aagcggcggg cgctgccctt   32220
gagggtcgtc cgcgtctccc gcaggcgcg  cgctatcagg cggcacgcgg cgatgagcag   32280
ggccagggcc ccgagtccgg tggcgcgcat gtaccgcctg ttgatgagcg tgtccgactc   32340
caccacgcgc ggggggagca gctcctgggc cagagagacg tcctcgtccc cctcctcgtc   32400
ctccaggccc caggggtccg gctcgggcgc ctcctcggcg ggctcgcggg tcaagtcctc   32460
ccgggtgggc cagacgcggc cgaggccgcc caggggagag gccggcggcg gaggtctctg   32520
ctgctgccgc cgcggcggag gatgggcggg agggacgagc gccgtcaggt cgtcgaacca   32580
cgccgggggc tggtgggggt ccgccagcgg ggagcgcggg gccggcggcg caaactccgg   32640
cgggagctcg ggggtggtgc cgggcgcctc caacggcggc ggccacggca tccgctccag   32700
cggcgagcgc ggcggggtcg ccggggtctc ggcctctccc ccgctcgccc atagcggctg   32760 aggggcggc  ggtggcggca gcggcggctc ctctcgcccg gggaactgga acggcgggtc   32820
cgacggcggc ggggtgaaga gcgcgggcgg gccggcagag tccctcggct cgggccacgt   32880
ccacggcgcc tccggggggc gctgctgaga cggctgcggc ggcagcggcg gaggtgtgaa   32940
catgagccgc gggggctccc cgtgccgctc cggcgtcggg gccggccgcg aaggtggtgg   33000
ggccggcggt ggtgcggccg ccgcgaagg  tggtgggggcc ggcggtggtg cggccggccg   33060
cgaaggtggt ggggccggcg gtggtgcggc ggggcggaa  gaggtggtgg cggaagacga   33120
ggaggtggtg gtggttgttg ccgccgccgc tgctgccgcc gaggcggcgg gccgctcgat   33180
ctcggagggg gcggccagcg acgtcgggc  cgccagcgga gaccgcggcg gctgggtctg   33240
cgccggggcg ggagtctctg gcgaggccgg gcagaggcacg acgactccct ccagctgcac   33300
aggctgcggc ggcgggatgt ggagacggag gtgcccggcc ggcgggcgcg ggccggcggc   33360
tcgcctcact gggcctccgg gggccgggac cacatcatct ccggggccga ctccggggc    33420 ggggacggct gctgtagctg ctgctgctgc cgccgccggt gggcccgctg gagcagtcgc   33480
cggcgcttgg gcttgggctt gaggcgggcg cggttcaagt cctccgggag gacggccctc   33540
gggttgagcc gcgggcggaa gacccccggt ctggcgcggg gccgatacgg gccttcgcgg   33600
aacaagagcc atggatttc  ggcgactgtg gtctctaata cccaccgacg ttcgcgcctt   33660
ggtgcgtaga acagcggagg gaaggggctg cgccactggg gccgcgggga gatgtcccgc   33720
aggttgatct ccacggctcg catccgcagc cgggccaccg tctcctcggc gctgccacc    33780 actcccgggg gctccaggag gtgctcgggc cgccgctccg gctgctgagg ggggacctcc   33840
gcgggcgcca tcgctcggtg ttccggccgg ggaagaagag gatgaggcgg cttctcggga   33900
cggggtcgag gcggcggagg aggacgcgga cgcgggctcg gagtccgatg tccccggagg   33960
agagcgggtc cgatgctggt ctggtccgac cgtgtgttcg cacttgtctg cgcgccccgc   34020
tttataccgt tcgtcatcga gggggcggcc cggggaggcg gttcccgccg ccttcccacc   34080
aaatttggcg tcgcggacgt ccggcggtgc accggccctc ggctctacga tgcggtcacc   34140
atcggatttc ttggccgatg gggcgggccc gggcgcgggg ggcgtggggg tcgccgccgg   34200
ggcagacggt ggtggagggg cgggcctggg gagcgtagtc tgagcagacg gtggtggagg   34260
ggcgggcggt gcgcgcgggcc tggggagcgt agtctgagca gacggtggtg gggggcgggg   34320
cggggcgggg ggagcacccc gcggcttggc ggccggttgg gacgacgggg gctgaggggg   34380
gacctgcgcg gccgcggtcg cggcggatgg tggaggggggg gcggtctgcg tctgggcccg   34440
```

```
ggtcggcggc tgagtctggg gggtggcctt gggcgcggtg gtggcggcgg cggtggcggg   34500
ctgcgccggg ggcttctggg caaggggggc ctgggccgac gggggctgcg gcggcggtgg   34560
gggaccctgg ggttgggggg tcggcttggc cgcggcgggc ggctgggcct gggggggcctc  34620 cggggggggcc gtctcgggcg ccggggccgt cgccgggtag ggcgggttga tgaccggcgg  34680
cgggggctcg atgcgcgcct tgagcgatgg ctggatcttt cgcggcgacg agtgcggctt   34740
gggggcgggc tcccgggggct gctgcttggg ggccgcggcg gccttggtgc cggcggcggg  34800
cttcttgggg gcggcggggg gccctgctg cggctgcggc tgcggcttgg tgagcggggt    34860
cgtctccacg ggcttggcgg gcggcggcgc cggcggggcc agcttggcgg cgggagtcgt   34920
ctccacgggc ttggcgggcg gcggcgccgg cggggccagc ttggcggcgg gagtcggctc   34980
cgcgggcttg gcgggcggcg gcgccggcgg ggccagcttg gcggcgggag tcggctccgc   35040
gggcttggcg ggcggcggcg ccggcggggc cgccggggcc aacggcggga gcgtgggcgg   35100
gtcgaccggc ggcgacgggg gcggcggcag cgcgctggcc accaggtcgt cgccgagcag   35160
gtccagccac gggttggcgc caaagtcgtc gtccgggacg aacccgtcgt cctcccccgc   35220
caactcgggg ggcagcccgg ggatcggggt cgcgggccgg gtgggcgtcg ccgacacggc   35280
gtacgggaac gggtcgccca ggttgcggaa gctcggccgg ccgtacagct cctccgaggt   35340
ggccgggtcc acgcgggcgt cgcccatgat gatggaggtg aacagcgggt ccgcggggtc   35400
catctccggc agctggtcct ccgtcgtctc caggaagggg atctcccgca gcagcgggtc   35460
gtcctcgagc gtgaagcccg ggcgtcgcgg cggctcgggc ggcgcccaga gcacgcgcga   35520
caccgccagc tgcgagtcca ccagcacgag gcaggccggc tcgccggcca ggggccgcgc   35580
cgcgatcagc gccgagagcc gctccagctg cggcgccagg cacgcgttct cgatgggggtt  35640 gtcgtcgagc gccagcaggc gctcgcccca ggagctgagg tccgtggaca cgccgcggtg   35700
cagcgcgggg tcgcgcaggt cgcacagcgt cacggccagg gtcaggcccg agccgggcga   35760
gtacacgtcc aggttctcca tggcgatcac cagcggggcc ccgacgagca ccgccgccgc   35820
ggccaggtcc atggcgctca cgcgcgtcgc gctgctcggc ggcgagcccg tgacggtgaa   35880
cgtcatgccc gtgcccacgg gcgcgtacag gtcgccgggc gccggcgcgc cgagcgccgc   35940
ggcctcgcgc acgtgcgccg cggcgtccag gcgctcggtg accgcggcgt cgtacgcggc  36000
gttcgcctcc ggctgcaggg cggaccacac cgccgagagc agccgcgggg ggatgcacat  36060
gcgcgccagc acggtgaagg tggccagcgc gcccggcacg gcgcgcgcca gccgctggcc  36120
cgtctccgtg tgcgcccagg gcgcccacag ctccgtctcc gagaagcggc cctcggtcca  36180
gtcggcgacg cgcagcgtga acagcgcctg cccgtcgcgc agcgggcgcc cggcggggcg  36240
cgcgcccgcg tccagcgtgt ccaccgcgtc cagcgcgcgg tccagcaccg cgtccagcgt  36300
cttggccatg tactcgtgct gcccggccag gtccacgcgc gtaaagttga acaggtgcgt  36360
cggctcgccg gccaccgcgg ccaccatcag gtcggggagg gcgagccgca ccgccggctc   36420
cagcggcggg tgcgcgacgc ggtccagcgc cccgaaggtg cgcgagagcg tcgtggccag  36480 cacgccgcg tacgtctccg cggcggcctt ggccgccgag tcccagtcgg cgcggcggtg   36540
gcgcacgaag cgcgcgaagg tggcgaagcc cgtgtcgcgc gccttctcgt agttgagccg   36600
caggtggatg atctcgttca tgaggcgcat gcccgccacg gtcgccgtct ccatgagccc   36660
ctcggtgagc ggcgggcgca gctcggcgcc ctcgtcggtg cacagcatgg ccgccagctt   36720
gtcgccgacc gcgcggtagc acacctggta ctccacgggc acgttgttgt cgtccaggaa  36780
```

```
gaccgtgggg aacaccgcgt ccgcgtcgct ccgcgcctcg cgcaccgtgc agatgacgtc   36840
gcggtcgccc aggcgcgccg ccacgcgctg cttcaggcgc gcgcacggcg ccgtcgaggc   36900
gcgcggccgc gccggcgtcg gccccgcgcc gccgtaggcc gcgtagaact gcaggcgcag   36960
cgtgagcagc tcgcggtagg cggcgtactt gggcgggatc caccgcggca gccgctccgc   37020
gcgcgcgtcg aaggcggccg ccagcgcgcg cagggcgtcg tgccgcagct cgggcccgat   37080
gcgcgccgcc atgcggtcga gctcgcgcac gtcctcctcg acggcgcgg cgtcgcggaa   37140 gaagtcgccc agggccccgg cgcgcgccga gtacttgctc tcgatgcgcc ccacgaactt   37200
ggcgggcagg cgcgggtaga cggcgtcgct gcgcagcgcc agcacctcca tggtcgccgt   37260
ctgcagcgcg cgcgcgcggg cctcggccag gcgcgcctcg tcctcggagg cgccggcgcg   37320
gccgcgcgcg cgcccaaagt cctcccaggc ctcgtcccag gcgacctcgg cggccgtcag   37380
ccgctgccgc agcgtgtccg cctcctggcg cagcgtctgc agcgcctcga tgcgctcggc   37440
gaactcgtcc atgggccgc ggccgtcgac gcgcgtcgtc agcgggtgcg tgtcgatgat   37500
gagccgcgcc tggtgcagcc actcgacggc ctgcacgtcc agctcgggcg cctcctcgac   37560
ggcgccgagc agcagcgccg cctgcgtcac cagctcctcc gcggaggcgg cccggtcgat   37620
gttgagcgag gccggcggcg gcgtcacccg cagcaggttc ttgaggttgg ccagctcgag   37680
ggccccgtcg cggtcgcgcg ccgccgccgc gtccaccacc tcgcgcagca ggcgcgtggc   37740
gcgctccgtc gccgcggcct ggtccgcctc cgccgcggcg aggccgtcgc gcgccgccgc   37800
caggtcgcgg cgcacgagcg cgcgcatggc ctccgcgtac gccgtgcgct cgaagcgcgc   37860
aaagtcgaag cgctccaggt aggtcacggc gccgcgcagc agctcggtgc tcggcacgtg   37920
caggtgcacc ccctcgtcga gcgcgcgcgc gcgtcggcg gccgcgcgca cgtacgtcac   37980
ctcctcgagc gcgcggcaga tctcggcgcc gcggctgccg ccggcctgca gcacgtccgc   38040
gcgccgcgcg cccagggcgg ccagctcggc ctcgtactcg gggaagccgc ggcggtaaaa   38100
gtccacgtac ttggccaggc ggggcacgtg cgccatgtcc gccccgacga agcccacggc   38160
gtcgtagtag ctgaagcgcc ccatgccggc ggcggcgcgg gccagcacgc cgccggcgat   38220
gcgggccagc cgcgagagcg gctccgtgtc ggcgccgaag agcgacccga tgacgggcgc   38280
cgcgacggcg tagtcgtcga gccacgtcag ccgctgcagc gcctgcagcg gcgggcccgc   38340
cgccgcgccg gcgttctcgg gcaggtgcgg gttgaaggcg aacacggcgt ccagcgccgt   38400
ggtcacggtc tcggcgttgg cgccgagcgc gcgctcggcg gcggggcgca gctccgcggc   38460
gtcgtagccg cggtcggccg ccacgtcgcg caggcgcacg aactcggccg cgtcgaaggc   38520
gtgctgctcg gcgcggcgca gcgccgcgtc ggcggcgcgc gcccagagct ggcgctgcgc   38580
gcgctccacc tccgccgcgc ggcgcgcctc cacggccgcc acggccgcct ccagctcgcc   38640
gacgcgctgg cgcgccgcga gcgccatctt ctgcagctgc ggctcctcca cggcggccgc   38700
gcgcgccacc tccagcgcca ggtgccgcgc ctcgaccagc gtccctcgt cgggctgcgc   38760 gcgcagccgc ccgagcatct ccacggccgc cgccacggcc gccacagcg cggcctgcag   38820 cgccgccacg cgctccgact cgcgcagcgc gcggcgcgc tcctcgcact gccgcgccag   38880
cggctccagg aagcccagct ccgggtgctc cacggcggcg cgcagcaccc ccgccgcgcg   38940
cgccgccttc tccgccgtgt ccgcgtccgc cagcgccgcc gccaccgcgt cggcgtgcgc   39000
gaggaagaag cgcgtgatgg gcgggttgtc cgcgagcgcg ttgaccagcg ccccgagcgg   39060
ctgcccggcg cccaccagcg cgccggggtc ggacgtcagc agctcgcggt agcgcgccac   39120
caggcgccac agcgccgcga gcaccgcgcc cggcacgggc gtggccgtga tgtgcgcgag   39180
```

```
caggtccacc gccgggccca gcgtggcaaa gtcgcccagc agcgcgcgca gccgcatgta   39240
gaggtcgttc tgctcggcgg cgcgctgctg cgccgcctgc accagcgtgc gcagctcggc   39300
gtcgcgccgc gcgagccgcg cgccgcgtct cctggctcag cacgtggccg ccatggcgcg   39360
gatgtgccga agcaggtcct ccatcgcgcg cacgcgcgtc tcctcgtccg gggcggccgc   39420
cagggcggcg tccatggcgt cgaagcgcgc caggtcggcg tcggccgagg cgcgcttggc   39480
cgcgcgctcg ttgatctggg tcacgtcgcg cgtgagcgtg tccagctcgc gccgctccag   39540
gtgcccgtgc gcctgcgcct cggccagcag cgcgaaccag gccccgaggc gctcgtccgt   39600
gctcacgtcc tcgcccgcct ccagcagctg cgccagcagc gcgccgtcgt gggcggcggg   39660
cgccgcgtcc agcgcgcgca gccgctcctc ggcggccgcc agcgagtcga cgaggcggcg   39720
caggcccgcc accgcggcgt tggcacgcgc gaagcgctgc gcgccgttgc ggtccatcag   39780
catggccttg gcgctgtact gcgcgccgcg cagaaagtac tcgcggatgg cgtcgccgac   39840
catcagcgcc agcttgcgcg gcagcttggc cgcgcgctcc ttgacgtcgc gcgtgttcgg   39900
ctcggccgcg ccgcccgcgc ccggcgcccc cgcgtccacg gcgtcaaagt tggcgtgggc   39960
ggcctcgagc gccgcctcga gcgcgctcac gtcgcgcgcc cgctcgagcg cccgctgcga   40020
ctcgcgggac tcgcgcgcgc gggcgcgcgc aaacagggcc cgcgcgcgcg ccaccaccgt   40080
ctggtcgtag acgccgccgg ggtcccgcgc cgcggcgtcc atgaagcacg ccgagagctg   40140
cgcgtaggag ccctcggact cgagcgcgtc cagcgcccgg tgcatggcct cgttcgcggg   40200
ccgcgcgacg cgcgccgcga ccagcgccag cttggccacg ggcgcggacg cgtcgtcgcc   40260
ggccacgtcc agcagcgcgc gcgcctccgt cagcaccatg tgcgtggcgg ccacaaagtc   40320
cccggccggg ccgcgctccg gcagcgcgcc caggatgggc tcgaagagcg cggcgacggc   40380
gcacggcgcc tccccgtggg tgcgggcgcc gttctccacc agaaagtcct gcaggtgccc   40440
gaagaggagc tcggcgaagc gctccagcag cccggcgcgc ccggggaaca ggctccggcc   40500
cgcgcacgcg accacgtgct cctcgagctc gtcggcgtgg gcctgcagcg ggcccaggtc   40560
gagcggggcc agctccagct cccggacggc gaagcccatg ggctcgcggg tgcgcgggcg   40620
gaacttgcgc gacggccgcc cgccgaccgt gtgcgtgctg ctcaggtcct cctggctcgc   40680
cggccacggg ggccggcgcc gcttgggcat gctcggccgc ttctggaccc gcggcggcgg   40740
cgggagcggt gcgccgccgg gtgccggggc ggggcggcg gccgccgaga cggggacggc   40800
ggggacgggg gcgacggcga ggacggggat ggccccgggg ccccgcgtcg gcggcgcggc   40860
ggccgccggg tccggcggca gggccatcgg gtgcacggag gcaccgcccg ctccacgta   40920 cggctcgtcc acgaggtacg tctcgcccac gccgtagagc gcgggcacgg cggcgaactg   40980 gtcgtgggc aggaagaaca cgaaggcccc ggcccaccgg agctcgctgg cggcgtagcc   41040
cgcgacgtgc gcgtacacgt ccgccgggcg caggcgcgcc acgaaggcct gggtgatctg   41100
cccgtggccg tgcgggtcga agacgtacac gacgtcgccg cggcggtaga ggcccaggcc   41160
cacggcgccg accacgacca gcgtgaagga ctcggcgcgc tgcgcccaga ggccgtcgaa   41220
gaaggcgcgc gccgtgatct gcgtgctctg gaaaccctcg gcgggcggcg tgaaaaagtt   41280
gcactcgccg tgcacccgcg agaagacgca gtgcagcgcg gcgccgcccg cgccctcgta   41340
gacgatcttg ttcgggagct cgctgatggc gcacatgccc ccgccgggcc ccgtccacgc   41400
ctggccctcg cgcaggcacg cgtccacggc gtcggccgtc agggcggcct ccacgccgtt   41460
cgtgaagacc aggcgcagga aggagaggga ggagcgcagg cacgagacgc ccgacccggg   41520
```

| | |
|---|---|
| ccccaggtcg gggtcatact gattacgata gccgacgacc accgcgtcgg ccgtcatggc | 41580 |
| tgaaataaca cacgcgcgtg ggggaaaaat cttttttattt ggacacggcg tcgacctcgg | 41640 |
| ccaggagccg atccacgggc acccacgttt gcgcgagcag gggcacgccc gcgctcgcgt | 41700 |
| cgtcgggcgc gcgcgcgccg cggcgcagca cctccaggtt cacggcggcc cagtcgcgca | 41760 |
| cgttgacgct cgccgagagc ggcacggcgt cggggcccgc ctcgccgtcg cccgccacct | 41820 |
| cgtggtagtc gcccaggacg cggtccgcgg cctcgcgcag ctcctcgggc gtgaaggcgg | 41880 |
| gcgcgggcgg cgcctgctcc tcgcgcgcct cggtccaggt ctcgcggagc gtcgcgacga | 41940 |
| gcgccagcac gccgcgctcg tcgacggcgc ggcgcagcgc ggcgctgacc aggtcccagc | 42000 |
| gcgccaggaa gcgctccacg ggccgcagga cggtggcggc ctgcaggcgg ccggccgtga | 42060 |
| gggcggcgct cgtctgcagc ttgctcaggc gcgcgtggtc ggcgcacagc gtccggaaca | 42120 |
| cgggcgcctg caggcccagc gcctcgcact cgcgcagcgc ctccgtcgtc tgcgccatca | 42180 |
| cgccgcgcag cgccccgcg tcggcgcgca tgtccgagcg gtgcgtgttg acctcggcgc | 42240 |
| ggaaggcgcc cacggcgtcc acgacgtccg ccagacgcca cgtgcccagg cagggcccac | 42300 |
| cctcccccggg cgcgaagacg gaggccgtgc gcccgcggaa gacgaagcgg caggtgaaga | 42360 |
| ggcgctcgag cgccaccacg cgctcggcca cggcgcccgc ggccgtggcc atcgagtcca | 42420 |
| gcaggtcgcc cgtgtgggtg gccatgtcct ccaggcggcg ccggagggcg cgcgccagca | 42480 |
| ggtccccgag gaaggcgctg gcggccagcg agggcggcgc cggcgccggc gcctcgagca | 42540 |
| cctcggcggc cgcgcgcacg accccgtgca gctcgtgcgc gagcgcctcg acgttgcgcg | 42600 |
| cgtgcgccac cgtcaggtcc tcgcgcgcca gcgccgccac gagcgcggcg agcttggtgc | 42660 |
| ggtagccgct gacgttgggg atgaggccgg cgccgtagtc gcgcgcccac gtcagcacct | 42720 |
| gcgccaggtc cgcgcggcgg tcgtaggagg ccgtcaggag gcagttgtag gcgtcggcca | 42780 |
| cggccgtcac gacgaagaag ggcgcgaagg acgggtcggc catggcctcg aggtgcacca | 42840 |
| tggacgggta gttcacgagg tccgcggcgg cggcgaggtc gacgagcgcc gcgctcgtcg | 42900 |
| gcgcctccat gggcgtctcc ccggcgccgt cggcgcgcag gccccagcgg ctctgcgcgc | 42960 |
| ggaaggcgag ccacgtgttg agggcctcgc gcgcggcgct gtgcgccagc ccggcgcggc | 43020 |
| gctcggccgc cgccacctcg cgcagcagcg ccgcgcgcgc cgcgcccacg tgctccgtgg | 43080 |
| gcgggcgcgg cgccatgcag tggcgcacca cgtgctccac gcccttctcg gggagcccca | 43140 |
| gcgccgccgt cacgtccccg tagaggggct ccagcgtgtc cgcgacgtcc gtgtaggcgc | 43200 |
| gcacgtagtc cagcccgggc ccgtagtcgt cgaggaggcg gtgcacgacg ccgccgacga | 43260 |
| ccgccgtgca gccgacggcg cgctgcgcgt ccgtcaggcg gggcgcgcgg tccagcacgg | 43320 |
| cgcgctcgag gaggtcgcag tggcggcgcg tgaagcccgc ggtcacgagc gcctccacga | 43380 |
| cctgcagcgg cgaggcgctg gcctgcaccg cctcccacac gcccgtggcg tccacctgcg | 43440 |
| tgtggtcgag gtccgcggcg gcggccacgt gcacggcctg cgccccgggg tccagcagcg | 43500 |
| ccagcacgcc ctggtccgtg cgcaggcgcc gcgccacggt gcccgggcgc agctcgcgca | 43560 |
| cgtacgcgtc cccgtgcgcg agggccgcgg agacgcgcac ctcgacggcc gtgcgcggcg | 43620 |
| tggcgttgac ctcgcccacg ggcaccagcg ccgcctcgtc cacggcccgc gccgcctcgg | 43680 |
| cgaactgctc gcgcagcgtc gggttctggc ggtcgtggaa gaactcgtcg gcgatcgtga | 43740 |
| gggcaaagag cgcgcgcgtc agcggcttca ggccctcgtt ctgcatctgg cgcaccgcca | 43800 |
| acgccagcgc cagcgcccag ttggtgtgct gcgcacgta gcgcaggccg tcctgcacaa | 43860 |
| agtccatgtc gtagagcgtc gcgaagcggg gctgcacgag cgcgcgcgcc gtctgctccg | 43920 |

```
ggggcacgac gcggggcgcg gccaggacgt cgtcggcgga gcgcgcgccc gccagggcct    43980
cgtcgaaggc ggcgcaccac tcgctcacga ggcggaacat ggcgtcgggg ccgaactcgg    44040
ccgaggtgcg cagcccggcc tcggtgaggg cggccgtggt gtcgtcgccg ttgacgaccc    44100
ccaggagctc cagcagcggg gccgtgccct cgtcccagtc gtggcgcagg cgccacagcg    44160
ccaggccggc caggttctcg gcgagcacgg ccgcctcgca ggtgcccgtc tcgacgtagg    44220
cgcggcaggc caggcgcagc gcgcgcgccc agagcccgcg cacgcccgcg ggcgtctcgc    44280
ggcccgcggc catgaagaac tccaggatgc gcgactgcac caccgtggcg acggcgtggt    44340
cggcctcctc gagcgcgcgc acgagcgcct ccattataag agggtccgcg cgcgggcgcc    44400
gccgcgcact cgaccccgcg cggcgcgacg atgagcgtgc agatcggcaa cgggctgctg    44460
atggtggtcg cgccgggcac actaaccgtg ggctcggcgc gcgcgcgcct tatacgccag    44520
gtgacgctgg cggacttctg cgagccccag gccgagcgcc cggggctggt ggtgctcgcg    44580
ctgcgccacc ccgcggacct ggccggcgcc gcctacgcgg ccacgccgcc cggcaagaac    44640
caccgcgacc tggaggaggc gtggctcgcc ctcgacgagg gcgggcgcgg cctcggcggc    44700
gacggcatcc gcgcctccgt cgtctcgctc aacttcctgg tggcgccgcc cgagaacgcg    44760
gacgacgcgc tgcgcgcgca cgtgacgacc aactaccgcg accggcgcac ggccgcgcgc    44820
ctcgagcgct tcgcgaccgt gctgcgcgcc atgatccgga gccacgtgtt cccgcaccgc    44880
gcgctgcacg tcctcggggg gctcctgggc cacgtgacgc aagaccggct ggccagcgtc    44940
acgtgcgtgg cccgcggcga ccaggaggcg gcgcgcacca acgacatggc cgcgcgccgc    45000
tcgcaggtgc acgtgcccgc gtgcgcgctg atggacgtgg accgcgagct gcgcctcggc    45060
ggcgacgacg gcctccgctt cgcgtacctg gtctttgtct acacgcagcg ccaccgccgc    45120
gaggcgctgc gcgtccacgt ggcggtgagc cgcctgcccg agctcggcga cgccctcagc    45180
ttcctcctgg ccggcacgcg cgtcgacaac gcgatccacg gcacggacga ggccgacgcc    45240
cccgccgcgc ccgccgccgc cgcggccttc cccgcgtacc tgttcaacga cccgcgcagc    45300
gcgcgctgcc cgacgggccg gctcaacacg cccgccgccg aggcgctgcc cgtgtgggcc    45360
cccgacatgc gcggccgcgc cacccggaac tcgtgcatgt acgccgccta cgtgcgcctc    45420
ggcaccgtcg agcgcgtcgt gcgccgggcc gagcgctgcg gctcggtgga cctgccgctg    45480
gcccacatgg agcgcttcac ctgggacgtg ggggcgtggg aggagtgttt cttctgaaaa    45540
aaccgggggg cgggtgtgtg agacggatgt gatgttgctg acgaggctaa taaaaggcg    45600 ggcacacgcg cgcgtgtccc cccgctgacc ctccgtgccg cgtccgtgtc gtgtgtgact    45660
caccccatcg tctctcccgc ccgcgatccc ggcccgtccc ggcttgtccc gccccgccca    45720
gacacgtccc atcatgtccc cgcgcgcgcc ccgcccgccg ggcgcggttt ccccgcccct    45780
tcccccattg gcggccccgc cgctaaaagc ccgcgcgccc cgagctcggg actctccgct    45840
cacctccccg cgtcgagcac acgcgcgcat ggcctccgtc gtcgcgcccg ccgcctcctc    45900
gtccgccgcc gccccggcg cggacgcatt cctcgacgcc gcctgccccg aggacgtcgc    45960
ccgggccctc gccgccgagc tcgaggcgct gcgcgccctc gggcacgacg tcggcgcgcc    46020
cgcgcccggc gcctcgcgcc gcgaggcggc gctgtttatc acgcgcgccg tggacgggct    46080
caaggccttc tcccgggtgg acgagcgcgt gtacgtggcc tgcggcaagc tggtgcacct    46140
gcgcgtgcgg aaccgcgagg cggacctgga cgcctggctc gcctcgccgg agctcgcgct    46200
gatccccgcg gtggcggccg ccgtgcgccg gcaccgcgcg cgcgtggagg cggccctccg    46260
```

```
ctggttctgg cgggaggcct acccggcgct ctacgcgcgc ggcctgcagt cggcgctcaa    46320
gtacgaggag atgtacctgg cccgcctcga gcacgggcgc tgcgaggcca tggaccagtt    46380
ctttgtgcgc ctcgccgcgg ccgccgccac ggcgacgcgg cgcccatgg cgctcgtgct     46440 ctgcggctcg gacgcgtggc ccgaggtctt tgacgcgtac tttcgcgcgc tggccacgca    46500
ggcgatcgtg cccgcaaccc cgctcatgct cttcgccggc cgcgcgcgcg gctcgctcgc    46560
cagctgctac ctgctgaacc ccctgccgcg caccaccgag gaggcggtgc gcgccatcac    46620
ggacgaggtg gcccccatcc tgctgcgccg cggcggcgtc gggctctcgc tgcagagctt    46680
caaccgcacg ccctcgggcg actgcacgcg cggcatcatg gccgtgctca aggcgctgga    46740
ctcgatggcg gcggccatca acagcgacag cgagcgcccc acgggcgtgt gcgtgtacgt    46800
cgagccgtgg cacgcggacg tgcgcgccgt gctgaacatg cgcggcatgc tcgccgccga    46860
cgagagcctc cgctgcgaca acatcttcag ctgcctctgg acgccggacc tgttcttcca    46920
gcgctaccag cggcacctgg acggcgagcg cgccgtcaag tggacgctct ttgacgaccg    46980
cgcctcgcac ctggcctcgc tgcacgggcc cgactttgcg cgcgagtacg agcgcctgga    47040
gcgcctcggc ctcggcgtcg agtccctgcc catccaggac atggccttcc tcatcgtccg    47100
cagcgccgtc atgacgggca gcccttcct catgatgaag gacgcgtgca accggcactt     47160
ccacacggac acgcgcggcg ccgccctcgc cacgtccaac ctctgcacgg agatcgtgca    47220
gcgggccacg cccggcgaga acggcgtctg caacctggcc agcgtgaacc tgcccgcgtg    47280
cctggcgggc ggcgccttcg actttgccgc gctgcgccgg gccgcgcgcg tcgccgccgt    47340
cttcgtcaac gccatgatgc gcatcgggaa ctacccgacg ggcgcctcgg tcgagggcgt    47400
gcggcgcagc cgctcgctgg gcatcggcct gcagggcctg cacacgaccg tgctggcgct    47460
ggacatggac atggccgacc cggcggcgcg gcgcctcaac gccgccatcg ccgaggagct    47520
gctctacggc gtcatggacg ccagcgtgga gctctgcgag cgcggcctgc gcccttcga    47580 cggcttcgag cacagccgct acgcgcgcgg ggtcatgccc tttgacgcct acgagcgcgt    47640
ctcgctccgc gagccgatgc gctgggacgc gctgcgcgtc cgcatcgcgg agcacggcgt    47700
gtacaacgcg cagtttgtgg cgctgatgcc caccgtgtcc tcgtcgcagg tcaccgagag    47760
cagcgagggc ttctcgccca ccttcaccaa catgttcagc aaggtcacca tctcggggga    47820
gctcctgcgc cccaacctgc cgctcatgga cgctgcgg cgcctgtttc cgcgcgagtg      47880
cgcgcgccgg gacgccgtgg cgcggctgga gcgcgcgcag tggtccgtgg ccgcggcctt    47940
cggggagctg cccgccgggc acccgctggc caagttcaag acggccttcg agtacgacca    48000
ggagctgctc atcgacatgt gcgcggaccg cgcccccttt gtggaccaca gccagtccat    48060
gtccctcttc ctgaccgagc ccgccgacg gaagttacac gcctcccgcg tcatgggcct     48120
cctcatgcgg gcatataacc tgggcctcaa gacgggcatg tactactgca agatcaggaa    48180
ggccaccaac aacgggggtgt tcaccggcgg ggacctggtc tgcacgagct gccacctgtg    48240
agcgcgcgcc atggagtact tttacacgtc ccagtgcccc gacatggacc acctccgctc    48300
gctgagcgtg gccaaccgct ggctcgagac ggacctgccg ctgggcgacg acgccaagga    48360
cgtgccgccg ctcagcgagg ccgagctcga gttctaccgc ttcctcttcg ccttcctctc    48420
cgccgcggac gacctcgtca acgtcaacct gggcagcctc tcggagctct tcacgcagaa    48480
ggacatcctg cactactaca tcgagcagga gtgcatcgag gtggtgcact cgcgcgtgta    48540
cagcgccatc cagctgatgc tgttccgcgg cgacgccgcg gcgcgcgagc gctacgtgcg    48600
cgcggcgctg cgggacgagg ccatccgccg caaggtggag tggctcgact cgcgcgtcgc    48660
```

```
cgagtgcgcc tccgtcgcgg aaaagtacct gctcatgatc ctcatcgagg gcatcttctt   48720
cgcctcctcg ttcgcctcca tctcgtacct ccgcacgcac aacctctttg tggtgacctg   48780
ccagtccaac gacttcatca gccgcgacga ggccatccac acctcggcct cgtgctgcat   48840
ctacaacaac tacctggggg acgccccgcg ccccgacgag gcccgcatcc accagctctt   48900
cgccgaggcg gtggagatcg agtgcgagtt tctgcgggcg cgcgccccgc gcgacagcct   48960
cctgctggac ctgccggcca tcatctcgta cgtgcgctac agcgcggacc ggctgctgca   49020
ggccatcggc gcgagcccgc tctttgacgc gcccgccccc gcggcggact ttcccatggc   49080
gctgatggtc gccgagaaac acaccaactt tttcgagcgg cgcagcacca actacacggg   49140
gaccgtcgtg aacgacctgt agccccggcg accccgcccc tcccccctct tctctctctg   49200
cggcaaaaca ctaataaagc gttgagacac tagcgcgcgc ctccggccgt catccttggg   49260
gcgagggtga gacgggaacg gggatgggag agtgggatgg ggaaatgggg gatgatgacg   49320
ggggaaggga gatggggccg gcgggggtgg acttggactg gggaaggatg gtggcggccg   49380
gcgcagagtg ggaggcggtg aggtggacgg aggggaggac cgatgtggga cggcggaggg   49440
acggcggagg gacggcggag ggacggcgga gggacggcgg agggacggcg acgacggaga   49500
gagaaggtgg gggagagggc gagcatcaca cgggccgcac aaccgaggat ttttttcaagt  49560 tttttattt tctcctatgg gcgttacagt cgtcccagta cgccacgagg acggcctggt   49620
agttcggggg cggggggtatg tgtttccaaa acaggcccgc cagctccttc gcccgcgtct   49680
cgttcttcac gtgccgcagc agcgagccaa agaccttgtt cacgtccgag ggctcctgca   49740
cgatggggac gcgccgcagc acgctcaggt gcccgtgccg cgccggcgtg agcatggcca   49800
ccacgtgctg gatgaactcg cgctcggcgc ggcgcgagcg cgcgtccccg gccgccggca   49860
gcagggcgag cgccttgccg gcgtcgcgca tgatgtcggg gcagcgggag gcgtacttga   49920
gcttgacgtc ctcggggggcc acctcgcggc cctccagcga ctcggccacc tgctgcaccg   49980
agtccacgtc cggcgcccgg tgcaggtccg tgtggcagcg cacgaacgcg gccaggaact   50040
ccgagtagtc caccccagg ctcgcgagga cgtcgcggca gcgcagcacc agcgggaaca   50100
cgggcgcgat gtcgaggatc atgtcgcacc cggtgaggat catgtccgtg tcggtcgtgt   50160
gcacctgcgc gaccgtgttg gtgtggtaga ggttggcgca gacgtcgtcc gcctccatgt   50220
ccgacacgtc cacgtaggcg tagcccatgt ggcggatgag gttgacgcag aggcggtgga   50280
cgatgcgcgg cgcgtgcagc atcgtgctcc agcgcggccg cggcggcgcg tcggcggccc   50340
cgtcgccgtc ggcgcgcacg gccgcggcca tgatggcctt ggcgccgcgc gcgatgcggc   50400
cgttcccgaa gatgccgcgg tccgagacga agatggggaa gtaggtgcgc ttgtgcagca   50460
tgcgcagcag gcgcagcagg cagcgggcgg tcgtggtcgc gttgtcctcg gtcgtctcct   50520
ggtagtgctt ctccatgagg gtgtacatga cgttccacag gtcgatggcg attggcgtga   50580
ggacccccgg cggcgtggag atggcctccg agcgcaccag acgtggcgg tgtgcgtact   50640 ttaaaaggcc aaagagcccc atgtctccgc tcgcacaccg aggcgccggt ctaaaatacg   50700
catgtggcgg ggcggggcca tccgcgcata taagccgggc ggtgattggt ctggcgcaca   50760
ccgcccgccc gagcccgctc gcccgccgcg atgtcgctgt tcgacgacgg cctcgaggac   50820
ctggaccgcc accccaccca cgcgcaccac ccggcgcagg tgatccacga cgggcccttc   50880
gtgctggagg acgcgagcc cctgcagcgc accggcatgc tggtgctcag cgacgagcac   50940
ctggagcacg cgcgcgccgc catcgccccg ctggccgcgc acctcgcgca cgccttcctc   51000
```

-continued

```
gtcttcagcg aggccgggct gctggtgcac gccagcgtgc gcggcgagca ggtctacgtg     51060
accctggccc cggaccagtt cagcacgttc gtgtggagcg ggcccaggc cgtgttcctg      51120
ggcaacgtcg acggcagcgg cggcgtgctc gacgcgctca aggtcgaccg gcggcggacc     51180
gtcttcaacg tcaccttcga ggtgtacggc gccttcccgg cgcggctgct gacgcggcgc     51240
gcgtactttg cggacgcggg cgtcctcgcg acggggcccg gctccccgag cgtcgcctgc     51300
gtctacaagc acgagttcaa cgactactgc atcatgctcc cctcgcgggc gcccgacgtg     51360
agcctgacgc tctcgcgccc ccaggtggcc aagctcgccg ccgtggcgaa gggcgccgcg     51420
gccgggacga ccttcgcgct cgcccgcggc ctcgacttct ccgtctcctc cagcgccggg     51480
gtcgtgacct tcccggcgcg cgaccgcgac gggaccgccg tgctggagcg cgccagccag     51540
cggcgccagg gcgtcgacgc ggtcggcgcg acggagccct tcgccatgac gctcgagacg     51600
gcgcacgggc tgctgacgct gctgcagcgg ctgcgggccg ggaacgccga gctcacgttc     51660
aacttttca cgacgccgcg gcaggcgccc ctgttcagcg tgaccacctg cggcccggtg      51720
agggcgacca ccttcttctt ctgcgcgccc gccgaccccg ccaccgtgcc cgccgccccc     51780
gcaggcgccg ccgccaccgt cgccgccgcc tgcggggcgg gcgcgtccgc cgcccccgcc     51840
gcgggggaca agcggcccgc cgcccgcgc atgtacacgc ccatcgccaa cgcccgcgg      51900
gccgcctcgg gggaagggg ccacgcctac ggagatttat tctaataaag tgtgcaggtg      51960
tataaagag aggtcgcacc tccgcgtctt tactcgccgt cgcgatgatc tcccagggga      52020
acggagggg ttgccgcccc ggcgagccat gctggcgctg cgcgctcgag tccacccgct      52080
gcatcacgct gatgggcgtg ctcgtcgcgc tcctcgccgc ttgcatgctg tccgtcccgc     52140
ccgcggcgtc gacgatgctg ctcggcgtcg ccagcctcat ggccatgctg cgcctgccca     52200
tgcccctcgt ggaccggttc atcccgcgcg tcatgggcct ccagtcgtc ggcgccgccg      52260
tcttcgccgc gggctgggcg ctggccagcc gcgacgcgat ctcggccggc gtcctgctgt     52320
gggcgtctg cgcgctcatc tcgcacatgt acaacgtcgt ctgcgtcgcc agcgggcccg      52380
acgcgcacta ccgccccgcc tgcctcgtca tgggcgtcgc cgcggcctgc ggcgcggcgg     52440
gggccctcgt gaacgtgcgc accgaggcgc gcctcggcat cgccctgggg ctggccgtca     52500
catgcgccac gaacaacgtc gcccgcagcc tgcgcggcac gtgcacctac gtcgccagcc     52560
gcgcccggtt cctggccgcg cccgcggacc tggggcgcgg ctacagcgtg gagaacgcgg     52620
acgccgaccc caccgccgag cccgagcggc gcgtctacga ggcgaccgtc cgcacacccc     52680
acgcctacgc cggcagcatc gcgctcttcg ccctcgtctt atcggccgcc tcctccctcc     52740
agtggatggt ctcccagatg gtgggccgcg gcaaccagct cgtctcgccc accaccgcgg     52800
ccgcggccgg cgccgccggg ttcctggacg cggcggcgct ctcgctcttt gtgcgcccga     52860
gcacgcgcca cctctcggtg gccgtcaagg gcgcgcacac gctcctcatc ctcgcggcca     52920
tcgtcctcac ggccgtcggc gagcccatgg gcgtgcccat cagccgcgcg gcctccaccg     52980
gcctcgcgct gctcgaggcg gaccacgtcc gcctgcgcca caccgcgcg taccggctcg     53040
ccgccgcgca cgtgacgcgg gccctgctgg tgcaggcgta cgtgaccgtc gccatgtgcg     53100
ccactagcat taaatccgtt tcctgattca cgcccacgct cgcgtcgttt ttaaaaccgc     53160
gatgggggga cgggggcca ttcgcacgcg ccatggcctc gctcgcgcgt gcgatgctcg      53220
ctctgctggc gccctacgcg gcggccatcg ccgcggcgcc gtcgaccacg acggcgctcg     53280
gcacgacgcg caacggggc ggcggcggca acagcagcgc gggcgaactc tcgccctcgc      53340
cgcccccgac cccgcgcccc gcctcgcccg aggcgggcgc ggtctccacg ccccgggccc     53400
```

```
cgccgccctc ggtctcgcgc aggaagcccc cgcggaacaa caaccggacg cgcgtccacg  53460
gcgacaaggc caccgcgcac gggcgcaagc gcatcgtgtg ccgggagcgg ctgttctcgg  53520
cgcgggtggg ggacgcggtc agcttcgggt gcgccgtctt cccgcgcgcc ggggagacct  53580
tcgaggtccg cttctaccgc cgcgggcgct tccgctcgcc cgacgccgac cccgagtact  53640
ttgacgagcc cccgcggtcg gagctcccgc gggagcggct cctcttcagc tccgccaacg  53700
cctccctcgc ccacgcggac gcgctcaccc ccgtcgtcga ggacgagggc gggcgcgcga  53760
ccgtcgccaa cgtctcgggc gaggtgtccg tgcgcgtggc cgcggcggac gccgagaccg  53820
agggcgtcta cacgtggcgc gtgctgtccg ccaacggcac cgaggtccgg agcgccaacg  53880
tctcgctcct cctgtacagc cagcccgagt tcggcctgag cgcgccaccc gtcctcttcg  53940
gtgagccctt ccgggcggtg tgcgtcgtcc gcgactacta cccgcggcgc agcgtgcgcc  54000
tgcgctggtt cgcggacgag cacccggtgg acgccgcctt cgtgaccaac agcaccgtgg  54060
ccgacgagct cgggcgccgc acgcgcgtct ccgtggtgaa cgtgacgcgc gcggacgtcc  54120
cgggcctcgc ggccgcggac gacgcggacg cgctcgcgcc gagcctgcgc tgcgaggccg  54180
tgtggtaccg cgacagcgtg gcctcgcagc gcttctccga ggccctgcgc ccccacgtct  54240 accaccggc ggcagtctcg gtgcgcttcg tcgagggctt cgccgtctgc gacggcctct  54300
gcgtgccccc ggaggcgcgc ctcgcctggt ccgaccacgc cgccgacacc gtctaccacc  54360
tcggcgcctg cgcggagcac cccggcctgc tcaacgtgcg gagcgcccgc ccgctgtcgg  54420
acctcgacgg gcccgtcgac tacacctgcc ggctcgaggg cctgccctcg cagctgcccg  54480
tcttcgagga cacgcagcgc tacgacgcct ccccgcgtc cgtgagctgg cccgtcgtga  54540
gcagcatgat cgtcgtcatc gccggcatcg ggatcctggc catcgtgctg gtcatcatgg  54600
cgacgtgcgt ctactaccgc cgggcggggc cgtgacgccc cgcgcgttcc cccccacgt  54660 cgaatcaata aacgacagcg agtccgaccc gagccctcgc gtcttgtgtg tgtttgcgcg  54720
cgccctcccc caccctctcc cacccacact ctctcccgcc ccaccacacc ccgcaataaa  54780
ccacacgaga cggcggcgtg tacagcgcga ccgggcaatc tttattggtc gtcggggggcg  54840 ggcgggaagg gagcgggggcg cggcatcctc atcgctggga catcatctgc gagacgaaga  54900
tgtcggcgcc gcgctggcag gccacggcgcg ccgagctggc gtcgatggtg ccggcggaga  54960
cgtccgccgg ggccgagacc gaggcctgga cgggcggctg gggggccgag gcgggcgcgg  55020
ccggggcggc ggcctgaacg ggggcggccg cggcggctgc cgctgctgga gccggagcgg  55080
gggcggccgc ggcggcggcg ggcacggcca ccggctgggc ctgcaccacc accggctgct  55140
gcgggaccac ctgggcgggg acgtgcgcga cggggccgc caggccctgg aggcccggca  55200
ggcccgggag cgccggcacg gcgtgcgcca cgggcgaggg gggcggcgcg tgcagccccg  55260 gctgggggc gtacatcggc gggtacagcg ccccggctgc gtggtgcggg tgcgggtgtc  55320
ccacgacggc cccgggtggc agcagctgct cggcggcgc cgcggcgcg tagtacggcg  55380 tcgggtagcg gagctgctgg gcgcgcaggt ggctgatctc gcgctggagc gacgagacca  55440
cggcggcgag gtcgctcgcg gggggcggcg cctccccggg gtagtacgcg ttgtcctggg  55500
cgtagtcgtc gtagcggcgc ttcctggcgg ggggccgggg ctcggcgag ggcgagcggc  55560 ggtggcggcg gtccatggcg gccgagacga tggcgccgag ctgggactcc aggctgggcg  55620
ccgggcgctg gttgaccacc agctggttgt actgcgccgc gggcacgaag atgtagtcgc  55680
cgggcgctgc gctcggcggg gctgccatgg ccgcactggg cccggggcgcc ggggaggccc  55740
```

```
cgcttttagg cagaagcccc gcccacatcg tcgcctgcag gtaggtgtgt ccgcgcacgc    55800
cggcctcgcg gcggcgcgcc gcgaccagct cccagcggtc gcgcagcagc atgttgttca    55860
cggccgtcga gagcagcgcg cgcgtgagcg cctcctcgct catgtgccac acgcgctcgc    55920
ggtccggcga ctcggcggcg cgcgccagca gctcggagcg cgcccgcgcc gagagctgcc    55980
ggaacggcgc cacggcggcc tcgggcgagg cgtcgtacac cacgatggtg cccacgcgcc    56040
gcccgatcac gcagagcgcc acgtgcgcaa agagcgtctc gtcggggggcc tcgccgggcg    56100
ccaggcgccg cgaggacagg gacgccgagg gcaggtagtt gctcagcagg tacagcagcc    56160
gctcctcgtc cgagagccgc atgtcccga agaagtccgg gcccacggcg cgggcgagca    56220
cggcccccag ctgcgggcag ttgacgacgc cgaggaagaa ggggccgcgg tcgtcgtcga    56280
ccacggccag cacggcgccg atgtcgcagc gcggcggtg gtcgatgttg atgggcagcg    56340
ggcccgccgg gggcagcgcg gcggccacga tctcgcgcgt cagcgcgagc tccccgccgt    56400
ccctatcgta cagggccagg tagcggaca cgtacacggg ccccatggcg gcggcggcgc    56460
gcgcggagac tgcgggctca ggcggcggcg aactgcggga tatagcccag gcagagaaag    56520
tacaggaggt cgtagtcgct ggagacgcca aactgcccga ggcgcttgtc cgccgcgttg    56580
cgcaggtgcg gctgctgcag cagcaggccc agccctcct cgtactgcac ggccacggcg    56640
tcgtgcgccg cgatgacctc gttgacgggg gccgtcacgc gctggcggtt ctgcagctcc    56700
agcgccacca ggcgcaccag gttgagctgg tggcgctgca cgcgcgcgcg gatcgagtgc    56760
gcgtccagcg ccagcgcggc cagcccgggg aagagctgcg tgagctccgt gcgctcgtcc    56820
gcgcggtagg ccacgacgac gtagtgggcc agcaggaagc gcaggttgcc gtcgccgctg    56880
cgcgaggcgg gcgcgtcccc gctggcgccg cgcggcggcg gcgcgttggg cacgagcgcg    56940
ccgagctgga agttgttgcg caggcggtcc ccgtacacgt tgccgttgtg cagcaggcgc    57000
cgcagcagca gcaggcccgt gatggtgttc accgtggcgc gcagcagcgg cgcgtcctcg    57060
ccgaggaaga ggttctggcc gcggcccagg aaggcggccg cggcgcggtt gacctcgtcc    57120
acgaagcccg cgccgtcgac ctcgttggcg ccgacgttcg cgccggggac cacgcgcagg    57180
cgcgccagcg cggcgagcac gctgtggccc tccagcgcgt agcgcccgtg gagctgctcg    57240
cgcggcacgc gcgcgtagtt gtagcggtac gagatgcgcc cgccctcggc cagcgcctgg    57300
ctcagcgcgt ccaggtactc ggggacccgc tccagcaggt ccgcgatgcc cagcggggcg    57360
gcggcgcccg cggcgccggg cccctgccgc gcgcggtgca ccaggtgcag gcacagcgcg    57420
gcgctctcga gcgccgagta gtgccggttg cccacgtaca gacgcccgca ggcctgcagc    57480
gccgtggtcg tcacgcccat gaaggtgcgc gacatgcggc cgtcgcgcga gtcgatggcg    57540
cgcgagacct gcgggcgctc cgcgacgagc gtggcctgga gcgtggcgta ccacgtgccg    57600
aagagcacgc cggaggcggc gccgcgcgcg gcgtacacca tggccaggaa gtccagcgag    57660
aggttggcgt cgtaggcgag cgccacgtcg ttcttggcga tctgcacctc gcggccctcg    57720
tccgcggccc cggtcgcctc gggcgcctcc tcggcggcgc gcgccgcgtc cgcctcctcg    57780
gcggcgcgcg ccgtctcctc gagcaccacg agcgcttcgg ccacgcgctc cacctgccgc    57840
tccagcggcc gcagctgctc gtccacctcg gcctcgaggc gcgcgcccgc ggccatggcg    57900
ttgtccagcg ccgcggcggc gcgcgcggcg gcgcgcgttcg cgtgcgccag cgcgaggcgc    57960
ggcgtcgagg cctcgccgaa gcccgggcgg gcccagaagc ccacggggaa cggggcgcg    58020
atgaagtggc gcgcgctgcc cgggatcgca gcggcctcga aggcgaacca cgcgcggtcc    58080
atggcgcggg gggacatggg ccgcgcgccg ccgcgcgccg ccttatcatc cccgctcccc    58140
```

```
gccgccgccc ggccccacgc gcgccgcgat cgcgatcacc gccgcggccc ggcgacgtac   58200
tcggcgaggc cgcgcacggt cgcggccatc gcgctcgcgt tgccgcgcgt ctgggtgcag   58260
ggcaggcgcg tcacgtcgag cacgcgcatg ctccgctggg ccacaaacac cagcaggggc   58320
acgagcgtga tctcctcgcc gcccgggggc acggcggcgg cgaggaggcg cgccgagtcg   58380
cgcagctggc acagccctc gtgccgctgc ccgcgcttgc tgggcgtgtt gaggttccgg    58440
gggaagcggc acgtcttgag ctcgatgacg aagcacaggt gcggcccac ccccagccgc    58500 accacgcaca cgcagtcggg gcggcgcacc ccgaggttga cttcaaaggc cagggtcaag   58560
gacgccttct taagcgtctc gcggggaagc ccgaagagac tctcgccgta cgcggacggg   58620
tcgcggcgca ggcgttcgta gaagcggttg tggcagcgga tccccgcccg gaagcgcgcc   58680
gggatgcgca tcctccggat ctacctcgac ggcgcctacg gcaccggcaa gagcaccacg   58740
gcccgggtga tggcgctcgg cggggcgctg tacgtgcccg agccgatggc gtactggcgc   58800
actctgttcg acacggacac ggtggccggt atttacgatg cgcagacccg gaagcagaac   58860
ggcagcctga gcgaggagga cgcggccctc gtcacggcgc agcaccaggc cgccttcgcg   58920
acgccgtacc tgctgctgca cacgcgcctg gtcccgctct tcgggcccgc ggtcgagggc   58980
ccgcccgaga tgacggtcgt cttgaccgc cacccggtgg ccgcgacggt gtgcttcccg    59040
ctggcgcgct tcatcgtcgg ggacatcagc gcggcggcct tcgtgggcct ggcggccacg   59100
ctgcccgggg agccccccgg cggcaacctg gtggtggcct cgctggaccc ggacgagcac   59160
ctgcggcgcc tgcgcgcccg cgcgcgcgcc ggggagcacg tggacgcgcg cctgctcacg   59220
gccctgcgca acgtctacgc catgctggtc aacacgtcgc gctacctgag ctcggggcgc   59280
cgctggcgcg acgactgggg gcgcgcgccg cgcttcgacc agaccacgcg cgactgcctc   59340
gcgctcaacg agctctgccg cccgcgcgac gaccccgagc tccaggacac cctcttcggc   59400
gcgtacaagg cgcccgagct ctgcgaccgg cgcgggcgcc cgctcgaggt gcacgcgtgg   59460
gcgatggacg cgctcgtggc caagctgctg ccgctgcgcg tctccaccgt cgacctgggg   59520
ccctcgccgc gcgcctgcgc cgcggccgtg gcggcgcagg cgcgcggcat ggaggtgacg   59580
gagtccgcgt acggcgacca catccggcag tgcgtgtgcg ccttcacgtc ggagatgggg   59640
gtgtgaccct cgcccctccc acccgcgccg cggccggatg gagaccgcga cggaggcaac   59700
gacgacggcg tgggaggggg ctcggggcgc gtataaagcc atgtgtatgt catcccaata   59760
aagtttgccg tgcccgtcac catgcccgcg tcgtccgtgc gcctcccgct gcgcctcctg   59820
accctcgcgg gcctcctggc cctcgcgggg gccgccgccc tcgcccgcgg cgcgccgcag   59880
ggtgggccgc cctcgccgca gggggtccc gcgcccaccg cggcgcccgc gcgcgggccc     59940
accctgttcg tcctggacgg cgacggctcc gcgtggttcg tcttccagct cggcgggctg   60000
ggggcgctca acgacacgcg catccgcggg cacctgctcg gccggtacct cgtctcgtac   60060
caggtggtgc cccgcccgt ctccgcgtgg tactttgtgc agcgcccgcg cgagcgcccg     60120
cgcctctcgg ggccgccctc gggcgcggag ctcgtggcct tcgacgcgcc cggcgtccgg   60180
cgcacgtaca ccacggcggc ggtgtggccc gcggaggtgg ccgtcctcgc ggacgcggag   60240
gcgcgctgcc ccgcggccgt cttcaacgtg acgctgggcg aggccttcct cggcctgcgc   60300
gtcgcgctgc gctccttcct gccgctggag gtcatcatct ccgccgagcg gatgcgcatg   60360
atcgcgcccc cggcgctcgg ctcggacctg gagccgccgg gccgcccgc gggcgcttc     60420 cacgtgtaca cgctcggctt cctctccgac ggggccatgc accagacgat gcgcgacgtg   60480
```

```
gccgcctacg tgcacgagag cgacgactac ctcgcccagc tgtcggcggc gcacgcggcc    60540
gccctggccg ccgtggtgca gcccgggccg tactactttt accgcgcggc ggtgcgcctc    60600
ggcgtggccg ccttcgtctt ctccgaggcg gcgcgccgcg accggcgcgc ctcggcgccg    60660
gcgctcctgc gcgtcgagag cgacgcgcgc ctgctctcgc gcctgctcat gcgcgcggcc    60720
ggctgccccg cgggcttcgc cgggctcttc gacgggcgcg ccgagcgcgt cccggtggcg    60780
cccgcggacc agctccgcgc cgcctggacc ttcggcgagg acccggcgcc ccggctggac    60840
ctcgcgcggg cgaccgtcgc cgaggcgtac cgccgctccg tgcggggaa gcccttcgac     60900 cagcaggcgc tcttcttcgc cgtcgccctg ctgctgcgcg ccggcggccc cggcgacgcg    60960
cgcgagaccc tgctccgcac cacggccatg tgcaccgcgg agcgcgccgc cgcggccgcc    61020
gagctcacgc gggccgcgct ctcgccgacg gccgcgtgga acgagcccct cagcctgctc    61080
gacgtcctct cgtcgtgcgc cgtctcgctg cgccgcgacc tcggcgggga cgccacccctg   61140 gccaacctgg gcgccgcggc gcggctcgcg ctggcgcccg ccggggcccc gggcgcggcg    61200
gcggcgacgg acgaggggc gggggaggag gaggaccccg tcgcgcgcgc cgcgcccgag    61260
atccccgccg aggcgctgct cgccctgccc ctgcgcgggg gcgccagctt cgtgttcacg    61320
cgccggcgcc cggactgcgg cccggcgtac acgctcggcg gcgtggacat cgccaacccg    61380
ctcgtgctcg ccctcgtcag caacgacagc gccgcgtgcg actacacgga ccgcatgccc    61440
gagtcccagc acctgccggc gacgacaac ccgtccgtgt gcgtgtactg cgactgcgtg    61500
ttcgtgcgct actcctccgc gggcacgatc ctggagaccg tcctcatcga gtccaaggac    61560
atggaggagc agctcatggc cggcgccaac tccaccatcc ccagcttcaa cccgacgctg    61620
cacggcggcg acgtcaaggc cctgatgctc ttccccaacg gcaccgtggt cgacctgctg    61680
tcgttcacgt cgacgcggct cgcgcccgtg tccccggcct acgtggtggc ctccgtcgtg    61740
ggggcggcca tcaccgtggg gatcctgtac gccctattca agatgctctg cagcttctcc    61800
tccgagggct attctcggtt aataaacgcc aggtcgtgag gccgcgccg ggccgcgaac     61860 ccagactctc tgcgtgcgcg tgttttcct tgtcgggcgc gggagagacg ggggggagac    61920
gggagggggg agagggacgg cacgggcgcc gtccgtcggg gagacggcgg gatgacatca    61980
cgagagtcgg gtggagggga tgcggggagc gccatccacg ggggaaggct gctggatgac    62040
ataactagag ccaggatga ggatccccctt tccccgttc cccgagtata caccactctc     62100
tccccgcaca catttcccac cgggcgccta acgtggattg caccccggtc cgcgctaccc    62160
ggttgtgtgt gagacgggcg gagagccgcc ctcgccccgg tcccccaaa actcctgcgg     62220 atgtgtggtc cgacgaagcc tccgcggatg tgtccgccgt accctcgtcc ccctctctcc    62280
cacagccctc tctcccacag ccctctctcc cacagccctc tctcccacag ccctctctcc    62340
cacagccctc tctcccacag ccagactccc gcctcccccg tccccgatcg ccgaacgcct    62400
tcaagaattt tttacccgct ccgaggaagg ggtctctaag gggtctctaa ggggtctcta    62460 agggtctct aagggtctc taagggtct ctaagggtc tctaagggt ctctaagggg          62520 tctctaaggg gtctctaagg ggtctctaag ggggaaccag agagtaaaga ccggagagta    62580
aagaccagag agtaaagacc agagagtaaa gaccggagag taaagaccag agacacattt    62640
tacaatttcg ttgtacccgg gtttattgaa aactttgttc aagagttaaa gtgtctgccg    62700
cttgccggtg tgccgcgccg aggccgcgat ccggccgccg tggaccgggg gcccgcgggc    62760
ctggattcga cgggacggcg ggtccgagcg acggcggtcc ggcggcgttt cggctcgcgg    62820
tcctcgcggc ggcgacgatc cggcggtccc acgacgatcc tggtccgggg gatccagcgg    62880
```

```
cgacggcggc gctccgggtt gtggcgccgg gctccggctc cccggtcttt tatacccaca   62940
cctcatgaat attcatgaat ggttggtatg tgcgaatttt tcggcgttcg cacttgttgt   63000
atataaaata ttatatccta tatatattag caattggtgc gaacgtgacg tggcccaatc   63060
attttccttg gatttgccca tgtgaccgag tttccaatag ctccgcccag atcgatcgcg   63120
gggccgatat tttgccgata atccatcaat attttcttcg gccgacgcgg gtttcacccg   63180
gccgtcccgc cggggaggcc cgtcccgggg cgcgggactc tcctctccgg acgccgcgcg   63240
gcgtcgagac cgcgccggga cgatggtgtc tgcgcatgcg cggctggggc cgagcgaccg   63300
ggaatcccct ctcatgacca gctccaccca tcgtcacatg cccgctcgct caccccttc   63360 tcccgcgacc ggcgacgatg gggcggccgt ggcccagcca cgacggaggg gcgctcgctc   63420
gcgcgcgcgg gggcggtggg ggttgggttc tcgggcttcg gggcggatgt gtgtgttgtg   63480
cgtcggggga ctgggggcga gcgagcgggg ggtgttgtgg acggggacg atccggggg    63540 gccaccgaga ccgaggcggg cgggcgcgcg cgtgtgtgcg tgtcgcggat agagaacgga   63600
cgggggcgcg gacgtggtgt ttggttaacg gttttttattg aggacgatgg agatgttggc   63660
gcgggtcagg cgcgcccgaa acagctgaaa caggtactgg gccccgcgga gggccgcggg   63720
cgagtcgccg aaggcggtca ggagcgccgc ctcggcgcag acgcggacg tgggccgcag   63780 cgcgcgcccc acgggcgccg tcggccgac gaggccccgg ccggcgtaga gcccgtccag   63840 caccccgcgcc ccggccgcct ccaccagctc gcacgcgtcg gcgtccggcg cgttcgtctc   63900
cgcgtcgctc atcatgaccg ccagctccag gcccgtcgcc gcgtcctccc gggcgtgctt   63960
cgtcgtcggg ggcgaggccc ccgccgggtc cgcgatcgcg ggggcgtgca ccacggcggc   64020
gttcacgagc atccgcatca cctcgccgaa gacggtcgcc tcgcgcagca cgcggttggc   64080
ggcgtgggcc acggcgctcg cggcccgaga ccgccgtgg ccgcccctc ctccccgtc    64140 tcctccgtcg tcgtcgtcgt cgtcgcccgc gcccgcccg gggcgctcgt ccagcctgtc   64200
gagcatgccc tccagcgcgg cgtagcagct cggcaggtgc cagcgggcca ggatgaactg   64260
gtacagcgcg aaccgctgcg cgcccgtgag cgacgtggag cccgtcccga agaaggggtc   64320
cgccgcgacg gcggacacgg cctcgaccac ggcggccgag gcgtcgtccg aggcgcccgc   64380
ggcccgccgc aggatggcgt ccgccccggc cacgaggtcg cagagcatct gcagggacag   64440
gctcccgccg cgcgtcgccc agatgcgccg cgtcgccggg atgtagcgca cctgcacaaa   64500
gtcgctgacc accgtcgcgc gcagcgcgcg ctcggcgtac cggcgcgggc gcacgctcag   64560
cgtgggggcc gcgcgcccgc ccttcaccac cacggccgtg ggccgcgtct cgccgctgag   64620 cgggggggcgc acgccgggga tgccgtcaaa gagcccctcc gtcagcacct gcagcgagct   64680
gggcagctcg gagaggtacg cctgcaccag cgcgaagcag gcctcgttca cggcgtacac   64740
gaagcccgag gagggggtgca cgatggcggg ctcggccagg agctccagga cgcggtcctg   64800
ctggcggtcg tgcacgagcg tcagcgagag cgccgacgcc ggcagcgaga ccatgcactc   64860
gacgaggtag gggtcgtaca cgtccagctc cgcgcggccg cagaggtcca gctccgtcag   64920
cggcagcagc agcccccaggg cgtccacgaa gacgtcgtcg ctcccctgcg ggcggccca   64980 cgcgcggccg aggcgcgcca gctccgtgcg cacgtagttg gcgacgacgc ggttcccggg   65040
cgcgttcccg cgcagcgtga gcccgaactt gccgatctcc cgcgagcgcc ggcgcacgga   65100
cacgatgcag ccccgtgca caaagtacgc gcggtccccg ccgtcggcga cgtagaacag   65160 cacccccctgg tgcacgatcg tgctctggta ctcaaactcc atggcggcgg gcacacgcgg   65220
```

```
cgcggcaaat gggtgagcga ggcggcgcga ccactccttt aaacccgccg ggggcgcct    65280 cccgccgcac acacgcggcg gcgcggggat ggaggacgcg gcggcggacg tggacgcggc    65340
ggcggacgcg aagatgacgg gggagaacga cgcgctgctg agctcggcct ttgtgggcgc    65400
gcgcccgccg cgcccgcgct tcagctcgca cgtggtgagc ctcctggccc tggcgctcgc    65460
gctccggccc gcgtgctgcc tcgtcctggc gctccacggc tcgcgggcca ccctcgcggc    65520
gctcctcacc gcgctggcct tctacgcgcg cgcggccgtc tgcgccgtcc tcgtggcgcg    65580
gaacgtggcc cgggaccgga tgccgctctc gccggcgcag caggcggcgc tgggctcct    65640 ggcggcggcg cggctggcct tcctgtacgt cgccctggac gcgggccgcc actacgcgcc    65700
cgccctcgcc ggggcgctgt acggcgccga ctgcgtctgc gacgcgctcg ccttcctgct    65760
gccgcgcgcg tacgcgcgct ccatcatgca ttaaaaggcg gccgcggcgc gcccgcgcca    65820
ctctcccccc tgctcccccag cgaccgcgca cacgcgcccg cacgcggtcg tcgccacacg    65880
atggagcgcc cggccatcct gccgtcgggg cagatcctgt ccaacatcga ggtgcactcg    65940
caccgcgcgc tgttcgacat cttcaagcgc ttccgctcgg acgacaacaa cctctacggt    66000
gccgagttcg acgcgctgct cggcacctac tgcagcacgc tctcgctcgt gcgcttcctg    66060
gagctcgggc tctcggtggc ctgcgtgtgc accaagttcc cggagctcag ctacgtggcc    66120
gagggcacca tccagtttga ggtgcagcag ccgatgatcg cgcgcgacgg gccgcacccg    66180
gccgaccagc ccgtgcacaa ctacatgatc aagcgcctcg atcgccgctc cctcaacgcc    66240
gccttctcga tcgccgtcga ggccctcggg ctcatctcgg gcgagaacct cgacggcacg    66300
cacatctcgt cggccatgcg gctgcgcgcc atccagcagc tcgcgcgcaa cgtgcaggcg    66360
gtgctggact cgttcgagcg cggcacggcc gaccagatgc tgcgcgtcct gatggagaag    66420
gcgccgcccc tgtcgctgct ggcgcccttc acgctctacg agggcggct cgcggaccgc    66480 gtggcctgcg ccgcgctcgt gtcggagctg aagcgccgcg tgcgcgacga caccttcttc    66540
ctcacgaagc acgagcgcaa caaggacgcg gtcctggacc ggctctcgga cctggtgaac    66600
tgcaccgcgc cctcggtggc cgtcgcgcgc atgacccacg cggacacgca ggggcgcccc    66660
gtcgacgggg tgctggtgac cacggccggc gtgcgccagc ggctcctgca ccacgtgctg    66720
acgctggcgg acacgcacgc ggacgtgccc gtgacctacg gcgagatggt gatcgccaac    66780
accaacctcg tgacgcgcgt ggtgatgggc aaggccgtca gcaacatgga cgacgtggcg    66840
cgctacctgc tcggcggcga gccggccccc gacgacggca agcccgtggg ctcggcgcgc    66900
gtgcgcgccg acctcgtcgt cgtcggcgac cgcctggtgt tcctcgaggc cctcgagaag    66960
cgcgtgtacc aggccacgca ggtgccgtac ccgctggtgg gcaacctgga cgtgaccttc    67020
gtcatgcccc tgggggtctt caagccggcc gccgaccgct acgcgcgcca cgccggcagc    67080
ttcgcgccca cgccgggcct cccggacccg cgcacgcacc cgccccgcgc cgtgcacttc    67140
ttcaacaagg acggcgtgcc ctgccacgtg accttcgagc acgccatggg caccctctgc    67200
cacccctcct tcctggacgt ggacgccacg ctggcggcgc tgcgccagga gcccgcgag    67260 gtgcagtgcg ccttcggcgc ctacgtggcc gacgcgcgcc ccgacgccct cgtcgggctc    67320
atgcagcgct cctcgaggga gtggcccggc atgatgcccg tgcgcccgcg ctgggccgcg    67380
ccggcggccg ccgaccagct gctggcgccc ggcaacgccg acctgcgcct ggagctgcac    67440
ccggcctttg acttcttcgt cgcgcccgag gtggacgtcc ccgggcccctt cgccgtgccc    67500 caggtgatgg gcaggtgcg cgcgatgccg cgcatcatca acggcaacat cccgctggcc    67560 ctgtgcccg tggactttag ggacgcgcgc ggcttcgagc tcagcgtgga ccggcatcgg    67620
```

-continued

```
ctggccccgg ccacggtggc cgcggtgcgc ggcgccttcc gcgacgccaa ctaccccatg    67680
gtgttctaca tcatcgaggc cgtgatccac gggagcgagc gcaccttctg cgcgctcgcg    67740
cggctcgtgg cgcagtgcat ccagagctac tggcgcaaca cgcacaacgc cgccttcgtg    67800
aacaacttct acatggtcat gtacatcaac acctacctgg gcaacgggga gctgcccgag    67860
gactgcgccg ccgtgtacaa ggacctgctg gagcacgtgc acgccctgcg gcgcctcatc    67920
ggcgagttca cgctgcccgg ggacccgctg gcaaccagc cccaggagga gctcaaccac    67980
gcgctggcgg acgccacgct gctgcccccg ctcatctggg actgcgaccc catcctgtac    68040
cgcgacgggc tcgccgagcg cctgccggag ctgcgcgtca acggcgcgca ctttcagcac    68100
atcctgtggg tcgagatggc ccaggtgaac tttcgcaacg tcggcggcgg cctggtgcac    68160
aaccggcccg tgcggaacga gaaccagccc ctgcacccgc accacgacgc cgagtggtcg    68220
gtgctgtcca agatctacta ctacgccgtg gtgcccgcct tctcgcgcgg caactgctgc    68280
accatgggcg tgcgctacga ccgcgtgtac cagctggtgc agacgatggt ggtgcccgag    68340
acggacgagg aggtgggcac ggacgacccc cggcacccgc tgcacccgcg caacctcgtg    68400
cccaactcgc tgaacgtgct cttccacaac gcctgcgtcg ccgtggacgc ggacgccatg    68460
ctgatcctgc aggagacggt gacgaacatg gccgagcgca cgacgcccct cctggcctcg    68520
gtggcgccgg acgcgggcat ggccacggtg gccacgcggg acatgcgcac gcacgacggc    68580
tcgctgcacc acggcctgct catgatggcc taccagccca cgacgccac gctgctcgag    68640 ggggccttct tctacccggc gcccgtgaac gcgctctttg cctgcgccga ccacctcggc    68700
gccatgcgcg acgtgggcgc cgaggtgcgc gccgccgccc agcacgtgcc ctgcgtgccc    68760
cactttctcg gggccaacta ctacgccacg gtgcgccagc ccgtggccca gcacgcggcg    68820
cagagccgcg ccgacgagaa cacgctctcg tacgcgctca tggcgggcta cttcaagatg    68880
agccccgtgg ccttcaccca ccagctgcgg cgccagctgc accccggctt cgccctgacg    68940
gtggtgcgcc aggaccgctt cgccacggag aacgtgctct ttgcggagaa ggccagcgag    69000
tcgtacttta tgggccagat gcaggtggcg cgcaccgaga gcggcggcgg gctgcacctg    69060
cagctcacgc agccccgcgc caacgtgaac ctggcgtgg gcttcacggc cgcgtacgcg    69120
gcggccgcgc tgcgcgcccc cgtgacggac atgggcaacc tgccgcagaa cctcttcgcc    69180
acgcgcggcg ccccgcccat gctggacgcg gacgcggacg actacctgcg ccgcacggtc    69240
aacgccggca accgcctggc gcccgtgccc gtcttcggcc agatgctgcc ccaggtgccc    69300
gcgggcctgg cccgcgggca gcagtcggtg tgcgagttca tcgccacgcc cgtctcggtc    69360
gacctggcct actttcggcg cgcgtgcaac ccgcgcgggc gcgccgccgg cgaggtgcac    69420
ggcgaggagg ggctgatgtt cgaccacagc cacgcggacc ccgcgcaccc ccaccgcgcc    69480
accgccaacc cctgggcctc gcagcggcac tcgtacgcgg accggctcta caacggccag    69540
tacaacatga gcgcccggc ctacagcccc tgcttcaagt tcttcacgcc cgccgaggcg    69600
gtcgccaaga gccgggggct ggcgcggctc atcgccgaca cgggcgccgc cgcctcgccg    69660
acgagcaacg gcgagtacca gttcaagcgg cccgtgggcg ccggcgagct cgtcgaggac    69720
ccgtgcgcgc tcttccagga ggcgtacccg ccgctgtgcg ccagcgactc ggcgctgctg    69780
cggacgcccc tcggggccga ggagcacttt gcgcagtacc tcatccgcga cgagtccccg    69840
ctgaagggct gcttccagca cgcgagcgcc tgagccgcag gaccgcggga ccgcggacc    69900 gtcgtctccg ccctgccccc ctcacccga ctctgtcacc cgcccccacc ctcccgcgcg    69960
```

```
gcgcgcgccg cgcgtgtata taaactgtgt acacggcacc cgcccgcgtc agtgtcttct    70020
ttcgcccgcg ccgccatgga ggtggacatt gcgctgccta cgctgtcccc cggggatctg    70080
tcggccctgc agaggtgcga gggccgcgtg gtgtttctgg agacgctgcg gcggcacgcg    70140
acgctgcgcg aggtcgcgct gccctgcggc ggcgacgtgc tcgcggccat ggccgcgtac    70200
aggcggcgct tcgcggccgt catcacgcgc gtgacgccgc accgcatgct ggccacgccg    70260
ctcggcgtcg gcggccgcgg gcagtcgctg gtgctgcaga acacgggccc cttcgacctg    70320
accaacgggg accacgtgtg cctcgtcccg ccgctgctcg gcgacgagtg cctgcggctc    70380
acgtcggcca acctggagct gcgcttcccc atgacgctgc cgctcgccca ggcccgcgag    70440
ctgacggcgc gggtggtggc gcgcgccgcc gagacgctgc gcggcgggc gcccgcgcgg    70500 ggcgccgacg tggtcttcag caacggccgg cgctaccagc tgcccccgcc gcaccgcgac    70560
aacgccgagg cggccacgcg ctcgctggtg ctgaacatga tcttcctgct caacgagggc    70620
gccgtgatcc tgctgtcgct catcccgaac ctgctgacgc tgggggcgca ggacggctac    70680
gccaacgccg tgatccagct gggcagcgcc acgcgcgagc tcggccagct ggtgcggcag    70740
cccccgccgc cgctgccgca agaccacgcg cggcgcttct gcgtgttcga ggcgctggag    70800
gcctggatcg cctcggcctc gcggctgggc gacacgctcg gcacgcggcc cgtggcgcgc    70860
gtgtgcatct tcgacggccc cccgaccgtc cccccggcg agaaggccgc ggtggtggag    70920
gtgtgacgac gcggcgcccg cggaggatga ccgcccgtcc ccctcgcccc ccctccctcg    70980
caaataaacc cgtgaaggaa aaaaacaaga gaaacgagtc gtgcgtgtct ggcgtttatt    71040
ttccgggccg gggtggcgag gcggggcgag ggaggagggg gcgcggggtg gccccgggag    71100 agggggggcgc gcgtcctccc ctcaggcaaa cagcccgtcg gcagcgtgc tcaggtgcac    71160 ggccatgacg agggccacgg cgaggtcgtc ggcgcagccg ccgcgcttgc cggtgaagac    71220
gcggtgctcg ccggccccg aggccgtctc cacgaggttc ccgagctggg cgttcaggta    71280
ctcgacgggg tcgcgcgcg cgcccacggt cacggacacg agctcctgcg aggccatgac    71340
ggcgcccgag ttgaactgct tgacgaaaaa gtcgaaggcg ggggtctttt gcttctgcag    71400
caggaagaag gggtagcgca cggcgcccgc gcccgcggcg ccgtggtggt agaagaccac    71460
ggccgggtcg gcgacgacgc gcgcggcgcg cagctccgcg agctcgcggc gcatggcgcc    71520
cacgatggcc acgccgagt cctggctgct gttgccctcg acggccacgc gcaccgccga    71580
gaaggcgccg tcgtgcagcg ccagcacgcg cgccaggcag cgcacgacgc agcgcgcgat    71640
ctcgtcggcg gaggcgcccg tgagcgcgcg caggaaaaag tgctccaggc cgagcacgat    71700
ccagctgcgc cggtagctgc ccacgacggc cacgccggtg ccggaggcgc gcgcgttggc    71760
cgtgaaggcc gggtccacgt acacgtgcag cgtgccggcc agcaggcggc ggttggccac    71820
cgaggagggg cggtagagca ggaagcgctc gccggcggcg cgcgtgagga cgggcgcctc    71880
gcgcgcggcc acggcgccgc cgaggatctc ctgcatgaag gagtccggga gcagccgctc    71940
ggccgtggtg cgcgtggcgg cgtccatggt gatgaagacg ggcttgttga gcacgtagca    72000
cgagcaggcg gtggcgtcgg tgtgcgccac cacgcggcgc atgtgctcgt cgcagacgta    72060
cgtgaccacg ttgagcatgt cggtgccgcg gaggttggtg aggaagctgg tgctggccct    72120
gccggtgttg gtggaggaga cgaagatgat cttgcagctg gcctggttca tgaagccgag    72180
gatggtctgc acggcatcgg ggcgtataaa gttggcctcg tcgacaaaga gcaggttaaa    72240
gtcctgtccg cggatcccct gtaacgacac gcggggagag agagggggg acggtgagcg    72300 gcgccgcgat ggacgcccac atcgccaacg agaccaagca gcagatgacg cgcttcgcgc    72360
```

```
ccgcgctcgt gcacgtcatc gtcccggacc ccctcctggc gcgcgcgggc gtggacccgc   72420
tcgcgcccct cgccgcccac gcgcagacgc gctaccacgg ctcgggcgtc tgcgagccgt   72480
gggtctccgt gttcgcgggc cacgtgcaga cgggcgccgt cgagagcgtg ctgacgctgc   72540
cgccgctgca gcgcccgcgc ggccccgggg gctgttcgt ctcgctgccc ctggcgctcg   72600
gcgcccactt tgacggcttc acgacggcgg cgctgcgcgt gggcgcgcgc gagctggtct   72660
tcacctacga cgagctcctg ccggcccgca cgcgctacaa cgtggacggc gagcgcctgg   72720
agcgcctgtg ccgccagttc gccaactacg cgcgcgcgcg gcgcgtggcc ccggcggtcg   72780
cggccgcggg gggccacatc gacgcgctgc tgccccccgc ggcggccacc atcgacggcg   72840
aggcgcagct gacgcgcggg ggcttcgacg acccggcggc gccgcacgcg cgggacgccg   72900
accgcgagat cctgtcgctg gtgcgccgcg cggccgagct cgtcgcggcg cggcacccgg   72960
tgcgcagcca cgtggcgagc gggctgatgc agggcgccct cgcgcggcgc ggcggcggag   73020
gagacggcgc gggggcgctc gaggcggcgg cgacggtgcc ggcgcccgcg gcgcgcgagg   73080
acgcgaacgg cggcggcgcc gcctggcgcg acgagctcct gctcacgccc caggaccccc   73140
ggccgctgac ggcgctcgac tggctggacg cgggctacgc cgcgctcgcg ggcggcgacg   73200
cgcccgcgca cgtgtggcgc cggcggcccg tgtccctggt ggcgcgccgc cactaccaga   73260
ccggcgagac gttcgtcgtc gtcgcctacg agcactccac cgcctggggc ggccggcgcg   73320
ggccccgggg cgagcccctg gcgcgcgtgc tcgccgagga gtgcgagcgg cacggcgtcg   73380 agcaccccgcg cgccctgccc gcggaggcgc ggcgggagct ggtgcggcgg cacgccgagc   73440
tggccgtgcc gctgggggac gaggagccgc cgctgccggt ctttgacgcc accgcggagc   73500
tggtgctgct ggagcgcttc cgcaacgcct gcgtgcgcgc gctgctggcc ggcgtccgcg   73560
agtccgtgcg ccgcgagccg cgcatgcgcc agatcatcga gttcgcgatc cgcccgcgcg   73620
accgcgaggc cgtcctcgac gtggccgggc gcgccccggc gctgctggac gcgttcgcgc   73680
ggcgcctcga gcacacgccg gcgcgggaga tggtcgactc gggcctgatg acggccgcgg   73740
cggcgcacct cgccgcgcgc gccaccgccg gctacgtgac cttcgagagc ggcccgctgc   73800
tgggcggcgt tttcctcttc gactactaca gcgccggcgg ggaggttata agggtgacgc   73860
gggccccgct ggccgtggca gtggagccgc cgacgcgcgg gcagttcgcg tgtcgcttcc   73920
gaggcgcgtc gcatcgctgt ctcccgggcg agagctacgc gtacctctgc gtcggcgtgt   73980
cgcgggacct gcgcgcgctg gtggtgctgc ccggcggctt cggcttcttc gcgaccctcc   74040
ggctggagtg gccccgccgcg ctggtggacc ccgtgctcga gcgcctgtgc cgccgcgtgt   74100 agcgggggcga ggggggcggg cgcgcgccat ggaggtggcc gcggccctga cggaggactt   74160
tgccgcctgg cggctgctgc gctccgactc gcgcgtcaag gtctacgccg ccctcgccgt   74220
cgtgggcgcg cgcctggccg ccgtggcgcc cggcgccgcg accgtcgccg cgcgcgtcta   74280
cctgacgcgc ccgcgggcgc tgcgcctggc gcagggccgc ttccacgtcg tggtcctgct   74340
caacgacgcc gcctacgcgc tggtggcggc cgtgaccacg accacgctcc gcgggagcgg   74400
cggcgagctc gtgcgcctga cgctgggcga cgcgagcctc gaggcgctgc cgccgacct   74460 gcccgtcgcc gagcccgtgc ccgccgcgcc ggcgggccgc ctggacctgg acgccgccga   74520
gcccgtggcc gccggcgcgg cgggccgccg cgactgcgtg gtcctggccc ccggcgcgtg   74580
gtgggcgcgc ggccgcgtct acttcctgca gatggaccgg aggctgctgg cgctgtgccc   74640
cgcgggctgg cgcgcgcgcc acctcggcgc cgtgctcgcc gggctgctga gccccgcga   74700
```

```
cgacgacggc ggcagctgct gccgcgagtg ccgcgtggag cacgtggacg ccctcaacgc   74760
gacgccgcac cccgacgggg ccgccgcgcc gtgcctgtgc gccgcgccgt gcctgtggcg   74820
ccaggcggac aagcgggagc tgcgcgcgag cgactcgggc ctcttccgcg tgctgttcct   74880
ggacgccgtg cggttcgtgc gcatgctccc ccgccgcaag atcgtcgacg tcgcctccga   74940
gctcatcggc gggctggacg cccgcgggcg ccacgtggtg gtcaacgacg ccggctggcg   75000
cctggtggcc ctggacccgg acgcgagccg cgcgctcgtg tgcgggtgcc cgctgctgcg   75060
cgcgctctgc gaccccccg cccgcgccat ccccgagcta ataaacgatt attgaaatga    75120
aaaaaatggg tacttgcgtt tgtattgtgg ctggaggcga acacgatggt gctgcgcgcg   75180
ccgtcgggga aggtgacggt gatgttctcg cccttgacgt ggtccacgcg cgcgtcgcgg   75240
caccagcggc gcaggcgcgc gtggatctcc tcgaacacgg gctccgtggc cttgcggatg   75300
tgggccgtgt agccgacgcg gatgccgcgg aaggtggcca gcgcgagggc gatgagcggg   75360
accaggaacc aggtcttgcc gtggcgccgc ggcacgagga agaccgtgac gcgctggcga   75420
aagtggcgca ccgcgtcctc ggagaagagc ggcgtgtcga aggccgccag caggtaggcg   75480
gtggcgcgct cggcgtggtc cccgagcagc accgtggcca gaaagtacac cgcgtgcatg   75540
aggatcatct tctggaagag ctccagcgtg ccgcgcccgc cgccgccttt gccctcgccc   75600
ccgcctccgc ggccgcgccc gcctccatcg tggccctcct cggcggcgtc ctccggcgcg   75660 gggccggggcg cgcccttcgc gccgcccggg ccctctcgt ccttctcctc ttccccccca   75720
tcctcctcgt cgccgtcgtc gtccccgggc cccgccgccg ccgccgtccc gagggcggcc   75780
gtcgcggcgt cgcggaagga gcgccgcgac aggagcgcga agcggttgac gaagcgccgg   75840
agctggcgga aggccccgga cgtccgcatg gcgtccaccg ccgccatggc gctcgtgtac   75900
gcgttgcggt ggaaggccag gcgctcgccg tcgtaggcgg cgaagtcgag cgcctcggcc   75960
gcgcgcgcga gcgccgggtc cacggcggcg cggccgcgcg cgcccccgaa gagcgcggcg   76020
cgcgcgagcc cggcgaagat ccgcgcgctc tcgcagcagt tgtgcagcgt gccgaccgcc   76080
gggaccaccg tctggtggcg ctgtggggcg gcgatggcaa agttgaaaaa gcgggcctcc   76140
tcggcgcagt cgcgctcact ggcctcgcgc ttgcgcttga ggtccgcgta gtagcgccgc   76200
gtcgcgtcgc ccaggccgaa catgctcgcc tcggaccgcc gggagcgccg cgtgcgcctc   76260
gaggaggcct ttcggcgcga gagcgtcttc aaggcgcgca ccgtcgagct tctgcgcggg   76320
cgcgccgaca agaaaaaccc cgagttcgtc cgggcctttta tggcggccaa acaggcccgg   76380
cgggatgtag agcgccacct gcggctggcc gcccgggtgg agtctgtgga acaaaaagcg   76440
cgcgcgctgc aggcccgcgt ggaagcccag gcggccgtcc gcggggtcct ggacaggcac   76500
cggcggttca cgcgggcgga ctttgcggag gcgctcgacg ccgcggagga cgcgctcgcg   76560
gccggcgagg accggctcga cgacgcggcc gcgctcgacg aggactgggc cggcggcggg   76620
gcgcccgacg aggacgaggg ggaggaggcg gacgaggccc tgctgaccca atggctgctg   76680
gaggaggcgg aggaggcgtg agccgggtcg cgctggcgcg gccgcccatc caccgcggca   76740
cgtccgcgcc gggcggcgcc atcgccgccg ccggcggcga cggggacggg gacgaggcct   76800
cccggctcct gggccgcgcg cagccgcgcg aggcccccta cctgatcccg cgcccggacg   76860
gggacctcgc cgtgccggac gacctgcagt acgcgaccct cgacctcacg ggcgaccccg   76920
tggccgtcgg ggccggatcg tacgcagcgc tgctcgtgta cggctcggtg gccgtgaaga   76980
cgctccgcgc cggcttcggc cacgaggccg tcatgacgct gctggccgcg gaggaggcgc   77040
gctccgccgg cgtccgcgcg gtggtgcgcc tgatgggact ctcggcgccg ctgcgccagc   77100
```

```
tcatgttccc ggcctacgag atggacatgg acgcgtaccg ccgctcgctc acggcgcgcc    77160
cggggcacgt ggtgcacgcc ctggggcgcg tcttcaccga gctcggccgc gcgctcgtgt    77220
tcctcaacgg ccgcgggctc agccacctgg acgtcaaggg cggcaacatc tttgtgcgca    77280
cgtgcggcaa catggtcgtg acggccgtca tcggggactt tagcctcatg gccctcaact    77340
cgcgcagcgc gctcgcggac ccgcgcttcc gcctcgcgcg ccgcaaggcg ctgaagatca    77400
cgtcgctggc gcggagcccg ccgacggggcg tcctcctggg gcatgcgcgc gaccggccca   77460
cgcgggtgct gatggacttt attaacgggc gcccgccgcc gcgggcccc ctgccgtacg     77520
aggtgggcct ggcgatcgac ctgtgcgcgc tgggccacgt gctgctggac gtggcgctcg    77580
gcctgcgccc gcagcgcggc caggcgctga cgcgcgagta cgccgtggag gtgctcgcgc    77640
gccgctgcgt gctcttcgcg gccctgctcc cgccgggcag cggcccctcc gccgaggccc    77700
tcgccgggga catcctcgag gaggagctgg ccgccggctt ccgcgagggc gtggccagct    77760
cgcgcccccgg caaccagccc ccgcgcacgg tggcccccgct gctcgagctc gtggcccggt   77820
tctgcggcga ggatggcggc gctcgttttg ccgaactcgc tgcctgagga gctggccgcg    77880
cgcaccttcc tgcggttcct gcgcggggcg ccgcgcccg cggccggcgg cgcggcgccg     77940
ctggcgtacc gcctggcgta cgtgcacgac ctgctcgtcg agctggcgcg ccacggcctc    78000
gccgcccccg acgcggccgc ggcggccttt ggcggcgcgc gcccgccgcc cgcgcccgcg    78060
ggcgtccccg ccgcggcggc gcgcgccgcc atcctgacgg tggaggcggc cacgcgcgcg    78120
cagagcgaga gcgacctgtg gacgctgctg cgccgcgggc tggccacggc ctcgaccgtg    78180
cgctggggggg cggacggccc gcgcttcccg ccgacgtggt gcgaggccag cacggcgcgc    78240
tgcggcacgc ccgacaacgc ggcgctcatc tttggccgcg tcaacgagag cgtggcccgc    78300
gccgccgtcg cggccctgta cgccgaggcg cccacgccgg acctgccccgg ggcgatcgcg    78360
ggcggcggcg acgatggcgg cggggacggg gcgaaggagg agatgttcac cttcgacgag   78420
acgggcgcgc cccgccggg ccacgacctc ttctcgtgcg ggctgctgct ggacccgcgc     78480
accggcatgg tcggggcctc gctgacctg ctggtgtgcg atcgcgacgc gatcgggcgc     78540
ctggcgccgc accgcacgca gacggagatg cgcttcttcg agatcaagtg ccgcgccaag    78600
tacctgttct cggcggacga cgcgagcccc acggcgcgcg cgtacgcgcg cctgctcgag    78660
cgccccgacg cggacacgct gcgcgggttc ctgtactcca tcgcccggcc gggcgtggag    78720
ttcttcgagg gcgccccggg gcccggcgag gcgctggcga cggcagaccc cgcctggcga    78780
cgcgggggcg ccgaggacgc cccgccgacg cgccggaggt gtggcgcctt cgacgggcgc    78840
cacgtcgccg cgaacgcgca cgcccagtcg gaggtctggc tatttagcga cccggtggac    78900
ggccgtcagg acattgtgcc ctgggcctcg ggcgagcgcg cgctgagggt gcccgtgttc    78960
gcgaacccgc gccacgccaa ctttcggcag atcctggtgc agagctacgt ggtcgccggc    79020
gtcttccccg accgccccgc gcgccccac ctggccacct tcttcggccg tcgccgcgc     79080
ccctgcgagc agaaccggac gctcgacctg gcctcgctgt gcgacgtgcc gccgcctgc    79140
gccgtgcccg tgctgctgat cgtcacgccc gtctccgtgt gcgaggaggc gttcgaggac    79200
ctgcggggcgc gcgccgagga ggcctttcgc gtcaccgcgt cgcggacatg ggacagtgct    79260
gctgccgatt ctccagcaac cgcgtcgtga cgagctccgg cgaggtgctg accttcgacg    79320
cggacgcgtt cgaggacttt gagctcgagc ccatggtcgg cgagcccggc cccgtgcgcc    79380
ccaaggcccc gtgccgcgtg tcgcgcggga acctccgcga agcctcgcgg gcgtactgac    79440
```

```
tgcaataaac ccgtttgtca tactatcgca tcgttcccgt ctggtgtctg ggggagagga    79500
tgggggagag gatggggag aggatgggg agaggatggg ggagaggatg ggggagagga     79560
tgggggagag gatggggag aggatgggg agaggatggg ggaagagagc cgtggggtgg     79620
ggcgagatgg aatggcacac gggccgcaaa gtgggacgat ggggacgggc ctcaacgcgg    79680
gacgagggcg gcggggcggg accggggaca agggacaagg gcggcgagag acggacacga    79740
gaggaccatg tgccgatcgaa acagaacgtt tattcaaagc cgaggttctc gtacacgacc   79800
tcgtcgccgt cgtcaaactc gtcgtcgccc gacccggggg ccagcaggta ctcgtcgttg    79860
ccccggccgt gcaggcgctt ctgcaggtac cgccgggccg tcgtccgcgc cttgtccacg    79920
ttggcgtaga accggctgcc ccgggcgcgg tgggcgatgc aggcgcggac caggcgcacg    79980
acgatcatcg ccagggcgat cagcgacagg accgccagga cggcgcgcgt cccgatgacg    80040
acgccgtgcg tctccccgag ggcctcgctg aacttggcga agtagcggtg ggcggacacg    80100
ccgaaggccg cgctggccac gagcacgcag aaggccggcg tggggagcac ctgcacgtag    80160
ccggacacga cgacctcgac gaacaccatc agcgccagcc ccagcagcgt gaacacggcc    80220
agggcggcct ccgccgtctt ccagaggctg atgtggaagc tgttggccag gagcacgccg    80280
agcatcagcc cgaccacggc cgcgcccagg ccgaccgcgc cgaggacgac gttcgtcacg    80340
acggcgcgcg cgtgcaccgc cacgcggcgc agcgggggc tggccgccag ggcggcgcgc     80400
acgtcacccg tgcccttgca ggcgtggcac gccccaaaga gggcgagaaa cacaaaatgg    80460
gtgatgtagg cggcggcggc cagacccgcc tgcttgtggg ccatcagcag caccacggcc    80520
tggagggtcc aggcgcagag cgcgccgagc atcagggtcc ccggggcggc caccgtcgac    80580
gccgcgtaga gcaccacgct gggctggaac gccagccggc cggcctcgcg ccgcagcacc    80640
acggcccccg cgaccgcgta cagggcgtgc gccagcagca cggtggccgt gaagccgaag    80700
aagctggtca cggtgggcgt ttccagaaac agggcggggg ccacgagcgg ctggcgcgtc    80760
cacacgccgc cggggcgtc gttgagcgtg tcgtagtcgg ccacggtcgc gtaaaagcac     80820
gggaacccca tttccgggag cgaggcgaag ataagggtga ggaccagcgt cagggcggcc    80880
agggcgaacc cgcagacctc tatcagccag gagcgccagc tcacggcctc ggcgttgcgc    80940
ggcccgcaca tggcggcgcc cgcccgcgtc cgccgcggcg gggccgagga ggacggcggg    81000
gcgttcgcct cgagcgtgtc gctcgcgcgg atgctatacg gttgcgacct cccgccgtg    81060 gtgcgcagcc gctggccggg cgtctccctg gacctgcagc gcgacgcgcc cgtcgagctt    81120
ccgtccccgc acgataccgc ctgccgcgc gtcctcgtgg cgcgcgctcc gatgggctcg     81180
ggcaagacga cggcgctgtt gaaatggctc tccgcggcgc tggcggccac tgatatgagc    81240
gcgctggtcc tgtcctgccg acgcagcttc acccgcaccc tggcgagacg aatgacgac    81300 gcgggcctgg gatttgtgac gtacttcgac tcggacgcat acgtcatgac gggccggccc    81360
taccgccggc tgctggtgca gatcgagagc ctgcaccgcg tggacgagca cctgatcaac    81420
aactacgacg tgctcgtcgt cgacgaggtc atgtccacgc tcgggcagct ctactcgccc    81480
accatggcgc ggctggcccg cgtggacgcc ctgctcgcgc ggctgctgcg cggctgcccg    81540
cgggtcctcg tcatgacgc cacgatcaac gcgcagctcg tggagctgct cgtggagctg    81600
cgcggcgagc ccagcgtgca cgtggtggtg agcgactacg ccacggccgc cttcgcgagc    81660
cgccgctgcc tcgtgctccg gcacctcggg gccgaggtcg cggcgggcgc ggcgggcgcg    81720
cgggaggacg gcggcggcga cgggagcgag gacgcggcgc gggccgggag ccccgccccg    81780
acgacggcgg cggcgacgac ggcggtggag gcggcggggg cggcggggga cagcttcttc    81840
```

```
ggcctcctgg gcgcgcgcct cgccgcgggg gacaacgtct gcgtcttctc gtcgacgctg    81900
gccttctccg agctcgtggc gcgcttctgc gcgcgcttca cgcctccgt  gctggtgctc    81960 aactcgcagc ggccccccga ggacgtgggc cgctgggccg tgcgcgccct cgtctacacc    82020
accgtggtca ccgtcgggct cagcttcgac gcgccgcact ttcacagcat gttcgcctac    82080
gtgaagccga tggcgcacgg cccggacatg gcctccgtct accagtccac ggggcgcgtg    82140
cggcggctgc tgcgcgacga gctcttcgtg tacgtggacg gctccggcgc gcgcggcgag    82200
cccatcttca cgcccgtgct gctgaaccac gtcgtgggct cgggctggcc ggcgcgcctg    82260
tcgcaggtga cgaacctcgt gtgcgcgcag ttccagcgcc gctgccgccc ggcgttcgcg    82320
gcggcgcgcg ggatgcgcct cttctcccgc ttcaagttca agcacctgtt cgagcgctgc    82380
acgctgacga gcgtcaacga cagcctcaac atcctgcacg cgctgctgga gaacaaccgc    82440
ctgcgggtgg cgctcgaggg ctgcgagccg ccgctgacgg cgcgcgcctt ctgcgacttt    82500
ctgcgcgacg cgcgcctgga cgccttcgcc agccagcagg tgctgcggca gctgcgcccc    82560
ccggaccggc cggtggcggc cgacatcgcg gacagcggcg aggtggccac cttcgtggag    82620
aagtacctcg tggccgacgt gcccgaggac gagctgcagg agctgctgcg cgcgctcgcc    82680
aaccccgtga cgcgggagca gtttgtgggc ctggccgtgc tcggcgcgtg cgcgcgcgtc    82740
cccgaggcgc tgcgcagcga gcgcgtcttc ggggccgtgt acgggcacta cgcctccggg    82800
gccgtgcccg tggtggccga cgggcggctg gagctggcgg cgctggcccc cgacttcaac    82860
gtgcccgcgc gctgggccct cacgcggcgc tgcgcgcgcg tcgcggaggc cgccgggctc    82920
ttcgagggcg cctcgccgga ggtggactcg gccgcggtcg cggcggcggc ggccgacgcc    82980
gagctggcgc cgctgctgct cgaggtgctg cggtgccacg tgctggacgc gacgacggcc    83040
gcgcggcgcc ccgtgcgcgc ggccctgagc gcgctggggg cgggcgggg  gcgcgggcccg    83100 ctgagccgcg ggcgccacgc cgcgctcgtg ttcaaggtga tgtgggagga ggccttcggc    83160
gtgcgcgtcg gccgcagccg gcagacgttc ccggggccca cgcgcgtgaa gaacctgcgc    83220
aaggccgaga tcgccgcgct gctgcgcgac gccggcctgg acccgcccgc gggcgccacc    83280
caccggcagc tgtacgccct gctgatggaa cgccgggggg actttgcggg ggagaggtat    83340
aaactgcgcc tgcccgcctg gagccggctc atgtacctga cccagggcgg cttcgacgcg    83400
ccgctggacg ccgcgctctc gctcgtgccc gcggaggcgt ggccgcgcac cgaggggccc    83460
gtggactttg cggcgctatg acggccgcgg cggggagcg  cgtgtgcgcg gccgggatct    83520
acacggcctg gacggagccc ggcgcgccgg gcgagctcca cgcgctggcg cacctgctgt    83580
gccgcgacgg ggccggcgcg tacgggcgc  gcttcgtcca cgtgacggcg gtgccgtgga    83640
cgggctcggc ggccgcggtg gccgcggcgc tgcgcgacgc gagcggcacg ggggcgctgg    83700
cggacccggc gctgtggcgc ggcgcgcacg cgcggtcat  gcggccctg  cgccgcgccc    83760 tcccggcgct ggccttctac gagccgctgc gcttcgagac ggaccccggcc acgaacctgg    83820 tcacggccgc gacgccggcg ggcggcggcg gcgaagagga gacgaccggg gagggcggcg    83880
aggaggacga ggacgaggcc ggcccgcgcg cgggcatcat ccacgtggac gccgacgtcg    83940
tcgtggaccg cgacgccgcg cgcgcgcacg ccaccgagcc gtggctgccg cacgcccagc    84000
tgcgcgccat ggccggctgc gccgcgctct ccgtcgagat cacgacgcgg cggaccagct    84060
tcgcgcgcgc ctacgcggag gccggcgcgc cgccgctgaa cgccggggc  gagatgagcg    84120 acctctttga cgtgcgcgag acggtgctgc ggcccgcggg ccggcgcgtg gcggcgcgcg    84180
```

```
tgctcgtccc gcgcggcttc gactgcctgg tggcccacgg cgtgagcaac gcggcgctgg   84240
tggcgctcta ccgccggtgg cacgcggccg cgtacggcgc gggcgacgcg accccgcccg   84300
tcttcgcctt cctggggccc gagctcgccc gcgagggcgc ggacgaggac tactactgcg   84360
cgctgggctt ccccctgttt gcgacgatca aggtggccgc ggccgcgccg gaggcggtcc   84420
gcggcgcgct cgccgcccac cggctcacgg acgggctgtg gcccgcgctc ggcttccgcg   84480
ccttccacgc cctcgggccc gtgagctgcg gcctgcgcct cgcgctgcgac gtctggccgg   84540 cggggcgcgc gaccagcgcc gtggagcacc cgtgcgccct ccgcggggcc tggctggcca   84600
agtttgactt cgcggccttc ttccccaacc tgtttctggc cctgtgcccg gccacgagc    84660 ggctgcggcg cgccgtgcgg gcgcgcgcgg tcaagccggc gctcgtggcc ttcttcggcg   84720
ggctcaagca cacgtgcccg gaggcgtacc acagcgtcat cgcgctggcc aacggcgtct   84780
cgcgcgccgt cgaggcggcc gcggccgagg ccggcctggt cacgtgcgcc tacgtcaagg   84840
acggcttctg gggcgtgctc ggcgacgtgc ccgcggccgc gccggaggcg ccgccgcgg    84900 ccgcggccga gcgcgtgcgc gtcgcctgcg aggccgccgc ggcgcggcac ctggccgacg   84960
cgggggccgc cgcgacggac gtgacgctgc gctgcgaggg catcttcgac gcggccctgg   85020
cctggtcctg ccacgcctac tggctgcggg ggcgcgaggg ccccgcggac tttgtcggct   85080
tcccgtcgcg cagcggcttc ggccgcgccg ccaaggccgc gctggacgcc ctgctgcgcg   85140
aggccgtcga gggccgcgcg gacgccgagg ccgcgcgcgc cgcctgcgac ggcctcgtcg   85200
agcgggcctt cgcctcgcgc cacgaccccg acttctgggc cgcgccgggg gacgccctcg   85260
cccccgccgc gtgcgcaggg gcgaccgccg ggcgcggcgg cgcgcgctgc tcgcggcgct   85320
gcgtgcgcct gcgcggcgcc ggccggtgc cctacgagca gctgcgcccc cgctgatcc    85380 tgccctggat agactgtctg gcccacatgg agcccatctt cgccgccctc gtcggcatgt   85440
acaaccgcgc gctcgaggcg ctgagcgccg gcgacgcccc ggcgcccttt gtgtttacat   85500
acacgccgga cgcgtttctg tttgggtaaa caataaagtc tgtttattgt cagaacgagc   85560
cacggggtcc cgcgtcttgc tctcgtccgc ggtcgggggg gagcgagaga ggggagagg   85620 ggggagggg tgagggaaga gagggatggg gaagggaag agggagagga gggtgggggg   85680
aggaggggcg cgcttcactc gtagcgcaca aacatggtct tctcggtgag cgcgcgcggc   85740
gccgtcgtcc accagcggta cacggcctcg gccatctcgg gcgtgcgcag gggcgcggtg   85800
agcgcgccgc cggggcgcgt ccgcaccagc ccgtcgggcg gcggcgcgtc gcccggcagg   85860
ccgagcaggg gcccgaaccc ggcggcgaag agggcgtcca cgacgggcgg ggcccggggg   85920
gccgacagca ggcgctgggc gatggggtag tggggcagca cgcgcgtctc gtcgagcggg   85980
ctgaggtggg ccgcgaacat gagcgtgttg agcgcgcgcg tggcgccgac gtgcagcagg   86040
cgccgcagct tccgcgccgg cggggcgcgc gcgcgctcca gccaccggcc caggctcagg   86100
caccgcgcgg cgtccgcctc cgccgcgggg cagttctcca ggaacatctg cagcacgcag   86160
agcgcgaact ccgtcgggtc ctcggggcgc accagggcca ggcggtgcgg cagcgccacc   86220
ggcggcacgg ccagcgagag cacgcggtcc tcggcggccg tgaccaccgc gaaggcgaac   86280
ccgcggaagg cctccccggc gaggcagcgg cggcggtact cgtcgcagga caccgtctcg   86340
ccgctctcga ggcgcagcgt cagcgcgccg ccctcgacgc gcgcgtcagt caccgaggcg   86400
ctcgtgaaga ccgggatcag cccgggcacc tcgcgcacct cgcacaccag ccgcgggagg   86460
gcgtgccagg tcagctcgtc catcacggcc tccatcgcgg agccgctcgg tcgcccggcg   86520
cacgtccgcc gcgaacagcg ccgcgatctc ggtcaggtag gcctcgaggc gcgtcttctt   86580
```

| | | | | | |
|---|---|---|---|---|---|
| aaacaccacg | ccgcacaggt | cctcctccga | gcggtacacc | tcctggctgg | tgatgaggaa | 86640 |
| gccgaggtgg | cgcacgcgca | ggatggagaa | gaagtacggc | gcgaggatga | gcagatgga | 86700 |
| gctgttggag | tacgagacgg | acacctcctg | gccctggttg | ttggccacgc | gcgtcagctt | 86760 |
| gaagcagcgg | atcagctcct | gctcccagag | ccgcgagagg | cgctccacgt | ccgactcgta | 86820 |
| cggcggcacg | tagcgcgact | ggaagctgtt | ggccacgtag | gcgtcgtcgc | ccatggcgcg | 86880 |
| cgtgatgtcg | atgacctcgt | ggccgaggtc | ccgcggcggc | tggccgtccg | cggcgccggg | 86940 |
| cgcgcgcccc | ccggcggggc | cggcggcgcc | ggtcccgtcc | gcgcccgcct | gcgcggcgcg | 87000 |
| cagggcctgc | tcgcgcaggc | gccgcacctc | ctgctcgcgc | tcgcgcacct | gctcgcggag | 87060 |
| gcccccgttg | tccgccttca | ggctctcgat | ggtcttgaag | aggttgttga | cgtagccctc | 87120 |
| gagcatgccg | ttgatgctgt | tgaccacgga | ggtgcggaag | gcgtcctgca | ccggctgcgc | 87180 |
| gccggcgccg | tggtgcccga | agcccggctg | cgacgtgtcc | acgctgtcca | ggatgcgcgc | 87240 |
| cccggtctcg | tcgaggtacg | agcgcaccgt | ctccgtgatg | tcgccgatgt | ggcgcatgcc | 87300 |
| cttcatgttc | acgatgaggc | gcacgaggcg | cgccgcggcc | gagcccgccg | ggtcctcgcc | 87360 |
| gagcatcttc | tccacggcgc | cggccgggtg | cccctcggcg | ggcttgcgcc | cgacgagcac | 87420 |
| cttcaccggc | gccgtgttga | gcagctggca | gaggcgcgcg | tgctcgcgca | gcgcgtggca | 87480 |
| cgccagcacc | tcgccgtgca | cgcgctgcgc | cggcgagtca | aagagcagct | cgccgtcgcg | 87540 |
| ccacagcggc | tgccagagca | ccaggcactc | cccgcgctcg | cccgtgagcg | cgtcgcgcgc | 87600 |
| cagcacgcgc | cggtgccggg | gctcgtagta | gagctcacg | cggtcgtagt | ccatgatggt | 87660 |
| gacgccgcgc | atggcctcgg | cgagctcggc | cacctcgtcc | aggccctggc | ccagcacgct | 87720 |
| gccggcgacg | cgcaggtgcc | cggccaggtc | gtgctcgtcc | acgcagcgct | cgcgccgccg | 87780 |
| cttcccccg | gggcgcgccc | ggcgcaccgg | gaccacgccg | aggcacacga | tccagtcgat | 87840 |
| gtacttggcg | aagctggccg | tgccgttgga | ctcgctggcc | gagaagcagg | ccgcgatgcc | 87900 |
| gcgcacaaag | tccaggaggg | ccatctgcag | cgtgcggtac | caggtgtcga | agaggcgctc | 87960 |
| ggccacggcg | ggcgcctcgt | cgccgaagcg | ccgcggccagc | gcctcggcgc | cgaggccgcg | 88020 |
| cgcgcgcagg | tgcgccatcc | agtcccgggc | cacgtcctcg | tagcgcgccg | cgttgagcgt | 88080 |
| gcgcgtgagc | agcgtggact | ggatctgccg | cacggcggcc | tcggtggagc | gcaccgagtt | 88140 |
| gtagatgccc | tggccctcgg | tgtagcccag | gttgcccatg | aggatctcct | tgaagaccat | 88200 |
| ggtgcgcggc | gtggggtgga | tgaggatccg | cgagggggcg | cccaacaggt | tattagcctc | 88260 |
| ctccgcggcg | ccgccgggc | agagcccgtc | cgcagccgcc | gccgtcgcag | ccgcagccga | 88320 |
| catggccgcc | gccgccgcag | agggtccgcg | cgccaccaac | gccacctatc | tgaactttac | 88380 |
| gtccatgcac | ggcgtcgagc | cgatcgtgga | gcgcgtccgg | gagctcgccg | cgacgcccgc | 88440 |
| ggaggcgccg | ccgccgctgg | cgtggttcaa | gtccctcgcc | gcggcggaca | acccggtgga | 88500 |
| tatagaggcg | ctggagctgc | ccttcgccgc | gtacctgatc | agcggcaatg | ccggctccgg | 88560 |
| caagagcacg | tgcatccaga | ccctcaacga | gaccatggac | tgcgtcatca | cgggctcgac | 88620 |
| gcgcgtcgcc | gcccagaacg | tctacgccaa | gctctcggcg | gcgtactcga | gccgctacgt | 88680 |
| gaacaccatc | ttccaggagt | tcggcttccg | cgggaaccac | gtgcaggcgc | agctcggcg | 88740 |
| ctacagctac | gcgtgcccca | cgagcccgcc | gacggtgcgc | gagctgcaga | agcgcgacct | 88800 |
| ggtgtactac | tgggaggtgc | tgcaggacat | ctcgcgcgc | gtgctcgcgg | ggagccacga | 88860 |
| ggagtttgcg | cgcctgcgcg | ccctggagcg | gctcacgggg | cgcgcggcgg | agcacctggc | 88920 |

```
cttcgcgtgc cacggctcgc tgccggcgtt cgcgcgcagc aacgtcatcg tgatcgacga   88980
ggccgggctg ctcgggcggc acctgctcac ggccgtcgtc tactgctggt ggctgatcaa   89040
cgccgcgtac gacacgacgc agtacgcggc gcgcgcgcgc cccgtgctcg tctgcgtggg   89100
ctcgcccacg cagacggact cgctcgagtc gcgcttcgag cacgcgcggc agctgtgccg   89160
cgtgcgcgcc agcgagaacc tgctcacgta cctgatcacc aaccgcgcgc tgcgcgagta   89220
cacggacctc tcgcgcaact gggccatctt catcaacaac aagcgctgcc aggagtacga   89280
gttcggcgag ctcatgaagg cgctcgagta cggcctcccg ctgacggacg agcacctgcg   89340
cctcgtcgac agcttcgtgg tgcccgaggc ctacatcaac aacccggcga acctgcaggg   89400
ctggacgcgc ctgtactcgt cgcaccgcga ggtcagcgcg tacatgagcc gcctgcacgc   89460
gcacctcaag gtggcgggcg acgcgcagtt tgtggtcttc acgctcccgg cctacaccat   89520
cgtgcgcacg gcggccttcg accggtaccg cgaggccacg cagcagccgc acctgacgct   89580
ggaccgctgg ctcgcggcca acgccggccg catcaccaac tactcgcaga gccgcgacca   89640
ggacgccgcg gcgctgcgct gcgaggcgcg cgcgcagcag ggcgtcgtgc tcgcccgctg   89700
cgaggtcacg tacgtgctca acagccaggt ggccgtcacc acgcgcctca agaagctggt   89760
catcggcttc agcggcacct tcgaggcctt cgcggccgtc ctgcgcgacg acgccttcgt   89820
ccacgcgcag ggcggcagcg ccgagtacac gtaccgcttc ctgtcgagcc tgctgtttag   89880
cggcatgatc gccttctaca acttcctgca gcgccccggg ctggcgcccg aggccgtgac   89940
ggcggcctac cggcgcctgg ccgccgtcac ggcggcggcg ctgcgcgtgc ccgaggagca   90000
ctttgacttc tcgggcgcgg cggcgcccgc cgccccgcg ggccccgggg gcgcgccggc   90060
ggacgacgac gacgacctct ttgcggcgct cagcgagaac atgctggaca tgctctactg   90120
ccactacgac tttgcgcgcc ccgagaccac gagcgaggtg tacgcgcagt tcctgatgct   90180
caagacgctc ttcgccgacc gctacgcggc gctctccgag ctcttcgggc ccgcgttcgc   90240
gcgcgcgccc ttcgagacgc acgtggacag cgtctcggtg cgcggggtgcg aggtgtttgt   90300
ggggggggctg cgcggcgcgc tgctctcgac ggcgctgcag acggacagct acacgctcgt   90360
gggctatacg cacgcgacgg cgccggcctt cgccgaggag ctggcgcggc gcaagctgca   90420
cgccggcacc gcggagctgc tcgcctcgct ggacacgccg cgcgtggtgc tgcgcgacca   90480
gagcggcttc ctgtccatcc tcaacgtcaa cctcagcgac tttgtcgagt cgctggacga   90540
cctggagctg gacatggcca cctacgtcga ctacggcatc agctccaagc tggccatgac   90600
catcgcgcgg tcgcagggcc tgagcctgga gcggtggcc gtgtgcttca cgcgcgccaa   90660
cctgcgcatg aacagcgtct acgtggccat gtcccgcgtg atctcgtcgc gcttcctgcg   90720
catgaacatg aacccgctgc gcgaggagcc cgagcgggac aacggcatca gcgagcatat   90780
attggccgcg ctgcgcgacg cgcggtgca catcgtgtac tgacccgccg tccacccgcc   90840
cgaggggggc cgaggaccca agggaccgag cgagaccgac catgacgcg ctggtggcct   90900
actcgttta cgaaataaag ctgcccggcg gctgggcgca gtcgggctgt gggcagaccg   90960
tgtgcgagta cgagcgcggc gtccgcgtca tggccacgga cgggtgcacg cgctgcgacg   91020
cgctcgcccc gggccgcgtc acgatccagc acgggcggt gctcacggtc ctggccgtgg   91080
acggggagcc ggagcggtgc tcgtacgtgt tcgcgcggac ctggccggcg ccccgagg   91140
gcgcgctcgt gatgcccttc tcgacctgga gctgcgccga gcgctcgcgc cgcctgcgcg   91200
ggcccgcggg cggcctgctg gccacccgt cgtggagcg ggcctgcac gtcaccatca   91260
ccgcgtaccg gcccgacgtg ctccgggacg ccctgcgcga ggccccgcatc ctggagtgag   91320
```

```
aggcggagag gggcgggcga gcggaggagg ccgccgccat caccatcgcc accaccgtca   91380
ccatccccat cccaccccga caataaacga cgacggccgc gcgtgcgcgg aaagagagac   91440
cgaaccggtt gtgtcttttg tctggtccgt gggcatccgc cctttattga tcgcggtagc   91500
aacaggaggc gggggggcgcg cgccggcccc gggacgggt ccggggggcgc gggagggcgg   91560 ccgccgaggg gacggcggcg tgggccgagg cgtggacgct gcgctggcgg ggtctcggca   91620
gctggggcgt cggggcggcc gtcgtcgagg cgttgatgct ccgttgccgg ggccggggca   91680
gctggaccgc cggggcggcc gtcgccgagg cgtggacgct gccgcggcgg cgcggggggtg  91740 cggccgcgca cgactcgggt ccgcccgcgg ccgtcgccga ggcgtgcacg ctgccgcggc   91800
ggcgtggggc ccgctgctgt tgttgttgct gctgctgctg cggatgctga gagcggtggt   91860
ggtgctgctg ctgctggtgg tggtgggtag gctggacgac ggtggcgtag acggggtccg   91920
gctcggtcgc gccgcgctgg cgcgagcgcc ccgcgggcggt gcccaggccg ccggcgcgca   91980
ggggcgcctc ctcgtcgggg gggccgcgcg aggaccgcgg ggcccgcgtc tcgccccgc    92040 cggcggagac gcggcgggag ccgcgcgcca ggcgccgggc ggccgtctcg ttggcctgca   92100
ggaaccggtg gtagtcatcg accgtggcca cggacgcgcg tccgaaggtg ctcatggcgc   92160
cgcaaacacg ttgtcccggt gcagccgcac cggctcgggg gtgatgaact cgtggatgaa   92220
caccggcgcg gccggccgcg ctcgtccgct cgtcggcgc gcgcggggct cgcgtgggcg    92280
tcgggcgcgc accgcggacc ggagctgatc gcgtacgcgc gccgcgtggg ctctgcggca   92340
caggataaac atctgcaggc ttttatggcc gcgcccgggg gcgccgcgcg ggccgcgcgc   92400
gcggcgcgca aacgcggacg tcttggtgca ggcgacgggg aggccggcca gggccgcggc   92460 caggtccccgg cggatcgtgt ccgtcagccg ccggcgcccg agctcgtcca cggacgcgac  92520
cataaacagc gtgtcaaact ccacgtgctg cgcccgcgc gggcccgccg ccgccgtcgt   92580
cccttcgtcc ccccgtcttt cctcgtcttc cgtctcctcc ttctccgtcg ccttcccctc   92640
ctcgccgtct tccacgtccc cctctccgtc ttcgctcccg cgcaccccct ccggggagg    92700 gggtgcgctc tccgggggcg cgtccgcgtc ctccgggcac ggcccggagg gctcgacctc   92760
ctccacggcc catcccact cgcgcagcac cgccaggacc ggcagcgcgc tggccggggc    92820
gccggcgagc gcgggctcca tcatccgctc tcctccgtcc atcccaccca ccccctccc    92880 cccctcctcg tcctccgccg gcggtgtgcg cgcacgcccg actcagtcca cgctccagtc   92940
gacgggggcc cggcccgtct ggacgaggta cgcgttcgcc tctccaaagt gcgggcaggt   93000
cctgaagggc gtgcgggaca gcggcgacg atggctgaag gtgagcacct tgtggcggcg    93060
cgggtccggc gcgcaggcct tttgagcgtg ggcgccccag agcatgaaca ccagcttggg   93120
gcgggtctcg cagagccgct ggacgacggc gcgcacgagc cgcgcccagc cgagcggggc   93180
gtgggagccg gggaccccgc gccgcacggt cagcgtcgtg ttcagcagca gcaccccgcg   93240
gcgcgcccag gcctccaggc agccgtgggc gggcgcgggg agcgtcgggt acgtcgcccg   93300
gaccgccgcg aagatgttgg ccaggctcgg ggggatcggc accccgcgcc ggacgctgaa   93360
ggccagcccg tgggcctggc ccggcccgtg gtacgggtcc tggccgatga tgaccacctt   93420
gacgtcctcg ggcgccgtga ggcgcgtcca ggcgaacacg tcctcgcgcg cgggcagcac   93480
ctcctcggtc aggcagcggc cgcggtactc ggccagcagc aggcgcgcgt acggcttggc   93540
gatctcgggc tccagcagcg cgcgccacga ggggccacg tcgaactcgg cggcgaaggc   93600
gtcccacgtg ggcgccccgg ggtcggggc cggggcggag gcgtcggccc ccgtggctgt   93660
```

| | |
|---|---|
| tgttgccgcc gacgccgcgg gcgtgcccct tcgcgggccgg gcggcggcgg agggtcgggc | 93720 |
| cggcttcgag gcccccgccc ctgcccggc ggggctgct gctgcagcgg cggtggcggc | 93780 |
| gttagaggca gaagcggcgg cggcggcagg cacgacgagg cgcaccccgg gcggcaggcc | 93840 |
| gcagggtctc ttactcggcg gggggccctc cattatagcg cagcggcggc agggagtcct | 93900 |
| tgtgcacggc cacctctccg agctccttca gggccgcctc atttaagggc tctccgatgg | 93960 |
| ccagggcctg gatggcgaca aaggggttga ccaggtaggc ggtgcccgac gcccacagga | 94020 |
| tgacctccgg tggcgagcag tagggcttca cgaccacgct cgtgacggcg gtcatgtccg | 94080 |
| gcggcagcga gtacgcgatg tagggggtggc agcgcgatcc cacggcggc tcgaggccca | 94140 |
| gcagcgggtg gtcttcatcg tcccattcca gctcctcgcg ccggggagcg cgggtggggg | 94200 |
| gcgcgggcgt gaccggcggc tcgaagatgg catcgagccc atgggggttt ccgcgacgc | 94260 |
| cggtgccagg aacccccagc gccgccgaaa aaaacaccag caccgccacg agcggcgaca | 94320 |
| tcgcggctgg tgtatccttt ttcggcgcgg ggtcccggct tttatctccg gaaagaggaa | 94380 |
| attgagacat aaactagacg tccgcataat ccccttgat ttacggggg gaaatacgtg | 94440 |
| ccacgtgccg gggggcgggg caactggagc gtggcgaagc ggaacggggc gcgatggggc | 94500 |
| gcatcgaggc gcgacgcgt cccggggag tcggggggga gtcgggggg agtcgggggg | 94560 |
| gagtcggggg ggagtcgggg gggaattcca gctcggcgcg atcgccgcat cgcgcaaagt | 94620 |
| ccggctgcag taaatttact gcggatgcag ttcccgggac ggccgcaccg gccaaatggc | 94680 |
| gctgcagtat agatactgcg gctgcagttt actacagttg cagtaccgcg cgccgccgcc | 94740 |
| aaatactaca gtagatttcc tgcggccgcc gcgtactgca gtttaccgcg gctgcagtaa | 94800 |
| actgcagtat cgcgcggtaa attgtagtct ggcagccgcg cgttactgca attagcggtg | 94860 |
| gctcccgaca ctctggccaa ttggtgctaa tgggccgtga tggtccacgc gggggtgatg | 94920 |
| taaccgccgg gccccggttg ggcactcaga tggtagccgg gcgccaggcc aaagtgctgt | 94980 |
| ctgagtgcca ctttatgact tgttttttct caaacaacat caattatgga tgcacatcgt | 95040 |
| gtatataatc cccggtccgc gctccgccca cccatcacag cagccgcgga cgctgcgcgc | 95100 |
| cggagcggtc catctcgcca gccagccaac cagccgagcc gcccagccga cccgagagcc | 95160 |
| ccgagagcca gactccctca tccatagaag acaccgggcg ggagagacgg actgaaaaaa | 95220 |
| tatatcttt tttattttgt ctgggcctgg agacccgcag caggagcgga ggtgggtgcg | 95280 |
| gggccgggag ccggagcagg accgggaaca ggaacaggaa caggagtggg gccggagca | 95340 |
| ggagcaggag cgggagccga agtggggca ggagcggcgg cggccgcggc agcaacaggg | 95400 |
| tcgcccccagt ccgcggcgag gaagagggag cttacttgta cagctcgtcc atgccgtggg | 95460 |
| tgatgccggc ggcggtgacg aactccagca ggaccatgtg gtcgcgcttc tcgttcgggt | 95520 |
| ccttggacag ggcggactgg gtggacaggt agtggttgtc cggcagcagg accgggccgt | 95580 |
| cgccgatcgg ggtgttctgc tggtagtggt cggctagctg gacgccaccg tcctcgatgt | 95640 |
| tgtggcgggt cttgaagttg gccttgatgc cgttcttctg cttgtccgcg gtgatgtaga | 95700 |
| cgttgtggga gttgtagttg tactccagct tgtgcccag gatgttaccg tcctccttga | 95760 |
| agtcgatgcc cttcagctcg atgccggttga ccagggtgtc gccctcgaac ttgacctcgg | 95820 |
| cacgcgtctt gtagttaccg tcgtccttga aggagatggt gcgctcctgg acgtaaccct | 95880 |
| ccggcatggg ggacttgaag aagtcgtggc gcttcatgtg gtccgggtag cgggagaagc | 95940 |
| actgacgcc gtaggtcagg gtggtgacca gggtcggcca cggaccggc agcttaccgg | 96000 |
| tggtgcagat gaacttcagg gtcagcttgc cgtaggtggc gtcgccctca ccctcgccgg | 96060 |

```
agacggagaa cttgtggccg ttgacgtcac cgtccagctc gaccaggatc gggacgacgc   96120
cggtgaacag ctcctcgccc ttcgacatga cggtgagtgg cagtgacagg cgctgcggcg   96180
gcggcgaggg gcttctgggg cggtagaagc caaagatccc ccaggcgctg gaagcctcgg   96240
cggtggtcgt ccgtctccga gagaccgtgc agcccatggt gtcgagggcc ccgttttta   96300 accgggtgcc cggcccctt gtttgtcttc gcccggggcg tccacgcccc cttccgcccg   96360
ccccgtcggg gctcccccg ccccctcggg ccgtcccggg acgatggccc gggcgcgccg   96420
tcgtgggaag cgggccctcc cgcggtgggt cgacggctcc tgggtctgaa agcggcgctg   96480
cggatccccc gctctcaccc ctgggtccgt cgccgcccg cggtgcgtgc gacgcccgcg   96540 aaccccggc ccacaacaca ccggcaccac caccaccatc atcgtccccc ctctccacat   96600
acacgctcgc actcgggcca cacgctcccg tcctccgccg ccaccctccc agcctcccgg   96660
cctcgcgggt cctcgggacg accgccgctc accccgacgg ggggactggg acagggagca   96720
aggggggagg aggacggggg ggggggagag gggaacgcga gcgggcgca ccccgtcgcc   96780 gtccgtggtg gcgggcacgc caccccgtcc gtccatccag ccccctcc cttttccgc   96840 ctcccgtccc acggcacggc cccatcgacg ccacaccgcg cggtgcgcgc cctccagccg   96900
tcccatcccc ccacaccccc cacgcttccc ccattcgctt ctcatcccgt cagacctgcg   96960
ccatggagtt cgaggacggg cgcggggcaa cggtggtgag aggcgagccg gggggtcga   97020 gtgggcctcg cactttacgc gcacacgccc ctctcgcgca ccacacacca ccgcacaccg   97080
ccgaggtcgg gcgagagagg gcgccccccc ctccacgacc ccgctcgccc cggtcccgac   97140
gccctcgcac ccccacagca ccccctttca cccccgctt ctccccgctc tctccgcgcg   97200
atcgcacaca caacccgc gcgcatgctc ggcttcttca cacggaggac accatgggca   97260
gcagatggta cggtcagccg ccggccgccg tgcgcatgtg tcgggctgcc gcggccaaga   97320
gtatcagcgt ggctttttg ttggtcaggg tgtgaaaaag gcacgctgat gcgtccgccg   97380
ctgcagcgga gctcctcggc agcgagatca tcgaccacca ccaccaccac atcgctcttc   97440
tcgcccgcgc ttccccaccg ccaccccaca ccatccccca ccccccccgt ccaccctcac   97500
cccccatcgc gtcgcgagag ctctcaacac atgcttacat gcacatgcac acgcgcccct   97560
ccctcctcgg cgccccgcg gcgggaccgt cgcaaccctc tcccccgccg tcccaccgt   97620 ccgcggccct cctctccttt tcccttccc ctcccctcg catccccgtt ccccctgtt   97680 ccgcatttcc ccgctccctc caccatcgac tctcatcgac gggcttctcc gccatcatca   97740
ccaccaacca ccatcaccat ctcccgccgc cgcccgacg gcgacccgcg gtgctcccag   97800
gggcgcgttc ccactcacaa cccggtggtt tcgatggccg ccccggggg gttgatgggg   97860 atgggcgctc gggggtgatc gtctgctacc aaaccgcacc accgtccccc tgtccctcat   97920
ccacttctcg acggccggct ccccgcgggg cgggggctgc tggggggtgg gtgggtgggt   97980
gatagagcag gcgggcaggt cggggcggcc gggagggcc cccggcccct ctccctcctc   98040
tctcttcccc cccccctacc ccctctccgc gccgactcga cgagcggggg cgaggcaggg   98100
tgcgtaccga cccgcctacc aggcaggcta gaagcctcac gctgctgctt ggcagcgggt   98160
gggtacccaa ccccctcccct caggacgcga ccgaccggtg tgaagagaga aagatgcccg   98220 tctccccgc ccccaccgtc cccgattttt cggttcctct cccgtcgcg ccggcgggcc   98280 cctcgtcgcc aggggttt tggtggaagg cccgccgggg taagggggg tgggtggtgt   98340 gtgtgcgacg gaacgggccg caggaggatc gggatgtatg cacggtcgtc cccgtctcaa   98400
```

```
acttcctcgt gtccctgtt ccccatcctt ccacccatgc attcatccgt gcggtggtgg    98460
ggatgagtgg atggatggag gcagggacg cggtggacca tgccaggcaa gacctgcatc    98520
actcgaagaa agggtgcctg gattggcctt cgcatctttg ccggccacga gcgacggcca   98580
ccaccgcccc cgacggtctc tccccccctc ccgcttctcc tctttcctct ccggcgcgta   98640
ccccccccc gttttctcga cgaggttcga ggacccccc ccaaagcaga gcgagagcac    98700
cccacacccg cacgcactcc ccggtgtcgc tccttttccc ccccggcagc gccggaaccg   98760
ggtgcgggcg gtgggggcga agattgggtt gggtgagaga ctagaaccgg tgttctcaac   98820
ccttctggag ccctaccctc tgtgcctgga ctttccagcg cgcgacacgg ggggagcgg    98880
gcacgcggcg gtggcgatgg tggcgacggc ggtggctggg cgcgatcgag gagatgtgga   98940
ggggtgccaa gcgcccgccg ccctccccg catctcttct ctctcgcaca cgcacacgac   99000
ccgcggatgg cgaggatgtg gggggagagg tctcccggcg ttagtgggtg ctatttgatt   99060
ctcctctaac cccctctccc tcgcggcccc ctcgaccatc gtcgtgcagc ggcgacggcg   99120
gctcccactc cgtctctctc ccccacacga cctcgacgcg tccgccacc ccgcccagtc    99180
acgtcccacc ccccggggag aggggagagg gatgcacggg ggtaggggtc ccgcccct    99240
ctctctgatt ccaagacggt gattgttgtc tccgtcccg gctcgcacgc acacatcccc    99300
gccgcgggat gcccgccag accaaccgag gggggggagg agaggggag gaggaggagg    99360
aagtataggc ctctcgggga cgggcggcgc gtggcgccgg agaggggggt ggcggggaag   99420
agggaaacct agaaggcggc ccatccccg agatgacgag agaggagaga ggcgctaaac    99480
ggcgcccggg gagttggggg aggaggagac ggcgcgcgag gagctggggg aggaggagga   99540
gacggcgcgc gaggaggaag acgaccggtc caacccttgg gacgagaggt ctcgaatctt   99600
gacaccattt cccctcccct ccgctccact cccgtcgcag cttcgcgcgg ggaggaaaat   99660
aatccgatcc gaccccgggg gcgagaggct cgcgatccca cccccgct ccccggggc     99720
cgcgaaaaaa gggggcgggg cttaaagggg gggggctaat ttgcataaat ttgcatacat   99780
ttgcatagcc ccgccccctc atttgcataa attagcatgg ccctcccccc tcatttgcat   99840
gcatttgcat aacccctccc cctgatctgc ataaccccac ccctcattt gcatacattt    99900
gcatagcccc gccccctaat ctgcataacc cctcccccta atctgcataa cccctccccc   99960
taatctgcat aaccctccc cctaatctgc ataaccctc cccctaatct gcataacccc   100020
tccccctaat ctgcatatga caacttcctc cggaagtgac gctctggccc ctcccccccc  100080
atttaaatat gaccgcttcc cccggacgtg acgccgggct cctccccccc ccatttgcat  100140
atgaccgctt cccggacgtg acgttttgc cgatgacgac ttccgcctca tttgcgtatg   100200
accgcttccc gcgcgcaact tccgccggac gtgacgccgg ccccacggga tctcatctgc  100260
atatcgcgcc ggcccttcc gcttccccg gacgtgacgc cggcttccgg ggcgcggccg   100320
gggcgggctc cgcggatcgc atcgcgcgc cgagcctgcc ccttccgtcg caccgggggt  100380
ccgcgggcgg gggcttccgc tccgcggcgc ccgcccatt ggctcccctc gcgccacgcg   100440
gtcgccgtcg tcatcgtccc gccggccaat cgtggcagc gggggaggct gggagtgggg   100500
acggaagacg gaagccagat gaacctgttc cgccgctct cccaccgcct ttccgcccc    100560
tccacgacga ccaccggga ccaccaccac caacaacacc accaccccc cccccccc     100620
tcacgcacac gctttactac tatcaccacc agggggcgat ggttgcaacg gcagttccct  100680
gtactgacca ccaccgtgtt ttttctctc tttctctctt tcccccacc ccctcgacc    100740
accgcaggac caccatcgtc caactcccgc ccgggaccac cgggacccctc gggaccatct 100800
```

```
acctcccacc aggacccgcc gggaccacca acgccgtcca cctcccacca ccaccatcaa 100860
ggaccccccaa catccccaag accctctact tcttcccacc aagaccctcc gggaggaggg 100920
cccccatctg ctaagaccca ccagggaccc ccatctgcta agacccacca ccaccaagac 100980
cctccaggag gaggaccccc atccacttct tcccaccacc accaccacca ccaagaccct 101040
ccaggaggag gaccccgtc accctcacca agaccctcca cctcttcttc ttcctcccac 101100
cagggacccc catccacaag accacctcca ccccagagac caccgccaag atggccgcct 101160
ccatctcccc aaaaaatctc agagactcga gccggttcag aaaatacagc acaaactttta 101220
ttttctcgct ctgaaaataa actcttttct cacccgatgg gagaaggagg agaagggac 101280
cgggggaccg cgggaggagg aggagaaggg gaccgggacg atcctccgcc gccgagccct 101340
ccgccgcggc cgccgccgcc gcttccacca ccgccgccac ctccgccgcc gccgcagcca 101400
cctccggccg ggggatccgc gcggaggaga aggagaggag gaggaggagg gccaccgggc 101460
cggggaggca ggcgccgggg aggcaagcgc cgccgggccg aggggaccga ggccgccgcc 101520
gcggacgcag aggaggagga ggacggggac gaggacgagg accgggccga gggcgagggg 101580
agagaagacg gaggagaagg gcctcgagga gccggcggag gggccggaga gtcagagtca 101640
gagtccggcc gggccgaggg ggcgccccgc tcagcggagc agcaggtagg ggttgccggc 101700
gtcctcggcc tcctcgtcgt ccgagatggc ctccaccttg atgggcccga gcgggccgcg 101760
gggccggccg tcgccgccgc ggacgccgac gatctccaca gagtccccgt cctcgccggg 101820
gccggcccg cgcccgagg cccccgcggg ccggcgggtc tccacggcgc ccccggcggc 101880
ggcgcggacg ctggtctcga agggcgcaaa gtcccagagc acgccggcg gggcgcccgc 101940
ggcggcgacg gcgccggggg tcagcaccag cggggcggcc tcggcgtcgg gctccagcag 102000
cgccgcggcg cagaaggcgc gcagctcggc cggcaggccc tcggggccgc ggagctcggc 102060
gaggcccccgg cggccgcagg agacgaagac gggccgcagc ggggcgccga gccccagcg 102120
gttggccgcg cggtgcccga aggcggcgcc cgcgtcaaag tccgggtccc cgagcccgag 102180
cgcggagcgc tggcgggcca tgtccttgca gccgtccacg gtgggagca cgcgctggcg 102240
gtaggcgcgc ggcggcagcg ggaccggggt ccggggcccg gcgcgggtgc tcaccgtgta 102300
gcgcacgttg tcctggcggc agaggcgcag cggctcggcc ccggggtgca ggcgggcgaa 102360
ggaggcctcc gcgcgggcga agcaggccgg gcccacgatg gagctagagt ccagcacggc 102420
cgcgcggagc tcgcggcacc cgggccagcg cacggcgcac tgggcggccg gtccaggcg 102480
ggcgcggacg tagacgtggt agtccccac ggccgggcc tccgcgggcc agtcctcgat 102540
ggtgtccagc acgatgagcc ggcgccgcgc cgcgccgagc cgcgagcaga ggtactccac 102600
ggccgccggc aagccgaggt cccgcgccga gagcagcagc accccctggg cgttgaggcg 102660
gccgatgtcg gggcgcccgg tccagttccc ggcccaggcg tgcgagtccg gcgtgcagag 102720
gcggtgggcg aaggcggcga gcagcgccga gaggccgccg cggcgcgggt ccaggccgg 102780
gcgcggggcg ccctcggcgg gctcggcgca gagctcctcg tggggcagcg ggtcgtagag 102840
caccaccacg cgcacgtcct cggggtcggc tatctgccgc atccaggcgg cgcggcggcg 102900
gagcggggcg cccgcggccc cgcggcgcgc ggcgatgtgc gccagggcgg ccgggtcgaa 102960
ggtgagcgcc gggcgccaga gttcggggaa gacctcctgg tccacgaggg cgcgggccac 103020
ctcgggcggg cagtaggcgg cgagggccgc ctcggagggc cgcggcgtgt gggtctcgcc 103080
ggccgggacg cggcggaagc cgccgtcggg cgcggggtgc tcgggcatgg gcccgagcgg 103140
```

```
gcgccggagc cggtcgtcct cggaggagga ggaggaggac agcagcgcgg gagcggggtc 103200
cggagcgggc ccgagtccga gggagcggcg cttgcgccgg gccccccggt cctcttcgtc 103260
gtcgcggtgg ccgtggccgt ccccgcggag ggccgcgccg gagagcccct cgtcctcctc 103320
gccgtccccg gggcggcggg ccccgggcgc gcggcgcttc ttcttgcgcc gctcgggcgc 103380
tgggtccggg ccggcggcgg gggagctggc gtagccggag gagccggaga ggccggactt 103440
ggtgccggag ctggacttgg tgctggagcc ggactcggtg ctggagctgg acttggtgct 103500
ggcggggctg gagggcccgg agccggggag gccgagggg gcgcccgccg ccgccggcgc 103560
cggcgctggg acgacgaggc cgggctgctc gggccagagc gggggcaggc cgggcgcggg 103620
ctccgcgggc ccgggccgcg cggcggcctc ggcgagccgg gccgcggcca cgttggccgg 103680
ggcgaagagg gccgcggcgt aggtccaggc ggcctcgcgg gcgcgggccc cgtccacgct 103740
gtagcgcacc agcggcgcca cggtgcgggc gacgagggcg acagcgtccg cggcctgctg 103800
ccgctcggcc gggccggccc cggggatcgc gtcgcggagc gcgagcagcg cggccgtcac 103860
ctcctcgagg caggcgggcc cgaggcggc cggggcgcgg gcgggcgcgg gcagccggag 103920
cgggcagggc agcaggcgct cgaggacgcc gcggcaggcc aggacgcagg cgtccgccag 103980
ctcgcggggc acgcggccgg gctgcgcggc ggcgaaggcg gcgcggacgc gggcgcagag 104040
ggcctcgacg gtcgcctccc cggcgcgggg gtccgcggcg cggcccgggt aggccatgtc 104100
ggcgtaggcc cggcggaggc tctgcaggat gaaggtcttc tgggtgcgat cgtagccggc 104160
gctcatggcc acggcgctca ccgcgtgcgg cagggcccag agcgggtcct gggcggccat 104220
ggcgtccccg atgtgcggca gcggcggggt cacgctgccg gtgatgaagg agccgtggcc 104280
gtggggcgcg tggacccggc gctggcagaa ctggttgaag cgctggtcgg gggcctgcat 104340
ccgcgggttc tgcagccagg acatggcctc gccggcggcc ccgctgtaga tgaggcgcac 104400
gagggcctcg tgctgcttcc tcgagtcccc catctccggg atgaagacgg gcacgggccc 104460
ggccgcggcc cggtagcggg ccgcggcctg gcggacgtcg tcctcgtccc agagcccctc 104520
gcgggagtcc ccggcgccgc cgtagcggac gcggccgtcg gccggagggt cggagccggg 104580
ccagggctcc ccgagcgggg tgagcagcgg cccgtcggtc ggcgggggcc cgtcggccat 104640
gagcgagagg tggttgttgg tggagcggcg cttcctgcgc gggggccggg cgggctccgg 104700
ggccggggcc ggggaggccg cggcggagga ggaggcggag gaggccgagg gccgcggggc 104760
cgcggcgggc gccggcggag acggtggcgg cccgcgcgg gcgagtgggg cgccgggccg 104820
gactccttcg tcttcttctc cctcggagga ggacgaggac gaggaggacg aggaggacga 104880
ggacgaggag gaggccgagc gccgcgcggc ggcggcggcg agggcccggg gggcggaggg 104940
cgagcgggcc ggggagaggt ccgagtcgct gccgccgctg ctggagctgc tgaagccgcg 105000
gccgcggcgg agggcgccct ctccggccgc ggcgccggcg ggctgtctct gcgggggcgc 105060
cccgccgtcc ccggcggggc cgagtccgtc ctcgtccttc tcggggccgc gggcgacggg 105120
ctcgacggcg acggtggtgg tggagctgga gttgagttg gggttggagg agacgggct 105180 ccgggcgcca gcggccgag gatcgagccg cctcgcggcg gcgggctcgt cgagcagggg 105240
ctcgcggtgc tggtgatggt gacgaccgcg gtccctccg gcgaggggg cgccgccgcc 105300 gccgggcgcc gagaccggcc cggcggcggg ggggctgggg gaagcgggcc cccgccgtgc 105360
cggcgctgcg gccaccgctg ctggctgtgc tggtggcgcc gggtccgag gccgcgccgc 105420 cggcccggc tcaccgaccg ggtccccgc ggggaccat ctccgcgggg ctgccgaggg 105480
gccgggggag ccggaggagg aggccgggga ggccgcgag ggggacgagc gcccggggcc 105540
```

```
gccgggggcc ccggcctctg ccgctgcgag tgctgccggg gtcggcggcc ggggcccgga  105600
gccggcccgg gaccggggcc cgaggacgag gtgaccgtgc tcggagccct gatggagagc  105660
ccgaccgggg gacccggcgg ccggggaccc gggctcgtcc tcctcctcgt cttcgtcgtc  105720
tagcaccacg atctcgcccg agcccggcg gggctgctgc tgctgggccg aaggaggacg  105780
gggcggcctc gtggctccgg ccgcggccgc gaggacggcg gcctcggcct cggcctcggc  105840
ggcgtcgtcg gagaagaggc cgcccgggcc gaagaggaga tcctcgccgg aggagccgcg  105900
gcgccgggag ccctggctgc cgccgtcggg gccggacgcg atgccctctt cctcggccgc  105960
ggcggcggcg gccgccagga gctggctgaa gttgccctcg gtctcgatga agtcaaagag  106020
atcgtcggcc atggtctcga tcgggtctt tctgcctgag cgaggctggg cgccgagcgc  106080
ggagagcggg cggcggagaa gaaggaggaa ggcggccgga ggaggagaag aagaagactc  106140
ttctctggtg ggccgagagc ctcggtgggt cgggcgtccg tcgagggctg atagccgccg  106200
gagagccgga gtcttcagag tccgcgccgg agcggagacg gtcggatccc ctcgggttgg  106260
cagagaacga tgctgtccgt acctgcaccg cagtgaagtg ctacgatgga gaccgcgctt  106320
ataagcgccc cgaggagagc ccgccccag gtaagcggac caatggccga ttttcgccgc  106380
ggacttcccc gacggccggc caatgggatt tttctcgccc gcttcctctc gcgtctgctt  106440
tgcatgcccg gccaagatg gcggccgccg gccaatggga tttcgcgagg aacttcctcg  106500
cgaggaccat ttgcatgccc ggcccccgcg gcggccatct tgcccactcg acggccaatg  106560
ggatttctct cgcccacttc ctctcgcgtc tactttgcat gtccggcccc gagggcgcca  106620
tcttggcccc tcgacggcca atgggatttc tctcgcccac ttcctctcgc gtctactttg  106680
catgcccggc cccgcggcg ccatctcgg cccgccgggg ccaatgggcg cgcggaggcg  106740
tctcccgcgc gcctctgatt tgcatgcccg gccgctctg cggccatctt ggccgcgggc  106800
ggccaatgag attgtccgaa aatccctcgc gcgggcgcga ggcgcatgct cggcacgcga  106860
cccaccccgt ggtgctagcg agccaatcag atgattttcg gggaagcttc cgtgtgcacg  106920
tcatttgcat gctcgcccca cgtggccgcc ctcggccaat ggggcctcac ggtgcaagct  106980
tccgtgtgtc tgcacgtggt ccgcatgtgt tgtggtggtc tctgtgttgt ggtggtccgc  107040
atgtgttgtg tggtggtctc tgtgttgtgg tggtccgcat gtgttgtgtg gtggtctctg  107100
tgttgtggtg gtctctgtgt tgtgtggtgg tctctgtgtt gtggtggtct ctgtgttgtg  107160
tggtggtctc accgcctccc cctgccactc gcgagacccc gagaccccg tttcccctc  107220 cccgagaccc ctgagacccc cgagaccctc ccgcgacccc cgcggtcgcc ccacccgcgc  107280
ctgcgcgctc ggcgcgcgct ccgagggcgc ccccagccgg tcggagagac gagcggaacc  107340
gccgtcggac cggggaccgg cgaccggacc cgaaccggga agcgacgccg gggcgggaga  107400
accggacccg aacctcgagc ccggacccgc ccggacccgg aaggaaggag ccggacagcc  107460
acgccttgga tacttttgtc gcccacccac ccctcctct cccccccccc ctctatctct  107520
ctctcccggt cccccctccc accccacgag acacgcccca gagtgaaaaa aataaaagtt  107580
gttctcgttg caccgtcttc cggctcgtgt cgtccttccg cggtacctcg ggcgggcggg  107640
agggggcgcg agaccggctc ggcctcgtcg ggagagaggg agttgggggg aggggagcca  107700
agatggcgac ggggcgtggc ggggcgtggc agagggggag gggggggggt cggagcgcgg  107760
accccgcccg gtggggggg gcgggtgcaa agggcgggg cccaaaatgg acctcggcc  107820 gggacccgg gggcgctccg ggagacgaag agggccgggc cccttcccg gcggggaggg  107880
```

```
ccgggccggc gcgccgggac gccccctccgg gggaaagcgt gtccccgcgc gggcgccgcg   107940
tcccgccccg agccccgggg ggcgcgcggg cctcgatcgc gcccgccgga cgcggaggcg   108000
cgaggccccc gcccccgggg gggtccggga tgggggggt caattttgc tgtgtgtgca    108060
gggaaggctc gctctctctc tctcgtggag ggtcggagg acggatggtc ggtcggacgg    108120
ggcgggcggg gagggtgtcg tctgtgtgtc tgtgcgcggg gagcgtgtga tgtggggtg    108180
tgcgagagag agcgtgcgtg cgtgtgggtg ggtgtgaggg ccggtgcgag tatgggggcc   108240
ggtgcgggtg tgagggtccg tgtgggtgtc ggtggtgcgg gtgttactgg cgataccggt   108300
accgacggtg gtggccgggc gggcggtctc tccgtctccg tctccgccgt cgcctcggtc   108360
cgaggagggg gggtgcccgg gcgtgtctcg cctttcccce agttcgcctc ctccttctcc   108420
tcctctctcg cctctcctct ctctccgc gtgtgtgcgc gcgcctctcc ccgtgcgtgt    108480
ctcgctcgcc ctctccgcct ctgtcctccg cccgactttc cgactctcct ccgtctcctc   108540
tcctccgtct cctctcctcc tctccccgcc ccgcccccg ccccgcccc ctgtcccggt    108600
cccggtcccg gtcccggtcc cggtcccggt cccacgcgcg cgcgcccgg ggaagggtcg    108660
ggcgatggcc gccgccaccg ccccaccctt cccccggacc ccctcccgcc cgccggggcg    108720
ccccgcgtgc tccggggcgc ccggccggcc atcccccac acctcccttc ctcccccgcc   108780
cccgacccgc ctcgcactcg cccgacactc ggcccgcggc acgcgcgccc agaccttcct   108840
ctccccccctc caccgcccgc cctcgccccc ctccgtctca tgccacccgc ggcagcatcc    108900
ccccctcccc gtcgtcctca gccaacggcc aacagccgac aacccacagc cgacagcctc    108960
actctcgcgc tctccccgtc gcgggaaaaa aacacggcac cacaggcggg agcggggtcg    109020
ctcgggggaa ggtttcattc aaacgacagg cgacaggagg gggccccgc gcgggtcggg   109080
ccttcttccc catccccgcc ggccccccctc tttctctctc tctcttcttc cgcgtcttct    109140
tccgcgtccg cttcggcccc ccgcggccgc ggcgtgggag agcggggcgt gtgggaagg    109200
aagaggggac ggggggggga agaagaagaa acggggaagc gggggaagga acagacgggg    109260
aaggggggaa agggaaacgg ggaaacgggg aaggggccgg cgggggggg ggaagcggga    109320
gggagaggcg cggcgccccg cgcttcccct tcccgcttcc ccctccgccc ggccgcgggt    109380
gcccgggaga cgggagcgaa aggaggagag gggaggaaaa aaagtctaga gcggggagga    109440
gaagtcaccg tagtagtcat agtagtagtc atagtagtag tcatagtaat atagtaggag    109500
taggagtagt aggagtagta gtaggagagt ctgtgcttac cgagagagga gaataagaag    109560
cagaagccgg ggcgcttcct ccccggcggt ccgggaagaa agccccggcg cctcgggcct    109620
cggagatggg gacgcggaga aggaaacacc caaaggcgga ggaggaggag gaagaaggag    109680
aggaaggaaa aaaaaaccte gagagcggcg cggcggtcg ccgcggccag gaggaaaaac    109740
gggggagcgg gagcggctcc cgagtccggg aatgaaaggc gggcggagga aggcgggtgc    109800
ggaggaggaa gcgctcgcgc ccctcgctct ctctccccct gtccccctct ccgcgtctct    109860
tccccgcgtc ccctctctgc gttcgccggt cgcggcgcgg gcggcggctg cagaggcggc    109920
tgcggacgcg gaggggggcg aggggacaca gaactctttt tgtcctcctc gccggctccc    109980
aggcggcggc cgcgtcccgc gtcccggcg tcatcacgcg ggaccccccg gtcccgtga    110040
cgcaggacgc gggaggggag gggggtcggg gggaagggag ggagggggg ggaatgaggg    110100
ggagagcggg gtgacgccgc gggtgggccg aggccggcgg ggaggagga ggaggacgcg    110160
gcggcggtga aggaggaaag ccgccgcgcg cgcgcccgcc gccgcaggcg cgtccccggc    110220
gcgggcgcct ctccacgccc cgttccgccc ggcgcccaat ggcgcggccg gctcggcggc    110280
```

```
ccggcccttc ctccgccctc ctccctcccc gccgcccgcg cgcccgcgtg cgctcgtgcc    110340
ggcgcggcat ccccgcccag gcggcggggg agcgcggagc gcgccgcccc cccgtgatca    110400
cgttcgcgca ccgcggcgcc agcaggaaaa aaacaacaca gagacacacc tccctctccg    110460
tctccctcgc cttctccgtt ttgggggag accgatgccg gtgccacata cacatacaca    110520
cacgcgcgcg caccccgtcc ccccccccc ttccccttcc ccttccccctc gccccggccc    110580 cccggcttgg tgccggagaa aaggggtgc cggcgcggac cggggtcggg cccgcggcgc    110640
cgagggtggg cgcgcgtgtc cgtgtgagag tttacggtgt gggtgggtgt cacggtggag    110700
cgggccgggg cccccggctc gcccgctcgc tcgctcgctc gccgggccgg cctggacgcg    110760
ggccacactg tgcggcggac cgtgccaagt ttagggcgct gcgacccaga gagagcgccg    110820
agctaaaagc tattttatcg ccgctgcggt ttcccctggc gcggcgccta gacaccgttt    110880
ctgcagacag agccctctct aatggcgcgt ccgggaaggc ttctcccggg ccgcgagggc    110940
cgcggcggcg accccctccc tccctcctcc tcccgtccc cgtccccgtc ccgcccgc    111000 tctcccgggc cgccgcgata ccgcgcgggc gataccgcgc gggccgcccg cgggcgctac    111060
cgcgccgctc cgctcgccgc ctcttccccc ctcctcctcc gccgccgccg ccagtcctcc    111120
tcgctcctct ccgcccacgc aactcctccc gcccgcgtgc ccccggggcc atcggctgga    111180
acaccccgag ccttcgctga gtgctgcccc cgccccgccc gcggcactcc gggcccgcgt    111240
gagagggtac agagcgaacc cggccccgac ccccccccg cccgccgggg gaggcttccc    111300
ggaaccggcg cggccatcaa ccccctcccc cacccacccg cacagcgcgc acgccgaccg    111360
cccgcgtttg ctacgatccc tgcgcccgac ggggccgcgg gacggcgcgt gcggcgcgga    111420
acgagagggg gagcggggt gcggggcggg ggcgcgggcg agtgagcgtg cgcgaagggg    111480
ggagagggcg cgtgggcgag aggggcgggg tggggtgggg ggcggcggcg gctcgccctc    111540
cgtcctcccc tccttcctct ccccgtcgac tcgcgtcgcg gcgattcggg ccgcatcgag    111600
gcgcgtcggg gttttcgcgc cctcgcgccg ccgccgcctc ctcatctttc gtggttaaca    111660
cacaccacca cacatacaca ccctcccccc gcgccgctgt ctgtggcgcc cgtcgtctct    111720 ccgccggcg caaccccggg ccctgagagc tttctccgct ttctatttcg gccccggcct    111780
ccccgacctc tctcacccgc cctcccgcgc tctctttccc acacacacaa gaggctcgcc    111840
ctcgttccat catctcggcg tactcgccgc ctcgtacact acatccgtct accgccgcca    111900
gcaacccttt ttttttcccg ctcactcctc ctccccccctc ctcctcctcc tcctcctccc    111960
ccctcctgcc tccattcatc aatctcgtcc aggccgcggg cccattcacc atcgccgcgg    112020
tccgagctcg gccaggagag atggatggat ggattggggg aaggagggc ggggagcgcg    112080 agcgggagaa ggttggcgaa ggagagagcg agagcgggaa ctgagagggg ggctgggtgg    112140
ggtgaggcga gtgaccgcca ccgccctcta ccaccaccac ccctcccctc cctctcctct    112200 ctctcccgg tccgtgtgc acacacagag agtgtttttt tttccttctt cttcccggtt    112260
cctcttcgtc ctccgggccc tcggtgccgc gatcccccac cccgccccgc ccccttcct    112320 cctccccca tttccccac ccccaattcc cccactcctc ccacaccagc ccccaccgcc    112380
gcggccgcag ccgccgcgat ccgtcctccc cattcatctt ttttccagag gccattcatc    112440
gccccgctca tccgtcttca tcgccgcgga gggctggctc gaggccagcg cgccctttcc    112500
tctcccggcg cgcccgctcc ctccgcgtcc cctctccccg ccgccccccg cggccacacc    112560
gagccttctc cgcgcggtcc cgcctctcct ctcctctccc cccatcccgc cccgctcccc    112620
```

```
gcccctctc  ccccccctc  tcccgccggt  gttttcccac  gcccacactc  actttctccg  112680
ctcccacccc  accctcctga  ctcaccgtc  ccgggggatt  ccctgtccct  cggggcgcgg  112740
ccgacccggc  ggtgacccat  ccccaccccg  ccgcgcccct  ttttcctcga  gagcgggcgt  112800
ccgggaaggg  agaggtcgcg  gcgggtcacg  cgcgctcccg  cgacttcccg  gcccgcgatg  112860
cggtcccgga  aatttccggg  acggtcgccg  cggccgtctc  ggggcccgcg  gcgccgccaa  112920
ctcgagtctt  ggcacgctgc  cagcgttcgc  acttgttgta  tataagatat  aatactagta  112980
tatattagca  attggtgcga  acgtgacgtg  gcccaatcaa  atccggccct  cgggcccacg  113040
tgccccattg  gcaatttatc  gaccgctttc  cgaagggatc  gaaccccggg  gcacccgcct  113100
ccggggacgc  gccagccaat  gcgggctccc  gggacgcggg  cacggctccc  ccattggccg  113160
gtcccggacg  cccgtcccgc  gggccggacc  gcccccttcc  cgggacttgg  cacgcatcca  113220
gcgttcgcac  ttgcggtata  taagatataa  actagtata  tattagcaat  tggtgcgaac  113280
gtgacgtggc  ccaatcaaat  ctctccacgg  gccccacgtg  ccccccattgg  cgatttatcg  113340
atcgcttttcc  gaagggatcg  aacccgggg  gcggcgcccc  cggggacgcg  ccggccaatg  113400
ggggagccgg  gcccgcgtcc  cggggcccca  cgtgtgaggc  cccggccaat  gggcccgtcg  113460
gcccggcccc  ctcgacgggg  cgataaaggg  gtgcgcggcg  gcccggccga  cggcactcgc  113520
cgccccaacg  acgccgacgg  ggatcgaccg  ggagaggcgc  gagcgcgccc  cgagccgacg  113580
aggagccgcg  ccccgctcga  ggacgcccgg  acgacgacg  tgacgtcggc  atcggcttcg  113640
acgacgacga  tcgcgggacc  cgacggtacc  ggatgcgggg  gatcccccgg  tcggggtggg  113700
ccgggagtgg  gcgtggcaac  tcctccccgt  cccccctccc  caccccgcgc  gatcgcgctc  113760
atcgtatccg  ttctcgtttc  aggtgccgca  tcgttccgga  agaaacgcct  cggggggtcgc  113820
gcgtccgtcg  cctaggtgag  tcgggggggct  tcccgggtgc  ggctccccccc  ctcccccctc  113880
ccctcccccg  ggttgggttg  ggcgggtggg  cggggtcgg  gagggatcgg  gggaagggga  113940
gggggtcgtg  gctcacgctg  acgtcatgcg  ttttcttccc  ccccccaca  gggacgcgag  114000
cgggaccggc  tggtcgacca  cccattcaat  ccatccaatc  catccagcca  ccccaccccg  114060
tcggggcggc  cgggctcggt  tccgggtcgg  cgtcggggag  cctcgcccac  cacccggcc  114120
cccgtcccag  cccagccccc  cccacgcccc  catcgcaccc  cctcccaccc  cacccgttc  114180
ccaccacccc  gccgacccccc  cgctcgaccg  cccgcccccg  acccaccgcg  tccgccgcgc  114240
ccatggaccg  ggtctgggcc  gactggtacg  agcccgtgcc  ctccccgccg  ttctcgcccg  114300
tcgacccgcc  cgggcccgg  cccacgaccc  cgctcccggg  gagcagcccc  ccgtcccccg  114360
cctcgacccc  cacgcccccc  aagcgcgggc  gctacgtcgt  cgagcacccc  gagtacgggc  114420
cccgcccga  ccccgaggag  gtgcgcgtcc  acgcgcgcg  gggccccggc  gccttctgcg  114480
cggccccctg  gcgcccgac  acgcggcgcc  tcggggccga  cgtgaaccgc  ctctttcgcg  114540
gcatcgccgt  tcggccgcc  gacgtgacgg  gcgacacgcg  cgccctgcgc  gcgcccctct  114600
ttgactttta  cgccatgggc  tacacgcgcc  agcgcccctc  ggcccctgc  tggcaggccc  114660
tgctccagct  ctcgcccgag  cagagcgccc  cgctgcgcag  cgcgctgcgc  gagctcaacg  114720
agcgcgacgt  ctacgacccg  cgcgtcctct  ccccgccggt  catcgagggc  ccgctctttg  114780
gggaggagtg  cgacgtcgac  gaggacgacg  ccggctcgga  caccaccgtc  gcgtccgagt  114840
ttagcttccg  cggctcggtg  tgcgaggacg  acgggagga  cgaggacgaa  gaggaagacg  114900
gggaggagga  agacgaggac  gaggaggggg  aagaggaaga  agacgaggag  gaagaggaag  114960
acgaggacga  ggaggaagag  gaagggggacg  aggacgggga  gacggacgtg  tacgaggagg  115020
```

```
acgacgagga cgaggacggg ctctgtgagg acgaggccga ggacgaggag gacgaggagg    115080
acggggacga ctttgacggg gccagcgtgg gcgacgacga cgtgtttgag ccccccgagg    115140
acggctcgga cggagagggc tcgggctcgg acgacggcgg ggacggggaa gaggaagacg    115200
aagatgaaga cgaggacgag gacgatggag aggacgagga ggacgaggaa gaggaggacg    115260 gggggaaga cggcgaagac ggtgaagaag acgaagacga agacggagag ggcgaggagg    115320
gcgggaagga cgccgcccgc cggggggacgc gcgcccgac gcggcccgcc gccgcccgt    115380 gaggcgggcc tcgccccgcg ctgttcttcc cactcccccc cccccccacc ccaccgtccg    115440
ccccatcgtt tgcccctctc cccttcccct ctgttgtgcc ctcaataaac acggcggccc    115500
gccgctcgaa cctcaactct ctcgtctctc gggcgttttt tccctcccgg ccctcgtggg    115560
gaagggagat ggggtggggg agaggggggac ggtgggggag agggggtggag ggagagaaag    115620 gacagaggcc gggcgcgtcg ggttcgagag cgagggcgtt tattgttaaa gttgttggtg    115680 gggggagtc cgggggagtc cgggggagtc aggggagtc aggggagtc cgggggagtc    115740 aggggagtc aggggagtc cgggggagtc cgggggagtc ctcggcggct aggagatggt    115800
gcaaggagtg gggggggtgag gtcctcggcg gctattggtg ggaaggggga gtgacgtcag    115860
ggcagcgggg ggaaaggggg gggaaagggg ggagagcgag tgggtggcgg cggcgagagt    115920
ctgtcggatg gcgccagggg gggcgggcgg gcggccgcgg ggagggagga cgggcgcgcg    115980
tgaggcggcg gcgcccgtc gcggtcgaga accaccgccg ccgtcaccgc cgcctcccat    116040
ccgatgtgat atcgcggcac gccggccgtc ccggcgttca ttcacaccgc acccgttcgc    116100
ccacgtcccc gcgggcaagc acgcacacac ccggtcgcgc atcatgctgg cgatgtggag    116160
atgggtcacc aagaggtcgc ggctccgccg aggccacgcc catcttgggg gaaataaagg    116220
agtccgggga atttgttcct tataccttgc cgggctcagc agggggttgt cgcgcgtcca    116280
cgcccagcgc tcgcacgcag caacaatggc cgacgccgga atcccgacg agatcctgta    116340 ctcggacatc agcgacgacg agatcatcat cgacggcgac ggcgacagca gcggggacga    116400
ggacgacgat gacgggggggc tgacgcggca ggccgcggcg cgcatcgtca cggacctggg    116460
cttcgaggtg ctgcagcccc tgcagtcggg ctcggagggc cgcgtcttcg tggcccgccg    116520
gccgggcgag gcggacacgg tggtgctgaa ggtgggccag aagccctcga cgctgatgga    116580
gggcatgctg ctgcagcgcc tgtcccacga taacgtcatg cgcatgaaac agatgctcgc    116640
ccgggggccg gcgacgtgcc tggtcctgcc gcactttcgg tgcgatctgt acagctacct    116700
gaccatgcgg gacgggccgc tggacatgcg cgacgccggg tgcgtgatcc gggccgtgct    116760
ccgcgggctc gcctacctgc acgggatgcg catcatgcac cgcgacgtca aggcggagaa    116820
catcttcctc gaggacgtgg acacggtgtg cctgggggac ctcggggccg cgcgctgcaa    116880
cgtggcggcg cccaactttt acgggctcgc cgggaccatc gagaccaacg ccccgaggt    116940 gctcgcgcgc gaccgctacg acaccaaggt cgacgtctgg ggcgcggggg tggtgctctt    117000
cgagacgctg gcctacccca agacgatcac cggcggggac gagcccgcga tcaacgggga    117060
gatgcacctg atcgacctca tccgcgccct cggggtgcac cccgaggagt tcccgcccga    117120
cacgcgcctc cggagcgagt tcgtccggta cgccgggacc caccgccagc cgtacacgca    117180
gtacgcgcgc gtggctcgcc tcgggctgcc cgagacgggg gctttcctga tttacaagat    117240
gttgacgttt gatcccgtcc gccgcccttc cgctgatgag atactcaact ttggaatgtg    117300
gaccgtataa aacgggccgg ctccgagcgg taggacacac acacctttgc gcatctccac    117360
```

```
agctcaacaa tgaagtgggc aacgtggatc ctcgccctcg ggctcctcgt ggtccgcacc    117420
gtcgtggcca gagaggcccc tcgggagctc tgctacggcc accccgtcca cgacgaccgg    117480
cggcccgtcg ggcccgcgac cgacgcccag cccgtgaacc cgctcgcccc cgccaacgcc    117540
accgggacgg actactctcg cggctgcgag atgcgcctcc tggatccgcc tctcgatgta    117600
tcgtcccgct cctcggaccc cgtcaacgtg accgtcgcct ggttctttga cggcggccac    117660
tgcaaggtgc ccctcgtcca ccgcgagtac tacggctgcc cggggacgc catgccctcc     117720 gtcgagacgt gcaccggcgg gtactcgtac acccgcacgc gcatcgacac cctgatggag    117780
tacgccctcg tgaacgccag cctcgtgctg cagcccgggc tgtacgcgc cggcctgtac     117840 atcgtcgtgc tcgtctttgg cgacgacgcc tacctcggca ccgtctccct gtcggtggag    117900
gccaacctgg actaccccctg cggcatgaag cacgggctca cgatcacccg ccccggggc    117960 accctcccac ccatcgcccc cacggccggc gaccaccagc gctggcgcgg gtgcttcccc    118020
tcgaccgacg agggcgcctg ggagaacgtg accgccgccg agaagggcct gtccgacgac    118080
tacgccgact actacgacgc gcacatcttc cgcctggagt ctgacgacga ggtcgtccac    118140
ggcgatgccc ccgaggcccc cgagggcgag gaggtgaccg aggaggaggc cgagctgacc    118200
tccagcgacc tcgacaacat cgagatcgag gtcgtgggct ctcccgccgc tcccgtcgag    118260
ggcgccggcg acggcgagga ggggcacagg gacgaggagg acgaggagct gacctccagc    118320
gaccttgaca acatcgagat cgaggtcgtg ggctcgcccg cggccgcccg cttcttcgcc    118380
gcctccacca cccccgcgc cccaccccgc gcggccgaga tcacgaccat gaccacggtc    118440
accaccgtgc ggacgaccga ggaccccagc ggcatcaccg actgccgccg gagcgacttt    118500
gtctcgccct ctgacatctt cgtgaccccc accggcagcc ccgctctgct cctgggcttc    118560
ctgggcagcg cgctcgcctc gcgccccctg cacctgacgg ccggggagac ggcccagcac    118620
gtgcgcgagg cccagcagaa gagccgccac atccgctccc tcggcggcct ccagctctcg    118680
gtcgagaccg agaccaccaa caccaccacc cccagacgg gcctgtcggg cgacatccgc     118740
acctcgatct acatctgcgt cgccctcgcc ggcctggtcg tcgtgggcat cgtcatcatg    118800
tgcctccata tggcgatcac cagggcccgg gcccggaacg acggctaccg ccacgtggcc    118860
tccgcctgac ccggccccgc ccgactcccc cgcgatcccc ccctctcac cgggtgtcca     118920 tcttcaataa agtatgtctc aaacacctaa tttgcgtacg gccttgctta cggggtgcg    118980 ccccacgccc agcggtccat aaaattgggt tggggcccca ggttcccata cactcacccg    119040
ccagcgccat gctgctcgca gcgctattgg cggcgctggt cgcccggacg acgctcggcg    119100
cggacgtgga cgccgtgccc gcgccgacct tcccccgcc cgcgtacccg tacaccgagt    119160
cgtggcagct gacgctgacg acggtcccct cgcccttcgt cggccccgcg gacgtctacc    119220
acacgcgccc gctggaggac ccgtgcgggg tggcggcgct gatctccgac ccgcaggtgg    119280
accggctgct gagcgaggcg gtggcccacc ggcggcccac gtaccgcgcc cacgtggcct    119340
ggtaccgcat cgcggacggg tgcgcgcacc tgctgtactt tatcgagtac gccgactgcg    119400
accccaggca gatctttggg cgctgccggc gccgcaccac gccgatgtgg tggaccccgt    119460
ccgcggacta catgttcccc acggaggacg agctgggggct gctcatggtg gctccggggc    119520
ggttcaacga gggccagtac cggcgcctgg tgtccgtcga cggcgtgaac atcctcaccg    119580
acttcatggt ggcgctcccc gaggggcaag agtgcccgtt cgcccgcgtg accagcacc    119640 gcacgtacaa gttcggcgcg tgctggaacg acgagagctt caggcggggc gtggacgtga    119700
tgcgattcct gacgccgttc taccagcagc ccccgcaccg ggaggtggtg aactactggt    119760
```

```
accgcaagaa cggccggacg ctcccgcggg cctacgccgc cgccacgccg tacgccatcg    119820
accccgcgcg gccctcggcg ggctcgccga ggcccaggcc ccggccccgg ccccggccga    119880
agcccgagcc cgccccggtg acgcccgcgc ccccggccg  cctgcccgag ccggcgacgc    119940
gggaccacgc cgccggggc  caccccacgc cgcgaccccc gaggcccgag acgccgcacc    120000
gccccttcgc cccgccggcc gtcgtgccca gcgggtggcc gcagcccgcg gagccgttcc    120060
agccgcggac ccccgccgcg ccgggcgtct cgcgccaccg ctcggtgatc gtcggcacgg    120120
gcaccgcgat gggcgcgctc ctggtgggcg tgtgcgtcta catcttcttc cgcctgaggg    120180
gggcgaaggg gtatcgcctc ctgggcggtc ccgcggacac cgacgagcta aaagcgcagc    120240
ccggtccgta gcctccgcag taccggcgtc gatgatgatg gtggcgcgcg acgtgacccg    120300 gctcccgcg  gggctcctcc tcgccgccct gaccctggcc gccctgaccc cgcgcgtcgg    120360
gggcgtcctc ttcaggggcg ccggcgtcag cgtgcacgtc gccggcagcg ccgtcctcgt    120420
gcctggcgac gcgcccaacc tgacgatcga cgggacgctg ctgtttctgg aggggccctc    120480
gccgagcaac tacagcgggc gcgtggagct gctgcgcctc gaccccaagc gcgcctgctt    120540
gcggacgcgg tccgacccca cggcgccgtt ctacatcacc accgagacgc acgagctgac    120600
gcggcgcccc ccggcggacg gctcgaagcc cggggagccc ctccgtatca gcccgccccc    120660
gcggctggac acggagtggt cgtccgtcct gaacgggatc cagtacctga actcgggggc    120720
ccggggcacg gccccgatcc acctgtggat cctgggcgcc gccgacctct gcgaccaggt    120780
gctcctggcc gcctcccgca gcaccgccgc cggagccccc ggcgcccga  cgggcgcgcg    120840 cctgacccgg cggcggcccg ggctgacgga cgccgacgcc ctggacgtga tcgtcgccgg    120900
gatcccggcc accgcgcca  tgttcgcgcg ggtccacaac cgctcctggc gccacgccgg    120960
cgagtggacg gaggccctgc atgcccagat cgtgacccgg ggcgacgtgc gccggcgccg    121020
aggcgggcgc ggcaacggac gcgagcgcgc cccgcgatgt accatctcct agacggcagg    121080
atctctccgc atcccccaca cccccccaaa aaaacaaaca ataaacgctc tcgctctggc    121140
acccgatgac acgcctccgt cctctctctc cctcccccat ctcccccttt cccccccctt    121200
tccccccgct gccctgacgt cactcccccct tccaccaat  agccgccgag gacctcaccc    121260
ccccactcct tgcaccatct cctagccgcc gaggactccc ccggactccc ccggactccc    121320
cctgactccc cctgactccc ccggactccc cctgactccc cctgactccc ccggactccc    121380
ccggactccc cccaccaac  aactttaaca ataaacgccc tcgctctcga acccgacgcg    121440
cccggcctct gtcctttctc tccctccacc cctctcccc  accgtccccc tctccccac     121500 cccatctccc ttccccacga gggcgggag  ggaaaaaacg cccgagagac gagagagttg    121560
aggttcgagc ggcgggccgc cgtgtttatt gagggcacaa cagagggggaa ggggagaggg    121620 gcaaacgatg gggcggacgg tggggtgggg ggggggggga gtgggaagaa cagcgcgggg    121680
cgaggcccgc ctcacggggc ggcggcggcc cgcgtcgggg cgcgcgtccc ccggcgggcg    121740
gcgtccttcc cgccctcctc gccctctccg tcttcgtctt cgtcttcttc accgtcttcg    121800
ccgtcttccc cccgtcctc  ctcttcctcg tcctcctcgt cctctccatc gtcctcgtcc    121860
tcgtcttcat cttcgtcttc ctcttccccg tccccgccgt cgtccgagcc cgagccctct    121920
ccgtccgagc cgtcctcggg gggctcaaac acgtcgtcgt cgcccacgct ggccccgtca    121980
aagtcgtccc cgtcctcctc gtcctcctcg tcctcggcct cgtcctcaca gagcccgtcc    122040
tcgtcctcgt cgtcctcctc gtacacgtcc gtctccccgt cctcgtcccc ttcctcttcc    122100
```

-continued

```
tcctcgtcct cgtcttcctc ttcctcctcg tcttcttcct cttccccctc ctcgtcctcg   122160
tcttcctcct ccccgtcttc ctcttcgtcc tcgtcctccc cgtcgtcctc gcacaccgag   122220
ccgcggaagc taaactcgga cgcgacggtg gtgtccgagc cggcgtcgtc ctcgtcgacg   122280
tcgcactcct ccccaaagag cggggccctcg atgaccggcg gggagaggac gcgcgggtcg   122340
tagacgtcgc gctcgttgag ctcgcgcagc gcgctgcgca gcggggcgct ctgctcgggc   122400
gagagctgga gcagggcctg ccagcagggg gccgaggggc gctggcgcgt gtagcccatg   122460
gcgtaaaagt caaagagggc gcggcgcagg gcgcgcgtgt cgcccgtcac gtcggcgcc   122520
gagacggcga tgccgcgaaa gaggcggttc acgtcggccc cgaggcgccg cgtgtcgggg   122580
cgccaggggg ccgcgcagaa ggcgccgggg ccccgcgcgc cgtggacgcg cacctcctcg   122640
gggtcgggcg ggggcccgta ctcggggtgc tcgacgacgt agcgcccgcg cttgggggc   122700
gtggggtcg aggcgggga cggggggctg ctccccggga gcgggtcgt gggccgggc   122760
ccgggcgggt cgacgggcga aacggcggg gagggcacgg gctcgtacca gtcggcccag   122820
acccggtcca tgggcgcggc ggacgcgtg ggtcggggc gggcggtcga gcgggggtc   122880
ggcggggtgg tgggaacggg gtggggtggg aggggtgcg atgggggcgt ggggggggct   122940
gggctgggac gggggccggg tgggtgggcg aggctcccg acgccgaccc ggaaccgagc   123000
ccggccgccc cgacgggtgg gggtggctgg atggattgga tggattgaat gggtggtcga   123060
ccagccggtc ccgctcgcgt ccctgtgggg gggggaaga aaacgcatga cgtcagcgtg   123120
agccacgacc ccctcccctt ccccgatcc ctcccgaccc ccgcccaccc gcccaaccca   123180
acccggggga ggggagggg gaggggggga gccgcacccg ggaagccccc cgactcacct   123240
aggcgacgga cgcgcgaccc ccgaggcgtt tcttccggaa cgatgcggca cctgaaacga   123300
gaacggatac gatgagcgcg atcgcgcggg gtggggaggg gggacgggga ggagttgcca   123360
cgcccactcc cggcccaccc cgaccggggg atccccgca tccggtaccg tcgggtcccg   123420
cgatcgtcgt cgtcgaagcc gatgccgacg tcaccgtcgt cgtccgggcg tcctcgagcg   123480
gggcgcggct cctcgtcggc tcggggcgcg ctcgcgcctc tccggtcga tccccgtcgg   123540
cgtcgttggg gcgcgagtg ccgtcggccg gccgccgcg cacccctta tcgcccgtc   123600
gaggggccg ggccgacggg cccattggcc ggggcctcac acgtgggccc cggggacgcg   123660
ggccggctc cccattggc cggcgcgtcc ccggggcgcc cgcccccggg gttcgatccc   123720
ttcggaaagc gatcgataaa tcgccaatgg gggcacgtgg ggcccgtgga gagatttgat   123780
tgggccacgt cacgttcgca ccaattgcta atatatacta gtattatatc ttatataccg   123840
caagtgcgaa cgctggatgc gtgccaagtc ccgggaaggg ggcggtccgg cccgcgggac   123900
gggcgtccgg gaccggccaa tggggagcc gtgcccgcgt cccggagcc cgcattggct   123960
ggcgcgtccc cggaggcggg tgccccgggg ttcgatccct tcggaaagcg gtcgataaat   124020
tgccaatggg gcacgtggc ccgagggccg gatttgattg gccacgtca cgttcgcacc   124080
aattgctaat atatactagt attatatctt atatacaaca agtgcgaacg ctggcagcgt   124140
gccaagactc gagttggcgg cgccgcgggc cccgagacgg ccgcggcgac cgtcccggaa   124200
atttccggga ccgcatcgcg ggcgggaag tcgcgggagc gcgcgtgacc cgccgcgacc   124260
tctcccttcc cggacgcccg ctctcgagga aaaggggcg cggcggggtg gggatgggtc   124320
accgccgggt cggccgcgcc ccgagggaca gggaatcccc cgggacgggt gagtcaggag   124380
ggtggggtgg gagcggagaa agtgagtgtg ggcgtggaa aacaccgcg ggagagggg   124440
gggagaggg ggcggggagc ggggcgggat ggggggagag gagaggagag gcgggaccgc   124500
```

```
gcggagaagg ctcggtgtgg ccgcgggggg cggcggggag aggggacgcg gagggagcgg   124560
gcgcgccggg agaggaaagg gcgcgctggc ctcgagccag ccctccgcgg cgatgaagac   124620
ggatgagcgg ggcgatgaat ggcctctgga aaaagatga atggggagga cggatcgcgg   124680
cggctgcggc cgcggcggtg ggggctggtg tgggaggagt gggggaattg ggggtggggg   124740 aaatggggggg aggaggaagg ggggcggggc ggggtgggggg atcgcggcac cgagggcccg   124800
gaggacgaag aggaaccggg aagaagaagg aaaaaaaaac actctctgtg tgtgcacacg   124860
ggaccgggga gagagaggag agggagggga gggggtggtgg tggtagaggg cggtggcggt   124920
cactcgcctc accccaccca gcccctctc cagttcccgc tctcgctctc tccttcgcca   124980
accttctccc gctcgcgctc cccgcccctc cttccccaa tccatccatc catctctcct   125040
ggccgagctc ggaccgcggc gatggtgaat gggcccgcgg cctggacgag attgatgaat   125100
ggaggcagga gggggggagga ggaggaggag gaggagggggg gaggaggagt gagcggggaa   125160
aaaaaagggt tgctggcggc ggtagacgga tgtagtgtac gaggcggcga gtacgccgag   125220
atgatggaac gagggcgagc ctcttgtgtg tgtgggaaag agacgcgggg agggcgggtg   125280
agagaggtcg ggggaggccgg ggccgaaata gaaagcggag aaagctctca gggcccgggg   125340
ttgcgccggc ggggagagacg acgggcgcca cagacagcgg cgcggggggga gggtgtgtat   125400 gtgtggtggt gtgtgttaac cacgaaagat gaggaggcgg cggcggcgcg agggcgcgaa   125460
aaccccgacg cgcctcgatg cggcccgaat cgccgcgacg cgagtcgacg gggagaggaa   125520 ggaggggggag acggagggcg agccgccgcc gccccccacc ccaccccgcc cctctcgccc   125580
acgcgccctc tccccccttc gcgcacgctc actcgcccgc gcccccgccc cgcacccccg   125640
ctccccctct cgttccgcgc cgcacgcgcc gtcccgcggc cccgtcgggc gcagggatcg   125700
tagcaaacgc gggcggtcgg cgtgcgcgct gtgcgggtgg gtgggggagg gggttgatgg   125760
ccgcgccggt tccgggaagc ctccccccgg gggcggggggg ggggtcggggg ccgggttcgc   125820 tctgtacccct ctcacgcggg cccggagtgc cgcgggcggg gcggggcag cactcagcga   125880 aggctcgggg tgttccagcc gatggccccg gggcacgcg ggcgggagga gttgcgtggg   125940
cggagaggag cgaggaggac tggcggcggc ggcggaggag gaggggggaa gaggcggcga   126000
gcggagcggc gcggtagcgc ccgcgggcgg cccgcgcgt atcgcccgcg cggtatcgcg   126060
gcggcccggg agagcgggcg gggggacgggg acggggacgg ggaggaggag ggaggaaggg   126120
ggtcgccgcc gcggccctcg cggcccggga gaagccttcc cggacgcgcc attagagagg   126180
gctctgtctg cagaaacggt gtctaggcgc gcgccaggg gaaaccgcag cggcgataaa   126240 atagcttta gctcggcgct ctctctgggt cgcagcgccc taaacttggc acggtccgcc   126300
gcacagtgtg gccgcgtcc aggccggcc ggcgagcgag cgagcgagcg ggcgagccgg   126360
gggccccggc ccgctccacc gtgacaccca cccacaccgt aaactctcac acggacacgc   126420
gcgcccaccc tcgcgccgc gggcccgacc ccggtccgcg ccggcacccc cttttctccg   126480
gcaccaagcc ggggggccgg ggcgaggga agggaaggg gaaggggggg gggggacggg   126540
gtgcgcgcgc gtgtgtgtat gtgtatgtgg caccggcatc ggtctccccc caaaacggag   126600
aaggcgaggg agacggagag ggaggtgtgt ctctgtgttg ttttttttcct gctggcgccg   126660 cggtgcgcga acgtgatcac ggggggggcgg cgcgctccgc gctccccgc cgcctgggcg   126720 gggatgccgc gccggcacga gcgcacgcgg gcgcgcggggc ggcggggagg gagaggggcg   126780
gaggaagggc cgggccgccg agccggccgc gccattgggc gccgggcgga acggggcgtg   126840
```

```
gagaggcgcc cgcgccgggg acgcgcctgc ggcggcgggc gcgcgccggg cggcttcct    126900
ccttcaccgc cgccgcgtcc tcctcctccc tccccgccgg cctcggccca cccgcggcgt   126960
caccccgctc tccccctcat tcccccccc   tccctcectt ccccccgacc cccctccct   127020
cccgcgtcct gcgtcacggg gaccggggggg tcccgcgtga tgacgccggg gacgcgggac  127080
gcgcccgccg cctgggagcc ggcgaggagg acaaaaagag ttctgtgtcc cctcgccccc   127140
ctccgcgtcc gcagccgcct ctgcagccgc cgcccgcgcc gcgaccggcg aacgcagaga   127200
ggggacgcgg ggaagagacg cggagagggg gacaggggga gagagagcga ggggcgcgag   127260
cgcttcctcc tccgcacccg ccttcctccg cccgcctttc attccggac  tcggagccg    127320
ctcccgctcc cccgttttc  ctcctggccg cggcgaccgc cgccgccgct ctcgaggttt   127380
tttttttcctt cctctccttc ttcctcctcc tcctccgcct ttgggtgttt ccttctccgc  127440
gtccccatct ccgaggcccg aggcgccggg gctttcttcc cggaccgccg gggaggaagc   127500
gccccggctt ctgcttctta ttctcctctc tcggtaagca cagactctcc tactactact   127560
cctactactc ctactcctac tatattacta tgactactac tatgactact actatgacta   127620
ctacggtgac ttctcctccc cgctctagac ttttttttcct cccctctcct cctttcgctc  127680
ccgtctcccg ggcacccgcg gccgggcgga ggggaagcg  ggaaggggaa gcgcggggcg   127740
ccgcgcctct ccctcccgct tccccccccc ccgccggccc cttccccgtt tccccgtttc   127800
ccttccccc  cttcccccgtc tgttccttcc cccgcttccc cgtttcttct tcttccccc   127860
cccgtccct  cttccttccc cacacgcccc gctctcccac gccgcggccg cgggggccg    127920
aagcggacgc ggaagaagac gcggaagaag agagagagag aaagagggg  gccggcgggg  127980
atggggaaga aggcccgacc cgcgcggggg ccccctcctg tcgcctgtcg tttgaatgaa   128040
accttccccc gagcgacccc gctcccgcct gtggtgccgt gttttttcc  cgcgacgggg   128100
agagcgcgag agtgaggctg tcggctgtgg gttgtcggct gttggccgtt ggctgaggac   128160
gacggggagg ggggatgct  gccgcgggtg gcatgagacg gagggggggcg agggcgggcg  128220
gtggagggg  gagaggaagg tctgggcgcg cgtgccgcgg gccgagtgtc gggcgagtgc   128280
gaggcgggtc gggggggcggg gaggaaggga ggtgtgggg  gatggccggc cggcgccccc   128340
ggagcacgcg gggcgccccg gcgggcggga gggggtccgg gggaagggtg gggcggtggc   128400
ggcggccatc gcccgacccct tcccggggc  gcgcgcgcgt gggaccggga ccggaccgg   128460
gaccgggacc gggaccggga caggggggcgg gggcgggggc ggggggcgggg agaggaggag  128520
aggagacgga ggagaggaga cggaggagag tcggaaagtc gggcggagga cagaggcgga   128580
gagggcgagc gagacacgca cggggagagg cgcgcgcaca cacgcggaga gagagaggag   128640
aggcgagaga ggaggagaag gaggaggcga actgggggaa aggcgagaca cgcccggcca   128700
ccccccctcc tcggaccgag gcgacggcgg agacggagac ggagagaccg cccgcccggc   128760
caccaccgtc ggtaccggta tcgccagtaa caccccgcacc accgacaccc acacggaccc   128820
tcacacccgc accggccccc atactcgcac cggccctcac acccacccac acgcacgcac   128880
gctctctctc gcacaccccc acatcacacg ctcccgcgc  acagacacac agacgacacc   128940
ctcccgccc  gcccgtccg  accgaccatc cgtcctcccg accctccacg agagagagag   129000
agcgagcctt ccctgcacac acagcaaaaa ttgacccccc ccatcccgga cccccccggg   129060
ggcgggggcc tcgcgcctcc gcgtccggcg ggcgcgatcg aggcccgcgc gccccgcggg   129120
gctcggggcg ggacgcggcg cccgcgcggg gacacgcttt cccccggagg ggcgtcccgg   129180
cgcgccggcc cggccctccc cgccgggaag ggggcccggc cctcttcgtc tcccggagcg   129240
```

```
cccccgggt   cccggcccga   ggtccatttt   gggccccgcc   cctttgcacc   cgccccccc    129300
caccgggcgg  ggtccgcgct   ccgacccccc   ccctcccccc   tctgccacgc   cccgccacgc   129360
cccgtcgcca  tcttggctcc   cctccccca    actccctctc   tcccgacgag   gccgagccgg   129420
tctcgcgccc  cctcccgccc   gcccgaggta   ccgcggaagg   acgacacgag   ccggaagacg   129480
gtgcaacgag  aacaactttt   atttttttca   ctctggggcg   tgtctcgtgg   ggtgggaggg   129540
gggaccggga  gagagagata   gaggggggg    gggagaggag   ggggtgggtg   ggcgacaaaa   129600
gtatccaagg  cgtggctgtc   cggctccttc   cttccgggtc   cgggcgggtc   cgggctcgag   129660
gttcgggtcc  ggttctcccg   ccccggcgtc   gcttcccggt   tcgggtccgg   tcgccggtcc   129720
ccggtccgac  ggcggttccg   ctcgtctctc   cgaccggctg   ggggcgccct   cggagcgcgc   129780
gccgagcgcg  caggcgcggg   tgggcgacc    gcggggtcg    cggagggtc    tcggggtct    129840
caggggtctc  gggagggggg   aaacgggggt   ctcgggtct    cgcgagtggc   aggggaggc    129900
ggtgagacca  ccacacaaca   cagagaccac   acaacacag    agaccaccac   acaacacaga   129960
gaccaccaca  acacagagac   caccacacaa   cacatgcgga   ccaccacaac   acagagacca   130020
ccacacaaca  catgcggacc   accacaacac   agagaccacc   acaacacatg   cggaccacgt   130080
gcagacacac  ggaagcttgc   accgtgaggc   cccattggcc   gagggcggcc   acgtggggcg   130140
agcatgcaaa  tgacgtgcac   acggaagctt   ccccgaaaat   catctgattg   gctcgctagc   130200
accacggggt  gggtcgcgtg   ccgagcatgc   gcctcgcgcc   cgcgcgaggg   attttcggac   130260
aatctcattg  gccgcccgcg   gccaagatgg   ccgcagagcg   ggccgggcat   gcaaatcaga   130320
ggcgcgcggg  agacgcctcc   gcgcgcccat   tggcccgggc   gggccgagat   ggccgccgcg   130380
ggggccgggc  atgcaaagta   gacgcgagag   gaagtgggcg   agagaaatcc   cattggccgt   130440
cgagggcca   agatggcgcc   ctcggggccg   gacatgcaaa   gtagacgcga   gaggaagtgg   130500
gcgagagaaa  tcccattggc   cgtcgagtgg   gcaagatggc   cgccgcgggg   gccgggcatg   130560
caaatggtcc  tcgcgaggaa   gttcctcgcg   aaatcccatt   ggccggcggc   cgccatcttg   130620
ggccgggcat  gcaaagcaga   cgcgagagga   agcgggcgag   aaaatcccat   tggccggcc    130680
gtcgggaag   tccgcggcga   aaatcggcca   ttggtccgct   tacctggggg   cgggctctcc   130740
tcggggcgct  tataagcgcg   gtctccatcg   tagcacttca   ctgcggtgca   ggtacggaca   130800
gcatcgttct  ctgccaaccc   gagggatcc    gaccgtctcc   gctccggcgc   ggactctgaa   130860
gactccggct  ctccggcggc   tatcagccct   cgacggacgc   ccgacccacc   gaggctctcg   130920
gcccaccaga  gaagagtctt   cttcttctcc   tcctccggcc   gccttcctcc   ttcttctccg   130980
ccgcccgctc  tccgcgctcg   gcgcccagcc   tcgctcaggc   agaaagaccc   cgatcgagac   131040
catggccgac  gatctctttg   acttcatcga   gaccgagggc   aacttcagcc   agctcctggc   131100
ggccgccgcc  gccgcggccg   aggaagaggg   catcgcgtcc   ggccccgacg   gcggcagcca   131160
gggctccccgg cgccgcggct   cctccggcga   ggatctcctc   ttcggcccgg   gcggcctctt   131220
ctccgacgac  gccgccgagg   ccgaggccga   ggccgccgtc   ctcgcggccg   cggccggagc   131280
cacgaggccg  cccgtcctc    cttcggccca   gcagcagcag   cccgccgggg   gctcgggcga   131340
gatcgtggtg  ctagacgacg   aagacgagga   ggaggacgag   cccgggtccc   cggccgccgg   131400
gtccccggt   cgggctctcc   atcagggctc   cgagcacggt   cacctcgtcc   tcgggccccg   131460
gtccggggcc  ggctcggggc   cccggccgcc   gaccccggca   gcactcgcag   cggcagaggc   131520
cggggccccc  ggcggccccg   ggcgctcgtc   cccctccgcg   gcctcccgg    cctcctcctc   131580
```

```
cggctccccc ggcccctcgg cagccccgcg gagatggtcc cccgcggggg acccggtcgg    131640
tgagcccggg ccggcggcgc ggcctcggac cccggcgcca ccagcacagc cagcagcggt    131700
ggccgcagcg ccggcacggc gggggcccgc ttccccagcc ccccccgccg ccgggccggt    131760
ctcggcgccc ggcggcggcg cgcccccctc cgcggaggg  gaccgcggtc gtcaccatca    131820
ccagcaccgc gagcccctgc tcgacgagcc cgccgccgcg aggcggctcg atcctcggcc    131880
gcttggcgcc cggagccccg tctcctccaa ccccaactcc aactccagct ccaccaccac    131940
cgtcgccgtc gagcccgtcg cccgcggccc cgagaaggac gaggacggac tcggccccgc    132000
cggggacggc gggcgcccc  cgcagagaca gccccgccgg cgccgcgccg gagagggcgc    132060
cctccgccgc ggccgcggct tcagcagctc cagcagcggc ggcagcgact cggacctctc    132120
cccggcccgc tcgccctccg ccccccgggc cctcgccgcc gccgccgcgc ggcgctcggc    132180
ctcctcctcg tcctcgtcct cctcgtcctc ctcgtcctcg tcctcctccg agggagaaga    132240
agacgaagga gtccggcccg cgcgcccact cgcccgcgcc gggccgccac cgtctccgcc    132300
ggcgcccgcc gcgcccccgc ggccctcggc ctcctccgcc tcctcctccg ccgcggcctc    132360
cccggccccg gccccggagc ccgcccggcc cccgcgcagg aagcgccgct ccaccaacaa    132420
ccacctctcg ctcatggccg acgggccccc gccgaccgac gggccgctgc tcaccccgct    132480
cggggagccc tggcccggct ccgaccctcc ggccgacggc cgcgtccgct acggcggcgc    132540
cggggactcc cgcgaggggc tctgggacga ggacgacgtc cgccaggccg cggcccgcta    132600
ccgcgccgcg gccgggcccg tgcccgtctt catcccggag atgggggact cgaggaagca    132660
gcacgaggcc ctcgtgcgcc tcatctacag cggggccgcc ggcgaggcca tgtcctggct    132720
gcagaacccg cggatgcagg ccccccgacca gcgcttcaac cagttctgcc agcgccgggt    132780
ccacgcgccc cacggccacg gctccttcat caccggcagc gtgaccccgc cgctgccgca    132840
catcggggac gccatggccg cccaggaccc gctctgggcc ctgccgcacg cggtgagcgc    132900
cgtggccatg agccgccgct acgatcgcac ccagaagacc ttcatcctgc agagcctccg    132960
ccgggcctac gccgacatgg cctacccggg ccgcgccgcg gaccccccgcg ccggggaggc    133020 gaccgtcgag gccctctgcg cccgcgtccg cgccgccttc gccgccgcgc agcccggccg    133080
cgtgccccgc gagctggcgg acgcctgcgt cctggcctgc cgcggcgtcc tcgagcgcct    133140
gctgccctgc ccgctccggc tgccgccgcc gcccgcgcc  ccggccgccc tcgggccgcg    133200
ctgcctcgag gaggtgacgg ccgcgctgct cgcgctccgc gacgcgatcc ccggggccgg    133260
cccggccgag cggcagcagg ccgcggacgc tgtcgcccctc gtcgcccgca ccgtggccgc    133320
gctggtgcgc tacagcgtgg acggggcccg cgcccgcgag gccgcctgga cctacgccgc    133380
ggccctcttc gccccggcca acgtggccgc ggcccggctc gccgaggccg ccgcgcggcc    133440
cgggcccgcg gagcccgcgc ccggcctgcc ccgctctgg  cccgagcagc ccggcctcgt    133500
cgtcccagcg ccggcgccgg cggcggcggg cgccccctcc ggcctccccg gctccggcc   133560 ctccagcccc gccagcacca agtccagctc cagcaccgag tccggctcca gcaccaagtc    133620
cagctccggc accaagtccg gcctctccgg ctcctccggc tacgccagct cccccgccgc    133680
cggcccggac ccagcccccg agcggcgcaa gaagaagcgc cgcgcgcccg ggcccgccg    133740 ccccggggac ggcgaggagg acgaggggct ctccggcgcg ccctccgcg ggacggcca    133800 cggccaccgc gacgacgaag aggaccgggg gccccggcgc aagcgccgct ccctcggact    133860
cgggcccgct ccgacccccg ctcccgcgct gctgtcctcc tcctcctcct ccgaggacga    133920
ccggctccgg cgcccgctcg ggcccatgcc cgagcacccc gcgcccgacg gcggcttccg    133980
```

```
ccgcgtcccg gccggcgaga cccacacgcc gcggccctcc gaggcggccc tcgccgccta  134040
ctgcccgccc gaggtggccc gcgccctcgt ggaccaggag gtcttcccg  aactctggcg  134100 cccggcgctc accttcgacc cggccgccct ggcgcacatc gccgcgcgcc gcggggccgc  134160
gggcgccccg ctccgccgcc gcgccgcctg gatgcggcag atagccgacc ccgaggacgt  134220
gcgcgtggtg gtgctctacg acccgctgcc ccacgaggag ctctgcgccg agcccgccga  134280
gggcgccccg cgcccggcct gggacccgcg ccgcggcggc ctctcggcgc tgctcgccgc  134340
cttcgcccac cgcctctgca cgccggactc gcacgcctgg gccgggaact ggaccgggcg  134400
ccccgacatc ggccgcctca acgcccaggg ggtgctgctg ctctcggcgc gggacctcgg  134460
cttcgccggc gccgtggagt acctctgctc gcggctcggc gcggcgcggc gccggctcat  134520
cgtgctggac accatcgagg actggcccgc ggacggcccg gccgtggggg actaccacgt  134580
ctacgtccgc gcccgcctgg acccggccgc ccagtgcgcc gtgcgctggc ccgggtgccg  134640
cgagctccgc gcggccgtgc tggactctag ctccatcgtg ggcccggcct gcttcgcccg  134700
cgcggaggcc tccttcgccc gcctgcaccc cggggccgag ccgctgcgcc tctgccgcca  134760
ggacaacgtg cgctacacgg tgagcacccg cgccgggccc cggacccgg  tcccgctgcc  134820 gccgcgcgcc taccgccagc gcgtgctccc caccgtggac ggctgcaagg acatggcccg  134880
ccagcgctcc gcgctcgggc tcggggaccc ggactttgac gcgggcgccg ccttcggca   134940 ccgcgcggcc aaccgctggg ggctcggcgc cccgctgcgg cccgtcttcg tctcctgcgg  135000
ccgccggggc ctcgccgagc tccgcggccc cgagggcctg ccggccgagc tgcgcgcctt  135060
ctgcgccgcg gcgctgctgg agcccgacgc cgaggccgcc ccgctggtgc tgaccccggg  135120
cgccgtcgcc gccgcgggcg cccgccggcc cgtgctctgg gactttgcgc ccttcgagac  135180
cagcgtccgc gccgccgccg ggggcgccgt ggagacccgc cggcccgcgg gggcctcggg  135240
cgccggggcc ggcccggcg  aggacgggga ctctgtggag atcgtcggcg tccgcggcgg  135300
cgacggccgg cccgcggcc  cgctcgggcc catcaaggtg gaggccatct cggacgacga  135360
ggaggccgag gacgccggca acccctacct gctgctccgc tgagcggggc gcccctcgg   135420 cccggccgga ctctgactct gactctccgg ccctccgcc  ggctcctcga ggcccttctc  135480
ctccgtcttc tctcccctcg ccctcggccc ggtcctcgtc ctcgtccccg tcctcctcct  135540
cctctgcgtc cgcggcggcg gcctcggtcc cctcggcccg gcggcgcttg cctccccggc  135600
gcctgcctcc ccggcccggt ggccctcctc ctcctcctct ccttctcctc cgcgcggatc  135660
ccccggccgg aggtggctgc ggcggcggcg gaggtggcgg cggtggtgga agcggcggcg  135720
gcggccgcgg cggagggctc ggcggcggag gatcgtcccg gtccccttct cctcctcctc  135780
ccgcggtccc ccgtcccct  tctcctcctt ctcccatcgg gtgagaaaag agtttatttt  135840
cagagcgaga aaataaagtt tgtgctgtat tttctgaacc ggctcgagtc tctgagattt  135900
tttggggaga tggaggcggc catcttggcg gtggtctctg gggtggaggt ggtcttgtgg  135960
atgggggtcc ctggtgggag gaagaagaag aggtggaggg tcttggtgag ggtgacgggg  136020
gtcctcctcc tggagggtct tggtggtggt ggtggtggtg gaagaagtg  gatggggtc   136080 ctcctcctgg agggtcttgg tggtggtggg tcttagcaga tgggggtccc tggtgggtct  136140
tagcagatgg gggccctcct cccggagggt cttggtggga agaagtagag ggtcttgggg  136200 atgttgggg  tccttgatgg tggtggtggg aggtggacgg cgttggtggt cccggcgggt  136260
cctggtggga ggtagatggt cccgagggtc ccggtggtcc cgggcgggag ttggacgatg  136320
```

```
gtggtcctgc ggtggtcgag gggggtgggg ggaaagagag aaagagagaa aaaaacacgg   136380
tggtggtcag tacagggaac tgccgttgca accatcgccc cctggtggtg atagtagtaa   136440
agcgtgtgcg tgagggggggg ggggggggggt ggtggtgttg ttggtggtgg tggtcccggg   136500
tggtcgtcgt ggagggcgg gaaaggcggt gggagagcgg gcggaacagg ttcatctggc    136560
ttccgtcttc cgtccccact cccagcctcc cccgctgcca ccgattggcc ggcgggacga   136620
tgacgacggc gaccgcgtgg cgcgagggga gccaatgggg cgggcgccgc ggagcggaag   136680
cccccgcccg cggacccccg gtgcgacgga aggggcaggc tcggcgcgcc gatgcgatcc   136740
gcggagcccg ccccggccgc gccccggaag ccggcgtcac gtccggggga agcggaaggg   136800
gccggcgcga tatgcagatg agatccgtgg gggccggcgt cacgtccggc ggaagttgcg   136860
cgcgggaagc ggtcatacgc aaatgaggcg gaagtcgtca tcggcaaaaa cgtcacgtcc   136920
gggaagcggt catatgcaaa tgggggggggg aggagcccgg cgtcacgtcc gggggaagcg   136980
gtcatattta aatgggggggg gaggggccag agcgtcactt ccggaggaag ttgtcatatg   137040
cagattaggg ggagggggtta tgcagattag ggggaggggt tatgcagatt aggggggaggg 137100 gttatgcaga ttagggggag gggttatgca gattaggggg aggggttatg cagattaggg   137160
ggcggggcta tgcaaatgta tgcaaatgag ggggtgggggt tatgcagatc aggggggaggg 137220 gttatgcaaa tgcatgcaaa tgagggggag gggccatgct aatttatgca aatgaggggg   137280
cggggctatg caaatgtatg caaatttatg caaattagcc ccccccttt aagcccgcc     137340 cccttttttc gcggcccccg gggagcgggg gggtggg                              137377
```